US008338091B2

(12) United States Patent
Chesnut et al.

(10) Patent No.: US 8,338,091 B2
(45) Date of Patent: Dec. 25, 2012

(54) METHODS AND COMPOSITIONS FOR SEAMLESS CLONING OF NUCLEIC ACID MOLECULES

(75) Inventors: Jonathan Chesnut, Carlsbad, CA (US); Miroslav Dudas, San Marcos, CA (US); Adam Harris, Carlsbad, CA (US); Louis Leong, Junction City, OR (US); Knut Madden, Carlsbad, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/401,680

(22) Filed: Feb. 21, 2012

(65) Prior Publication Data
US 2012/0149069 A1   Jun. 14, 2012

Related U.S. Application Data

(63) Continuation of application No. 12/112,803, filed on Apr. 30, 2008, which is a continuation of application No. 10/913,501, filed on Aug. 9, 2004, now abandoned.

(60) Provisional application No. 60/493,322, filed on Aug. 8, 2003.

(51) Int. Cl.
C12Q 1/68   (2006.01)

(52) U.S. Cl. ..... 435/6; 435/320.1; 435/91.42; 536/23.1; 536/24.2

(58) Field of Classification Search .................. None
See application file for complete search history.

(56) References Cited

U.S. PATENT DOCUMENTS

| 4,216,245 A | 8/1980 | Johnson |
|---|---|---|
| 4,293,652 A | 10/1981 | Cohen |
| 4,372,745 A | 2/1983 | Mandle et al. |
| 4,458,066 A | 7/1984 | Caruthers et al. |
| 4,517,338 A | 5/1985 | Urdea |
| 4,525,048 A | 6/1985 | Wong et al. |
| 4,670,572 A | 6/1987 | Hinshaw |
| 4,683,195 A | 7/1987 | Mullis et al. |
| 4,736,866 A | 4/1988 | Leder et al. |
| 4,745,076 A | 5/1988 | Muller et al. |
| 4,859,587 A | 8/1989 | Roizman et al. |
| 4,873,191 A | 10/1989 | Wagner et al. |
| 4,987,071 A | 1/1991 | Cech et al. |
| 5,104,621 A | 4/1992 | Pfost et al. |
| 5,125,748 A | 6/1992 | Bjornson et al. |
| 5,139,744 A | 8/1992 | Kowalski |
| 5,206,568 A | 4/1993 | Bjornson et al. |
| 5,221,623 A | 6/1993 | Legocki |
| 5,242,681 A | 9/1993 | Elgavish et al. |
| 5,262,176 A | 11/1993 | Palmacci |
| 5,334,575 A | 8/1994 | Noonan et al. |
| 5,350,564 A | 9/1994 | Mazza et al. |
| 5,355,215 A | 10/1994 | Schroeder et al. |
| 5,464,764 A | 11/1995 | Capecchi et al. |
| 5,487,933 A | 1/1996 | White |
| 5,589,351 A | 12/1996 | Harootunian |
| 5,597,910 A | 1/1997 | Gudibande et al. |
| 5,601,980 A | 2/1997 | Gordon et al. |
| 5,622,821 A | 4/1997 | Selvin et al. |
| 5,624,803 A | 4/1997 | Noonberg et al. |
| 5,628,982 A | 5/1997 | Lauffer et al. |
| 5,631,153 A | 5/1997 | Capecchi et al. |
| 5,631,169 A | 5/1997 | Lakowicz et al. |
| 5,639,615 A | 6/1997 | Selvin et al. |
| 5,650,289 A | 7/1997 | Wood |
| 5,656,207 A | 8/1997 | Woodhead et al. |
| 5,656,433 A | 8/1997 | Selvin et al. |
| 5,672,344 A | 9/1997 | Kelley et al. |
| 5,674,713 A | 10/1997 | McElroy et al. |
| 5,683,888 A | 11/1997 | Campbell |
| 5,721,435 A | 2/1998 | Troll |
| 5,741,657 A | 4/1998 | Tsien et al. |
| 5,766,891 A | 6/1998 | Shuman |
| 5,777,079 A | 7/1998 | Tsien et al. |
| 5,789,375 A | 8/1998 | Mukae et al. |
| 5,789,573 A | 8/1998 | Baker et al. |
| 5,800,999 A | 9/1998 | Bronstein et al. |
| 5,804,387 A | 9/1998 | Cormack et al. |
| 5,807,746 A | 9/1998 | Lin et al. |
| 5,843,746 A | 12/1998 | Tatsumi et al. |
| 5,877,021 A | 3/1999 | Stinchcomb et al. |
| 5,888,732 A | 3/1999 | Hartley et al. |
| 5,917,012 A | 6/1999 | Nishikata |
| 5,932,474 A | 8/1999 | Tsien et al. |

(Continued)

FOREIGN PATENT DOCUMENTS

EP   1079520   2/2001

(Continued)

OTHER PUBLICATIONS

Abbas-Terki et al., "Lentiviral-Mediated RNA Interference", *Human Gene Therapy*, vol. 13, Dec. 10, 2002, 2197-2201.

Abremski et al., "Bacteriophage P1 Cre-loxP site-specific recombination Site-specific DNA Topoisomerase Activity of the Cre Recombination Protein", *The Journal of Biological Chemistry*, vol. 261, No. 1, Jan. 5, 1986, 391-396.

Adelman et al., "RNA Silencing of Dengue Virus Type 2 Replication in Transformed C6/36 Mosquito Cells Transcribing an Inverted-Repeat RNA Derived from the Virus Genome", *Journal of Virology*, vol. 76, No. 24, Dec. 2002, 12925-12933.

Araki et al., "Site-specific Recombinase, R, Encoded by Yeast Plasmid pSR1", *Journal of Molecular Biology*, vol. 225, No. 1, May 5, 1992, 25-37.

(Continued)

*Primary Examiner* — Kimberly Chong

(57) ABSTRACT

The present invention is in the fields of biotechnology and molecular biology. More particularly, the present invention relates to cloning or subcloning one or more nucleic acid molecules comprising one or more type IIs restriction enzyme recognition sites. The present invention also embodies cloning such nucleic acid molecules using recombinational cloning methods such as those employing recombination sites and recombination proteins. The present invention also relates to nucleic acid molecules (including RNA and iRNA), as well as proteins, expressed from host cells produced using the methods of the present invention.

20 Claims, 49 Drawing Sheets

U.S. PATENT DOCUMENTS

| | | | |
|---|---|---|---|
| 5,948,653 | A | 9/1999 | Pati et al. |
| 5,998,208 | A | 12/1999 | Fraefel et al. |
| 6,008,378 | A | 12/1999 | Tsien et al. |
| 6,054,271 | A | 4/2000 | Tsien et al. |
| 6,074,853 | A | 6/2000 | Pati et al. |
| 6,086,902 | A | 7/2000 | Zamb et al. |
| 6,088,214 | A | 7/2000 | Malone et al. |
| 6,121,043 | A | 9/2000 | Cochran et al. |
| 6,143,557 | A | 11/2000 | Hartley et al. |
| 6,143,577 | A | 11/2000 | Bisconte Sconte De Saint Julien |
| 6,171,861 | B1 | 1/2001 | Hartley et al. |
| 6,197,584 | B1 | 3/2001 | Bennett et al. |
| 6,200,812 | B1 | 3/2001 | Pati et al. |
| 6,228,646 | B1 | 5/2001 | Hardy |
| 6,261,797 | B1 | 7/2001 | Sorge et al. |
| 6,270,969 | B1 | 8/2001 | Hartley et al. |
| 6,277,608 | B1 | 8/2001 | Hartley et al. |
| 6,304,156 | B1 | 10/2001 | Ishizaki et al. |
| 6,319,703 | B1 | 11/2001 | Speck |
| 6,342,229 | B2 | 1/2002 | O'Hare et al. |
| 6,355,412 | B1 | 3/2002 | Stewart |
| 6,379,967 | B1 | 4/2002 | Meredith et al. |
| 6,410,255 | B1 | 6/2002 | Pollok et al. |
| 6,410,311 | B1 | 6/2002 | Cochran et al. |
| 6,509,156 | B1 | 1/2003 | Stewart |
| 6,586,180 | B1 | 7/2003 | Ruffner et al. |
| 6,720,140 | B1 | 4/2004 | Hartley et al. |
| 6,872,551 | B2 | 3/2005 | Lima et al. |
| 2002/0007051 | A1 | 1/2002 | Cheo et al. |
| 2003/0027337 | A1 | 2/2003 | Droge et al. |
| 2003/0124555 | A1 | 7/2003 | Brasch et al. |
| 2003/0139363 | A1 | 7/2003 | Kay et al. |
| 2003/0186233 | A1* | 10/2003 | Chesnut et al. .......... 435/6 |
| 2004/0002077 | A1 | 1/2004 | Taira et al. |
| 2004/0053112 | A1 | 3/2004 | Hartley et al. |
| 2007/0184451 | A1 | 8/2007 | Byrd et al. |
| 2007/0196838 | A1 | 8/2007 | Chesnut et al. |
| 2011/0046201 | A1 | 2/2011 | Chesnut et al. |

FOREIGN PATENT DOCUMENTS

| | | |
|---|---|---|
| EP | 1215748 | 6/2002 |
| WO | WO96/19497 | 6/1996 |
| WO | WO96/23569 | 8/1996 |
| WO | WO98/12372 | 3/1998 |
| WO | WO98/56943 | 12/1998 |
| WO | WO02/05294 | 1/2002 |
| WO | WO02/46372 | 6/2002 |
| WO | WO02/090495 | 11/2002 |
| WO | WO03/046173 | 6/2003 |
| WO | WO2004/046320 | 6/2004 |
| WO | WO2004/108897 | 12/2004 |

OTHER PUBLICATIONS

Argos et al., "The integrase family of site-specific recombinases: regional similarities and global diversity", *The EMBO Journal*, vol. 5, No. 2, 1986, 433-440.

Ausubel et al., "Introduction to Expression by Fusion Protein Vectors", *Current Protocols in Molecular Biology.*, John Wiley and Sons, Inc., 1994, 16.4.1-16.4.4.

Baek et al., "Sustainable Systemic Delivery via a Single Injection of Lentivirus into Human Skin Tissue", *Human Gene Therapy*, vol. 12, No. 12, Aug. 10, 2001, 1551-1558.

Baldwin et al., "Cloning and expression of the luxY gene from *Vibrio fischeri* strain Y-1 in *Escherichia coli* and complete amino acid sequence of the yellow fluorescent protein", *Biochemistry*, vol. 29, No. 23, Jun. 12, 1990, 5509-5515.

Banerjee et al., "Control of developmental timing by small temporal RNAs: a paradigm for RNA mediated regulation of gene expression", *Bioessays*, vol. 24, No. 2, Feb. 2002, 119-129.

Bath et al., "Many Type IIs Restriction Endonucleases Interact with Two Recognition Sites before Cleaving DNA", *Journal of Biological Chemistry*, vol. 277, No. 6, Feb. 8, 2002, 4024-4033.

Berger et al., "Structure of DNA topoisomerases", *Biochimica et Biophysica Acta*, vol. 1400, No. 1-3, Oct. 1, 1998, 3-18.

Berlman, "Energy Transfer Parameters of Aromatic Compounds", *Table of Contents, Academic Press*, 1973, 1-4.

Bernstein et al., "Role for a bidentate ribonuclease in the initiation step of RNA interference", *Nature*, vol. 409, No. 6818, Jan. 18, 2001, 363-366.

Boutla et al., "Short 5-phosphorylated double-stranded RNAs induce RNA interference in *Drosophila*", *Current Biology*, vol. 11; No. 22, Nov. 13, 2001, 1776-1780.

Broach et al., "Recombination within the Yeast Plasmid, 2 mu Circle is Site Specific", *Cell*, vol. 29, No. 1, May 1982, 227-234.

Brousseau et al., "Synthesis of a Human Insulin Gene. V. Enzymatic Assembly Cloning and Characterization of the Human Proinsulin DNA", *Gene*, vol. 17, No. 3, Mar. 1982, 279-289.

Bruchez, Jr. et al., "Semiconductor Nanocrystals as Fluorescent Biological Labels", *Science*, vol. 281, No. 5385, Sep. 25, 1998, 2013-2016.

Brummelkamp et al., "A System for Stable Expression of Short Interfering RNAs in Mammalian Cells.", *Science*, vol. 296, No. 5567, Apr. 19, 2002, 550-553.

Buchschacher et al., "Development of lentiviral vectors for gene therapy for human diseases", *Blood*, vol. 95, No. 8, Apr. 15, 2000, 2499-2504.

Bundgaard, "Bioreversible derivatives for various functional groups and chemical entities", *Design of Prodrugs, Chapter 1*, Amsterdam, Elsevier Science Publishers, 1985, 1-92.

Campbell, "Chromosomal insertion sites for phages and plasmids", *Journal of Bacteriology*, vol. 174, No. 23, Dec. 1992, 7495-7499.

Campbell et al., "Sheep cloned by nuclear transfer from a cultured cell line", *Nature*, vol. 380, No. 6569, Mar. 7, 1996, 64-66.

Caplen et al., "Specific Inhibition of Gene Expression by Small Double-Stranded RNAs in Invertebrate and Vertebrate Systems", *Proceedings of the National Academy of Sciences*, vol. 98, No. 17, Aug. 14, 2001, 9742-9747.

Caravan et al., "Gadolinium (III) Chelates as MRI Contrast Agents: Structure, Dynamics, and Applications", *Chemical Reviews*, vol. 99, No. 9, Sep. 8, 1999, 2293-2352.

Caron et al., "Appendix II: Alignment of primary sequences of DNA topoisomerases", *Advances in Pharmacology*, vol. 29B, 1994, 271-297.

Carver et al., "Transgenic livestock as bioreactors: stable expression of human alpha-1-antitrypsin by a flock of sheep", *Biotechnology*, vol. 11, No. 11, Nov. 1993, 1263-1270.

Cheng et al., "Conservation of structure and mechanism between eukaryotic topoisomerase I and site-specific recombinases", *Cell*, vol. 92, No. 6, Mar. 20, 1998, 841-850.

Colby et al., "Interferon Induction and Action", *Microbiology Section*. The University of Connecticut, Storrs, Connecticut 06268, 1971, 333-360.

Der et al., "A double-stranded RNA-activated protein kinase-dependent pathway mediating stress-induced apoptosis", *Proceedings of the National Academy of Sciences*, vol. 94, No. 7, Apr. 1, 1997, 3279-3283.

Dirac et al., "Reversal of Senescence in Mouse Fibroblasts Through Lentiviral Suppression of p53", *The Journal of Biological Chemistry*, vol. 278, No. 14, Apr. 4, 2003, 11731-11734.

Dykxhoorn et al., "Killing the Messenger: Short RNAs That Silence Gene Expression", *Nature Reviews, Molecular Cell Biology*, vol. 4, No. 6, Jun. 2003, 457-467.

Elbashir et al., "Duplexes of 21-nucleotide RNAs mediate RNA Interference in cultured mammalian cells", *Nature*, vol. 411, May 24, 2001, 494-498.

Erlich, "PCR Automation", *PCR Technology*, Principles and Applications for DNA Amplications, Chapter 3, 1989, 23-30.

Esposito et al., "The integrase family of tyrosine recombinases: evolution of a conserved active site domain", *Nucleic Acids Research*, vol. 25, No. 18, Sep. 15, 1997, 3605-3614.

Fire et al., "Potent and specific genetic interference by double-stranded RNA in *Caenorhabditis elegans*", *Nature*, vol. 391, No. 6669, Feb. 19, 1998, 806-811.

Freshney, "The Culture Environment: II. Media and Supplements", *Culture of Animal Cells: A Manual of Basic Technique*, Alan R. Liss, Inc., 1983, 74-78.

Gordon, "Transgenic Animals", *International Review of Cytology*, vol. 115, 1989, 171-229.

Gu et al., "Deletion of a DNA Polymerase Beta Gene Segment in T Cells Using Cell Type-Specific Gene Targeting", *Science*, vol. 265, No. 5168, Jul. 1, 1994, 103-106.

Gupta et al., "Eukaryotic DNA topoisomerases I", *Biochimica et Biophysica Acta*, vol. 1262, No. 1, May 17, 1995, 1-14.

Hallum et al., "Quantitative Aspects of Inhibition of Virus Replication by Interferon in Chick Embryo Cell Cultures", *Journal of Bacteriology*, vol. 92, No. 4, Oct. 1966, 1047-1050.

Herman, "Ch 8: Resonance Energy Transfer Microscopy", *Methods in Cell Biology*, vol. 30, 1989, 219-243.

Hoess et al., "The Cre-lox Recombination System", *Nucleic Acids and Molecular Biology*, vol. 4, 1990, 99-109.

Hoess et al., "The role of the loxP spacer region in P1 site-specific recombination", *Nucleic Acids Research*, vol. 14, No. 5, Mar. 11, 1986, 2287-2300.

Horton et al., "Engineering hybrid genes without the use of restriction enzymes: gene splicing by overlap extension", *Gene*, vol. 77, No. 1, Apr. 15, 1989, 61-68.

Invitrogen Corporation, *Invitrogen Catalogue*, 2003, 11791-019.

Invitrogen Corporation, *Invitrogen Catalogue*, 2003, 12535-019.

Invitrogen Corporation, *Invitrogen Catalogue*, 2003, 12536-017.

Invitrogen Corporation, *Invitrogen Catalogue*, 2003, 12537-023.

Invitrogen Corporation, AcTEV TM Protease, *Invitrogen Catalogue*, 2003, 12575-015.

Invitrogen Corporation, Cloning—Chapter 1, *K4550-40: Invitrogen Catalogue*, 2003.

Invitrogen Corporation, Cloning—Chapter 1, *K4560-40: Invitrogen Catalogue*, 2003.

Invitrogen Corporation, Cloning—Chapter 1, *K4500-05: Invitrogen Catalogue*, HTP TOPO Cloning Kits, 2003.

Invitrogen Corporation, Cloning—Chapter 1, *K4550-01; Invitrogen Catalogue*, TOPO TA Cloning Kits, 2003.

Invitrogen Corporation, Cloning—Chapter 11—Gateway Destination Vectors, *Invitrogen Catalogue*, V496-10, 2004.

Invitrogen Corporation, DNA Purification—Chapter 9, *K1900-01; Invitrogen Catalogue*, 2003.

Invitrogen Corporation, Enzymes—Chapter 8, *Invitrogen Catalogue*, 2003, 15224-025.

Invitrogen Corporation, Gateway Entry Vectors, *Invitrogen Catalogue*, 2003, 11813.

Invitrogen Corporation, Gene Expression, *V494-20: Invitrogen Catalogue*, 2003.

Invitrogen Corporation, Gene Expression—Chapter 10, *K4944-00; Invitrogen Catalogue*, 2004.

Invitrogen Corporation, Gene Expression—Chapter 10, *K4945-00; Invitrogen Catalogue*, 2004.

Invitrogen Corporation, Gene Expression—Chapter 4, *K4950-00; Invitrogen Catalogue*, 2003.

Invitrogen Corporation, Gene Expression—Chapter 4, *K4960-00; Invitrogen Catalogue*, 2003.

Invitrogen Corporation, Gene Expression—Chapter 4, *K4970-00; Invitrogen Catalogue*, 2003.

Invitrogen Corporation, Gene Expression—Chapter 4, *V790-20 : Invitrogen Catalogue*, 2003.

Invitrogen Corporation, Gene Expression—Untagged pcDNA Vectors, *V795-20 : Invitrogen Catalogue*, 2003.

Invitrogen Corporation, Invitrogen Online Ordering: GripTite 293 MSR Cell Line, *R795-07 : Invitrogen Catalogue* https://catalog.invitrogen.com/index.cfm?fuseaction=viewCatalog.viewProductDetails&pr..., 2007.

Invitrogen Corporation, *K4520-01: Invitrogen Catalogue*, 2003.

Invitrogen Corporation, *K4520-40: Invitrogen Catalogue*, 2003.

Invitrogen Corporation, *K4540-01: Invitrogen Catalogue*, 2007.

Invitrogen Corporation, *K4560-01: Invitrogen Catalogue*, 2003.

Invitrogen Corporation, MultiSite Gateway Technology, *Invitrogen Catalogue*, 2003, 12538-013.

Invitrogen Corporation, Products for High-throughput, *K4500-01; Invitrogen Catalogue*, 2003.

Invitrogen Corporation, Sequencing Products, *N530-02; Invitrogen Catalogue*, 2003.

Invitrogen Corporation, Transformation—Chapter 3, *C4040-03; Invitrogen Catalogue*, 2003.

Invitrogen Corporation, Transformation—Chapter 3, *C4040-06; Invitrogen Catalogue*, 2003.

Invitrogen Corporation, Transformation—Chapter 3, *C4040-10; Invitrogen Catalogue*, 2003.

Invitrogen Corporation, *Y90001: Invitrogen Catalogue*, 2007.

Kasim et al., "Control of siRNA expression utilizing Cre-loxP recombination system", *Nucleic Acids Research Supplemental*, vol. 3, 2003, 255-256.

Kawasaki et al., "siRNAs generated by recombinant human Dicer induce specific and significant but target site-independent gene silencing in human cells", *Nucleic Acids Research*, vol. 31, No. 3, Feb. 1, 2003, 981-987.

Keil et al., "Synthesis and Characterization of 1,3 Bis-(2-dialkylamino 5 thienyl) substituted Squaraines—A Novel Class of Intensively Coloured Panchromatic Dyes", *Dyes and Pigments*, vol. 17, 1991, 19-27.

Kirby et al., "RNA interference-mediated silencing of Sod2 in *Drosophila* leads to early adult-onset mortality and elevated endogenous oxidative stress", *Proceedings of the National Academy of Sciences*, vol. 99, No. 25, Dec. 10, 2002, 16162-16167.

Kleinschmidt et al., "Biochemistry of Interferon and its Inducers", *Annual Review of Biochemistry*, vol. 41, No. 10, 1972, 517.

Lakowicz, "Emerging applications of fluorescence spectroscopy to cellular imaging: lifetime imaging, metal-ligand probes, multi-photon excitation and light quenching", *Scanning Microscopy Supplement*, vol. 10, 1996, 213-224.

Lakowicz, "Topics in Fluorescence Spectroscopy", vols. 1-3, Plenum Press, 1991-2000.

Lakso et al., "Targeted Oncogene activation by site-specific recombination in transgenic mice", *Proceedings of the National Academy of Sciences*, vol. 89, No. 14, Jul. 15, 1992, 6232-6236.

Lampson et al., "Inducers of Interferon and Host Resistance, I. Double-Stranded RNA From Extracts of *Penicillium funiculosum*", *Proceedings of the National Academy of Sciences*, vol. 58, No. 2, Aug. 1967, 782-789.

Landy, "Dynamic, structural and regulatory aspects of lambda site-specific recombination", *Annual Reviews of Biochemistry*, vol. 58, 1989, 913-949.

Landy, "Mechanistic and structural complexity in the site-specific recombination pathways of Int and FLP", *Current Opinion in Genetics and Development*, vol. 3, No. 5, Oct. 1993, 699-707.

Lauffer, "Paramagnetic Metal Complexes as Water Proton Relaxation Agents for NMR Imaging: Theory and Design", *Chemical Reviews*, vol. 87, No. 5, 1987, 901-927.

Lavitrano et al., "Sperm Cells as Vectors for Introducing Foreign DNA into Eggs: Genetic Transformation of Mice", *Cell*, vol. 57, No. 5, Jun. 2, 1989, 717-723.

Lee et al., "Expression of Small Interfering RNAs Targeted Against HIV-1 Rev Transcripts in Human Cells", *Nature Biotechnology*, vol. 20, No. 5, May 2002, 500-505.

Lee et al., "MiRNA maturation: stepwise processing and subcellular localization", *The EMBO Journal*, vol. 21, No. 17, 2002, 4663-4670.

Lewis et al., "Passage through Mitosis Is Required for Oncoretroviruses but Not for the Human Immunodeficiency Virus", *The Journal of Virology*, vol. 68, No. 1, Jan. 1994, 510-516.

Liu et al., "The univector plasmid-fusion system, a method for rapid construction of recombinant DNA without restriction enzymes.", *Current Biology*, vol. 8, Research Paper, Nov. 19, 1998, 1300-1309.

Lo, "Transformation by iontophoretic microinjection of DNA: multiple integrations without tandem insertions.", *Molecular and Cellular Biology*, vol. 3, No. 10, Oct. 1983, 1803-1814.

Lomniczi et al., "Biological properties of avian coronavirus RNA", *Journal of General Virology*, vol. 36, No. 3, Sep. 1977, 531-533.

Lomniczi et al., "Interferon Production by Temperature-sensitive Mutants of Semliki Forest Virus", *Journal of General Virology*, vol. 8, No. 1, Jul. 1970, 55-68.

Luo et al., "Small interfering RNA production by enzymatic engineering of DNA (SPEED)", *Proceedings of the National Academy of Sciences*, vol. 101, No. 15, Apr. 13, 2004, 5494-5499.

Lyer et al., "Modified oligonucleotides—synthesis, properties, and applications", *Current Opinion in Molecular Therapeutics*, vol. 1, No. 3, Jun. 1999, 344-358.

Maeser et al., "The Gin Recombinase of Phage Mu Can Catalyse Site-Specific Recombination in Plant Protoplasts", *Molecular and General Genetics*, vol. 230, No. 1-2, Nov. 1991, 170-176.

Maniatis et al., "Synthesis of cDNA", *Molecular Cloning: A Laboratory Manual*, Cold Spring Harbor Laboratory Press, 1982, 213 & 231.

Martinek et al., "Specific Genetic Interference With Behavioral Rhythms in *Drosophila* by Expression of Inverted Repeats", *Genetics*, vol. 156, No. 4, Dec. 2000, 1717-1725.

Matta et al., "Use of Lentiviral Vectors for Delivery of Small Interfering RNA", *Cancer & Biology Therapy*, vol. 2, No. 2, Mar. 2003, 206-210.

Miller et al., "Improved Retroviral Vectors for Gene Transfer and Expression", *BioTechniques*, vol. 7, No. 9, Oct. 1989, 980-990.

Miller et al., "Gene Transfer by Retrovirus Vectors Occurs Only in Cells that are Actively Replicating At the Time of Infection", Molecular and Cellular Biology, vol. 10, No. 8, Aug. 1990, 4239-4242.

Mullis et al., "Specific Enzymatic Amplification of DNA In Vitro: The Polymerase Chain Reaction", *Cold Spring Harbor Symposia on Quantitative Biology*, vol. 51, Part 1, 1986, 263-273.

Muyrers et al., "Rapid Modification of Bacterial Artificial Chromosomes by ET-Recombination", *Nucleic Acids Research*, vol. 27, No. 6, Mar. 15, 1999, 1555-1557.

Naldini et al., "Ch 3: Lentiviral Vectors", The Development of Human Gene Therapy Friedmann, T., ed., *Cold Spring Harbor Laboratory Press*, Cold Spring Harbor NY, 1999, 47-60.

Norris et al., "Nucleotide sequence of a cDNA clone encoding the precursor of the peridinin-chlorophyll a-binding protein from the dinoflagellate *Symbiodinium* sp.", *Plant Molecular Biology*, vol. 24, No. 4, Feb. 1994, 673-677.

Old, "Basic Techniques", *Principles of Gene Manipulation, An Introduction to Genetic Engineering*, 1981, 26-27.

Paddison et al., "Short hairpin RNAs (shRNAs) induce sequence-specific silencing in mammalian cells", *Genes & Development*, vol. 16, No. 8, Apr. 15, 2002, 948-958.

Padgett et al., "Creating seamless junctions independent of restriction sites in PCR cloning", *Gene*, vol. 168, No. 1, Feb. 2, 1996, 31-35.

Park et al., "Modified HIV-1 based lentiviral vectors have an effect on viral transduction efficiency and gene expression in vitro and in vivo", *Molecular Therapy*, vol. 4, No. 3, Sep. 3, 2001, 164-173.

Paterson et al., "Approaches to maximizing stable expression of alpha1-antitrypsin in transformed CHO cells", *Applied Microbiology and Biotechnology*, vol. 40, No. 5, Jan. 1994, 691-698.

Paul et al., "Effective Expression of Small Interfering RNA in human cells", *Nature Biotechnology*, vol. 20, No. 5, May 2002, 505-508.

Peng et al., "Organ distribution of gene expression after intravenous infusion of the targeted and untargeted lentiviral vectors", *Gene Therapy*, vol. 8, No. 19, Oct. 2001, 1456-1463.

Petersen et al., "Characterization of a DNA Topoisomerase Encoded by *Amsacta moorei* Entomopoxvirus", *Virology*, vol. 230, No. 2, Apr. 14, 1997, 197-206.

Pierce et al., "Construction of a directed hammerhead ribozyme library: towards the identification of optimal target sites for antisense-mediated gene inhibition", *Nucleic Acids Research*, vol. 26, No. 22, Jan. 1, 1998, 5093-5101.

Prasher et al., "Primary structure of the *Aequorea victoria* green fluorescent protein", *Gene*, vol. 111, No. 2, Feb. 15, 1992, 229-233.

Qian et al., "Reactions between Half-and Full-FLP Recombination Target Sites: A Model System for Analyzing Early Steps in FLP Protein-Mediated Site-Specific Recombination", *The Journal of Biological Chemistry*, vol. 267, No. 1, Apr. 15, 1992, 7794-7805.

Qin et al., "Inhibiting HIV-1 Infection in Human T Cells by Lentiviral-Mediated Delivery of Small Interfering RNA Against CCR5", *Proceedings of the National Academy of Sciences*, vol. 100, No. 1, Jan. 7, 2003, 183-188.

Rodems et al., "A FRET-Based Platform for Ultra-high density drug Screening of protein kinases and phosphatases", *Assay and Drug Development Technologies*, vol. 1, No. 1-1, Nov. 2002, 9-19.

Rubinson et al., "A lentivirus-based system to functionally silence genes in primary mammalian cells, stem cells and transgenic mice by RNA interference", *Nature Genetics*, vol. 33, No. 3, Mar. 1, 2003, 401-406.

Sambrook et al., "Ch: 16.30-16.60—Introduction of Recombinant Vectors into Mammalian Cells", *Molecular Cloning, a Laboratory Manual*, 2nd ed., Cold Spring Harbor Laboratory Press, Cold Spring Harbor, NY, 1989, 16.30-16.60.

Sauer, "Site-specific recombination: developments and applications", *Current Opinion in Biotechnology*, vol. 5, No. 5, Oct. 1994, 521-527.

Sen et al., "Restriction enzyme-generated siRNA (REGS) vectors and libraries", *Nature Genetics*, vol. 36, No. 2, Feb. 2004, 183-189.

Sharp, "RNAi and double-strand RNA", *Genes & Development*, vol. 13, No. 2, Jan. 15, 1999, 139-141.

Shuman et al., "Identification of a Vaccinia Virus Gene Encoding a Type I DNA Topoisomerase", *Proceedings of the National Academy of Sciences*, vol. 84, No. 21, Nov. 1, 1987, 7478-7482.

Shuman, "Novel approach to molecular cloning and polynucleotide synthesis using vaccinia DNA Topoisomerase", *The Journal of Biological Chemistry*, vol. 269, No. 51,, Dec. 23, 1994, 32678-32684.

Shuman, "Vaccinia virus DNA topoisomerase: a model eukaryotic type IB enzyme", *Biochimica et Biophysica Acta*, vol. 1400, No. 1-3, Oct. 1, 1998, 321-337.

Sioud, "Therapeutic potential of small interfering RNAs", *Drugs of the Future*, vol. 29, No. 7, Jul. 2004, 741-750.

Spatola et al., "Ch 5: Peptide Backbone Modifications: A Structure—Activity Analysis of Peptides Containing Amide Bond Surrogates, Conformational Constraints, and Rela", *Chemistry and Biochemistry of Amino Acids, Peptides and Proteins*, vol. 7, 1983, 267-357.

Stewart et al., "Lentivirus-Delivered Stable Gene Silencing by RNAi in Primary Cells", *RNA*, vol. 9, No. 4, Apr. 2003, 493-501.

Svoboda et al., "RNAi in mouse oocytes and preimplantation embryos: effectiveness of hairpin dsRNA", *Biochemical and Biophysical Research Communications*, vol. 287, No. 5, Oct. 12, 2001, 1099-1104.

Szybalski et al., "Class-IIS Restriction Enzymes—A Review", *Gene*, vol. 100, Apr. 1991, 13-26.

Szybalski, "Universal restriction endonucleases : designing novel cleavage specificities by combining adapter oligodeoxynucleotide andenzyme moieties",Gene, vol. 40, Nos. 2-3, 1985, 169-173.

Thompson et al., "Germ line transmission and expression of a corrected HPRT gene produced by gene targeting in embryonic stem cells", *Cell*, vol. 56, No. 2, Jan. 27, 1989, 313-321.

Tiscornia et al., "A General Method for Gene Knockdown in Mice by Using Lentiviral Vectors Exprerssing Small Interfering RNA", *Proceedings of the National Academy of Sciences*, vol. 100, No. 4, Feb. 18, 2003, 1844-1848.

Tsien et al., "Fluorophores for Confocal Microscopy, Photophysics and Photochemistry", *Handbook of Biological Confocal Microscopy*, Chapter 16, 1990, 169-178.

Turro, "Ch 9.1: An Energy-Surface Description of Electronic Energy Transfer and Energy Degradation", *Modern Molecular Photochemistry*, Menlo Park: Benjamin/Cummings Publishing Col, Inc, 1978, 296-361.

Ulmer et al., "Heterologous Protection Against Influenza by Injection of DNA Encoding a Viral Protein", *Science*, vol. 259, No. 4102, Mar. 19, 1993, 1745-1749.

Urdea et al., "Chemical Synthesis of a Gene for Human Epidermal Growth Factor Urogastrone and Its Expression in Yeast", *Proceedings of the National Academy of Sciences*, vol. 80, No. 24, Dec. 1983, 7461-7465.

U.S. Appl. No. 60/122,392, filed Mar. 2, 1999.
U.S. Appl. No. 60/475,004, filed Jun. 3, 2003.

Valeur, "Molecular Fluorescence: Principles and Applications", (*Textbook*), Wiley VCH, 2002.

Van Der Putten et al., "Efficient Insertion of Genes into the Mouse Germ Line Via Retroviral Vectors", *Proceedings of the National Academy of Sciences*, vol. 82, No. 18, Sep. 1, 1985, 6148-6152.

Verma et al., "Modified Oligonucleotides: Synthesis and Strategy for Users", *Annual Review of Biochemistry*, vol. 67, Jul. 1998, 99-134.

Voziyanov et al., "A general model for site-specific recombination by the integrase family recombinases", *Nucleic Acids Research*, vol. 27, No. 4,, 1999, 930-941.

Watson et al., "Ch 12: Transferring Genes into Mammalian Cells", *Recombinant DNA*, 2nd Ed.; W.H. Freeman and Co., 1992, 213-234.

Weber, "Ch 8: Polarization of the Fluorescence of Solutions", *Fluorescence and Phosphorescence Analysis: Principles and Applications*, 1966, 217-240.

Welker et al., "Vectors with hidden cloning sites", *Biochemical and Biophysical Research Communications*, vol. 271, No. 2, May 10, 2000, 534-536.

Wilbanks et al., "Rod Structure of a Phycoerythrin II-containing Phycobilisome", *The Journal of Biological Chemistry*, vol. 265, No. 2, Jan. 15, 1993, 1226-1241.

Wilmut et al., "Viable offspring derived from fetal and adult mammalian cells", *Nature*, vol. 385, Feb. 27, 1997, 810-813.

Wright et al., "High level Expression of Active Human Alpha-1-Antitrypsin in the Milk of Transgenic Sheep", *Biotechnology*, vol. 9, Sep. 1991, 830-834.

Yang et al., "Specific Double-Stranded RNA Interference in Undifferentiated Mouse Embryonic Stem Cells", *Molecular and Cellular Biology*, vol. 21, No. 22, Nov. 2001, 7807-7816.

Yee et al., "A general method for the generation of high-titer, pantropic retroviral vectors: Highly efficient infection of primary hepatocytes", *Proceedings of the National Academy of Sciences*, vol. 91, No. 20, Sep. 27, 1994, 9564-9568.

Yi et al., "Specific and Potent RNA Interference in Terminally Differentiated Myotubes", *Journal of Biological Chemistry*, vol. 278, No. 2, Jan. 10, 2003, 934-939.

Yon et al., "Precise gene fusion by PCR", *Nucleic Acids Research*, vol. 17, No. 12, Jun. 26, 1989, 4895.

Youngner et al., "Interferon Production by Inactivated Newcastle Disease Virus in Cell Cultures and in Mice", *Journal of Bacteriology*, vol. 92, No. 4, Oct. 1966, 862-868.

Yu et al., "RNA interference by expression of short-interfering RNAs and hairpin RNAs in mammalian cells", *Proceedings of the National Academy of Sciences*, vol. 99, No. 9, Apr. 30, 2002, 6047-6052.

Zhang et al., "A new logic for DNA engineering using recombination in *Escherichia coli*", *Nature Genetics*, vol. 20, No. 2 Oct. 1998, 123-128.

\* cited by examiner

```
  1 CTTTCCTGCG TTATCCCCTG ATTCTGTGGA TAACCGTATT ACCGCCTTTG AGTGAGCTGA
    GAAAGGACGC AATAGGGGAC TAAGACACCT ATTGGCATAA TGGCGGAAAC TCACTCGACT

61 TACCGCTCGC CGCAGCCGAA CGACCGAGCG CAGCGAGTCA GTGAGCGAGG AAGCGGAAGA
    ATGGCGAGCG GCGTCGGCTT GCTGGCTCGC GTCGCTCAGT CACTCGCTCC TTCGCCTTCT

121 GCGCCCAATA CGCAAACCGC CTCTCCCCGC GCGTTGGCCG ATTCATTAAT GCAGCTGGCA
    CGCGGGTTAT GCGTTTGGCG GAGAGGGGCG CGCAACCGGC TAAGTAATTA CGTCGACCGT

181 CGACAGGTTT CCCGACTGGA AAGCGGGCAG TGAGCGCAAC GCAATTAATA CGCGTACCGC
    GCTGTCCAAA GGGCTGACCT TTCGCCCGTC ACTCGCGTTG CGTTAATTAT GCGCATGGCG

241 TAGCCAGGAA GAGTTTGTAG AAACGCAAAA AGGCCATCCG TCAGGATGGC CTTCTGCTTA
    ATCGGTCCTT CTCAAACATC TTTGCGTTTT TCCGGTAGGC AGTCCTACCG GAAGACGAAT
                                     rrnB T2 terminator
301 GTTTGATGCC TGGCAGTTTA TGGCGGGCGT CCTGCCCGCC ACCCTCCGGG CCGTTGCTTC
    CAAACTACGG ACCGTCAAAT ACCGCCCGCA GGACGGGCGG TGGGAGGCCC GGCAACGAAG 361 ACAACGTTCA AATCCGCTCC CGGCGGATTT GTCCTACTCA GGAGAGCGTT CACCGCCAAA
    TGTTGCAAGT TTAGGCGAGG GCCGCCTAAA CAGGATGAGT CCTCTCGCAA GTGGCTGTTT 421 CAACAGATAA AACGAAAGGC CCAGTCTTCC GACTGAGCCT TTCGTTTTAT TTGATGCCTG
    GTTGTCTATT TTGCTTTCCG GGTCAGAAGG CTGACTCGGA AAGCAAAATA AACTACGGAC
          rrnB T1 terminator
                                                              M13 For(-20)
481 GCAGTTCCCT ACTCTCGCGT TAACGCTAGC ATGGATGTTT TCCCAGTCAC GACGTTGTAA
    CGTCAAGGGA TGAGAGCGCA ATTGCGATCG TACCTACAAA AGGGTCAGTG CTGCAACATT
    M13 For (-20)
541 AACGACGGCC AGTCTTAAGC TCGGGCCCCA AATAATGATT TTATTTTGAC TGATAGTGAC
    TTGCTGCCGG TCAGAATTCG AGCCCGGGGT TTATTACTAA AATAAAACTG ACTATCACTG
601 CTGTTCGTTG CAACAAATTG ATGAGCAATG CTTTTTTATA ATGCCAACTT TGTACAAAAA
    GACAAGCAAC GTTGTTTAAC TACTCGTTAC GAAAAAATAT TACGGTTGAA ACATGTTTTT
                                                          SENSE PRM
                             pENTR1a-462F                 hsU6-1wd
                                                         U6 PROMOTER
661 AGCAGGCTTT AAAGGAACCA ATTCAGTCGA CTGGATCCGG TACCAAGGTC GGGCAGGAAG
    TCGTCCGAAA TTTCCTTGGT TAAGTCAGCT GACCTAGGCC ATGGTTCCAG CCCGTCCTTC
    SENSE PRIV
    hsU6-1w
```

FIG.12A

```
                              U6 PROMOTER
 721  AGGGCCTATT TCCCATGATT CCTTCATATT TGCATATACG ATACAAGGCT GTTAGAGAGA
      TCCCGGATAA AGGGTACTAA GGAAGTATAA ACGTATATGC TATGTTCCGA CAATCTCTCT
                              U6 PROMOTER
 781  TAATTAGAAT TAATTTGACT GTAAACACAA AGATATTAGT ACAAAATACG TGACGTAGAA
      ATTAATCTTA ATTAAACTGA CATTTGTGTT TCTATAATCA TGTTTTATGC ACTGCATCTT
                              U6 PROMOTER
 841  AGTAATAATT TCTTGGGTAG TTTGCAGTTT TAAAATTATG TTTTAAAATG GACTATCATA
      TCATTATTAA AGAACCCATC AAACGTCAAA ATTTTAATAC AAAATTTTAC CTGATAGTAT
              U6-PSE                              PROMOTER E
                              U6 PROMOTER
 901  TGCTTACCGT AACTTGAAAG TATTTCGATT TCTTGGCTTT ATATATCTTG TGGAAAGGAC
      ACGAATGGCA TTGAACTTTC ATAAAGCTAA AGAACCGAAA TATATAGAAC ACCTTTCCTG
               ±1 base transcription starts
      U6 PROMOTER    Not1
 961  GAAACACCGG AGACCGCGGC CGCTGGATCC GGCTTACTAA AAGCCAGATA ACAGTATGCG
      CTTTGTGGCC TCTGGCGCCG GCGACCTAGG CCGAATGATT TTCGGTCTAT TGTCATACGC
              Bsa1
1021  TATTTGCGCG CTGATTTTTG CGGTATAAGA ATATATACTG ATATGTATAC CCGAAGTATG
      ATAAACGCGC GACTAAAAAC GCCATATTCT TATATATGAC TATACATATG GCTTCATAC 1081  TCAAAAAGAG GTGTGCTATG AAGCAGCGTA TTACAGTGAC AGTTGACAGC GACAGCTATC
      AGTTTTTCTC CACACGATAC TTCGTCGCAT AATGTCACTG TCAACTGTCG CTGTCGATAG 1141  AGTTGCTCAA GGCATATATG ATGTCAATAT CTCCGGTCTG GTAAGCACAA CCATGCAGAA
      TCAACGAGTT CCGTATATAC TACAGTTATA GAGGCCAGAC CATTCGTGTT GGTACGTCTT 1201  TGAAGCCCGT CGTCTGCGTG CCGAACGCTG GAAAGCGGAA AATCAGGAAG GGATGGCTGA
      ACTTCGGGCA GCAGACGCAC GGCTTGCGAC CTTTCGCCTT TTAGTCCTTC CCTACCGACT
                                                                    ccdB
1261  GGTCGCCCGG TTTATTGAAA TGAACGGCTC TTTTGCTGAC GAGAACAGGG ACTGGTGAAA
      CCAGCGGGCC AAATAACTTT ACTTGCCGAG AAAACGACTG CTCTTGTCCC TGACCACTTT
                                    ccdB
1321  TGCAGTTTAA GGTTTACACC TATAAAAGAG AGAGCCGTTA TCGTCTGTTT GTGGATGTAC
      ACGTCAAATT CCAAATGTGG ATATTTTCTC TCTCGGCAAT AGCAGACAAA CACCTACATG
                                    ccdB
1381  AGAGTGATAT TATTGACACG CCCGGGCGAC GGATGGTGAT CCCCCTGGCC AGTGCACGTC
      TCTCACTATA ATAACTGTGC GGGCCCGCTG CCTACCACTA GGGGGACCGG TCACGTGCAG
                                    ccdB
1441  TGCTGTCAGA TAAAGTCTCC CGTGAACTTT ACCCGGTGGT GCATATCGGG GATGAAAGCT
      ACGACAGTCT ATTTCAGAGG GCACTTGAAA TGGGCCACCA CGTATAGCCC CTACTTTCGA
```

FIG.12B

```
                              ccdB
                                    Bsal
1501 GGCGCATGAT GACCACCGAT ATGGCCAGTG TGCCGGTCTC CGTTATCGGG GAAGAAGTGG
     CCGCGTACTA CTGGTGGCTA TACCGGTCAC ACGGCCAGAG GCAATAGCCC CTTCTTCACC
                              ccdB
1561 CTGATCTCAG CCACCGCGAA AATGACATCA AAAACGCCAT TAACCTGATG TTCTGGGGAA
     GACTAGAGTC GGTGGCGCTT TTACTGTAGT TTTTGCGGTA ATTGGACTAC AAGACCCCTT
     ccdB         Pol III terminator
       Bsal
1621 TATAAGGTCT CATTTTTTTT CTAGACCCAG CTTTCTTGTA CAAAGTTGGC ATTATAAGAA
     ATATTCCAGA GTAAAAAAAA GATCTGGGTC GAAAGAACAT GTTTCAACCG TAATATTCTT 1681 AGCATTGCTT ATCAATTTGT TGCAACGAAC AGGTCACTAT CAGTCAAAAT AAAATCATTA
     TCGTAACGAA TAGTTAAACA ACGTTGCTTG TCCAGTGATA GTCAGTTTTA TTTTAGTAAT
                                                            M13 Rev
1741 TTTGCCATCC AGCTGATATC CCCTATAGTG AGTCGTATTA CATGGTCATA GCTGTTTCCT
     AAACGGTAGG TCGACTATAG GGGATATCAC TCAGCATAAT GTACCAGTAT CGACAAAGGA
     M13 Rev
1801 GGCAGCTCTG GCCCGTGTCT CAAAATCTCT GATGTTACAT TGCACAAGAT AAAAATATAT
     CCGTCGAGAC CGGGCACAGA GTTTTAGAGA CTACAATGTA ACGTGTTCTA TTTTTATATA
                                                                kanR
1861 CATCATGAAC AATAAAACTG TCTGCTTACA TAAACAGTAA TACAAGGGGT GTTATGAGCC
     GTAGTACTTG TTATTTTGAC AGACGAATGT ATTTGTCATT ATGTTCCCCA CAATACTCGG
                               kanR
1921 ATATTCAACG GGAAACGTCG AGGCCGCGAT TAAATTCCAA CATGGATGCT GATTTATATG
     TATAAGTTGC CCTTTGCAGC TCCGGCGCTA ATTTAAGGTT GTACCTACGA CTAAATATAC
                               kanR
1981 GGTATAAATG GGCTCGCGAT AATGTCGGGC AATCAGGTGC GACAATCTAT CGCTTGTATG
     CCATATTTAC CCGAGCGCTA TTACAGCCCG TTAGTCCACG CTGTTAGATA GCGAACATAC
                               kanR
2041 GGAAGCCCGA TGCGCCAGAG TTGTTTCTGA AACATGGCAA AGGTAGCGTT GCCAATGATG
     CCTTCGGGCT ACGCGGTCTC AACAAAGACT TTGTACCGTT TCCATCGCAA CGGTTACTAC
                               kanR
2101 TTACAGATGA GATGGTCAGA CTAAACTGGC TGACGGAATT TATGCCTCTT CCGACCATCA
     AATGTCTACT CTACCAGTCT GATTTGACCG ACTGCCTTAA ATACGGAGAA GGCTGGTAGT
                               kanR
2161 AGCATTTTAT CCGTACTCCT GATGATGCAT GGTTACTCAC CACTGCGATC CCCGGAAAAA
     TCGTAAAATA GGCATGAGGA CTACTACGTA CCAATGAGTG GTGACGCTAG CGGCCTTTTT
```

FIG.12C

```
                                kanR
2221 CAGCATTCCA GGTATTAGAA GAATATCCTG ATTCAGGTGA AAATATTGTT GATGCGCTGG
     GTCGTAAGGT CCATAATCTT CTTATAGGAC TAAGTCCACT TTTATAACAA CTACGCGACC
                                kanR
2281 CAGTGTTCCT GCGCCGGTTG CATTCGATTC CTGTTTGTAA TTGTCCTTTT AACAGCGATC
     GTCACAAGGA CGCGGCCAAC GTAAGCTAAG GACAAACATT AACAGGAAAA TTGTCGCTAG
                                kanR
2341 GCGTATTTCG TCTCGCTCAG GCGCAATCAC GAATGAATAA CGGTTTGGTT GATGCGAGTG
     CGCATAAAGC AGAGCGAGTC CGCGTTAGTG CTTACTTATT GCCAAACCAA CTACGCTCAC
                                kanR
2401 ATTTTGATGA CGAGCGTAAT GGCTGGCCTG TTGAACAAGT CTGGAAAGAA ATGCATAAAC
     TAAAACTACT GCTCGCATTA CCGACCGGAC AACTTGTTCA GACCTTTCTT TACGTATTTG
                                kanR
2461 TTTTGCCATT CTCACCGGAT TCAGTCGTCA CTCATGGTGA TTTCTCACTT GATAACCTTA
     AAAACGGTAA GAGTGGCCTA AGTCAGCAGT GAGTACCACT AAAGAGTGAA CTATTGGAAT
                                kanR
2521 TTTTTGACGA GGGGAAATTA ATAGGTTGTA TTGATGTTGG ACGAGTCGGA ATCGCAGACC
     AAAAACTGCT CCCCTTTAAT TATCCAACAT AACTACAACC TGCTCAGCCT TAGCGTCTGG
                                kanR
2581 GATACCAGGA TCTTGCCATC CTATGGAACT GCCTCGGTGA GTTTTCTCCT TCATTACAGA
     CTATGGTCCT AGAACGGTAG GATACCTTGA CGGAGCCACT CAAAAGAGGA AGTAATGTCT
                                kanR
2641 AACGGCTTTT TCAAAAATAT GGTATTGATA ATCCTGATAT GAATAAATTG CAGTTTCATT
     TTGCCGAAAA AGTTTTTATA CCATAACTAT TAGGACTATA CTTATTTAAC GTCAAAGTAA
                       kanR
2701 TGATGCTCGA TGAGTTTTTC TAATCAGAAT TGGTTAATTG GTTGTAACAC TGGCAGAGCA
     ACTACGAGCT ACTCAAAAAG ATTAGTCTTA ACCAATTAAC CAACATTGTG ACCGTCTCGT 2761 TTACGCTGAC TTGACGGGAC GGCGCAAGCT CATGACCAAA ATCCCTTAAC GTGAGTTACG
     AATGCGACTG AACTGCCCTG CCGCGTTCGA GTACTGGTTT TAGGGAATTG CACTCAATGC
                                                   pUC ori
2821 CGTCGTTCCA CTGAGCGTCA GACCCCGTAG AAAAGATCAA AGGATCTTCT TGAGATCCTT
     GCAGCAAGGT GACTCGCAGT CTGGGGCATC TTTTCTAGTT TCCTAGAAGA ACTCTAGGAA
                        pUC ori
2881 TTTTTCTGCG CGTAATCTGC TGCTTGCAAA CAAAAAAACC ACCGCTACCA GCGGTGGTTT
     AAAAAGACGC GCATTAGACG ACGAACGTTT GTTTTTTTGG TGGCGATGGT CGCCACCAAA
                        pUC ori
2941 GTTTGCCGGA TCAAGAGCTA CCAACTCTTT TTCCGAAGGT AACTGGCTTC AGCAGAGCGC
     CAAACGGCCT AGTTCTCGAT GGTTGAGAAA AAGGCTTCCA TTGACCGAAG TCGTCTCGCG
```

FIG. 12D

```
                                            pUC_ori
3001 AGATACCAAA TACTGTCCTT CTAGTGTAGC CGTAGTTAGG CCACCACTTC AAGAACTCTG
     TCTATGGTTT ATGACAGGAA GATCACATCG GCATCAATCC GGTGGTGAAG TTCTTGAGAC
                                            pUC_ori
3061 TAGCACCGCC TACATACCTC GCTCTGCTAA TCCTGTTACC AGTGGCTGCT GCCAGTGGCG
     ATCGTGGCGG ATGTATGGAG CGAGACGATT AGGACAATGG TCACCGACGA CGGTCACCGC
                                            pUC_ori
3121 ATAAGTCGTG TCTTACCGGG TTGGACTCAA GACGATAGTT ACCGGATAAG GCGCAGCGGT
     TATTCAGCAC AGAATGGCCC AACCTGAGTT CTGCTATCAA TGGCCTATTC CGCGTCGCCA
                                            pUC_ori
3181 CGGGCTGAAC GGGGGGTTCG TGCACACAGC CCAGCTTGGA GCGAACGACC TACACCGAAC
     GCCCGACTTG CCCCCCAAGC ACGTGTGTCG GGTCGAACCT CGCTTGCTGG ATGTGGCTTG
                                            pUC_ori
3241 TGAGATACCT ACAGCGTGAG CATTGAGAAA GCGCCACGCT TCCCGAAGGG AGAAAGGCGG
     ACTCTATGGA TGTCGCACTC GTAACTCTTT CGCGGTGCGA AGGGCTTCCC TCTTTCCGCC
                                            pUC_ori
3301 ACAGGTATCC GGTAAGCGGC AGGGTCGGAA CAGGAGAGCG CACGAGGGAG CTTCCAGGGG
     TGTCCATAGG CCATTCGCCG TCCCAGCCTT GTCCTCTCGC GTGCTCCCTC GAAGGTCCCC
                                            pUC_ori
3361 GAAACGCCTG GTATCTTTAT AGTCCTGTCG GGTTTCGCCA CCTCTGACTT GAGCGTCGAT
     CTTTGCGGAC CATAGAAATA TCAGGACAGC CCAAAGCGGT GGAGACTGAA CTCGCAGCTA
                                            pUC_ori
3421 TTTTGTGATG CTCGTCAGGG GGGCGGAGCC TATGGAAAAA CGCCAGCAAC GCGGCCTTTT
     AAAACACTAC GAGCAGTCCC CCCGCCTCGG ATACCTTTTT GCGGTCGTTG CGCCGGAAAA
                                            pUC_ori
3481 TACGGTTCCT GGCCTTTTGC TGGCCTTTTG CTCACATGTT
     ATGCCAAGGA CCGGAAAACG ACCGGAAAAC GAGTGTACAA
```

FIG.12E

```
5'-UUCAGUGAGUAGAGUCAUATT-3'      SEQ ID NO:36
   ||||||||||||||||||||
3'-TTAAGUCACTCATCTCAGUAU-5'      SEQ ID NO:37
   |------"CORE"------|
   1                 19
```

FIG.16

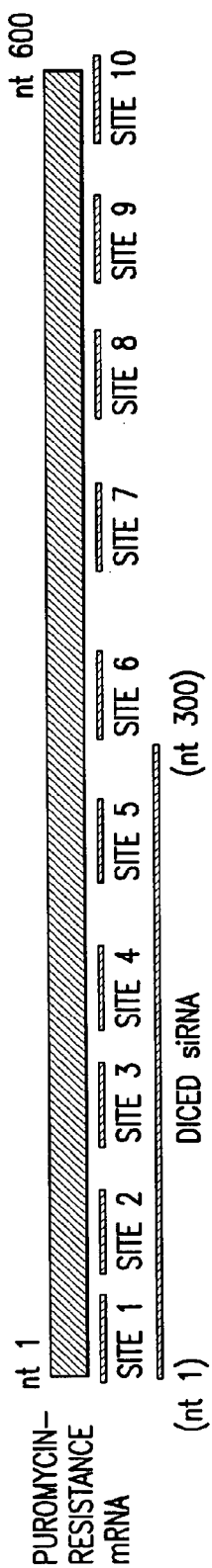
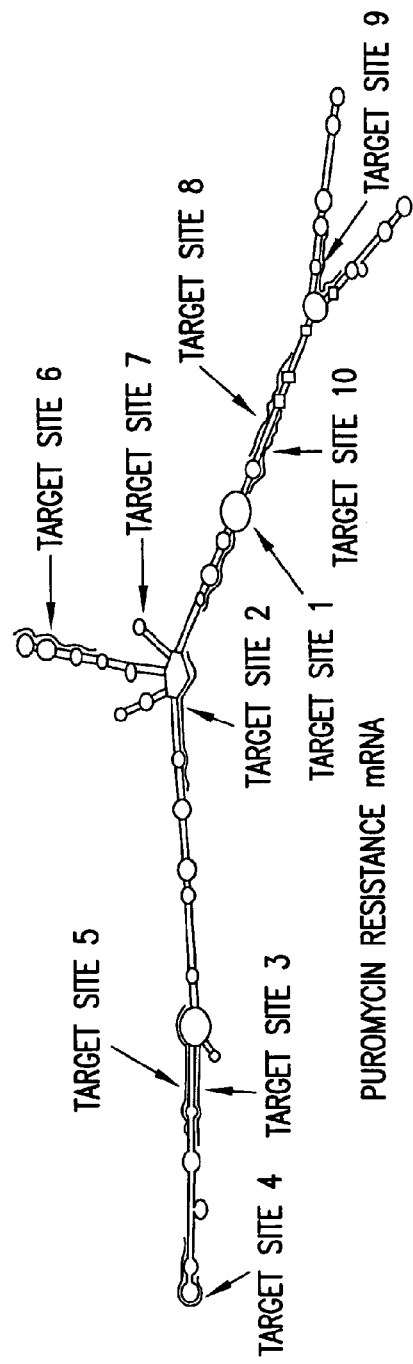
FIG.18A
FIG.18B

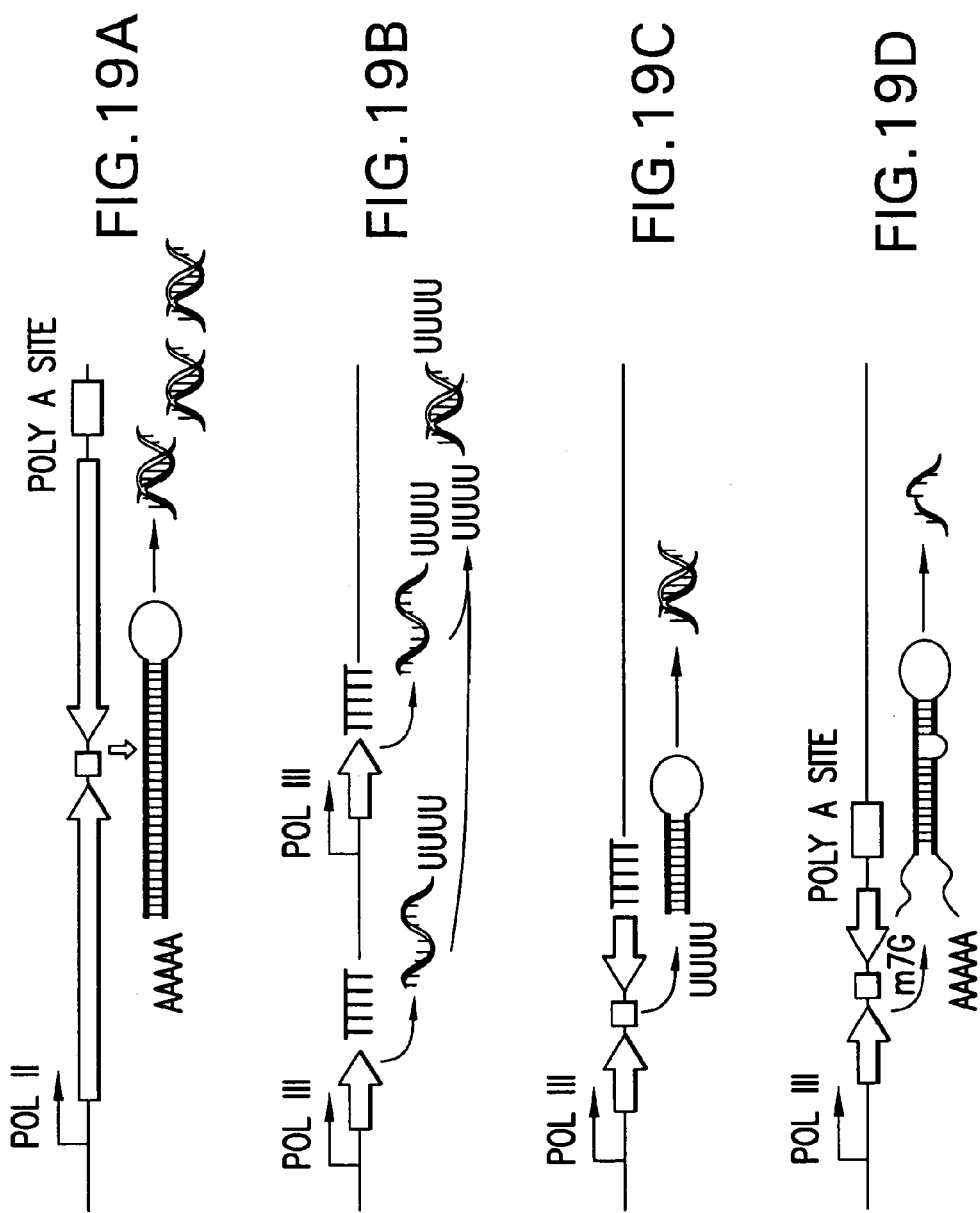

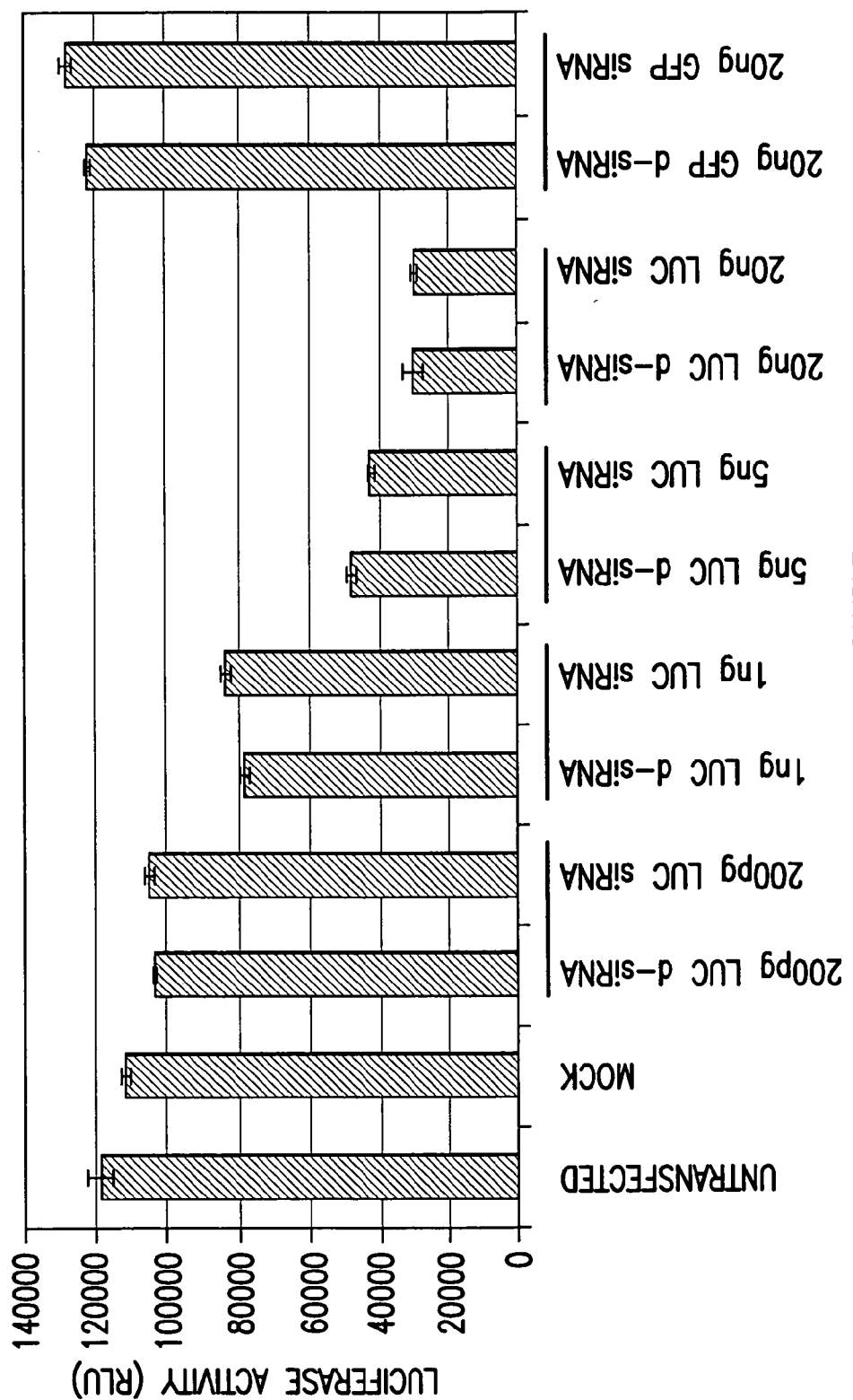

|  | TRANSIENT EXPRESSION | | STABLE EXPRESSION | | | |
|---|---|---|---|---|---|---|
|  | DIVIDING CELLS | NON-DIVIDING CELLS | DIVIDING CELLS | NEURONAL CELLS | DRUG OR GROWTH ARRESTED CELLS | CONTACT INHIBITED CELLS |
| ADENOVIRUS (DNA VIRUS) | YES | YES |  |  |  |  |
| RETROVIRUS (RNA VIRUS) | YES |  | YES |  |  |  |
| LENTIVIRUS (RNA VIRUS) | YES | YES | YES | YES | YES | YES |

FIG.29

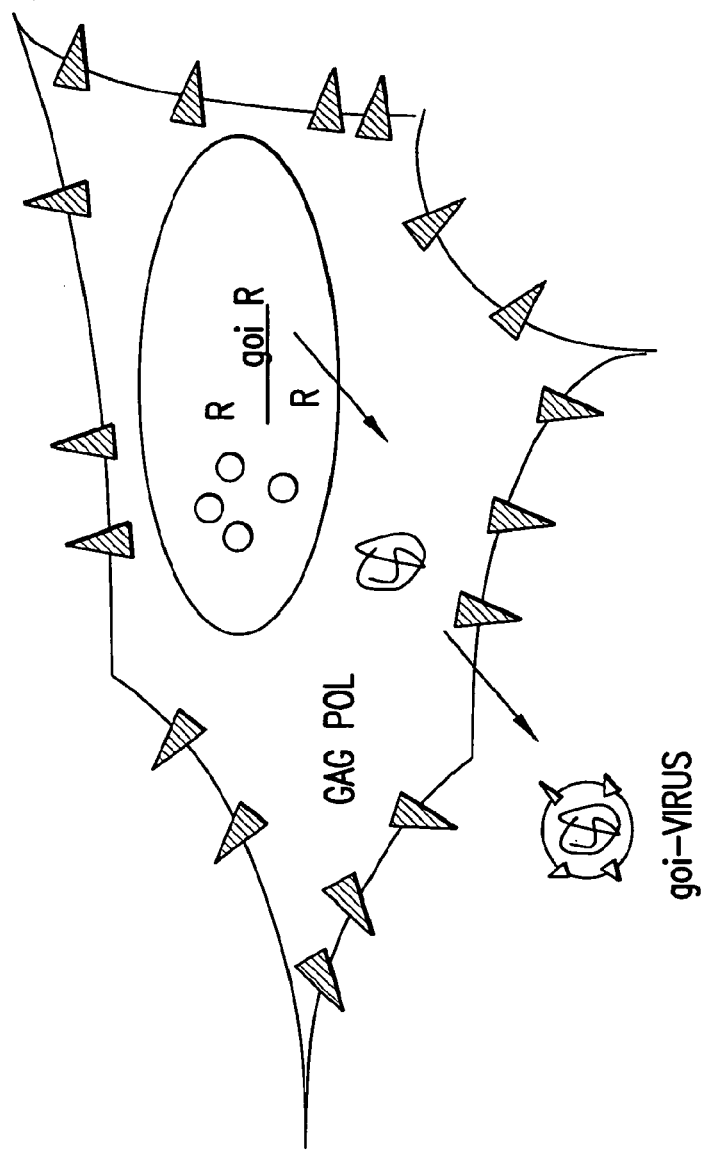
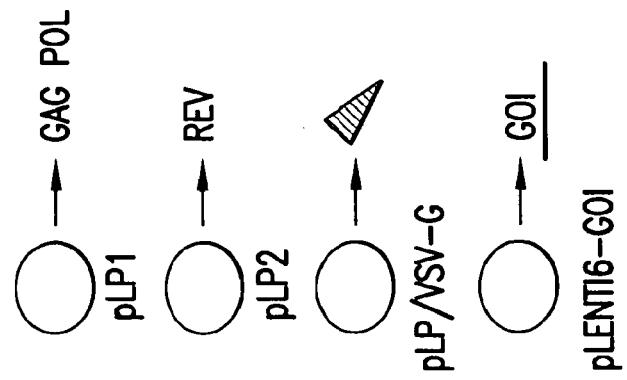
FIG. 31

METHODS AND COMPOSITIONS FOR SEAMLESS CLONING OF NUCLEIC ACID MOLECULES

CROSS-REFERENCE TO RELATED APPLICATIONS

This application is a continuation of U.S. application Ser. No. 12/112,803 filed on Apr. 30, 2008, which is a continuation of U.S. application Ser. No. 10/913,501 filed on Aug. 9, 2004, and claims priority to U.S. Application No. 60/493,322 filed on Aug. 8, 2003, which disclosures are herein incorporated by reference in their entirety.

BACKGROUND OF THE INVENTION

1. Field of the Invention

The present invention is in the fields of biotechnology and molecular biology. More particularly, the present invention relates to seamlessly cloning or subcloning one or more nucleic acid molecules. The present invention also relates to seamless cloning of nucleic acid molecules comprising one or more type IIs restriction enzyme recognition sites. The present invention also embodies cloning such nucleic acid molecules using recombinational cloning methods such as those employing recombination sites and recombination proteins. The present invention also relates to nucleic acid molecules (including RNA and iRNA), as well as proteins, expressed from host cells produced using the methods of the present invention.

2. Related Art

A significant problem with many of the currently available molecular cloning techniques results from the reliance upon restriction sites. These techniques result in the presence of extraneous polynucleotides in the amplification products even after restriction digestions. Such extraneous polynucleotides can introduce design limitations on the cloned product which often interfere with the structure and function of the desired gene products, be they RNA, DNA or protein.

One method of joining nucleic acids without introducing extraneous bases or relying on the presence of restriction sites is splice overlap extension (SOE) (Yon et al, *Nucl. Acids Res.* 17:4895 (1989) and Horton et al., *Gene* 77:61-68 (1989)). This method is based on the hybridization of homologous 3' single-stranded overhangs to prime synthesis of DNA using each complementary strand as a template. Although this technique can join fragments without introducing extraneous nucleotides (in other words, seamlessly), it does not permit the easy insertion of a DNA segment into a specific location when seamless junctions at both ends of the segment are required. Nor does this technique allow for joining fragments with a vector. Ligation with a vector must be subsequently performed by incorporating restriction sites onto the termini of the final SOE fragment. Finally, this technique is particularly awkward when trying to exchange polynucleotides encoding various domains or mutation sites between genetic constructs encoding related proteins.

Sorge et al., U.S. Pat. No. 6,261,797 describe a method by which polynucleotide sequences of interest are synthesized using one or more synthesis primers, wherein at least one of the primers is a releasable primer. After synthesis, the synthesis product is cleaved by a releasing enzyme. The releasable primers of Sorge et al. comprise a recognition site for a type IIs restriction endonuclease, principally Eam1105I. This then allows for "seamless domain replacement" where synthesis reactions allow the production of a polynucleotide of interest by synthesizing two different polynucleotide sequences using separate sets of primers, cleaving the synthesis products with a releasing enzyme, and ligating together the two sets of release synthesis products.

Type IIs Restriction Enzymes

Restriction enzymes can be grouped based on similar characteristics. In general there are three major types or classes: I, II (including IIs) and III. Class I enzymes cut at a somewhat random site from the enzyme recognition sites (see Old and Primrose, Principles of Gene Manipulation, Blackwell Sciences, Inc., Cambridge, Mass., (1994)). Most enzymes used in molecular biology are type II enzymes. These enzymes recognize a particular target sequence (i.e., restriction endonuclease recognition site) and break the polynucleotide chains within or near to the recognition site. The type II recognition sequences are continuous or interrupted. Class IIs enzymes (i.e., type IIs enzymes) have asymmetric recognition sequences. Cleavage occurs at a distance from the recognition site. These enzymes have been reviewed by Szybalski et al. *Gene* 100:13-26 (1991). Class III restriction enzymes are rare and are not commonly used in molecular biology.

Type-IIs endonucleases generally recognize non-palindromic sequences and cleave outside of their recognition site, thus producing overhangs of ambiguous base pairs. (Szybalski, *Gene* 40:169-173 (1985).) Additionally, as a result of their non-palindromic recognition sequences, the use of type-IIs endonucleases will generate more markers per kB than a similar type-II endonuclease, e.g., approximately twice as often. U.S. Pat. No. 4,293,652 discloses a linker with a type-IIs enzyme recognition sequence to permit synthesized DNA to be inserted into a vector without disturbing a recognition sequence. Brousseau et al. (Gene 17:279-289 (1982)) and Urdea et al. (*Proc. Natl. Acad. Sci. USA* 80:7461-7465 (1983)) disclose the use of type-IIs enzymes for the production of vectors to produce recombinant insulin and epidermal growth factor respectively.

Thus, there remains a need in the art for methods and compositions that allow for insertion of nucleic acid molecules into specific locations of other nucleic acid molecules with seamless junctions at one or both ends. There is also a need in the art for methods and compositions that allow for transfer of these seamlessly cloned sections from one nucleic acid molecule to another. The present invention fulfills these needs.

BRIEF SUMMARY OF THE INVENTION

The present invention provides methods of seamlessly cloning nucleic acid molecules. The seamless cloning methods of the present invention may utilize, for example, any restriction enzyme, including those which cleave nucleic acid molecules to produce blunt ends. Suitably, the methods of the invention utilize type IIs restriction sites and enzymes that recognize and cleave at such sites, which allow for the insertion of one or more (e.g. one, two, three, four, five, etc.) nucleic acid segments into specific locations of a second nucleic acid molecule with seamless junctions on one or both ends. The present methods are also suitable for the production of nucleic acid molecules (e.g. DNA, RNA, DNA hybrids and the like) that only contain nucleic acid sequences that are desired in the product molecule and that lack extraneous unwanted sequences, for example sequences comprising or encoded by restriction sites. The present invention also provides for protein molecules produced or encoded by the cloned nucleic acid molecules of the invention, that contain only amino acid sequences that are desired in the product protein molecule (e.g., a native or mature protein, a fusion protein, and the like), and that lack extraneous amino acids, for example amino acids encoded by restriction sites. In certain embodiments, nucleic acid molecules of the present invention are especially suitable for use as interfering RNA. The present invention also provides novel vectors comprising type IIs sites and, optionally, selectable markers for the production of seamlessly cloned nucleic acids, as well as compositions and kits for practicing methods of the invention.

In one aspect, the present invention provides methods for joining one or more (e.g. one, two, three, four, five, etc.) first nucleic acid molecules and one or more second nucleic acid molecules, comprising: (a) combining the first and second nucleic acid molecules under conditions sufficient to allow for the joining of at least one terminus of the first nucleic acid molecule(s) to at least one terminus of the second nucleic acid molecule(s), wherein the terminus of the first nucleic acid molecule(s) which is connected to the terminus of the second nucleic acid molecule(s) comprises a sticky end (e.g. an overhanging end) generated by a restriction enzyme (e.g. a type IIs restriction enzyme) and the terminus of the second nucleic acid molecule(s) is compatible (e.g. a blunt end or a sticky end) with this sticky end. In embodiments similar to the above and elsewhere herein, the sticky end may be on the terminus of the second nucleic acid molecule, and the first nucleic acid molecule may contain the compatible end.

In suitable such embodiments, the present invention provides methods of cloning or subcloning one or more desired nucleic acid molecules comprising: (a) combining in vitro or in vivo, (i) one or more first nucleic acid molecules comprising one or more sticky ends that have been generated by one or more restriction enzymes (e.g. one or more type IIs restriction enzymes); and (ii) one or more second nucleic acid molecules comprising one or more ends which are compatible with the one or more sticky ends on the first nucleic acid molecule(s) and, optionally, one or more selectable markers; and (b) incubating the combination under conditions sufficient to join the first nucleic acid molecule and one or more of the second nucleic acid molecules, thereby producing one or more desired product nucleic acid molecules.

In other aspects, the present invention provides methods for cloning or subcloning one or more desired nucleic acid molecules comprising: (a) combining in vitro or in vivo, (i) one or more first nucleic acid molecules comprising one or more sticky ends that have been generated by one or more restriction enzymes (e.g. one or more type IIs restriction enzymes); (ii) one or more second nucleic acid molecules comprising one or more restriction sites (e.g. one or more first type IIs restriction enzyme recognition sites) and, optionally, one or more selectable markers; and (iii) one or more restriction enzymes (e.g., one or more type IIs restriction enzymes) that are specific for the one or more restriction sites on the second molecules; and (b) incubating the combination under conditions sufficient to join the first nucleic acid molecule and one or more of the second nucleic acid molecules, thereby producing one or more desired product nucleic acid molecules.

In additional related aspects, the present invention provides methods for cloning or subcloning one or more desired nucleic acid molecules comprising: (a) combining in vitro or in vivo, (i) one or more first nucleic acid molecules comprising at least one nucleic acid segment that is flanked by one or more restriction sites (e.g. one or more first type IIs restriction enzyme recognition sites); (ii) one or more second nucleic acid molecules comprising one or more ends which are compatible with a sticky end on the segment and, optionally, one or more selectable markers; and (iii) one or more restriction enzymes (e.g., one or more type IIs restriction enzymes) that are specific for the one or more restriction sites on the at least one nucleic acid segment; and (b) incubating the combination under conditions sufficient to join the first nucleic acid segment and one or more of the second nucleic acid molecules, thereby producing one or more desired product nucleic acid molecules.

In related aspects, the present invention provides methods for cloning or subcloning one or more desired nucleic acid molecules, or portions thereof, comprising: (a) combining in vitro or in vivo, (i) one or more first nucleic acid molecules comprising at least one nucleic acid segment that is flanked by one or more first restriction sites (e.g. one or more first type IIs restriction enzyme recognition sites); (ii) one or more second nucleic acid molecules comprising one or more second restriction sites (e.g. one or more type IIs restriction enzyme recognition sites) and, optionally, one or more selectable markers; and (iii) one or more restriction enzymes (e.g. one or more type IIs restriction enzymes) that are specific for the first and/or second type IIs restriction enzyme recognition sites; and (b) incubating the combination under conditions sufficient to join the first nucleic acid segment and one or more of the second nucleic acid molecules, thereby producing one or more desired product nucleic acid molecules.

Type IIs restriction enzyme recognition sites and type IIs restriction enzymes that are useful in the present cloning methods, compositions, nucleic acids, vectors and kits include, but are not limited to, BsaI, BbsI, BbvII, BsmAI, BspMI, Eco31I, BsmBI, BaeI, FokI, HgaI, MlyI, SfaNI and Sth132I. The first, and second restriction sites, if present, utilized throughout the various aspects of the present invention may be the same or they may be different. In addition, the restriction sites on the same nucleic acid molecule (and/or nucleic acid segment) may be the same, or they may be different. The present invention also encompasses situations wherein one or both of the nucleic acid molecules involved in the various methods are vectors, and where one or both of the nucleic acid molecules are linear nucleic acid molecules. The present invention also encompasses the use of other blunt-end cleavage enzymes, including, but not limited to, ScaI, SmaI, HpaI, HincII, HaeII and AluI.

In certain embodiments, the nucleic acids and nucleic acid segments utilized in the cloning methods, compositions, kits, and vectors of the present invention may optionally comprise one or more selectable markers. Hence, the invention also provides such nucleic acids. The one or more selectable markers utilized in the present invention may be flanked by one or more (e.g. one, two, three, four, five, etc.) restriction sites (e.g. type IIs restriction enzyme recognition sites). Suitable selectable markers include, but are not limited to, genes that confer antibiotic resistance, genes that encode fluorescent proteins, tRNA genes, auxotrophic markers, toxic genes, phenotypic markers, antisense oligonucleotides, restriction endonucleases, restriction endonuclease cleavage sites, enzyme cleavage sites, protein binding sites, and sequences complementary to PCR primer sequences. Suitable antibiotic resistance genes include, but are not limited to, a chloramphenicol resistance gene, an ampicillin resistance gene, a tetracycline resistance gene, a Zeocin resistance gene, a spectinomycin resistance gene and a kanamycin resistance gene. In certain embodiments of the present invention, the selectable marker is a toxic gene. Suitable toxic genes include, but are not limited to, a ccdB gene, a gene encoding a tus protein which binds one or more ter sites, a kicB gene, a sacB gene, an ASK1 gene, a ΦX174 E gene and a DpnI gene. In additional embodiments of the methods of the present invention, the first and/or second nucleic acid molecules may comprise both one or more toxic genes and one or more antibiotic resistance genes, and these genes may further be flanked by type IIs restriction enzyme recognition sites. In suitable such embodiments of the present invention, the first and/or second nucleic acid molecules may comprise both a toxic gene and an antibiotic resistance gene.

In other aspects of the invention, nucleic acids and/or nucleic acid segments for use in the cloning methods, vectors, kits and compositions may further comprise one or more recombination sites and/or one or more topoisomerase recognition sites and/or one or more topoisomerases. The nucleic acids and/or nucleic acid segments of the present invention may also comprise two or more recombination sites. If a topoisomerase recognition site is present in a nucleic acid molecule or nucleic acid segment of the present invention, it may optionally be flanked by two or more recombination sites. Recombination sites suitable for use in the present invention include, but are not limited to, attB sites, attP sites, attL sites, attR sites, lox sites, psi sites, tnpI sites, dif sites, cer sites, frt sites, and mutants, variants and derivatives thereof. These one or more recombination sites may flank one or more selectable markers, if present, and/or restriction sites (e.g. type IIs sites). In certain embodiments of the present invention, the topoisomerase recognition site, if present, is recognized and bound by a type I topoisomerase, which may be a type IB topoisomerase. Suitable types of type IB topoisomerase include, but are not limited to, eukaryotic nuclear type I topoisomerase and poxvirus topoisomerase. Suitable types of poxvirus topoisomerase include, but are not limited to, poxvirus topoisomerase produced by or isolated from a virus such as vaccinia virus, Shope fibroma virus, ORF virus, fowlpox virus, molluscum contagiosum virus and *Amsacta morrei* entomopoxvirus.

The present invention also provides methods of linking nucleic acid molecules and/or nucleic acid segments which comprise one or more topoisomerases bound to one or both termini, wherein the topoisomerase adapted terminus or termini comprise a sequence compatible with that cleaved by a restriction enzyme (e.g. a type IIs restriction enzyme). In such suitable embodiments of the invention, a first nucleic acid molecule or nucleic acid segment may contain a blunt end to be linked, and a second nucleic acid molecule may contain an overhang at the end which is to be linked by a site-specific topoisomerase (e.g., a type IA or a type IB topoisomerase), wherein the overhang includes a sequence complementary to that comprising the blunt end, thereby facilitating strand invasion as a means to properly position the ends for the linking reaction.

The nucleic acid molecules generated using this aspect of the invention include those in which at least one strand (not both strands) is covalently linked at the ends which are joined (e.g. double-stranded nucleic acid molecules generated using these methods contain a nick at each position where two ends were joined). These embodiments are particularly advantageous in that a polymerase can be used to replicate the double-stranded (ds) nucleic acid molecule by initially replicating the covalently linked strand. For example, a thermostable polymerase such as a polymerase useful for performing an amplification reaction such as PCR can be used to replicate the covalently strand, whereas the strand containing the nick does not provide a suitable template for replication.

In certain embodiments of the invention, the first or second nucleic acid molecules or nucleic acid segments involved in the various methods of the present invention may not comprise a promoter. The present invention also allows for transfer of a promoter element into a second nucleic acid molecule that may not comprise a promoter, via seamless cloning. In this orientation, transcription of the second nucleic acid molecule from the promoter element located on the first nucleic acid molecule or nucleic acid segment may proceed such that no additional sequences are transcribed between the promoter element and the transcription initiation point of the second nucleic acid molecule. The present invention also allows for seamlessly adding a first nucleic acid molecule or nucleic acid segment into a second nucleic molecule that contains a promoter element such that the first nucleic acid molecule or segment will subsequently be under the control of the promoter element.

The present invention also provides methods for cloning or subcloning one or more desired nucleic acids: (a) combining in vitro or in vivo, (i) one or more first nucleic acid molecules that have one or more sticky ends that have been generated by one or more restriction enzymes (e.g. type IIs restriction enzymes); and (ii) one or more second nucleic acid molecules comprising one or more ends which are compatible with the one or more sticky ends on the first nucleic acid molecule(s) and further comprising one or more recombination sites; and (b) incubating the combination under conditions sufficient to join the first nucleic acid molecule and one or more of the second nucleic acid molecules, thereby producing one or more desired product nucleic acid molecules.

The present invention also provides methods for cloning or subcloning one or more desired nucleic acid molecules, or portions thereof, comprising: (a) combining in vitro or in vivo, (i) one or more first nucleic acid molecules comprising at least one nucleic acid segment that is flanked by one or more first restriction sites (e.g. one or more type IIs restriction enzyme recognition sites); (ii) one or more second nucleic acid molecules comprising one or more second restriction sites (e.g. type IIs restriction enzyme recognition sites) flanked by one or more recombination sites; and (iii) one or more restriction enzymes (e.g. one or more type IIs restriction enzymes) that are specific for the first and/or second restriction sites; and (b) incubating the combination under conditions sufficient to join the first nucleic acid molecule and one or more of the second nucleic acid molecules, thereby producing one or more desired product nucleic acid molecules.

As described above, the first and/or second nucleic acid molecules and/or nucleic acid segments involved in such embodiments of the present invention may optionally comprise one or more selectable markers. The first and/or second nucleic acid molecules and/or nucleic acid segments involved in such aspects of the invention may also, or alternatively comprise one or more topoisomerase recognition sites or topoisomerases as described above, and optionally or alternatively, two or more recombination sites, which in certain such embodiments may flank these topoisomerases or topoisomerase recognition sites.

The present invention also provides methods for cloning or subcloning one or more desired nucleic acid molecules, or portions thereof, via recombination cloning comprising: (a) combining, in vitro or in vivo (i) one or more first nucleic acid molecules comprising at least one nucleic acid segment that is flanked by one or more restriction sites (e.g. one or more type IIs restriction enzyme recognition sites) and that is further flanked by one or more recombination sites; (ii) one or more second nucleic acid molecules comprising one or more recombination sites; and (iii) one or more site-specific recombination proteins; and (b) incubating the combination under conditions sufficient to join the first nucleic acid molecule and one or more of the second nucleic acid molecules, thereby producing one or more desired product nucleic acid molecules.

The second nucleic acid molecule involved in such embodiments of the invention may also comprise one or more restriction sites (e.g. one or more type IIs restriction enzyme recognition sites). The first and/or second nucleic acids and/or nucleic acid segments involved may also optionally comprise one or more selectable markers as described above. The first and/or second nucleic acid molecules and/or nucleic acid segments involved in this aspect of the invention may also comprise topoisomerase recognition sites or topoisomerases as described above, as well as two or more recombination sites flanking these topoisomerase sites.

Suitable recombination proteins for use in the present invention include, but are not limited to, Int, Cre, IHF, Xis, Fis, Hin, Gin, Cin, Tn3 resolvase, TndX, XerC and XerD.

The present invention also provides methods for producing host cells comprising one or more of the nucleic acid molecules produced by the cloning methods of the present invention Suitable host cells that may be used throughout the present invention include, but are not limited to, bacterial cells, yeast cells, plant cells and animal cells. The present invention also provides methods for producing a subsequent nucleic acid molecule and/or protein by expression of the product nucleic acid molecule of the cloning methods of the present invention in a host cell.

Additional embodiments provide for nucleic acid molecules and proteins produced in and isolated from a host cell. In certain such embodiments, the nucleic acid molecules produced in the host cell may contain only desired nucleic acid sequences, i.e. they may not contain extraneous nucleotides, for example, nucleotides encoded by the restriction sites (e.g. type IIs restriction enzyme recognition sites). Similarly, the proteins produced from a host cell by these methods may only contain amino acid sequences that correspond to the desired native or mature protein, and may not contain extraneous amino acids, for example amino acids encoded by the restriction sites (e.g. type IIs restriction enzyme recognition sites). Nucleic acid molecules produced from a host cell by methods of the present invention may be useful as interfering RNA molecules.

Another aspect of the present invention provides methods of producing an RNA molecule for use as an interfering RNA comprising: (a) optionally, identifying one or more target nucleic acid sequences; (b) preparing one or more nucleic acid molecules which encode one or more interfering RNAs, wherein the interfering RNAs bind to the one or more target nucleic acid sequences; (c) combining in vitro or in vivo, (i) the one or more first nucleic acid molecules encoding one or more interfering RNAs that have one or more sticky ends that have been generated by one or more restriction enzymes (e.g. type IIs restriction enzymes); and (ii) one or more second nucleic acid molecules comprising one or more ends which are compatible with the one or more sticky ends on the first nucleic acid molecule(s), and optionally comprising one or more selectable markers; and (d) incubating the combination under conditions sufficient to join one or more of the nucleic acid molecules encoding the interfering RNAs and one or more of the second nucleic acid molecules, thereby producing one or more desired product nucleic acid molecules; (e) inserting the one or more product nucleic acid molecules into a host cell; and (f) expressing the one or more interfering RNAs in the host cell. As in other embodiments of the invention described herein, the second nucleic acid molecule may contain an end which is generated by digestion with a type IIs restriction enzyme and the first nucleic acid-molecule may contain a compatible end generated by other means.

The present invention also provides methods of producing an RNA molecule for use as an interfering RNA comprising: (a) optionally, identifying one or more target nucleic acid sequences; (b) preparing one or more nucleic acid molecules which encode one or more interfering RNAs, wherein the interfering RNAs bind to the one or more target nucleic acid sequences; (c) combining in vitro or in vivo, (i) the one or more first nucleic acid molecules encoding one or more interfering RNAs flanked by one or more first restriction sites (e.g. one or more type IIs restriction enzyme recognition sites); (ii) one or more second nucleic acid molecules comprising one or more second restriction sites (e.g. one or more type IIs restriction enzyme recognition sites) and optionally comprising one or more selectable markers; and (iii) one or more site-specific restriction enzymes (e.g. one or more type IIs restriction enzymes); and (d) incubating the combination under conditions sufficient to join one or more of the nucleic acid molecules encoding the interfering RNAs and one or more of the second nucleic acid molecules, thereby producing one or more desired product nucleic acid molecules; (e) inserting the one or more product nucleic acid molecules into a host cell; and (f) expressing the one or more interfering RNAs in the host cell.

In related embodiments, the present invention provides methods of producing an RNA molecule for use as an interfering RNA comprising: (a) optionally, identifying one or more target nucleic acid sequences; (b) preparing one or more nucleic acid molecules which encode one or more interfering RNAs, wherein the interfering RNAs bind to the one or more target nucleic acid sequences; (c) combining in vitro or in vivo, (i) the one or more first nucleic acid molecules encoding one or more interfering RNAs that have one or more sticky ends that have been generated by one or more restriction enzymes (e.g. type IIs restriction enzymes); and (ii) one or more second nucleic acid molecules comprising one or more ends which are compatible with the one or more sticky ends on the first nucleic acid molecule(s), and optionally comprising one or more selectable markers; and (d) incubating the combination under conditions sufficient to join one or more of the nucleic acid molecules encoding the interfering RNAs and one or more of the second nucleic acid molecules, thereby producing one or more desired product nucleic acid molecules; and (e) expressing one or more interfering RNAs in vitro or in vivo. In a first further embodiment, the one or more interfering RNAs may be produced in vitro or isolaged from a cell and then introduced into a second cell.

Another aspect of the present invention provides methods of producing an RNA molecule for use as an interfering RNA comprising: (a) optionally, identifying one or more target nucleic acid sequences; (b) preparing one or more nucleic acid molecules which encode one or more interfering RNAs, wherein the interfering RNAs bind to the one or more target nucleic acid sequences; (c) combining in vitro or in vivo, (i) the one or more first nucleic acid molecules encoding one or more interfering RNAs flanked by one or more first restriction sites (e.g. one or more type IIs restriction enzyme recognition sites); (ii) one or more second nucleic acid molecules comprising one or more second restriction sites (e.g. one or more type IIs restriction enzyme recognition sites) and optionally comprising one or more selectable markers; and (iii) one or more site-specific restriction enzymes (e.g. one or more type IIs restriction enzymes); and (d) incubating the combination under conditions sufficient to join one or more of the nucleic acid molecules encoding the interfering RNAs and one or more of the second nucleic acid molecules, thereby producing one or more desired product nucleic acid molecules; and (e) expressing one or more interfering RNAs in vitro or in vivo. In a first further embodiment, the one or more interfering RNAs may be produced in vitro or isolated from a cell and then introduced into a second cell.

In a related aspect, the present invention provides methods of producing an RNA molecule for use as an interfering RNA comprising: (a) optionally, identifying one or more target nucleic acid sequences; (b) preparing one or more interfering RNAs, wherein the interfering RNAs bind to the one or more target nucleic acid sequences; (c) combining in vitro or in vivo, (i) the one or more first nucleic acid molecules comprising one or more interfering RNAs that have one or more sticky ends that have been generated by one or more restriction enzymes (e.g. type IIs restriction enzymes); and (ii) one or more second nucleic acid molecules comprising one or more ends which are compatible with the one or more sticky ends on the first nucleic acid molecule(s), and optionally comprising one or more selectable markers; and (d) incubating the combination under conditions sufficient to join one or more interfering RNAs and one or more of the second nucleic acid molecules, thereby producing one or more desired product nucleic acid molecules; (e) inserting the one or more product nucleic acid molecules into a host cell; and (f) expressing the one or more interfering RNAs in the host cell.

The present invention also provides methods of producing an RNA molecule for use as an interfering RNA comprising: (a) optionally, identifying one or more target nucleic acid sequences; (b) preparing one or more nucleic acid molecules which comprise one or more interfering RNAs, wherein the interfering RNAs bind to the one or more target nucleic acid sequences; (c) combining in vitro or in vivo, (i) the one or more first nucleic acid molecules comprising one or more interfering RNAs flanked by one or more first restriction sites (e.g. one or more type IIs restriction enzyme recognition sites); (ii) one or more second nucleic acid molecules comprising one or more second restriction sites (e.g. one or more type IIs restriction enzyme recognition sites) and optionally comprising one or more selectable markers; and (iii) one or more site-specific restriction enzymes (e.g. one or more type IIs restriction enzymes); and (d) incubating the combination under conditions sufficient to join one or more interfering RNAs and one or more of the second nucleic acid molecules, thereby producing one or more desired product nucleic acid molecules; (e) inserting the one or more product nucleic acid molecules into a host cell; and (f) expressing the one or more interfering RNAs in the host cell.

Methods of the present invention may be used, for example, to prepare shRNA molecules in which the 5' and 3' termini contain none or few (e.g., one, two, three, four, or five) nucleotides which are not encoded by a first nucleic acid molecule referred to throughout. Thus, the shRNA may comprise from about 40 to about 60 nucleotides in which either none of all but a few nucleotides at one or both termini are encoded by a first nucleic acid molecule. In such instances, the first nucleic acid molecule may be composed of nucleic acid which upon transcription results in the production of RNA with three different segments: (1) sense RNA, (2) a loop/non-complementary RNA, and (3) antisense RNA. Methods of the invention include introducing into a cell (1) (a) nucleic acid which encodes the RNA described above or (b) the RNA itself, and (2) the measurement of inhibition of expression of a gene corresponding to the sense and/or antisense RNA.

In particular embodiments of the invention, the invention may be used to produce nucleic acid molecules which produce RNA molecules that do not form hairpins. As one example, methods of the invention may be used to produce two separate vectors, one or which may be used to produce a sense RNA molecules (e.g., a sense RNA molecule which is between about 18 and about 30, between about 20 and about 30, between about 22 and about 30, or between about 18 and about 25 nucleotides in length) and an antisense RNA molecules (e.g., a sense RNA molecule which is between about 18 and about 30, between about 20 and about 30, between about 22 and about 30, between about 18 and about 100, or between about 18 and about 25 nucleotides in length), wherein the two RNA molecules are capable of hybridizing to each other and/or share a region of sequence complementarity over at least 80%, 90%, or 95% of their full lengths (e.g., sequence complementarity over a 19 nucleotide stretch, wherein each molecule is 22 nucleotides in length). Alternatively, both sense and antisense RNA molecules, such as described above, may be produced by a single vector but as separate transcription products.

As a variation of the above, the invention may be used to produce either sense or antisense RNA molecules alone in cells. These RNA molecules may be of any length suitable for the particular application (e.g., expression of protein, antisense inhibition of gene expression, ribozyme production, etc.).

The invention may further be used to produce microRNA molecules. MicroRNA molecules are molecules which are structurally similar to shRNA molecules but, typically, contain one or more mismatches or insertion/deletions in their regions of sequence complementary. At least some microRNA molecules are transcribed as polycistrons of about 400, which are then processed to RNA molecules of about 70 nucleotides. These double stranded 70 mers are then are processed again, presumably by the enzyme Dicer, to two RNA molecules which are about 22 nucleotides in length and often have one or more (e.g., one, two, three, four, five, etc.) internal mismatches in their regions of sequence complementarity. Lee et al., *EMBO* 21:4663-4670 (2002). The invention also includes, for example, uses of microRNA molecules and nucleic acid molecules which encode microRNA molecules which are similar to the uses described those described herein for shRNA and non-hairpin doule stranded RNA molecules.

The present invention also provides methods of regulating the expression of one or more genes in a cell or an animal using interfering RNA, comprising: (a) identifying one or more target nucleic acid sequences; (b) preparing one or more nucleic acid molecules which encode one or more interfering RNAs, wherein the interfering RNAs bind to the one or more target nucleic acid sequences; (c) combining in vitro or in vivo, (i) the one or more first nucleic acid molecules encoding one or more interfering RNAs that have one or more sticky ends that have been generated by one or more restriction enzymes (e.g. type IIs restriction enzymes); and (ii) one or more second nucleic acid molecules comprising one or more ends which are compatible with the one or more sticky ends on the first nucleic acid molecule(s), and optionally comprising one or more selectable markers; (d) incubating the combination under conditions sufficient to join one or more of the nucleic acid molecules encoding the interfering RNAs and one or more of the second nucleic acid molecules, thereby producing one or more desired product nucleic acid molecules; and (e) inserting the one or more interfering RNA expression vectors into the cell or one or more cells of the animal, under conditions such that the one or more interfering RNAs bind to the one or more target nucleic acid sequences, thereby regulating expression of the one or more targeted genes.

In related embodiments, the present invention also provides methods of regulating the expression of one or more genes in a cell or an animal using interfering RNA, comprising: (a) identifying one or more target nucleic acid sequences; (b) preparing one or more nucleic acid molecules which comprise one or more interfering RNAs, wherein the interfering RNAs bind to the one or more target nucleic acid sequences; (c) combining in vitro or in vivo, (i) the one or more first nucleic acid molecules comprising one or more interfering RNAs flanked by one or more first restriction sites (e.g. one or more type IIs restriction enzyme recognition sites); (ii) one or more second nucleic acid molecules comprising one or more second restriction sites (e.g. one or more type IIs restriction enzyme recognition sites) and optionally comprising one or more selectable markers; and (iii) one or more site-specific restriction enzymes (e.g. one or more type IIs restriction enzymes); (d) incubating the combination under conditions sufficient to join one or more interfering RNAs and one or more of the second nucleic acid molecules, thereby producing one or more desired product nucleic acid molecules; and (e) inserting the one or more interfering RNA expression vectors into the cell or one or more cells of the animal, under conditions such that the one or more interfering RNAs bind to the one or more target nucleic acid sequences, thereby regulating expression of the one or more targeted genes.

Such methods of the invention can be used to knockout or knockdown one or more genes in vivo in a cell or animal. These methods of the invention may also be used to produce genetically modified animals by expressing interfering RNA in germ cells or somatic cells, and for preparation of transgenic animals.

In another embodiment, the present invention also provides isolated nucleic acid molecules comprising: (a) one or more sticky ends that have been generated by one or more restriction enzymes (e.g. one or more type IIs restriction enzymes); and (b) optionally one or more selectable markers. The present invention also provides isolated nucleic acid molecules comprising: (a) one or more restriction sites (e.g. one or more type IIs restriction enzyme recognition sites); and (b) optionally one or more selectable markers.

Suitable restriction enzyme recognition sites and selectable markers are described above. The isolated nucleic acid molecules of the present invention may also comprise one or more recombination sites and/or one or more topoisomerase recognition sites and/or one or more topoisomerases. If present, the topoisomerase recognition sites may be flanked by recombination sites. The isolated nucleic acid molecules of the present invention may be vectors or linear nucleic acid molecules. The present invention also provides isolated nucleic acid molecules comprising: (a) one or more sticky ends that have been generated by one or more restriction enzymes (e.g. one or more type IIs restriction enzymes); and (b) one or more recombination sites. The present invention further provides isolated nucleic acid molecules comprising: (a) one or more restriction sites (e.g. one or more type IIs restriction enzyme recognition sites); and (b) one or more recombination sites.

The present invention also provides vectors comprising: (a) one or more desired nucleic acid segments; (b) optionally one or more toxic genes; and (c) one or more sites that are compatible with a sticky end generated by a restriction enzyme (e.g. one or more type IIs restriction enzymes). Suitable desired nucleic acid molecules include genes (e.g. open reading frames) and promoters. The vectors of the present invention may also comprise one or more recombination sites, and one or more topoisomerase recognition sites and/or one or more topoisomerases, wherein, the topoisomerase recognition sites if present, may be flanked by recombination sites. In other embodiments, the vectors of the present invention may optionally comprise one or more selectable markers as described above. Suitable vectors of the present invention include, but are not limited to, pENTR/U6-ccdB (vector diagram for pENTR/U6-ccdB shown in FIG. 2A, vector sequence in Table 5, FIG. 12, and SEQ ID NO:1).

The present invention also provides vectors comprising: (a) one or more desired nucleic acid segments; (b) optionally one or more toxic genes; and (c) one or more restriction sites (e.g. one or more type IIs restriction enzyme recognition sites). Suitable desired nucleic acid molecules include genes and promoters. The vectors of the present invention may also comprise one or more recombination sites, and one or more topoisomerase recognition sites and/or one or more topoisomerases, wherein, the topoisomerase recognition sites if present, may be flanked by recombination sites. In other embodiments, the vectors of the present invention may optionally comprise one or more selectable markers as described above. Suitable vectors of the present invention include, but are not limited to, pENTR/U6-ccdB (vector diagram for pENTR/U6-ccdB shown in FIG. 2A, vector sequence in Table 5, FIG. 12, and SEQ ID NO:1).

The present invention also provides host cells comprising one or more of the isolated nucleic acid molecules or nucleic acid segments of the present invention, and methods of expressing the isolated nucleic acids of the present invention in one more host cells and isolating the expressed nucleic acids. The present invention also provides methods of expressing and isolating proteins from host cells comprising one or more isolated nucleic acids or nucleic acid segments of the invention.

Another embodiment of the invention provides methods of expressing desired product nucleic acid segments by introducing the nucleic acid molecules, nucleic acid segments, or vectors of the present invention into a host cell and expressing the product nucleic acid segments.

The present invention also provides for compositions comprising: (a) one or more first nucleic acid molecules that have one or more sticky ends that have been generated by one or more restriction enzymes (e.g. type IIs restriction enzymes); and (ii) one or more second nucleic acid molecules comprising one or more ends which are compatible with the one or more sticky ends on the first nucleic acid molecule(s). The first and second nucleic acid molecules may optionally comprise one or more selectable markers as discussed above. These first and second nucleic acid molecules may also comprise one or more recombination sites, one or more topoisomerase recognition sites and/or one or topoisomerases, wherein the topoisomerase recognition sites, if present, may be flanked by recombination sites. The optional selectable markers may be flanked by type IIs restriction sites and/or recombination sites. The compositions of the invention may also comprise one or more recombination proteins as described above.

The present invention further provides for compositions comprising: (a) one or more first nucleic acid molecules comprising at least one nucleic acid segment that is flanked by one or more first restriction sites (e.g. one or more type IIs restriction enzyme recognition sites); (b) one or more second nucleic acid molecules optionally comprising one or more second restriction sites (e.g. one or more type IIs restriction enzyme recognition sites); and (c) one or more restriction enzymes (e.g. type IIs restriction enzymes) that are specific for the first and/or second restriction sites. The first and second nucleic acid molecules and/or nucleic acid segments may optionally comprise one or more selectable markers as discussed above. These first and second nucleic acid molecules and/or nucleic acid segments may also comprise one or more recombination sites, one or more topoisomerase recognition sites and/or one or topoisomerases, wherein the topoisomerase recognition sites, if present, may be flanked by recombination sites. The optional selectable markers may be flanked by type IIs restriction sites and/or recombination sites. The compositions of the invention may also comprise one or more recombination proteins as described above.

The present invention also provides kits comprising the isolated nucleic acids or vectors of the present invention. The kits of the present invention may further comprise one or more type IIs restriction enzymes, one or more recombination proteins, and one or more host cells.

Other embodiments of the present invention will be apparent to one or ordinary skill in light of the following drawings and description of the invention, and of the claims.

BRIEF DESCRIPTION OF THE DRAWINGS

FIG. 12 depicts the nucleic acid sequence of the pENTR/U6 with annotations noting the various segments of the vector. SEQ ID NO:1

FIG. 16 depicts siRNA Molecules.

FIG. 19 depicts expression in vivo.

FIG. 23 depicts d-siRNA vs. siRNA.

FIG. 29 depicts Selecting a viral expression system.

FIG. 31 depicts Overview of Lentiviral Production.

DETAILED DESCRIPTION OF THE INVENTION

Definitions

Figure 1A:
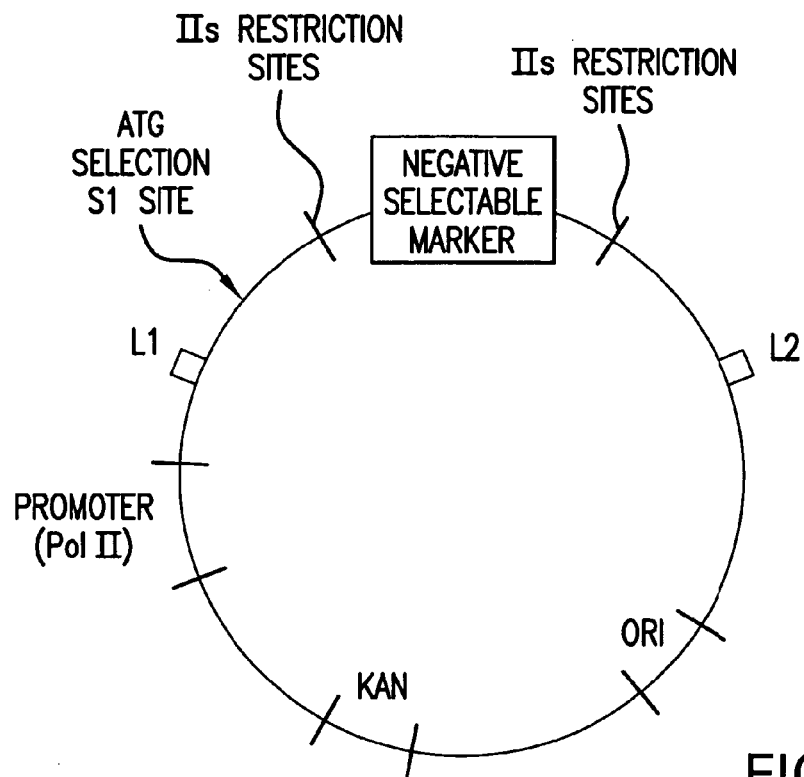
FIG. 1A is a schematic diagram of a vector of the invention comprising: an origin of replication (ori), a kanamycin resistance gen (kan), a Polymerase II promoter (polII), L1 (attL1) and L2 (attL2) recombination sites, an ATG translation initiation site/codon, a secretion signal, type IIs restriction sites, and a negative selectable marker.
Figure 1B:
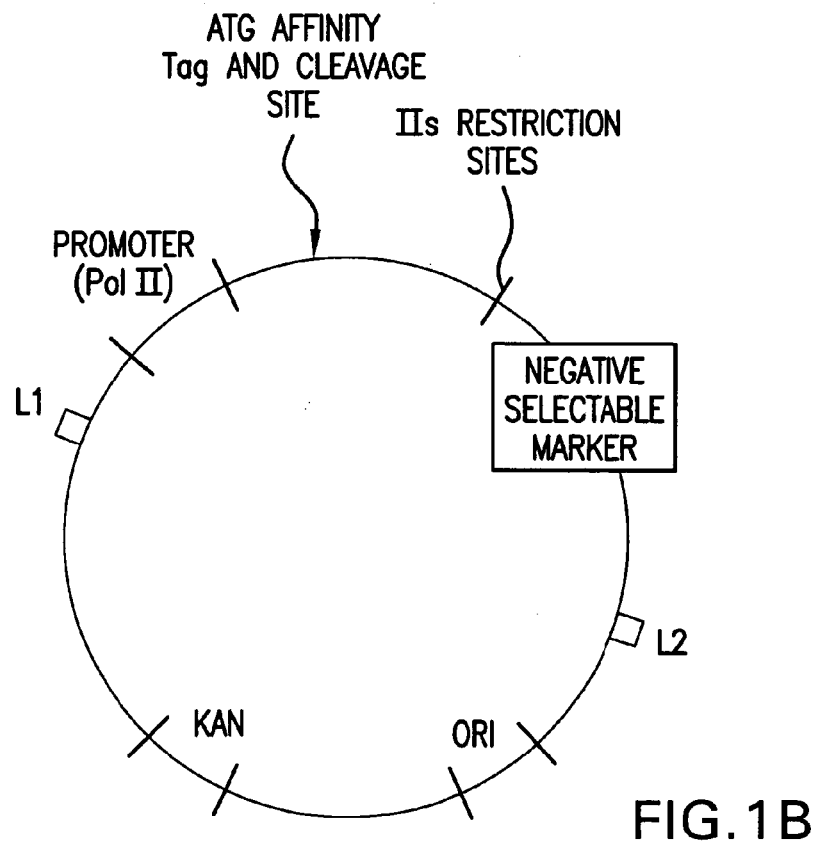
FIG. 1B is a schematic diagram of a vector of the invention comprising: an origin of replication (ori), a kanamycin resistance gen (kan), a Polymerase II promoter (polII), L1 (attL1) and L2 (attL2) recombination sites, an ATG initiation site/codon, an affinity tag, a cleavage site, a type IIs restriction site, and a negative selectable marker.
Figure 2A:
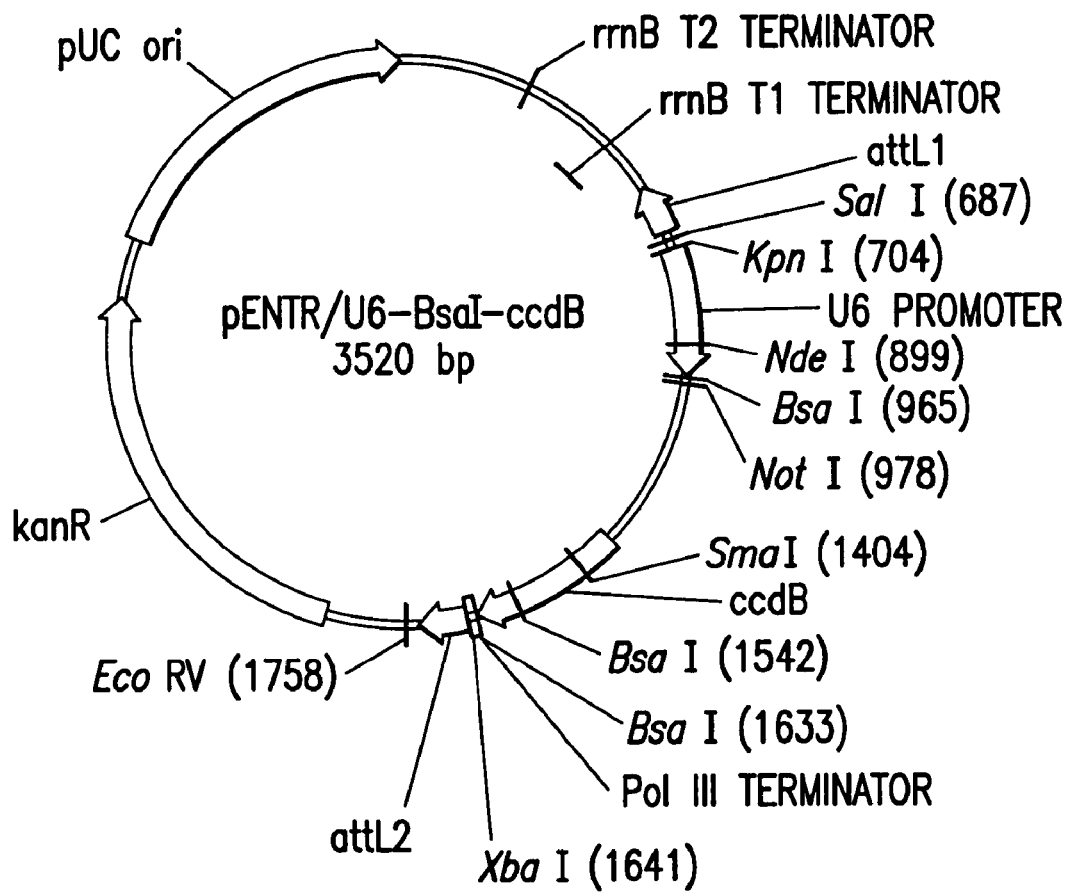
FIG. 2A is a schematic diagram of pENTR/U6.
Figure 2B:
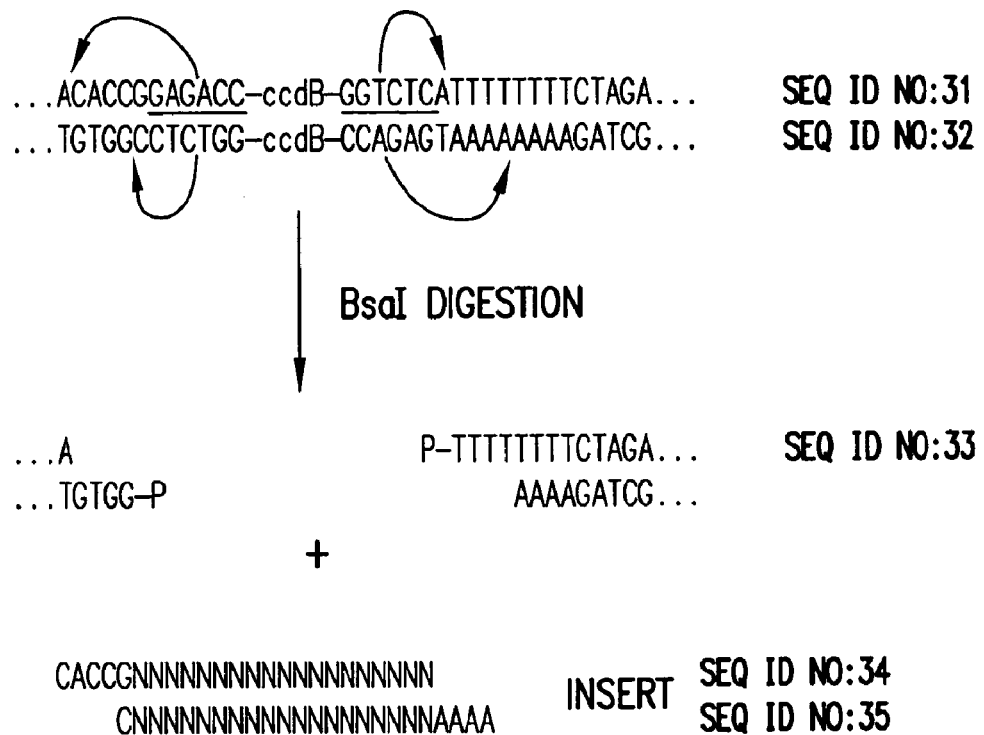
FIG. 2B depicts a BsaI digestion and cloning scheme using pENTR/U6.

Unless defined otherwise, all technical and scientific terms used herein have the same meanings as commonly understood by one of ordinary skill in the art to which this invention belongs.

One or more: As used herein, the term "one or more" includes at least one, more suitably, one, two, three, four, five, ten, twenty, fifty, one-hundred, five-hundred, etc., of the item to which "one or more" refers.

Nucleic Acid: As used herein, "nucleic acid" refers to polynucleotides such as deoxyribonucleic acid (DNA) and ribonucleic acid (RNA). The term should also be understood to include, as applicable to the embodiment being described, single-stranded (such as sense or antisense) and double stranded polynucleotides, including double-stranded DNA-RNA hybrids. The term "nucleic acid" also is synonymous, and may be used interchangeably with the term "nucleic acid molecule."

Gene: As used herein, "gene" refers to a nucleic acid comprising an open reading frame encoding a polypeptide, including both exon and (optionally) intron sequences.

About: As used herein, when referring to any numerical value, "about" means a value of ±10% of the stated value (e.g. "about 50° C. encompasses a range of temperatures from 45° C. to 55° C., inclusive: similarly, "about 100 mM" encompasses a range of concentrations from 90 mM to 110 mM, inclusive).

Host: As used herein, a "host" is any prokaryotic or eukaryotic organism that is a recipient of a replicable expression vector, cloning vector or any nucleic acid molecule. The nucleic acid molecule may contain, but is not limited to, a structural gene, a transcriptional regulatory sequence (such as a promoter, enhancer, repressor, and the like) and/or an origin of replication. As used herein, the terms "host," "host cell," "recombinant host" and "recombinant host cell" may be used equivalently and interchangeably. For examples of such hosts, see Maniatis et al., Molecular Cloning: A Laboratory Manual, Cold Spring Harbor Laboratory, Cold Spring Harbor, N.Y. (1982).

Derivative: As used herein the term "derivative," when used in reference to a vector, means that the derivative vector contains one or more (e.g., one, two, three, four five, etc.) nucleic acid segments which share sequence similar to the vectors represented in FIG. 1A, FIG. 1B, FIG. 2A, FIG. 6A, FIG. 6B, FIG. 8A, FIG. 8B, FIG. 8C, FIG. 8D, FIG. 9A, FIG. 9B, FIG. 9C, FIG. 10, FIG. 11, FIG. 12, Table 5, and any other vector encompassed by the present application. In particular embodiments, a derivative vector (1) may be obtained by alteration of a vector represented in FIG. 1A, FIG. 1B, FIG. 2A, FIG. 6A, FIG. 6B, FIG. 8A, FIG. 8B, FIG. 8C, FIG. 8D, FIG. 9A, FIG. 9B, FIG. 9C, FIG. 10, FIG. 11, FIG. 12, Table 5, and any other vector encompassed by the present application, or (2) may contain one or more elements (e.g., antibiotic resistance marker, recombination or restriction site, etc.) of a vector represented in FIG. 1A, FIG. 1B, FIG. 2A, FIG. 6A, FIG. 6B, FIG. 8A, FIG. 8B, FIG. 8C, FIG. 8D, FIG. 9A, FIG. 9B, FIG. 9C, FIG. 10, FIG. 11, FIG. 12, Table 5, and any other vector encompassed by the present application. Further, as noted above, a derivative vector may contain one or more element which shares sequence similarity (e.g., at least 50%, at least 60%, at least 70%, at least 80%, at least 90%, at least 95%, etc. sequence identity at the nucleotide level) to one or more element of a vector represented in FIG. 1A, FIG. 1B, FIG. 2A, FIG. 6A, FIG. 6B, FIG. 8A, FIG. 8B, FIG. 8C, FIG. 8D, FIG. 9A, FIG. 9B, FIG. 9C, FIG. 10, FIG. 11, FIG. 12, Table 5, and any other vector encompassed by the present application. Derivative vectors may also share at least at least 50%, at least 60%, at least 70%, at least 80%, at least 90%, at least 95%, etc. sequence identity at the nucleotide level to the complete nucleotide sequence of a vector represented in FIG. 1A, FIG. 1B, FIG. 2A, FIG. 6A, FIG. 6B, FIG. 8A, FIG. 8B, FIG. 8C, FIG. 8D, FIG. 9A, FIG. 9B, FIG. 9C, FIG. 10, FIG. 11, FIG. 12, Table 5, and any other vector encompassed by the present application. Derivative vectors include those which have been generated by performing a cloning reaction upon a vector represented in FIG. 1A, FIG. 1B, FIG. 2A, FIG. 6A, FIG. 6B, FIG. 8A, FIG. 8B, FIG. 8C, FIG. 8D, FIG. 9A, FIG. 9B, FIG. 9C, FIG. 10, FIG. 11, FIG. 12, Table 5, and any other vector encompassed by the present application. Derivative vectors also include vectors which have been generated by the insertion into another vector of one or more structural and/or functional components of a vector (e.g. one or more genes or portions thereof encoding one or more structural or functional proteins (or portions thereof) of a vector), including but not limited to the vectors represented in FIG. 1A, FIG. 1B, FIG. 2A, FIG. 6A, FIG. 6B, FIG. 8A, FIG. 8B, FIG. 8C, FIG. 8D, FIG. 9A, FIG. 9B, FIG. 9C, FIG. 10, FIG. 11, FIG. 12, Table 5, and any other vector encompassed by or suitable for use in the invention. Often these derivative vectors will contain at least 50%, at least 60%, at least 70%, at least 80%, at least 90%, at least 95%, etc. of the nucleic acid present in a vector represented in FIG. 1A, FIG. 1B, FIG. 2A, FIG. 6A, FIG. 6B, FIG. 8A, FIG. 8B, FIG. 8C, FIG. 8D, FIG. 9A, FIG. 9B, FIG. 9C, FIG. 10, FIG. 11, FIG. 12, Table 5, and any other vector encompassed by the present application. Derivative vectors also include progeny of any of the vectors referred to above, as well as vectors referred to above which have been subjected to mutagenesis (e.g., random mutagenesis).

Promoter: As used herein, a promoter is an example of a transcriptional regulatory sequence, and is specifically a nucleic acid sequence generally described as the proximal region of a gene located 5' to the start codon. The transcription of an adjacent nucleic acid segment is initiated at the promoter region. A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions. Suitable examples of promoters that may be used in the present invention include, but are not limited to polymerase III promoters such as H1 and U6.

Product: As used herein, a "product" is one of the desired daughter molecules produced after cloning process. The product contains the nucleic acid which was to be cloned or subcloned.

Recognition sequence: As used herein, a "recognition sequence" (alternatively and equivalently referred to herein as a recognition site) is a particular sequence to which a protein, chemical compound, DNA, or RNA molecule (e.g., restriction endonuclease, a topoisomerase, a modification methylase, a type IIs restriction enzyme, or a recombinase) recognizes and binds. In the present invention, a recognition sequence may refer to a recombination site (which may alternatively be referred to as a recombinase recognition site), a topoisomerase recognition site, or a type IIs restriction enzyme recognition site. For example, the recognition sequence for Cre recombinase is loxP which is a 34 base pair sequence comprised of two 13 base pair inverted repeats (serving as the recombinase binding sites) flanking an 8 base pair core sequence. See FIG. 1 of Sauer, B., *Current Opinion in Biotechnology* 5:521-527 (1994). Other examples of such recognition sequences are the attB, attP, attL, and attR sequences which are recognized by the recombinase enzyme. Integrase attB is an approximately 25 base pair sequence containing two 9 base pair core-type Int binding sites and a 7 base pair overlap region. attP is an approximately 240 base pair sequence containing core-type Int binding sites and arm-type Int binding sites as well as sites for auxiliary proteins integration host factor (IHF), FIS and excisionase (Xis). See Landy, *Current Opinion in Biotechnology* 3:699-707 (1993). Such sites may also be engineered according to the present invention to enhance production of products in the methods of the invention. When such engineered sites lack the P1 or H1 domains to make the recombination reactions irreversible (e.g., attR or attP), such sites may be designated attR' or attP' to show that the domains of these sites have been modified in some way. Examples of topoisomerase recognitions sites include, but are not limited to, the sequence 5'-GCAACTT-3' that is recognized by *E. coli* topoisomerase III (a type I topoisomerase); the sequence 5'-(C/T)CCTT-3' which is a topoisomerase recognition site that is bound specifically by most poxvirus topoisomerases, including vaccinia virus DNA topoisomerase I; and others that are known in the art as discussed elsewhere herein.

Recombination proteins: As used herein, "recombination proteins" include excisive or integrative proteins, enzymes, co-factors or associated proteins that are involved in recombination reactions involving one or more recombination sites, which may be wild-type proteins (See Landy, *Current Opinion in Biotechnology* 3:699-707 (1993)), or mutants, derivatives (e.g., fusion proteins containing the recombination protein sequences or fragments thereof), fragments, and variants thereof. Suitable recombination proteins for use in the present invention include, but are not limited to Int, Cre, IHF, Xis, Fis, Hin, Gin, Cin, Tn3 resolvase, TndX, XerC and XerD.

Recombination site: As used herein, a "recombination site" is a recognition sequence on a nucleic acid molecule participating in an integration/recombination reaction by recombination proteins. Recombination sites are discrete sections or segments of nucleic acid on the participating nucleic acid molecules that are recognized and bound by a site-specific recombination protein during the initial stages of integration or recombination. For example, the recombination site for Cre recombinase is loxP which is a 34 base pair sequence comprised of two 13 base pair inverted repeats (serving as the recombinase binding sites) flanking an 8 base pair core sequence. See FIG. 1 of Sauer, B., *Curr. Opin. Biotech.* 5:521-527 (1994). Other examples of recognition sequences include the attB, attP, attL, and attR sequences described herein, and mutants, fragments, variants and derivatives thereof, which are recognized by the recombination protein Int and by the auxiliary proteins integration host factor (IHF), FIS and excisionase (Xis). See Landy, *Curr. Opin. Biotech.* 3:699-707 (1993).

Recombinational Cloning: As used herein, "recombinational cloning" is a method, such as that described in U.S. Pat. Nos. 5,888,732, 6,143,557, 6,171,861, 6,270,969, and 6,277,608 (the contents of which are fully incorporated herein by reference), whereby segments of nucleic acid molecules or populations of such molecules are exchanged, inserted, replaced, substituted or modified, in vitro or in vivo. Suitably, such cloning method is an in vitro method, i.e., a method in which the recombination reaction takes place outside of or in the absence of host cells.

Selectable marker: As used herein, "selectable marker" is a nucleic acid segment that allows one to select for or against a molecule (e.g., a replicon) or a cell that contains it, often under particular conditions. These markers can encode an activity, such as, but not limited to, production of RNA, peptide, or protein, or can provide a binding site for RNA, peptides, proteins, inorganic and organic compounds or compositions and the like. Examples of selectable markers include but are not limited to: (1) nucleic acid segments that encode products which provide resistance against otherwise toxic compounds (e.g., antibiotics); (2) nucleic acid segments that encode products which are otherwise lacking in the recipient cell (e.g., tRNA genes, auxotrophic markers); (3) nucleic acid segments that encode products which suppress the activity of a gene product; (4) nucleic acid segments that encode products which can be readily identified (e.g., phenotypic markers such as β-galactosidase, green fluorescent protein (GFP), yellow fluorescent protein (YFP), cyan fluorescent protein (CFP), and cell surface proteins); (5) nucleic acid segments that bind products which are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g. restriction endonucleases); (8) nucleic acid segments that can be used to isolate or identify a desired molecule (e.g. specific protein binding sites); (9) nucleic acid segments that encode a specific nucleotide sequence which can be otherwise non-functional (e.g., for PCR amplification of subpopulations of molecules); (10) nucleic acid segments, which when absent, directly or indirectly confer resistance or sensitivity to particular compounds; and/or (11) nucleic acid segments that encode products which are toxic in recipient cells.

Examples of toxic gene products are well known in the art, and include, but are not limited to, restriction endonucleases (e.g., DpnI), apoptosis-related genes (e.g. ASK1 or members of the bcl-2/ced-9 family), retroviral genes including those of the human immunodeficiency virus (HIV), defensins such as NP-1, inverted repeats or paired palindromic nucleic acid sequences, bacteriophage lytic genes such as those from (ΦX174 or bacteriophage T4; antibiotic sensitivity genes such as rpsL, antimicrobial sensitivity genes such as pheS, plasmid killer genes, eukaryotic transcriptional vector genes that produce a gene product toxic to bacteria, such as GATA-1, and genes that kill hosts in the absence of a suppressing function, e.g., kicB, ccdB, ΦX174 E (Liu, Q. et al., *Curr. Biol.* 8:1300-1309 (1998), and other genes that negatively affect replicon stability and/or replication. A toxic gene can alternatively be selectable in vitro, e.g., a restriction site.

Selection scheme: As used herein, "selection scheme" is any method which allows selection, enrichment, or identification of a desired product or product(s). The selection schemes of one suitable embodiment have at least two components that are either linked or unlinked during recombinational cloning. One component is a Selectable marker. The other component controls the expression in vitro or in vivo of the Selectable marker, or survival of the cell (or the nucleic acid molecule, e.g., a replicon) harboring the plasmid carrying the Selectable marker. Generally, this controlling element will be a repressor or inducer of the Selectable marker, but other means for controlling expression or activity of the Selectable marker can be used. Whether a repressor or activator is used will depend on whether the marker is for a positive or negative selection, and the exact arrangement of the various nucleic acid segments, as will be readily apparent to those skilled in the art.

Fragments of selectable markers can be arranged relative to the recombination sites or restriction sites such that when the segments are brought together, they reconstitute a functional Selectable marker. For example, the linking event can link a promoter with a structural nucleic acid molecule (e.g., a gene), can link two fragments of a structural nucleic acid molecule, or can link nucleic acid molecules that encode a heterodimeric gene product needed for survival, or can link portions of a replicon.

Site-specific recombinase: As used herein, a "site specific recombinase" is a type of recombinase which typically has at least the following four activities (or combinations thereof): (1) recognition of one or two specific nucleic acid sequences; (2) cleavage of said sequence or sequences; (3) topoisomerase activity involved in strand exchange; and (4) ligase activity to reseal the cleaved strands of nucleic acid. See Sauer, B., *Current Opinions in Biotechnology* 5:521-527 (1994). Conservative site-specific recombination is distinguished from homologous recombination and transposition by a high degree of specificity for both partners. The strand exchange mechanism involves the cleavage and rejoining of specific nucleic acid sequences in the absence of DNA synthesis (Landy, A. (1989) *Ann. Rev. Biochem.* 58:913-949).

Figure 36:
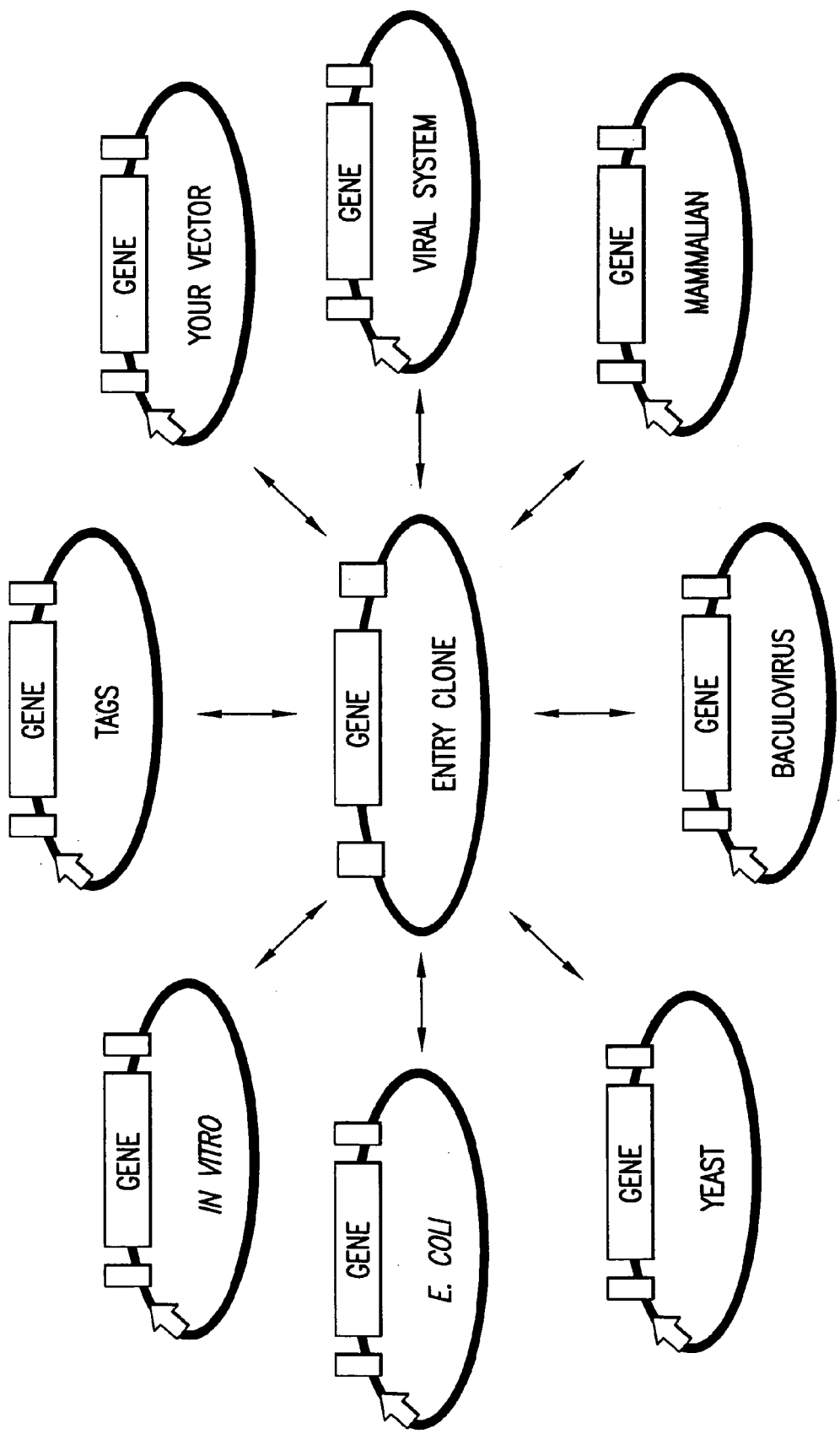
FIG. 36 depicts Subcloning an Entry Clone into Multiple Destination Vectors.
Figure 37:
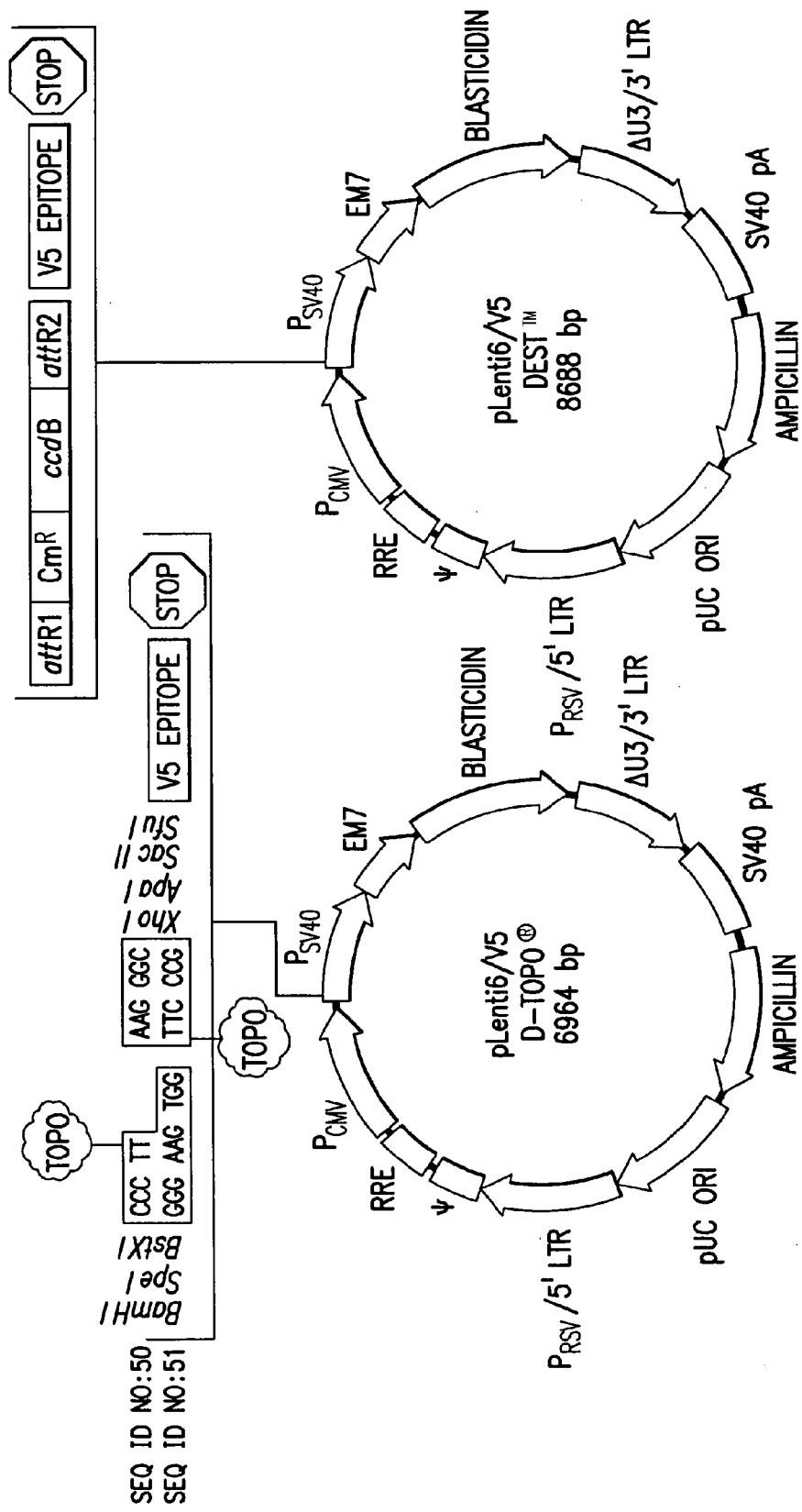
FIG. 37 depicts pLenti6N5 Expression Vectors.

Vector: As used herein, a "vector" is a nucleic acid molecule (preferably DNA) that provides a useful biological or biochemical property to an Insert. Examples include plasmids, phages, autonomously replicating sequences (ARS), centromeres, and other sequences which are able to replicate or be replicated in vitro or in a host cell, or to convey a desired nucleic acid segment to a desired location within a host cell. A Vector can have one or more restriction endonuclease recognition sites (whether type I, II or IIs) at which the sequences can be cut in a determinable fashion without loss of an essential biological function of the vector, and into which a nucleic acid fragment can be spliced in order to bring about its replication and cloning. Vectors can also comprise one or more recombination sites that permit exchange of nucleic acid sequences between two nucleic acid molecules. Such as, for example, subcloning of genes of interest between Entry and Destination vectors in the Gateway™ system (available from Invitrogen Corporation, Carlsbad, Calif. (see, e.g., FIG. 36)). Vectors can further provide primer sites, e.g., for PCR, transcriptional and/or translational initiation and/or regulation sites, recombinational signals, replicons, Selectable markers, etc. Clearly, methods of inserting a desired nucleic acid fragment which do not require the use of recombination, transpositions or restriction enzymes (such as, but not limited to, UDG cloning of PCR fragments (U.S. Pat. No. 5,334,575, entirely incorporated herein by reference), TA Cloning® brand PCR cloning (Invitrogen Corporation, Carlsbad, Calif.) (also known as direct ligation cloning), and the like) can also be applied to clone a fragment into a cloning vector to be used according to the present invention. The cloning vector can further contain one or more selectable markers suitable for use in the identification of cells transformed with the cloning vector.

Incorporating: As used herein, "incorporating" means becoming a part of a nucleic acid (e.g., DNA) molecule or primer.

Nucleotide: As used herein, a "nucleotide" is a base-sugar-phosphate combination. Nucleotides are monomeric units of a nucleic acid molecule (DNA and RNA). The term nucleotide includes ribonucleoside triphosphates ATP, UTP, CTG, GTP and deoxyribonucleoside triphosphates such as dATP, dCTP, dITP, dUTP, dGTP, dTTP, or derivatives thereof. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Portion: As used herein, the term "portion" refers to part, or percentage of a whole entity. For example, a "portion" of a nucleic acid molecule refers to 1%, 10%, 25%, 50%, 75%, 90%, 99%, etc., of the whole nucleic acid molecule.

Segment: As used herein, the term "segment" refers to part, or percentage of a whole entity. For example, a "segment" of a nucleic acid molecule refers to 1%, 10%, 25%, 50%, 75%, 90%, 99%, etc., of the whole nucleic acid molecule.

Other terms used in the fields of recombinant nucleic acid technology and molecular and cell biology as used herein will be generally understood by one of ordinary skill in the applicable arts.

The present invention relates to methods, compositions, isolated nucleic acids, vectors and kits for seamless cloning of nucleic acid molecules and production of nucleic acids and proteins.

The vectors represented throughout, specifically shown in FIGS. 1A, 1B, 2A, 6A and 6B, 8A, 8B, 8C, 8D, 9A, 9B, 9C, 10, 11, 28, 33, 37 as well as similar vectors and portions of these vectors, may be used in the practice of the methods of the present invention. In each case, these vectors are designed such that upon digestion with a restriction enzyme (e.g. a type IIs restriction enzyme), a sticky end is generated abutting and/or including nucleic acids which encode a peptide which may be cleaved from a protein or peptide encoded by a nucleic acid which is inserted into the vector. These, and other vectors of the present invention may further comprise one or more signal peptides and/or protease cleavage sites. The vectors of the present invention allow for the production of a protein that is exported from a cell and cleaved to generate a "mature" protein. The vectors of the present invention also allow for the production of a protein that is retained in the cell as a "native" protein.

In one aspect, the present invention provides methods for joining one or more (e.g. one, two, three, four, five, etc.) first nucleic acid molecules and a second one or more nucleic acid molecules, comprising: (a) combining the first and second nucleic acid molecules under conditions sufficient to allow for the joining of at least one terminus of the first nucleic acid molecule(s) to at least one terminus of the second nucleic acid molecule(s), wherein the terminus of the first nucleic acid molecule which is connected to the terminus of the second nucleic acid molecule(s) comprises a sticky end (e.g. an overhanging end) generated by a restriction enzyme (e.g. a type IIs restriction enzyme) and the terminus of the second nucleic acid molecule(s) is compatible (e.g. a blunt end or a sticky end) with this sticky end. In embodiments similar to the above and elsewhere herein, the sticky end my be on the terminus of the second nucleic acid molecule and the first nucleic acid molecule may contain a compatible end.

As in other embodiments of the invention described herein, the second nucleic acid molecule may contain an end which is generated by digestion with a type IIs restriction enzyme and the first nucleic acid molecule may contain a compatible end generated by other means.

In suitable embodiments, the present invention provides methods of cloning or subcloning one or more desired nucleic acid molecules comprising: (a) combining in vitro or in vivo, (i) one or more first nucleic acid molecules comprising one or more sticky ends that have been generated by one or more restriction enzymes (e.g. one or more type IIs restriction enzymes); and (ii) one or more second nucleic acid molecules comprising one or more ends which are compatible with the one or more sticky ends on the first nucleic acid molecule(s)

and, optionally, one or more selectable markers; and (b) incubating the combination under conditions sufficient to join the first nucleic acid molecule and one or more of the second nucleic acid molecules, thereby producing one or more desired product nucleic acid molecules.

In another aspect, the present invention provides methods for cloning or subcloning one or more desired nucleic acid molecules comprising: (a) combining in vitro or in vivo, (i) one or more first nucleic acid molecules comprising one or more sticky ends that have been generated by one or more restriction enzymes (e.g. one or more type IIs restriction enzymes); (ii) one or more second nucleic acid molecules comprising one or more restriction sites (e.g. one or more first type IIs restriction enzyme recognition sites) and, optionally, one or more selectable markers; and (iii) one or more restriction enzymes (e.g., one or more type IIs restriction enzymes) that are specific for the restriction enzyme recognition site; and (b) incubating the combination under conditions sufficient to join the first nucleic acid molecule and one or more of the second nucleic acid molecules, thereby producing one or more desired product nucleic acid molecules.

In another aspect, the present invention provides methods for cloning or subcloning one or more desired nucleic acid molecules, or portions thereof, comprising: (a) combining in vitro or in vivo, (i) one or more first nucleic acid molecules comprising at least one nucleic acid segment that is flanked by one or more restriction sites (e.g. one or more first type IIs restriction enzyme recognition sites); (ii) one or more second nucleic acid molecules comprising one or more ends which are compatible with a sticky end on the segment and, optionally, one or more selectable markers; and (iii) one or more restriction enzymes (e.g., one or more type IIs restriction enzymes) that are specific for the restriction enzyme recognition site; and (b) incubating the combination under conditions sufficient to join the first nucleic acid segment and one or more of the second nucleic acid molecules, thereby producing one or more desired product nucleic acid molecules.

In another aspect, the present invention provides methods for cloning or subcloning one or more desired nucleic acid molecules, or portions thereof, comprising: (a) combining in vitro or in vivo, (i) one or more first nucleic acid molecules comprising at least one nucleic acid segment that is flanked by one or more first restriction sites (e.g. one or more first type IIs restriction enzyme recognition sites); (ii) one or more second nucleic acid molecules comprising one or more second restriction sites (e.g. one or more type IIs restriction enzyme recognition sites) and, optionally, one or more selectable markers; and (iii) one or more restriction enzymes (e.g. one or more type IIs restriction enzymes) that are specific for the first and/or second type IIs restriction enzyme recognition sites; and (b) incubating the combination under conditions sufficient to join the first nucleic acid segment and one or more of the second nucleic acid molecules, thereby producing one or more desired product nucleic acid molecules.

The seamless cloning methods of the present invention may utilize any restriction enzyme, including those which cleave nucleic acid molecules to produce blunt ends. The term "blunt ends" as used herein is used to indicate a nucleic acid molecule which has been cleaved by a restriction enzyme in such a way as to produce a double stranded nucleic acid in which both strands stop "bluntly" and do not overlap or overhang the other. Suitably, the methods of the invention utilize type IIs restriction sites. The present invention also encompasses the use of blunt-end cleavage enzymes, such as, but not limited to, ScaI, SmaI, HpaI, HincII, HaeII and AluI.

Type-IIs restriction enzymes and recognition sites which are useful in all aspects of the present invention include, but are not limited to, EarI, MnlI, PleI, AlwI, BbsI, BsaI, BsmAI, BspMI, Esp3I, HgaI, SapI, SfaNI, BbvI, BsmFI, FokI, BseRI, HphI, Alw26I, BbvlI, BpmI, BsmI, BbsI, BsmBI, BaeI, BsrI, MlyI, BsrDI, Eco57I, GsuI, MnlI, PleI, TaqII, Tth111II and MboII. In all aspects of the present invention, the restriction enzyme recognition sites on the first and second nucleic acid molecules may be the same sites or they may be different. In addition, the restriction enzyme recognition sites may be the same or different on each nucleic acid molecule. This allows for selective cloning where only nucleic acid segments with complementary sites will transfer between nucleic acids molecules.

Cleavage of a polynucleotide sequence with a type IIs restriction enzyme leaves an overhang on one strand of the sequence, or a sticky end. Via the cloning methods of the present invention, this sticky end can be combined with a compatible sequence on a second nucleic acid molecule resulting in a cloned, co-joined molecule. Sequences cleaved by Type IIs sites may also be joined to blunt ended compatible nucleic acid sequences via the cloning methods of the present invention. The compatible sequences can be joined via various catalyzing enzymes, for example DNA ligase and topoisomerase. Certain type IIs enzymes (e.g. MlyI) cleave and leave a blunt end on a nucleic acid molecule that may then be combined with a sticky end on a second nucleic acid molecule.

Nucleic acid molecules of the invention to be cloned may contain a blunt end to be linked, and the second nucleic acid molecule involved in the cloning method may contain an overhang at the end which is to be linked by a site-specific topoisomerase (e.g., a type IA or a type IB topoisomerase), wherein the overhang includes a sequence complementary to that comprising the blunt end, thereby facilitating strand invasion as a means to properly position the ends for the linking reaction.

The nucleic acid molecules generated using this aspect of the invention include those in which one strand (not both strands) is covalently linked at the ends to be linked (i.e. double-stranded nucleic acid molecules generated using these methods contain a nick at each position where two ends were joined). These embodiments are particularly advantageous in that a polymerase can be used to replicate the double-stranded (ds) nucleic acid molecule by initially replicating the covalently linked strand. For example, a thermostable polymerase such as a polymerase useful for performing an amplification reaction such as PCR can be used to replicate the covalently strand, whereas the strand containing the nick does not provide a suitable template for replication.

Preferably, the 5' termini of the ends of the nucleotide sequences to be linked by a type IB topoisomerase according to a method of certain aspects of the invention contain complementary 5' overhanging sequences, which can facilitate the initial association of the nucleotide sequences, including, if desired, in a predetermined directional orientation. Alternatively, the 5' termini of the ends of the nucleotide sequences to be linked by a type LB topoisomerase according to a method of certain aspects of the invention contain complementary 5' sequences wherein one of the sequences contains a 5' overhanging sequence and the other nucleotide sequence contains a complementary sequence at a blunt end of a 5' terminus, to facilitate the initial association of the nucleotide sequences through strand invasion, including, if desired, in a predetermined directional orientation. The term "5' overhang" or "5' overhanging sequence" is used herein to refer to a strand of a nucleic acid molecule that extends in a 5' direction beyond the terminus of the complementary strand of the nucleic acid molecule. Conveniently, a 5' overhang can be produced as a result of site specific cleavage of a nucleic acid molecule by a type IB topoisomerase.

Preferably, the 3' termini of the ends of the nucleotide sequences to be linked by a type IA topoisomerase according to a method of certain aspects of the invention contain complementary 3' overhanging sequences, which can facilitate the initial association of the nucleotide sequences, including, if desired, in a predetermined directional orientation. Alternatively, the 3' termini of the ends of the nucleotide sequences to be linked by a topoisomerase (e.g., a type IA or a type II topoisomerase) according to a method of certain aspects of the invention contain complementary 3' sequences wherein one of the sequences contains a 3' overhanging sequence and the other nucleotide sequence contains a complementary sequence at a blunt end of a 3' terminus, to facilitate the initial association of the nucleotide sequences through strand invasion, including, if desired, in a predetermined directional orientation. The term "3 overhang" or "3 overhanging sequence" is used herein to refer to a strand of a nucleic acid molecule that extends in a 5' direction beyond the terminus of the complementary strand of the nucleic acid molecule. Conveniently, a 3' overhang can be produced upon cleavage by a type IA or type II topoisomerase.

The cloning methods of the present invention may be performed in vitro or in vivo. By in vitro and in vivo herein is meant cloning that is carried out outside of host cells (e.g., in cell-free systems, or in systems containing host cells in which the various cloning and recombination reaction(s) of the present invention take(s) place outside of the host cells) or inside of host cells (e.g., using recombination or other proteins expressed by host cells), respectively.

The nucleic acid molecules utilized and produced in the methods, compositions and kits of the present invention may be vectors or linear nucleic acid molecules. The term "vector," as used herein, refers to a nucleic acid molecule (preferably DNA) that provides a useful biological or biochemical property to an inserted nucleic acid. The terms "vector" and "plasmid" are used interchangeably herein. Examples of vectors include, phages, autonomously replicating sequences (ARS), centromeres, and other sequences which are able to replicate or be replicated in vitro or in a cell, or to convey a desired nucleic acid segment to a desired location within a cell of an animal. Vectors useful in the present invention include chromosomal-, episomal- and virus-derived vectors, e.g., vectors derived from bacterial plasmids or bacteriophages, and vectors derived from combinations thereof, such as cosmids and phagemids. A vector can have one or more restriction endonuclease recognition sites at which the sequences can be cut in a determinable fashion without loss of an essential biological function of the vector, and into which a nucleic acid fragment can be spliced in order to bring about its replication and cloning. Vectors can further provide primer sites, e.g., for PCR, transcriptional and/or translational initiation and/or regulation sites, recombinational signals, replicons, selectable markers, etc. Clearly, methods of inserting a desired nucleic acid fragment which do not require the use of homologous recombination, transpositions or restriction enzymes (such as, but not limited to, UDG cloning of PCR fragments (U.S. Pat. No. 5,334,575, entirely incorporated herein by reference), TA Cloning® brand PCR cloning (Invitrogen Corp., Carlsbad, Calif.), and the like) can also be applied to clone a nucleic acid into a vector to be used according to the present invention. The vector can optionally further contain one or more selectable markers suitable for use in the identification of cells transformed with the vector, such as the selectable markers and reporter genes described herein. Vectors of the present invention may be derivative vectors as described throughout the present specification.

Vectors known in the art and those commercially available (and variants or derivatives thereof) may be used in the present invention. Such vectors may be obtained from, for example, Vector Laboratories Inc., Invitrogen, Promega, Novagen, NEB, Clontech, Boehringer Mannheim, Pharmacia, EpiCenter, OriGenes Technologies Inc., Stratagene, PerkinElmer, Pharmingen, and Research Genetics. General classes of vectors of particular interest include prokaryotic and/or eukaryotic cloning vectors, expression vectors, fusion vectors, two-hybrid or reverse two-hybrid vectors, shuttle vectors for use in different hosts, mutagenesis vectors, transcription vectors, vectors for receiving large inserts and the like.

Other vectors of interest include viral origin vectors (M13 vectors, bacterial phage λ vectors, adenovirus vectors, and retrovirus vectors), high, low and adjustable copy number vectors, vectors which have compatible replicons for use in combination in a single host (pACYC184 and pBR322) and eukaryotic episomal replication vectors (pCDM8).

Vectors for use in the present invention may comprise all, or portions of viral genomes, for example an adenovirus genome, a baculovirus genome, a herpesvirus genome, a pox virus genome, an adeno-associated virus genome, a retrovirus genome, a flavivirus genome, a togavirus genome, an alphavirus genome, an RNA virus genome, etc.

The present invention also encompasses the use of recombinant retroviruses, e.g., lentiviruses, or any other type of retrovirus may be used in an analogous fashion to practice the present invention. A commercially available system for the construction of recombinant lentiviruses is ViraPower™ Lentiviral Expression System, available from Invitrogen Corporation, Carlsbad, Calif. The ViraPower™ system provides a retroviral system for high-level expression in dividing and non-dividing eukaryotic cells, e.g., mammalian cells (See FIG. 29). Examples of products available from Invitrogen Corporation, Carlsbad, Calif. include the ViraPower™ Lentiviral Directional TOPO® Expression Kit (catalog number K4950-00), the ViraPower™ Lentiviral GATEWAY™ Expression Kit (catalog number K4960-00), and the ViraPower™ Lentiviral Support Kit (catalog number K4970-00).

Figure 8A:
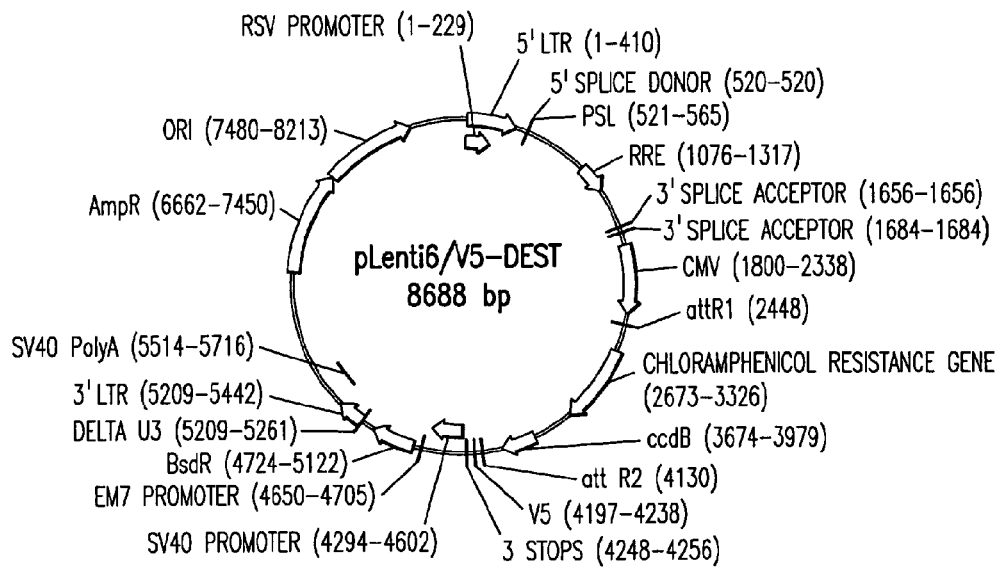
FIG. 8A is a plasmid map of pLenti6/V5-DEST.
Figure 8B:
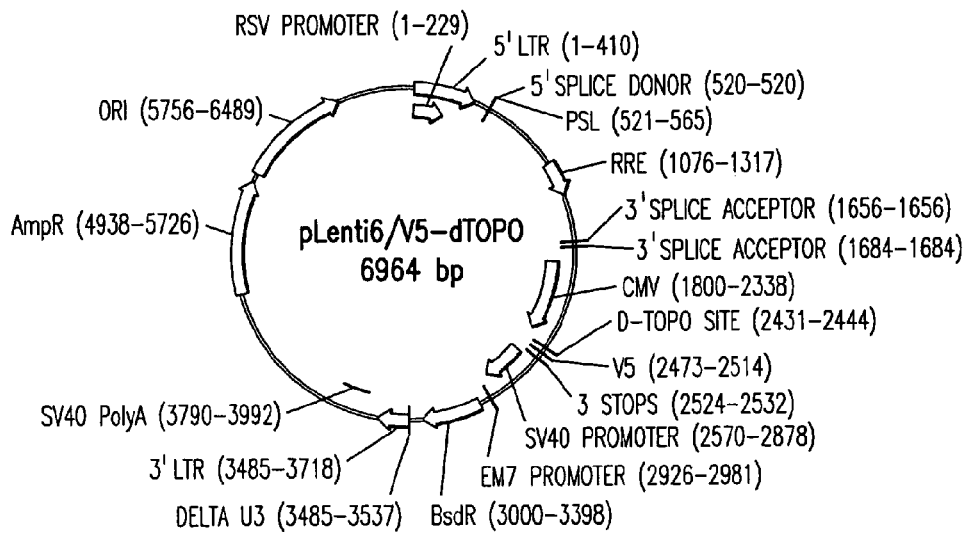
FIG. 8B is a plasmid map of pLenti6/V5-gTOPO®.
Figure 8C:
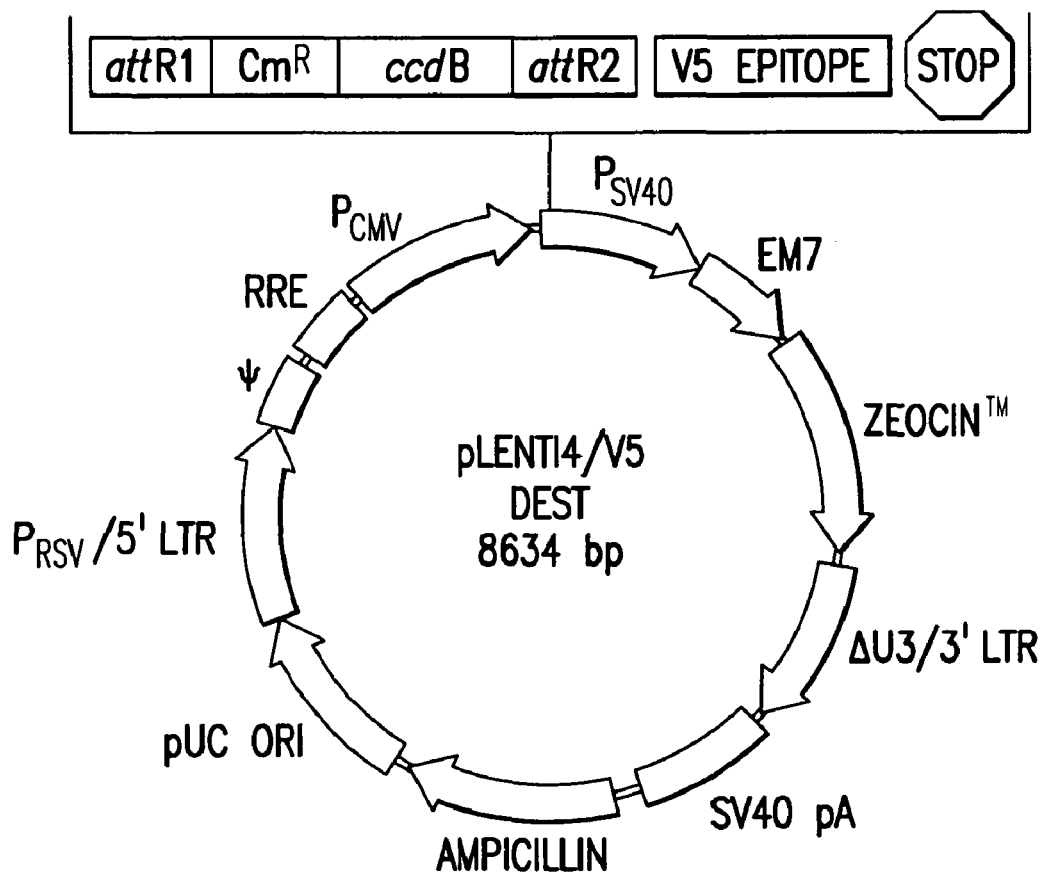
FIG. 8C is a plasmid map of pLenti4/V5-DEST
Figure 8D:
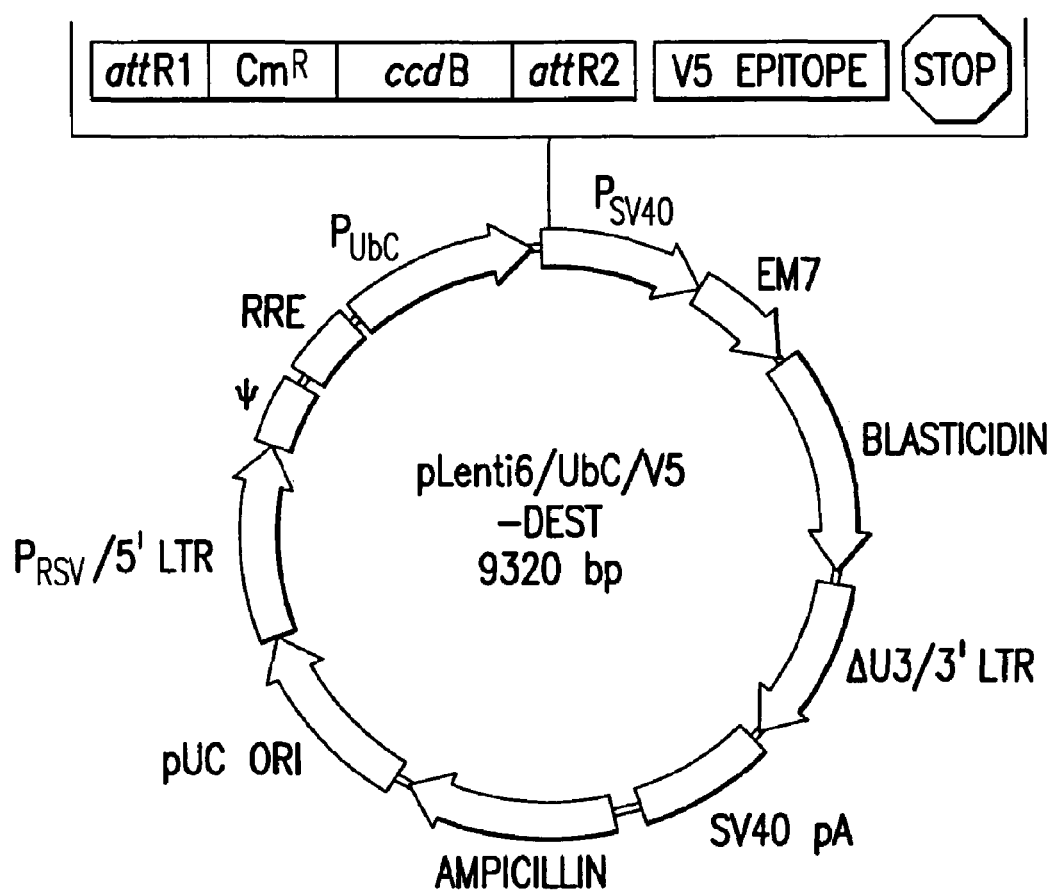
FIG. 8D is a plasmid map of pLenti6/UbC/V5-DEST.
Figure 9A:
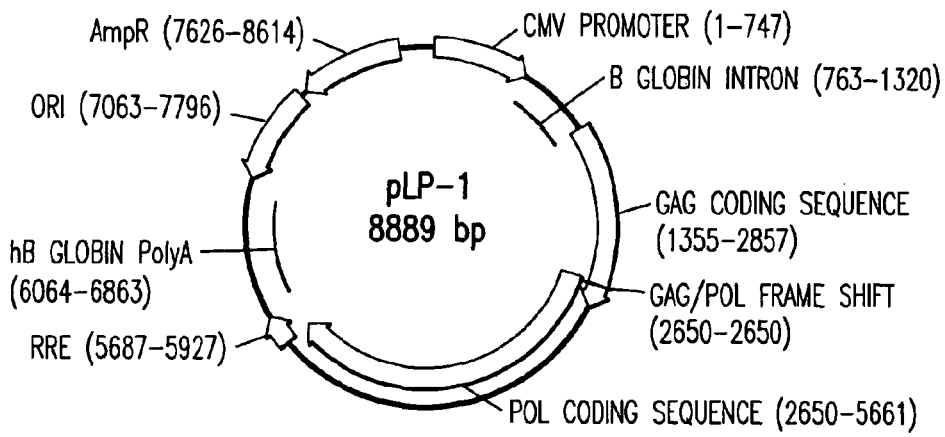
FIG. 9A is a plasmid map pLP1.
Figure 9B:
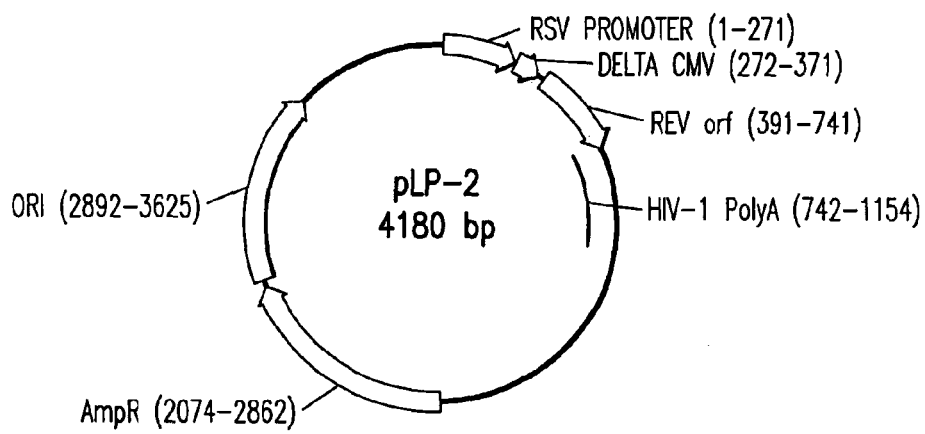
FIG. 9B is a plasmid pLP2.
Figure 9C:
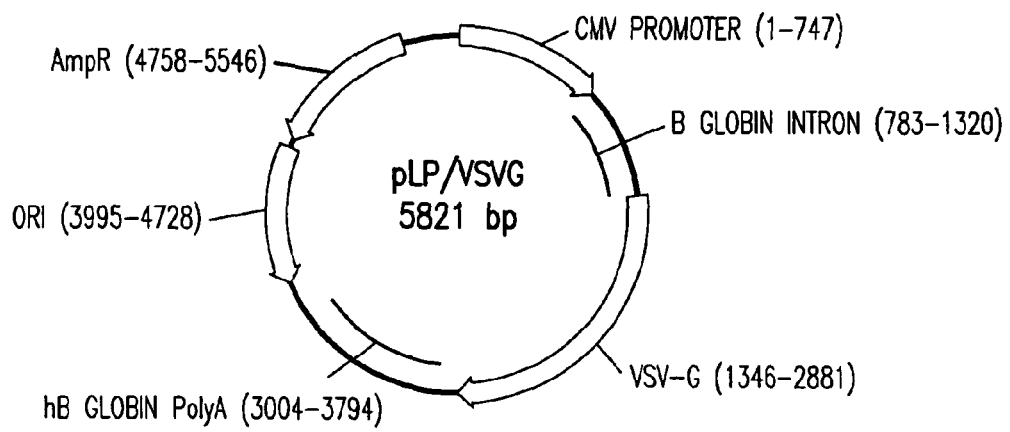
FIG. 9C is a plasmid map of pLP/VSVG.
Figure 10:
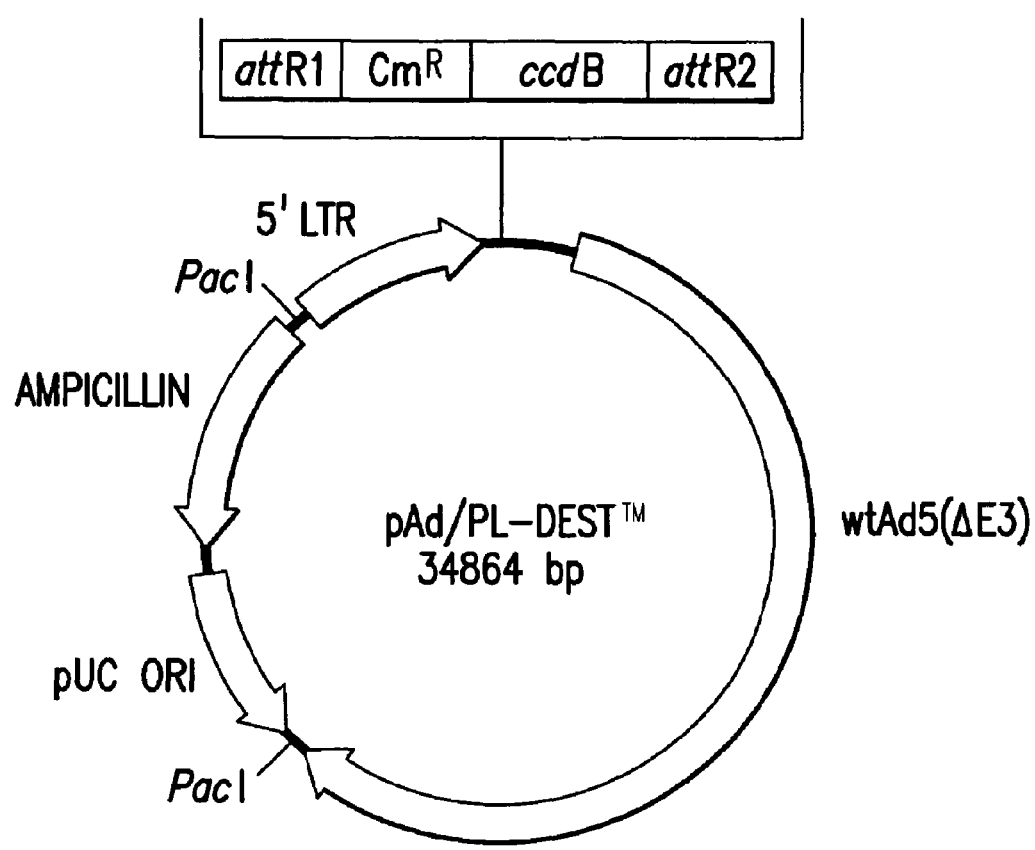
FIG. 10 is a plasmid map of pAd/PL-DEST.
Figure 30:
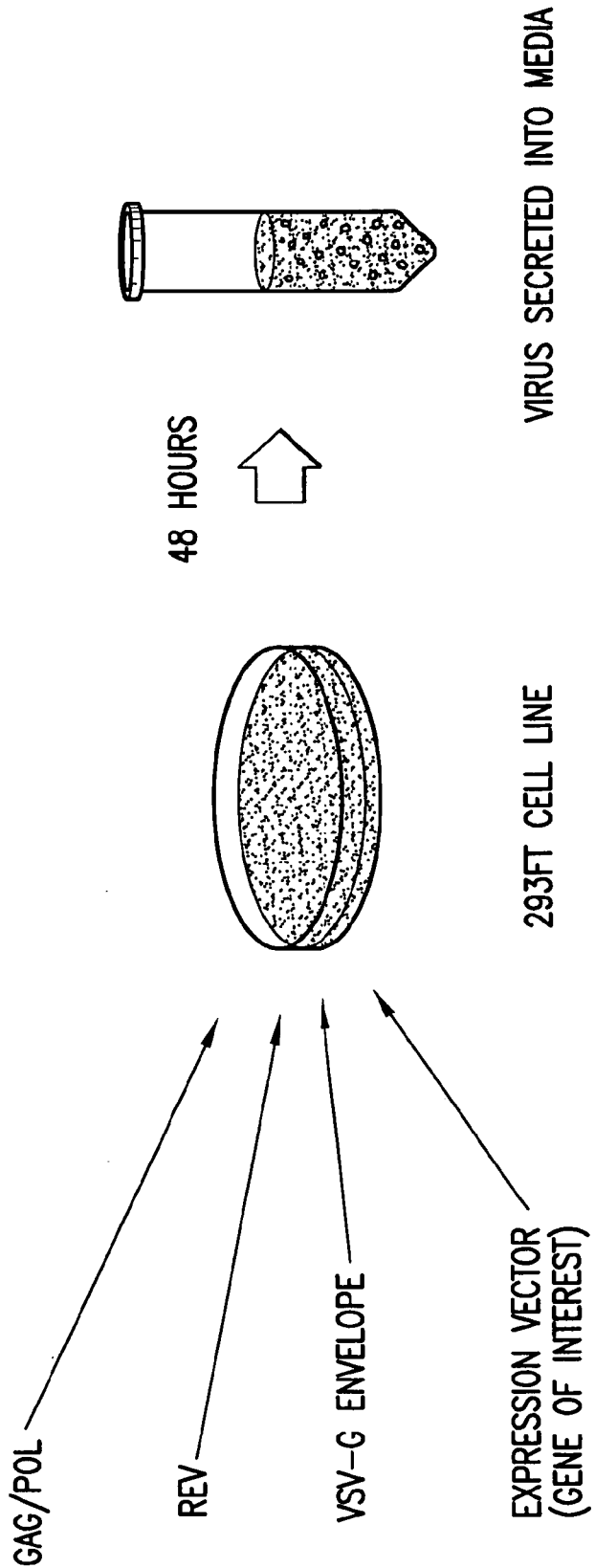
FIG. 30 depicts Outline for lentiviral production.
Figure 32:
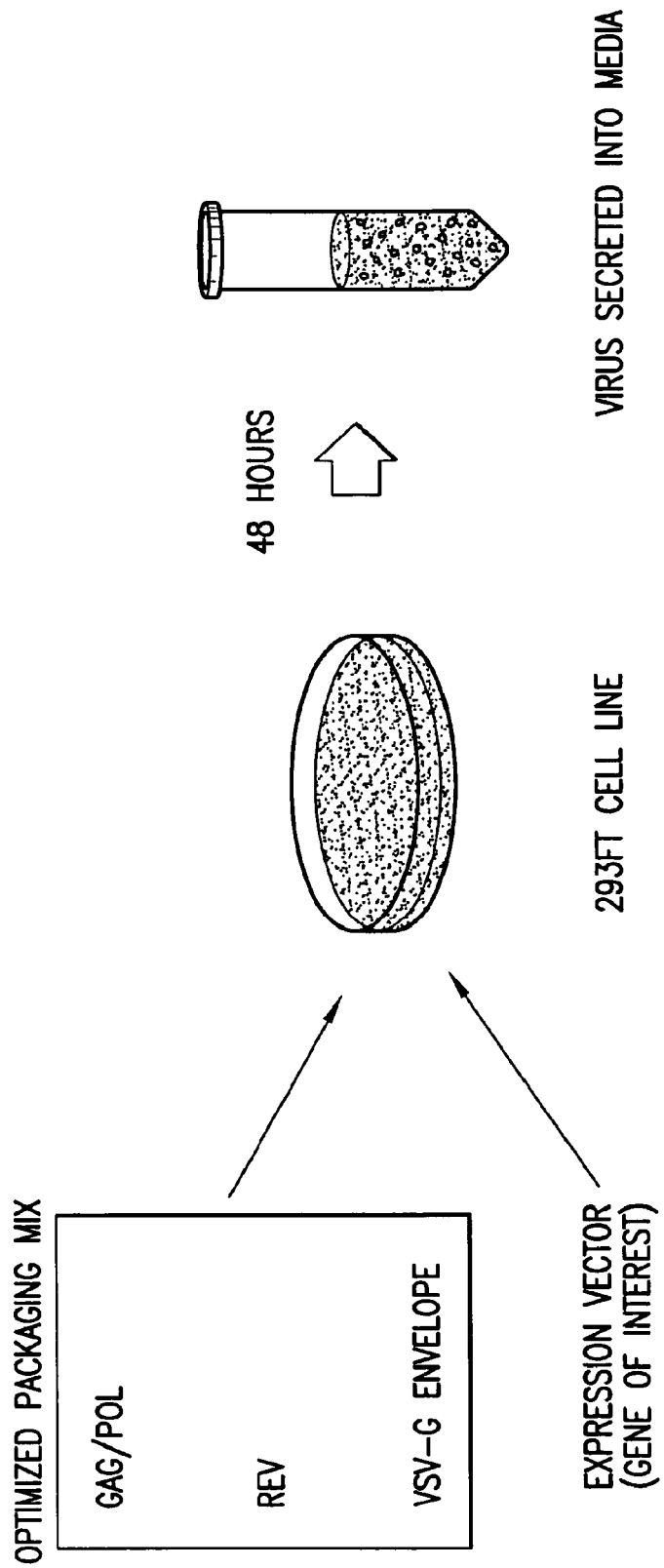
FIG. 32 depicts ViraPower™ lentiviral production.
Figure 33:
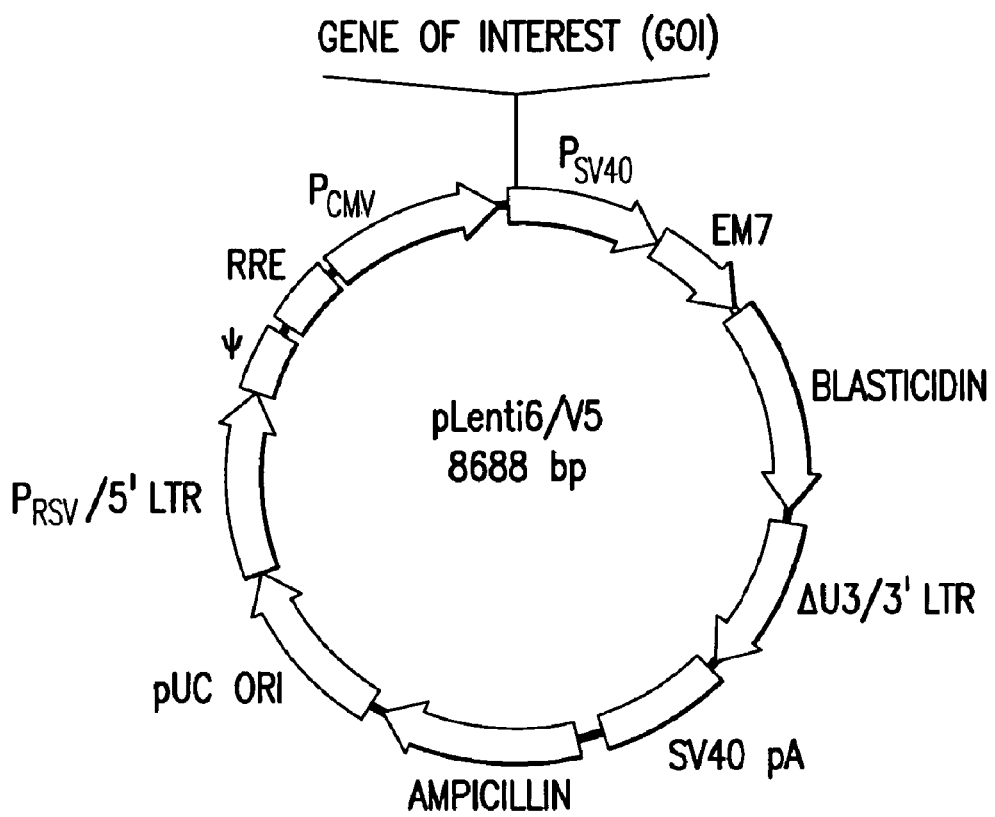
FIG. 33 depicts Clone your gene of interest into Lentivirus.
Figure 34:
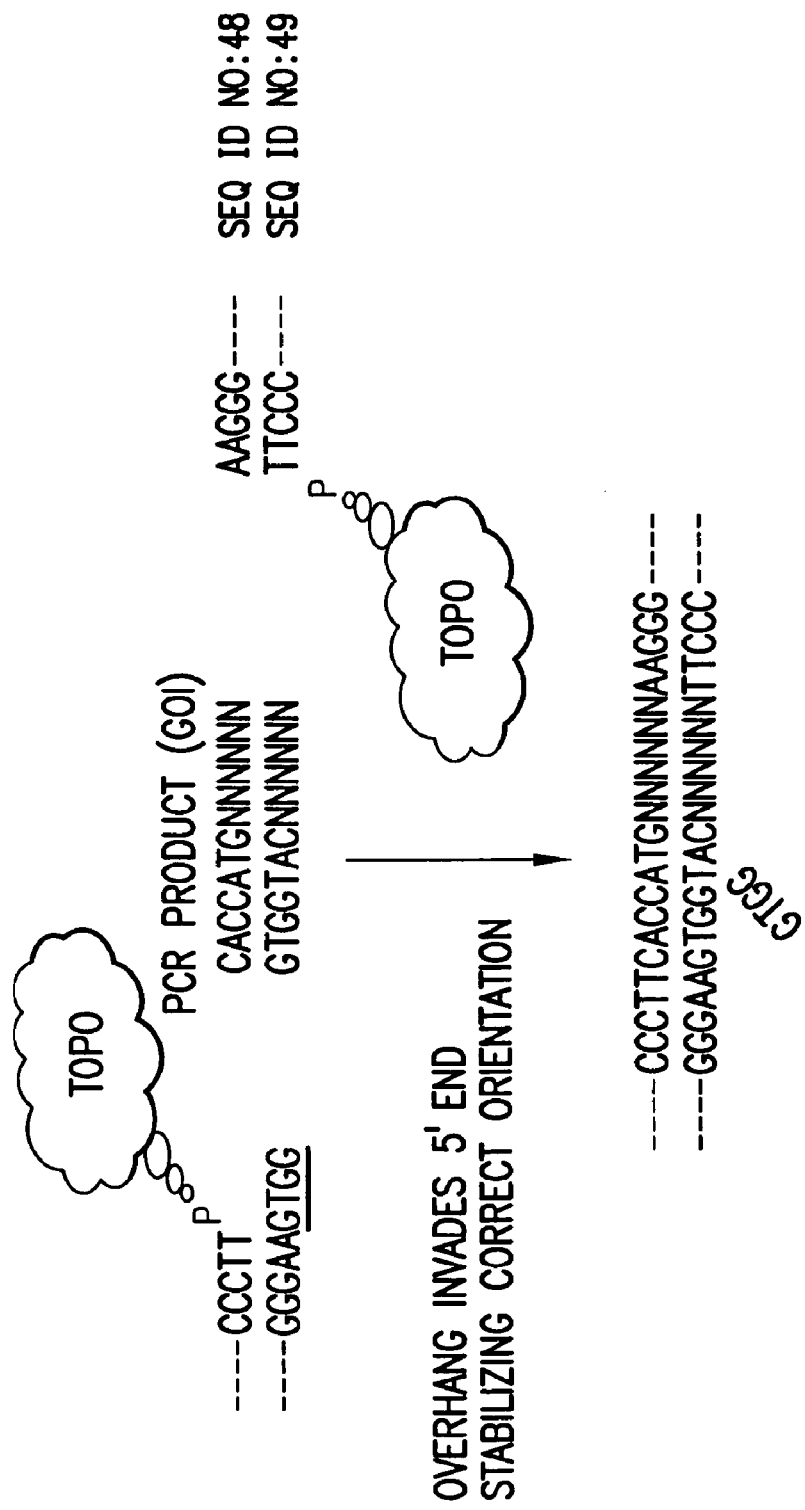
FIG. 34 depicts Two methods for fast cloning.
Figure 35:
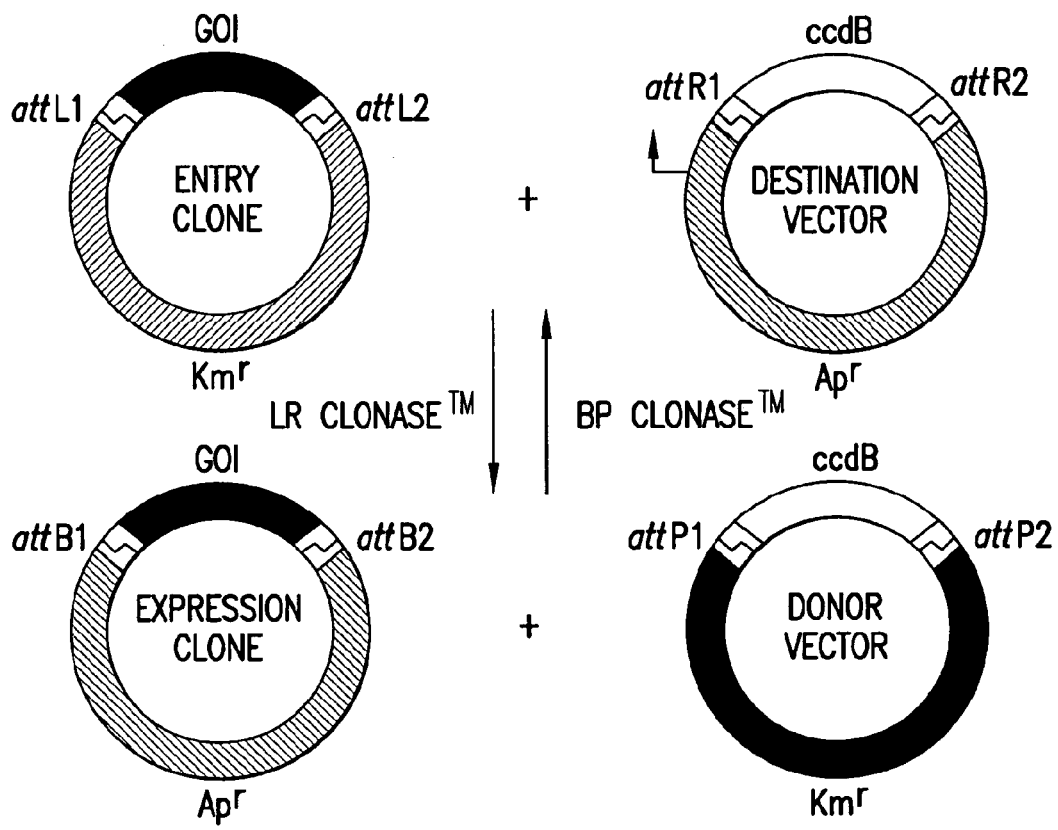
FIG. 35 depicts Two methods for fast cloning.

The present invention also encompasses replication-incompetent lentiviruses that can deliver and express one or more sequences of interest (e.g., genes). These viruses (based loosely on HIV-1) can effectively transduce dividing and non-dividing mammalian cells (in culture or in vivo), thus broadening the possible applications beyond those of traditional Moloney (MLV)-based retroviral systems (Clontech, Stratagene, etc.). Directional TOPO and GATEWAY™ lentiviral vectors have been created to clone one or more genes of interest with a V5 epitope, if desired. The Directional TOPO method involves a 5 minute bench-top ligation and results in 95% correct orientation (See FIGS. 33 and 34). The GATEWAY™ method involves cloning and sequencing a gene of interest only once into an entry clone and rapidly shuttling the gene of interest from vector to vector, or the destination clones. The GATEWAY™ method requires no restriction digests, gel purification or ligase. The GATEWAY™ method is 90-100% efficient and accurate and the gene of interest is cloned in the right direction and in-frame (FIG. 35). The vectors also carry the blasticidin resistance gene (bsd) to allow for the selection of transduced cells. Without additional modifications, these vectors can theoretically accommodate up to ~6 kb of foreign gene. Three supercoiled packaging plasmids (gag/pol, rev and VSV-G envelope) are provided to supply helper functions and viral proteins in trans (See FIGS. 30 and 32). Finally, an optimized producer cell line (293FT) is provided that will facilitate production of high titer virus. An Overview of lentiviral production is summarized in FIG. 31 and involves the following steps: 1) Co-transfect 3 packaging plasmids and pLenti6-GOI into 293FT; 2) VSV-G envelope becomes studded in cell membrane; 3) Rev transports viral genome RNA with gene of interest out of the nucleus; 4) gag protein packages: viral RNA and pol protein; 5) Virus buds off cell, picks up envelope (pseudotyping). Plasmid maps of vectors adapted for use with GATEWAY™ and topoisomerase cloning in the production of nucleic acid molecules comprising all or a portion of a lentiviral genome are shown in FIGS. 8A (pLenti6/V5-DEST), 8B (pLenti6/V5-D-TOPO®), 8C (pLenti4/V5-DEST), and 8D (pLenti6/UbC/V5-DEST) respectively. The nucleotide sequences of the plasmids are provided in Tables 6-9, SEQ ID NOS:2-5. Plasmid maps of the three packaging plasmids pLP1, pLP2, and pLP/VSVG are shown in FIGS. 9A, 9B, and 9C respectively and the nucleotide sequences of these plasmids are provided as Tables 10, 11 and 12, (SEQ ID NOS:6-8) respectively.

Retroviruses are RNA viruses that reverse transcribe their genome and integrate the DNA copy into a chromosome of the target cell. It was discovered that the retroviral packaging proteins (gag, pol and env) could be supplied in trans, thus allowing the creation of replication incompetent viral particles capable of stably delivering a gene of interest. These retroviral vectors have been available for gene delivery for many years (Miller et al., (1989) *BioTechniques* 7:980-990). One significant advantage of retroviral-based delivery is that the gene of interest is stably integrated into the genome of the host cell with very high efficiency. In addition, no viral genes are expressed in these recombinant vectors making them safe to use both in vitro and in vivo. However, one main drawback to the traditional Moloney-based retroviruses is that the target cell must undergo one round of cell division for nuclear import and stable integration to occur. Traditional retroviruses do not have an active mechanism of nuclear import and therefore must wait for the host cell nuclear membrane to breakdown during mitosis before they can access the host genomic DNA (Miller et al., *Mol. Cell. Biol.* 10:4239-442 (1990)).

Unlike traditional retroviruses, HIV (classified as a "lentivirus") is actively imported into the nuclei of non-dividing cells (Lewis et al., J. Virol. 68:510-516 (1994)). HIV still goes through the basic retrovirus lifecycle (RNA genome reverse transcribed in the target cell and integrated into the host genome); however, cis-acting elements facilitate active nuclear import, allowing HIV to stably infect non-dividing cells (for reviews see Buchschacher et al., *Blood* 95:2499-2504 (2000), Naldini et al., "The Development of Human Gene Therapy", Cold Spring Harbor Laboratory Press, pages 47-60 (1999)). It is important to note that, for both lentivirus and traditional retroviruses, no gene expression occurs until after the viral RNA genome has been reverse transcribed and integrated into the host genome.

Similar to other retrovirus expression systems, the packaging functions of HIV can be supplied in trans, allowing the creation of lentiviral vectors for gene delivery. With all the viral proteins removed, the gene delivery vector becomes safe to use and allows foreign DNA to be efficiently packaged. In addition, it has been shown that lentiviral (or any retroviral) envelope proteins can be substituted for ones with broader tropism. The substitution of envelope is called pseudotyping, and allows creation of lentiviral vectors capable of infecting a wider variety of cells besides just CD4+ cells. Many have found that the G protein from vesicular stomatitis virus (VSV-G) is an excellent pseudotyping envelope protein that imparts a very broad host range for the virus (Yee et al., *Proc. Natl. Acad. Sci. USA* 91:9564-9568 (1994)). The ability of pseudotyped lentivirus to infect a broad range of non-dividing cells has led to its extensive use in animal gene delivery and gene therapy (Baek et al., *Hum. Gene Ther.* 12:1551-8 (2001), Park et al., *Mol. Ther.* 4:164-73 (2001), Peng et al., *Gene Ther.* 8:1456-63 (2001)).

Figure 11:
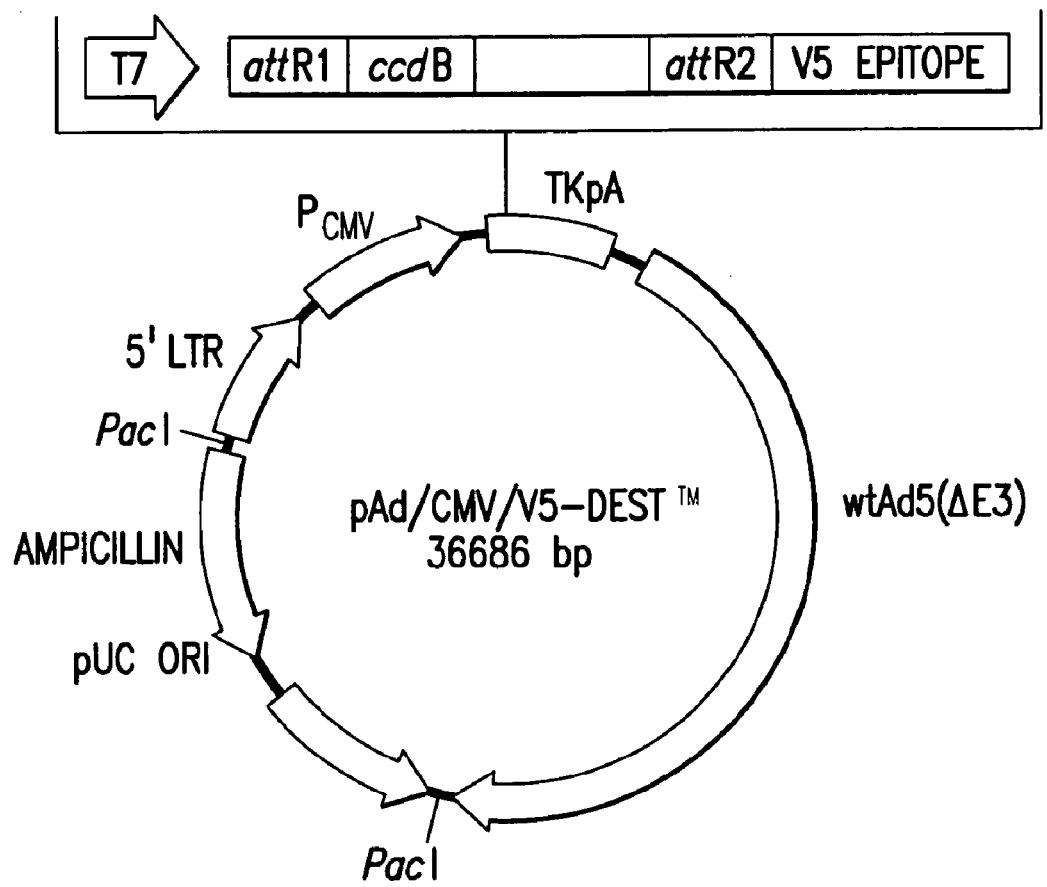
FIG. 11 is a plasmid map of pAd/CMV/V5-DEST.

The present invention also encompasses the use of adenoviral vectors, including but not limited to, a pAd/PL-DEST vector (Table 11, FIG. 10, SEQ ID NO:7) and pAd/CMV/V5-DEST vector (Table 12, FIG. 11, SEQ ID NO:8). Adenoviruses are non-enveloped viruses with a 36 kb DNA genome that encodes more than 30 proteins. At the ends of the genome are inverted terminal repeats (ITRs) of approximately 100-150 base pairs. A sequence of approximately 300 base pairs located next to the 5'-ITR is required for packaging of the genome into the viral capsid. The genome as packaged in the virion has terminal proteins covalently attached to the ends of the linear genome.

The genes encoded by the adenoviral genome are divided into early and late genes depending upon the timing of their expression relative to the replication of the viral DNA. The early genes are expressed from four regions of the adenoviral genome termed E1-E4 and are transcribed prior to onset of DNA replication. Multiple genes are transcribed from each region. Portions of the adenoviral genome may be deleted without affecting the infectivity of the deleted virus. The genes transcribed from regions E1, E2, and E4 are essential for viral replication while those from the E3 region may be deleted without affecting replication. The genes from the essential regions can be supplied in trans to allow the propagation of a defective virus. For example, deletion of the E1 region of the adenoviral genome results in a virus that is replication defective. Viruses deleted in this region are grown on 293 cells that express the viral E1 genes from the genome of the cell.

In addition to permitting the construction of a safer, replication-defective viruses, deletion and complementation in trans of portions of the adenoviral genome and/or deletion of non-essential regions make space in the adenoviral genome for the insertion of heterologous DNA sequences. The packaging of viral DNA into a viral particle is size restricted with an upper limit of approximately 38 kb of DNA. In order to maximize the amount of heterologous DNA that may be inserted and packaged, viruses have been constructed that lack all of the viral genome except the ITRs and packaging sequence (see, U.S. Pat. No. 6,228,646). All of the viral functions necessary for replication and packaging are provided in trans from a defective helper virus that is deleted in the packaging signal.

The present invention also encompasses the use of herpes viruses (see, for example, U.S. Pat. No. 5,672,344, issued to Kelly, et al.). The family Herpesviridae contains three subfamilies 1) alphaherpesvirinae, containing among others human herpesvirus 1; 2) betaherpesvirinae, containing the cytomegaloviruses; and 3) gammaherpesvirinae. Herpesviruses are enveloped DNA viruses. Herpesviruses form particles that are approximately spherical in shape and that contain one molecule of linear dsDNA and approximately 20 structural proteins. Numerous herpesviruses have been isolated from a wide variety of hosts. For example, U.S. Pat. No. 6,121,043 issued to Cochran, et al. describes recombinant herpesvirus of turkeys comprising a foreign DNA inserted into a non-essential region of the herpesvirus of turkeys genome; U.S. Pat. No. 6,410,311 issued to Cochran, et al. describes recombinant feline herpesvirus comprising a foreign DNA inserted into a region corresponding to a 3.0 kb EcoRI-SalI fragment of a feline herpesvirus genome, U.S. Pat. No. 6,379,967 issued to Meredith, et al., describes herpesvirus saimiri, (HVS; a lymphotropic virus of squirrel monkeys) as a viral vector; and U.S. Pat. No. 6,086,902 issued to Zamb, et al. describes recombinant bovine herpesvirus type 1 vaccines.

Herpesviruses have been used as vectors to deliver exogenous nucleic acid material to a host cell. In addition to the examples above, U.S. Pat. No. 4,859,587, issued to Roizman describes recombinant herpes simplex viruses, vaccines and methods, U.S. Pat. No. 5,998,208 issued to Fraefel, et al., describes a helper virus-free herpesvirus vector packaging system, U.S. Pat. No. 6,342,229 issued to O'Hare, et al., describes herpesvirus particles comprising fusion protein and their preparation and use and U.S. Pat. No. 6,319,703 issued to Speck describes recombinant virus vectors that include a double mutant herpesvirus such as an herpes simplex virus-1 (HSV-1) mutant lacking the essential glycoprotein gH gene and having a mutation impairing the function of the gene product VP16.

Suitable vectors for use in the present invention also include prokaryotic vectors such as pcDNA II, pSL301, pSE280, pSE380, pSE420, pTrcHisA, B, and C, pRSET A, B, and C (Invitrogen, Corp.), pGEMEX-1, and pGEMEX-2 (Promega, Inc.), the pET vectors (Novagen, Inc.), pTrc99A, pKK223-3, the pGEX vectors, pEZZ18, pRIT2T, and pMC1871 (Pharmacia, Inc.), pKK233-2 and pKK388-1 (Clontech, Inc.), and pProEx-HT (Invitrogen, Corp.) and variants and derivatives thereof. Other vectors of interest include eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMC1neo, and pOG44 (Stratagene, Inc.), and pYES2, pAC360, pBlueBacHis A, B, and C, pVL1392, pBlueBacIII, pCDM8, pcDNA1, pZeoSV, pcDNA3 pREP4, pCEP4, and pEBVHis (Invitrogen, Corp.) and variants or derivatives thereof.

Other vectors suitable for use in the invention include pUC18, pUC19, pBlueScript, pSPORT, cosmids, phagemids, YAC's (yeast artificial chromosomes), BAC's (bacterial artificial chromosomes), P1 (*Escherichia coli* phage), pQE70, pQE60, pQE9 (quagan), pBS vectors, PhageScript vectors, BlueScript vectors, pNH8A, pNH16A, pNH18A, pNH46A (Stratagene), pcDNA3 (Invitrogen), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSV-SPORT1 (Invitrogen) and variants or derivatives thereof.

Additional vectors of interest include pTrxFus, pThioHis, pLEX, pTrcHis, pTrcHis2, pRSET, pBlueBacHis2, pcDNA3.1/His, pcDNA3.1(-)/Myc-His, pSecTag, pEBVHis, pPIC9K, pPIC3.5K, pAO815, pPICZ, pPICZα, pGAPZ, pGAPZα, pBlueBac4.5, pBlueBacHis2, pMelBac, pSinRep5, pSinHis, pIND, pIND(SP1), pVgRXR, pcDNA2.1, pYES2, pZErO1.1, pZErO-2.1, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe, SV2, pRc/CMV2, pRc/RSV, pREP4, pREP7, pREP8, pREP9, pREP 10, pCEP4, pEBVHis, pCR3.1, pCR2.1, pCR3.1-Uni, and pCRBac from Invitrogen; λ ExCell, λ gt11, pTrc99A, pKK223-3, pGEX-1λT, pGEX-2T, pGEX-2TK, pGEX-4T-1, pGEX-4T-2, pGEX-4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE-4-abc(+), pOCUS-2, pTAg, pET-32LIC, pET-30LIC, pBAC-2 cp LIC, pBACgus-2 cp LIC, pT7Blue-2 LIC, pT7Blue-2, λSCREEN-1, λBlueSTAR, pET-3abcd, pET-7abc, pET9abcd, pET11abcd, pET12abc, pET-14b, pET-15b, pET-16b, pET-17b-pET-17xb, pET-19b, pET-20b(+), pET-21abcd(+), pET-22b(+), pET-23abcd(+), pET-24abcd(+), pET-25b(+), pET-26b(+), pET-27b(+), pET-28abc(+), pET-29abc(+), pET-30abc(+), pET-31b(+), pET-32abc(+), pET-33b(+), pBAC-1, pBACgus-1, pBAC4x-1, pBACgus4x-1, pBAC-3 cp, pBACgus-2 cp, pBACsurf-1, plg, Signal plg, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6xHis-GFP, pSEAP2-Basic, pSEAP2-Contral, pSEAP2-Promoter, pSEAP2-Enhancer, pβgal-Basic, pβgal-Control, pβgal-Promoter, pβgal-Enhancer, pCMVβ, pTet-Off, pTet-On, pTK-Hyg, pRetro-Off, pRetro-On, pIRES1neo, pIRES1hyg, pLXSN, pLNCX, pLAPSN, pMAMneo, pMAMneo-CAT, pMAMneo-LUC, pPUR, pSV2neo, pYEX4T-1/2/3, pYEX-S1, pBacPAK-His, pBacPAK8/9, pAcUW31, BacPAK6, pTriplEx, λgt10, λgt11, pWE15, and λTriplEx from Clontech; Lambda ZAP II, pBK-CMV, pBK-RSV, pBluescript II KS+/−, pBluescript II SK+/−, pAD-GAL4, pBD-GAL4 Cam, pSurfscript, Lambda FIX II, Lambda DASH, Lambda EMBL3, Lambda EMBL4, SuperCos, pCR-Scrigt Amp, pCR-Script Cam, pCR-Script Direct, pBS+/−, pBC KS+/−, pBC SK+/−, Phagescript, pCAL-n-EK, pCAL-n, pCAL-c, pCAL-kc, pET-3abcd, pET-11abcd, pSPUTK, pESP-1, pCMVLacI, pOPRSVI/MCS, pOPI3 CAT, pXT1, pSG5, pPbac, pMbac, pMC1neo, pMC1neo Poly A, pOG44, pOG45, pFRTβGAL, pNEOβGAL, pRS403, pRS404, pRS405, pRS406, pRS413, pRS414, pRS415, and pRS416 from Stratagene.

Two-hybrid and reverse two-hybrid vectors of interest include pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp and variants or derivatives thereof.

The present invention also embodies the use and production of chimeric vectors. Such chimeric vectors may comprise one or more sequences that encode one or more functional or structural component of a viral vector, wherein each component may or may not come from the same or different types of viruses. Suitable components that may be combined to create such a chimeric vector include, but are not limited to, gag, poi, env, and rev genes and capsid proteins.

The nucleic acid molecules produced and/or utilized in the cloning methods, compositions and kits of the present invention may additionally or alternatively comprise one or more promoter molecules as described throughout the present specification, including the Pol III promoters H1 and U6 as well as other promoters recognized by RNA polymerase III. The nucleic acid molecules and vectors of the present invention may also further or alternatively comprise one or more genes which code for signal peptides and/or protease cleavage sites. Examples of protease cleavage sites include, but are not limited to, TEV sites and EK sites. TEV cleavage sites useful in the present invention include:

```
Consensus sequence:
Glu-Xaa-Xaa-Try-Xaa-Gln//Xaa¹    (SEQ ID NO: 23)

TEV1:
Glu-Asn-Leu-Try-Phe-Gln//Xaa¹    (SEQ ID NO: 24)

TEV2:
Glu-Thr-Leu-Tyr-Ilue-Gln//Xaa¹   (SEQ ID NO: 25)

(Xaa = any amino acid; Xaa¹ = any amino acid,
except Pro; // = cleavage site).
```

EK cleavage sites useful in the present invention include:

```
    Asp-Asp-Asp-Asp-Lys//    (SEQ ID NO: 26)

(// = cleavage site).
```

Signal peptides utilized in the present invention may be removed by a signal peptidase or any protease (e.g. Precision, thrombin and factor X) specific for one or more motifs on a signal peptide to generate a mature protein, including a protein encoded only by the inserted nucleic acid. The present invention also encompasses methods for the production of fusion proteins, and the fusion proteins produced by those methods. In accordance with the present invention, the proteins of the present invention may comprise one or more signal peptides, or portions of signal peptides, as noted above. These signal peptides may be used to facilitate production of desired proteins (e.g. mature or native proteins) in vivo or in vitro. Proteins produced using the methods of the present invention comprising such signal peptides would allow for the production of mature proteins, in which proteins are exported from the cell upon cleavage of the signal peptide by proteases within the cell. In an in vitro setting, these signal peptides would facilitate the production of native or desired proteins outside of a cell. Cleavage of the signal peptide may occur using signal peptidases, such as those described above, thus producing a desired protein product. These signal peptides may also be used as tags to facilitate affinity purification of polypeptides or proteins, for example fusion polypeptides or fusion proteins, produced by the methods of the present invention.

Any number of different protease recognition sites may be used in the practice of the invention. These sites will often be selected by to fit particular criteria suitable for the specific application. Exemplary proteases and protease recognition sites include the following. Tobacco Etch Virus (TEV) protease recognizes the amino acid sequence Glu-Xaa-Xaa-Tyr-Xaa-Gln//Xaa¹ (SEQ ID NO:23), where Xaa is any amino acid; Xaa¹ is any amino acid except Pro and // indicates the cleavage site. Thus, for the amino acid sequence Glu-Asn-Leu-Tyr-Phe-Gln-Gly (SEQ ID NO:27), TEV cleaves between the Gln and Gly residues (see Invitrogen product literature associated with cat. nos. 10127-017 and 12575-015). Also, for the amino acid sequence Glu-Thr-Leu-Tyr-Ile-Gln-Xaa' (SEQ ID NO:25), TEV cleaves between the Gln and Xaa residues. Enterokinase (EK) recognizes the amino acid sequence Asp-Asp-Asp-Asp-Lys (SEQ ID NO:26) cleaves after the lysine (see Invitrogen product literature associated with cat. nos. E180-01 and E180-02, Invitrogen Corp., Carlsbad, Calif.). The ulp1 protease recognizes the amino acid sequence Gly-Gly-Ser (SEQ ID NO:28) and cleaves between the second glycine and the serine (U.S. Patent Publication No. 2003/0086918). Thus, the invention provides and includes nucleic acid molecules which may be used for producing proteins which may be processed by TEV protease, EK and/or ulp1 protease to generate proteins, as well as methods employing these enzymes and proteins or peptides produced using these methods.

In instances where the protein or peptide which is desired contains an amino terminal glycine, an amino terminal tag comprising and/or ending in a TEV protease recognition sequence may be used to generate a protein or peptides which contains no amino acids associated with, for example, cloning sites. Similarly, in instances where the protein which is desired contains an amino terminal serine, an amino terminal tag comprising and/or ending in a ulp protease recognition sequence may be used to generate a protein or peptide which contains amino acids associated with, for example, cloning sites. EK may be used to generate proteins or peptides which have an amino terminus other than glycine, as well as glycine.

The present invention also includes methods for joining two or more nucleic acid molecules using methods, for example, described elsewhere herein, wherein a first nucleic acid molecule contains a region which encodes a protease cleavage site and, optionally, a tag with a second nucleic acid molecule encodes a desired protein or peptide. In many instances, these nucleic acid segments are connected such that the desired protein is expressed along with amino acids of the protease cleavage site as a fusion protein such that upon processing with the cognate protease, the desired protein is produced. Often, the desired protein which results from proteolytic digestion will contain only amino acids encoded by the second nucleic acid molecule referred to above.

In many instances, when a desired protein is produced from a nucleic acid formed by the connection of two nucleic acid molecules, the generation of a "seam" is only relevant with respect to one end of the protein (i.e., the amino terminus or the carboxy terminus). In other words, in instances, where there is, for example, an amino terminal tag or a carboxy terminal tag, but not both, there is only a need to remove one tag. For example, when the translation product contains an amino terminal tag, the carboxy terminus of the translation product will typically terminate at a position in the mRNA which corresponds to the naturally resident stop codon. In such instances, a protease system may be used which will only amino terminal amino acids from the translation product.

The present invention also encompasses the production of a protein that comprises an expression enhancing amino acid sequence cleavable by ulp1 protease or an active fragment of ulp1 protease (for example the fragment from amino acid positions 403 to 621) and a poly-amino acid of interest, particularly one that is difficult to express in a recombinant expression system. The protein may also include a purification tag for ease of isolation. The ulp1 protease cleavable site may be any ulp1 cleavable site, such as for example a ulp1 protease cleavable site from a ubiquitin-like protein e.g. a SUMO (small ubiquitin-like molecule). The SUMO may be, for instance, Smt3 from yeast, or a fragment of Smt3 that retains the ability to be recognized and cleaved by Ulp 1. Examples of such a fragment of Smt3 include the fragment from amino acid positions 14-98 of Smt3 and the fragment from amino acid positions 1-98 of Smt3. Examples of such proteins can be found in WO 02/090495, the entire disclosure of which is incorporated herein by reference.

When nucleic acid molecules and/or methods of the invention are used to produce proteins or peptides, these proteins or peptides may be produced with an amino terminal and/or carboxy terminal tag. These tags may be used for any number of purposes, including to (1) increase the stability of the protein or peptide or (2) allow for purification. Thus, proteins or peptides produced by methods of the invention, as well as protein or peptides encoded by nucleic acid molecules of the invention, may contain affinity purification tags (e.g., epitope tags such as the V5 epitope). Affinity purification tags are often amino acid sequences that can interact with a binding partner immobilized on a solid support. Nucleic acids encoding multiple consecutive single amino acids, such as histidine, may be used for one-step purification of the recombinant protein by affinity binding to a resin column, such as nickel sepharose. A protease cleavage site can be engineered between the affinity tag and the desired protein to allow for removal of the tag, for example, after the purification process is complete or to induce release of the desired protein or peptide from the solid support. Affinity tags which may be used in the practice of the invention include tags such as the chitin binding domain (which binds to chitin), polyarginine, glutathione-S-transferase (which binds to glutathione), maltose binding protein (which binds maltose), FlAsH, biotin (which binds to avidin and strepavidin), and the like.

Epitope tags are short amino acid sequences which are recognized by epitope specific antibodies. Proteins or peptides which contain one or more epitope tags may purified, for example, using a cognate antibody bound to a chromatography resin. The presence of the epitope tag furthermore allows the recombinant protein to be detected in subsequent assays, such as Western blots, without having to produce an antibody specific for the recombinant protein itself. Examples of commonly used epitope tags include V5, glutathione-S-transferase (GST), hemaglutinin (HA), the peptide Phe-His-His-Thr-Thr (SEQ ID NO:29), chitin binding domain, and the like. As discussed above, these affinity tags may be removed from the desired protein or peptide by proteolytic cleavage.

FlAsH tags comprise the sequence a cys-cys-Xaa-Xaa-cys-cys (SEQ ID NO:30), where Xaa and Xaa are amino acids. In many instances, Xaa and Xaa, which may be the same or different amino acids, are amino acids with high a-helical propensity. In some embodiments, X and Y are the same amino acid. These peptides have been shown to bind to biarsenical compounds. The FlAsH systems is described in U.S. Pat. No. 6,054,271, the entire disclosure of which is incorporated herein by reference.

The nucleic acid molecules and/or nucleic acid segments utilized in the cloning methods, compositions and kits of the present invention may optionally comprise one or more selectable markers comprising at least one DNA segment encoding an element selected from the group consisting of an antibiotic resistance gene, a gene that encodes a fluorescent protein, a tRNA gene, an auxotrophic marker, a toxic gene, a phenotypic marker, an antisense oligonucleotide, a restriction endonuclease, a restriction endonuclease cleavage site, an enzyme cleavage site, a protein binding site, and a sequence complementary to a PCR primer sequence.

Suitable antibiotic resistance genes for use in the present invention are well known in the art and include, but are not limited to, chloramphenicol resistance genes, ampicillin resistance genes, tetracycline resistance genes, Zeocin resistance genes, spectinomycin resistance genes and kanamycin resistance genes.

Examples of toxic gene products suitable for use in the present invention are well known in the art, and include, but are not limited to, restriction endonucleases (e.g., DpnI), apoptosis-related genes (e.g. ASK1 or members of the bcl-2/ced-9 family), retroviral genes including those of the human immunodeficiency virus (HIV), defensins such as NP-1, inverted repeats or paired palindromic nucleic acid sequences, bacteriophage lytic genes such as those from (ΦX174 or bacteriophage T4; antibiotic sensitivity genes such as rpsL, antimicrobial sensitivity genes such as pheS, plasmid killer genes, eukaryotic transcriptional vector genes that produce a gene product toxic to bacteria, such as GATA-1, and genes that kill hosts in the absence of a suppressing function, e.g., kicB, sacB, ccdB, (ΦX174 E (Liu, Q. et al., Curr. Biol. 8:1300-1309 (1998)), and other genes that negatively affect replicon stability and/or replication. The present invention also encompasses the use of a gene that encodes the tus gene which binds to one or more ter sites. A toxic gene can alternatively be selectable in vitro, e.g., a restriction site.

Any of the nucleic acid molecules or nucleic acid segments used in or produced by the present methods, compositions and kits may further comprise one or more site-specific recombination sites. These recombination sites may flank the one or more restriction sites (e.g. one or more type IIs sites) if present in the nucleic acid molecules or segments of the invention. Site-specific recombinases are proteins that are present in or produced by many organisms (e.g., viruses and bacteria) and have been characterized as having both endonuclease and ligase properties. These recombinases (along with associated proteins in some cases) recognize specific sequences of bases (i.e., recombination sites) in a nucleic acid molecule and exchange the nucleic acid segments flanking those sequences. The recombinases and associated proteins are collectively referred to as "recombination proteins" (see, e.g., Landy, A., *Current Opinion in Biotechnology* 3:699-707 (1993)).

Numerous recombination systems from various organisms have been described. See, e.g., Hoess, et al., *Nucleic Acids Research* 14:2287 (1986); Abremski, et al., *J. Biol. Chem.* 261:391 (1986); Campbell, *J. Bacteriol.* 174:7495 (1992); Qian, et al., *J. Biol. Chem.* 267:7794 (1992); Araki, et al., *J. Mol. Biol.* 225:25 (1992); Maeser and Kahnmann, *Mol. Gen. Genet.* 230:170-176) (1991); Esposito, et al., *Nucl. Acids Res.* 25:3605 (1997). Many of these belong to the integrase family of recombinases (Argos, et al., *EMBO* 15:433-440 (1986); Voziyanov, et al., *Nucl. Acids Res.* 27:930 (1999)). Perhaps the best studied of these are the Integrase/att system from bacteriophage ((Landy, A. *Current Opinions in Genetics and Devel.* 3:699-707 (1993)), the Cre/loxP system from bacteriophage P1 (Hoess and Abremski (1990) In Nucleic Acids and Molecular Biology, vol. 4. Eds.: Eckstein and Lilley, Berlin-Heidelberg: Springer-Verlag; pp. 90-109), and the FLP/FRT system from the *Saccharomyces cerevisiae* 2μ circle plasmid (Broach, et al., Cell 29:227-234 (1982)).

Recombination sites are sections or segments of nucleic acid on the participating nucleic acid molecules that are recognized and bound by the recombination proteins during the initial stages of integration or recombination. For example, the recombination site for Cre recombinase is loxP which is a 34 base pair sequence comprised of two 13 base pair inverted repeats (serving as the recombinase binding sites) flanking an 8 base pair core sequence. See FIG. 1 of Sauer, B., *Curr. Opin. Biotech.* 5:521-527 (1994). Other examples of recognition sequences include the attB, attP, attL, and attR sequences which are recognized by the recombination protein Int. attB is an approximately 25 base pair sequence containing two 9 base pair core-type Int binding sites and a 7 base pair overlap region, while attP is an approximately 240 base pair sequence containing core-type Int binding sites and arm-type Int binding sites as well as sites for auxiliary proteins integration host factor (IHF), FIS and excisionase (Xis). See Landy, *Curr. Opin. Biotech.* 3:699-707 (1993). Suitable recombination sites for use in the present invention include, but are not limited to, attB sites, attP sites, attL sites, attR sites, lox sites, psi sites, tnpI sites, dif sites, cer sites, frt sites, and mutants, variants and derivatives thereof.

The present cloning methods also embody the use of nucleic acid molecules that include a DNA segment having one or more terminal 3'-deoxyadenosine monophosphate (dAMP) residues, as described in U.S. Pat. No. 5,487,933, herein incorporated entirely by reference. These DNA segments are generated by thermophilic polymerases during PCR amplification. Double-stranded nucleic acids are formed with a single overhanging 3'-AMP residue. Mixture of these molecules with a population of linear double-stranded DNA molecules with a single overhanging deoxythymidylate (dTMP) residue at one or both of the 3' termini of the DNA molecule allow for ligation of the 3'-dAMP containing nucleic acid molecules and the 3'-dTMP-containing DNA molecules to produce recombinant molecules. This approach is commonly known to those in the art as "TA Cloning," compositions and methods for which are available from Invitrogen Corporation (Carlsbad, Calif.).

The present invention also encompasses the use of cloning methods known to those skilled in the art as RecA cloning. The RecA cloning protein efficiently coats singly-stranded DNA. In the presence of ATP, this Rec-A coated single-stranded DNA can for triple-stranded nucleoprotein complexes with homologous double-stranded DNA. This RecA driven strand invasion and annealing can lead to high efficiency capture of DNA containing regions of homology with single-stranded DNA probes. This system can be used to increase the efficiency of recombination between a circular plasmid DNA molecule and a linear DNA "insert." Such suitable methods of RecA cloning can be found in U.S. Pat. Nos. 5,948,653, 6,074,853 and 6,200,812, the disclosures of each of which are hereby incorporated entirely by reference.

The present invention also encompasses the use of a method of cloning DNA molecules in cells comprising the steps: a) providing a host cell capable of performing homologous recombination, b) contacting in said host cell a first DNA molecule which is capable of being replicated in said host cell with a second DNA molecule comprising at least two regions of sequence homology to regions on the first DNA molecule, under conditions which favour homologous recombination between said first and second DNA molecules and c) selecting a host cell in which homologous recombination between said first and second DNA molecules has occurred.

In this method of the present invention, the homologous recombination suitably occurs via the recET mechanism, i.e. the homologous recombination is mediated by the gene products of the recE and the recT genes which are preferably selected from the *E. coli* genes recE and recT or functionally related genes such as the phage λ redα and redβ genes. In contrast to RecA cloning, the recET cloning system requires significantly fewer bases of homology for efficient recombination into the target molecule. These proteins facilitate the homologous incorporation of a double-stranded DNA fragment into a circular plasmid.

A host cell suitable for this embodiment of the present invention is a bacterial cell, e.g. a gram-negative bacterial cell. Suitably the host cell is an enterobacterial cell, such as *Salmonella, Klebsielia* or *Escherichia*. Most preferably the host cell is an *Escherichia coli* cell. It should be noted, however, that this method of the present invention is also suitable for eukaryotic cells, such a s fungi, plant or animal cells. Such suitable methods of recET cloning can be found in Zhang, Y. et al., *Nature* 20:123-128 (1998), Muryers, J. P. P., et al., *Nucl. Acids Res.* 27:1555-1557 (1999), and U.S. Pat. Nos. 6,509, 156 and 6,355,412, the disclosures of each of which are hereby incorporated entirely by reference.

The first nucleic acid molecule and/or segment, as well as the second nucleic acid molecule involved in the methods, compositions and kits of the present invention may further or alternatively comprise one or more topoisomerase recognition sites and/or one or more topoisomerases. In suitable embodiments, the topoisomerase recognition site(s), if present, may optionally be flanked by two or more recombination sites.

The term "flanked" as used herein is meant to indicate a spatial relationship wherein a restriction site (e.g. a type IIs site) and/or recombination site are located to one side of a nucleic acid segment (gene, selectable marker, etc.). As described above, recombination sites may also flank restriction sites (e.g. type IIs sites) utilized in the invention. In the situation where a nucleic acid segment is flanked by two or more recombination or recognition sites, each side of the nucleic acid segment may be flanked by one or more sites.

Topoisomerases are categorized as type I, including type IA and type IB topoisomerases, which cleave a single strand of a double stranded nucleic acid molecule, and type II topoisomerases (gyrases), which cleave both strands of a nucleic acid molecule. Type IA and IB topoisomerases cleave one strand of a nucleic acid molecule. Cleavage of a nucleic acid molecule by type IA topoisomerases generates a 5' phosphate and a 3' hydroxyl at the cleavage site, with the type IA topoisomerase covalently binding to the 5' terminus of a cleaved strand. In comparison, cleavage of a nucleic acid molecule by type IB topoisomerases generates a 3' phosphate and a 5' hydroxyl at the cleavage site, with the type IB topoisomerase covalently binding to the 3' terminus of a cleaved strand. The topoisomerase recognition sites of the present invention, if present, may be recognized and bound by a type I topoisomerase, and suitably by a type IB topoisomerase. Type IB topoisomerases useful in the present invention include, but are not limited to eukaryotic nuclear type I topoisomerase and a poxvirus topoisomerase. The poxvirus topoisomerase useful in the present invention may be produced by or isolated from a virus including, but not limited to, vaccinia virus, Shope fibroma virus, ORF virus, fowlpox virus, molluscum contagiosum virus and *Amsacta morrei* entomopoxvirus (see Shuman, *Biochim. Biophys. Acta* 1400:321-337, 1998; Petersen et al., *Virology* 230:197-206, 1997; Shuman and Prescott, *Proc. Natl. Acad. Sci., USA* 84:7478-7482, 1987; Shuman, *J. Biol. Chem.* 269:32678-32684, 1994; U.S. Pat. No. 5,766,891; PCT/US95/16099; PCT/US98/12372, each of which is incorporated herein by reference; see, also, Cheng et al., supra, 1998). Suitable type IB topoisomerases include the nuclear type I topoisomerases present in all eukaryotic cells and those encoded by vaccinia and other cellular poxviruses (see Cheng et al., *Cell* 92:841-850, 1998, which is incorporated herein by reference). The eukaryotic type IB topoisomerases are exemplified by those expressed in yeast, *Drosophila* and mammalian cells, including human cells (see Caron and Wang, *Adv. Pharmacol.* 29B, :271-297, 1994; Gupta et al., *Biochim. Biophys. Acta* 1262:1-14, 1995, each of which is incorporated herein by reference; see, also, Berger, supra, 1998).

In suitable aspects of the present invention, the one or more optional selectable markers of the nucleic acids or segment used in or produced by the present invention may be flanked by one or more restriction sites (e.g. one or more type IIs sites) and/or one or more recombination sites.

In other suitable embodiments of the present invention, the first nucleic acid molecule or segment and/or the second nucleic acid molecule may not comprise a promoter. The present invention allows for transfer of a promoter element into a second nucleic acid molecule that may not comprise a promoter via seamless cloning. In this orientation, transcription of the second nucleic acid molecule from the promoter element located on the first nucleic acid molecule may proceed such that no additional sequences are transcribed between the promoter element and the start codon of the second nucleic acid molecule. The present invention also allows for seamlessly adding a first nucleic acid molecule or segment into a second nucleic molecule that contains a promoter element such that the first nucleic acid molecule or segment will subsequently be under the control of the promoter element.

Incubation conditions suitable for use in the methods of the present invention comprise incubation with sufficient amounts of DNA ligases and buffers. Such incubation conditions are described in Maniatis et al., Molecular Cloning: A Laboratory Manual, Cold Spring Harbor Laboratory, Cold Spring Harbor, N.Y. (1982). The term sufficient amount as used herein means that the amount of DNA ligase(s) and buffer(s) present during the cloning and/or recombination reactions is such that these reactions proceed as designed. Suitable buffers include physiologic buffers such as, but not limited to, Tris-(hydroxymethyl)aminomethane-HCl TRIS®-HCl, Ethylene-diaminetetraacetic acid (EDTA) disodium salt, saline, Phosphate Buffered Saline (PBS), N-(2-Hydroxyethyl)piperazine-N'-(2-ethanesulfonic acid) (HEPES®), 3-(N-Morpholino)propanesulfonic acid (MOPS),2-bis(2-Hydroxyethylene)amino-2-(hydroxymethyl)-1,3-propanediol (bis-TRIS®), potassium phosphate (KP), sodium phosphate (NaP), dibasic sodium phosphate ($Na_2HPO_4$), monobasic sodium phosphate ($NaH_2PO_4$), monobasic sodium potassium phosphate ($NaKHPO_4$), magnesium phosphate ($Mg_3(PO_4)_2 \cdot 4H_2O$), potassium acetate ($CH_3COOH$), D(+)-α-sodium glycerophosphate ($HOCH_2CH(OH)CH_2OPO_3Na_2$) and other physiologic buffers known to those skilled in the art.

In additional embodiments of the present invention provides methods for cloning or subcloning one or more desired nucleic acid molecules comprising: (a) combining in vitro or in vivo (i) one or more first nucleic acid molecules comprising one or more sticky ends generated by one or more first restriction enzymes (e.g. one or more type IIs restriction enzymes); (ii) one or more second nucleic acid molecules comprising one or more toxic genes flanked by one or more second restriction sites (e.g. one or more type IIs restriction enzyme recognition sites); and (iii) one or more restriction enzymes (e.g. one or more type IIs restriction enzymes) that are specific for the first and/or second restriction sites; and (b) incubating the combination under conditions sufficient to join the first nucleic acid molecule and one or more of the second nucleic acid molecules, thereby producing one or more desired product nucleic acid molecules. Cloning via such methods of the invention allows for selection of successfully cloned nucleic acid molecules where the toxic gene originally present in the second nucleic acid molecule has been removed and replaced with a desired nucleic acid sequence from the first nucleic acid molecule.

In other embodiments of the present invention provides methods for cloning or subcloning one or more desired nucleic acid molecules, or portions thereof, comprising: (a) combining in vitro or in vivo (i) one or more first nucleic acid molecules comprising at least one nucleic acid segment that is flanked by one or more first restriction sites (e.g. one or more type IIs restriction enzyme recognition sites); (ii) one or more second nucleic acid molecules comprising one or more toxic genes flanked by one or more second restriction sites (e.g. one or more type IIs restriction enzyme recognition sites); and (iii) one or more restriction enzymes (e.g. one or more type IIs restriction enzymes) that are specific for the first and/or second restriction enzyme recognition sites; and (b) incubating the combination under conditions sufficient to join the first nucleic acid molecule and one or more of the second nucleic acid molecules, thereby producing one or more desired product nucleic acid molecules. As noted above, cloning via such methods of the invention allows for selection of successfully cloned nucleic acid molecules where the toxic gene originally present in the second nucleic acid molecule has been removed and replaced with a desired nucleic acid sequence from the first nucleic acid molecule.

The present invention also provides methods for cloning or subcloning one or more desired nucleic acid molecules comprising: (a) combining in vitro or in vivo (i) one or more first nucleic acid molecules comprising one or more sticky ends that have been generated by one or more first restriction enzymes (e.g. one or more type IIs restriction enzymes); (ii) one or more second nucleic acid molecules comprising one or more toxic genes and one or more antibiotic resistance genes all flanked by one or more second restriction sites (e.g. one or more type IIs restriction enzyme recognition sites); and (iii) one or more restriction enzymes (e.g. one or more type IIs restriction enzymes) that are specific for the restriction enzyme recognition sites; and (b) incubating said combination under conditions sufficient to join the first nucleic acid molecule into and or more of the second nucleic acid molecules, thereby producing one or more desired product nucleic acid molecules. This embodiment allows for additional selective screening via selection, for example, of antibiotic resistant host cells.

The present invention also provides methods for cloning or subcloning one or more desired nucleic acid molecules, or portions thereof, comprising: (a) combining in vitro or in vivo (i) one or more first nucleic acid molecules comprising at least one nucleic acid segment flanked by one or more first restriction sites (e.g. one or more type IIs restriction enzyme recognition sites); (ii) one or more second nucleic acid molecules comprising one or more toxic genes and one or more antibiotic resistance genes all flanked by one or more second restriction sites (e.g. one or more type IIs restriction enzyme recognition sites); and (iii) one or more restriction enzymes (e.g. one or more type IIs restriction enzymes) that are specific for the restriction enzyme recognition sites; and (b) incubating said combination under conditions sufficient to join the first nucleic acid molecule and one or more of the second nucleic acid molecules, thereby producing one or more desired product nucleic acid molecules. This embodiment allows for additional selective screening via selection, for example, of antibiotic resistant host cells.

Another embodiment of the invention provides a method for cloning or subcloning one or more desired nucleic acid molecules comprising: (a) combining in vitro or in vivo (i) one or more first nucleic acid molecules comprising one or more sticky ends that have been generated by one or more first restriction enzymes (e.g. one or more type IIs restriction enzymes); (ii) one or more second nucleic acid molecules comprising one or more second restriction sites (e.g. one or more type IIs restriction enzyme recognition sites) flanked by one or more recombination sites; and (iii) one or more restriction enzymes (e.g. one or more type IIs restriction enzymes) that are specific for the first and/or second restriction enzyme recognition sites; and (b) incubating said combination under conditions sufficient to join the first nucleic acid molecule and one or more of said second nucleic acid molecules, thereby producing one or more desired product nucleic acid molecules. Following cloning of the first nucleic acid molecule, the cloned portion of the sequence may be cloned into another nucleic acid molecule via, for example, recombination cloning as described below.

Another embodiment of the invention provides a method for cloning or subcloning one or more desired nucleic acid molecules, or portions thereof, comprising: (a) combining in vitro or in vivo (i) one or more first nucleic acid molecules comprising at least one nucleic acid segment flanked by one or more first restriction sites (e.g. one or more type IIs restriction enzyme recognition sites); (ii) one or more second nucleic acid molecules comprising one or more second restriction sites (e.g. one or more type IIs restriction enzyme recognition sites) flanked by one or more recombination sites; and (iii) one or more restriction enzymes (e.g. one or more type IIs restriction enzymes) that are specific for the first and/or second restriction enzyme recognition sites; and (b) incubating said combination under conditions sufficient to join the first nucleic acid molecule and one or more of said second nucleic acid molecules, thereby producing one or more desired product nucleic acid molecules. As noted above, following cloning of the first nucleic acid molecule, the cloned portion of the sequence may be cloned into another nucleic acid molecule via, for example, recombination cloning as described below.

The present invention also provides for a method for cloning or subcloning one or more desired nucleic acid molecules, or portions thereof, comprising: (a) combining in vitro or in vivo (i) one or more first nucleic acid molecules comprising at least one nucleic acid segment flanked by one or more first restriction sites (e.g. one or more type IIs restriction enzyme recognition sites) and further flanked by one or more recombination sites; (ii) one or more second nucleic acid molecules comprising one or more recombination sites; and (iii) one or more site-specific recombination proteins; and (b) incubating the combination under conditions sufficient to transfer the first nucleic acid molecule into one or more of the second nucleic acid molecules, thereby producing one or more desired product nucleic acid molecules.

This method of the present invention allows for the transfer of a nucleic acid sequence flanked by one or more restriction sites (e.g. one or more type IIs sites) that is further flanked by one or more recombination sites into a second nucleic acid molecule via recombinational cloning. Recombinational cloning is described in detail in U.S. Pat. Nos. 5,888,732 and 6,277,608 (incorporated herein entirely by reference in their entireties). Recombinational cloning as disclosed in U.S. Pat. Nos. 5,888,732 and 6,277,608 describes methods for moving or exchanging nucleic acid segments using at least one recombination site and at least one recombination protein to provide chimeric DNA molecules. Suitable recombination proteins for use in the present invention include, but are not limited to Int, Cre, IHF, Xis, Fis, Hin, Gin, Cin, Tn3 resolvase, TndX, XerC and XerD.

The methods of the present invention may further comprise introducing the product nucleic acid into one or more host cells. Host cells that may be used in any aspect of the present invention include, but are not limited to, bacterial cells, yeast cells, plant cells and animal cells. Preferred bacterial host cells include *Escherichia* spp. cells (particularly *E. coli* cells and most particularly *E. coli* strains DH10B, Stbl2, DH5, DB3 (deposit No. NRRL B-30098), DB3.1 (preferably *E. coli* LIBRARY EFFICIENCY7 DB3.1J Competent Cells; Invitrogen Corporation, Carlsbad, Calif.), DB4 and DB5 (deposit Nos. NRRL B-30106 and NNRL B-30107 respectively, see U.S. application Ser. No. 09/518,188, filed Mar. 2, 2000, the disclosure of which is incorporated by reference herein in its entirety), JDP682 and ccdA-over (See U.S. Provisional Application No. 60/475,004, filed Jun. 3, 2003, the disclosure of which is incorporated by reference herein in its entirety), *Bacillus* spp. cells (particularly *B. subtilis* and *B. megaterium* cells), *Streptomyces* spp. cells, *Erwinia* spp. cells, *Klebsiella* spp. cells, *Serratia* spp. cells (particularly *S. marcessans* cells), *Pseudomonas* spp. cells (particularly *P. aeruginosa* cells), and *Salmonella* spp. cells (particularly *S. typhimurium* and *S. typhi* cells). Preferred animal host cells include insect cells (most particularly *Drosophila melanogaster* cells, *Spodoptera frugiperda* Sf9 and Sf21 cells and Trichoplusa High-Five cells), nematode cells (particularly *C. elegans* cells), avian cells, amphibian cells (particularly *Xenopus laevis* cells), reptilian cells, and mammalian cells (most particularly NIH3T3, CHO, COS, VERO, BHK and human cells). Preferred yeast host cells include *Saccharomyces cerevisiae* cells and *Pichia pastoris* cells. These and other suitable host cells are available commercially, for example from Invitrogen Corporation (Carlsbad, Calif.), American Type Culture Collection (Manassas, Va.), and Agricultural Research Culture Collection (NRRL; Peoria, Ill.).

Additional host cells that are useful in the present invention include mutant host cells and host cell strains, as well as mutants and/or derivatives thereof, that are resistant to the effects of the expression of one or more toxic genes. Host cells of this type may, for example, comprise one or more mutations in one or more genes within their genomes or on extrachromosomal or extragenomic DNA molecules (such as plasmids, phagemids, cosmids, etc.), including mutations in, for example, recA, endA, mcrA, mcrB, mcrC, hsd, deoR, tonA, and the like, in particular in recA or endA or in both recA and endA. The mutations to these host cells may render the host cells and host cell strains resistant to toxic genes including, but not limited to, ccdB, kicB, sacB, DpnI, an apoptosis-related gene, a retroviral gene, a defensin, a bacteriophage lytic gene, an antibiotic sensitivity gene, an antimicrobial sensitivity gene, a plasmid killer gene, and a eukaryotic transcriptional vector gene that produces a gene product toxic to bacteria, and most particularly ccdB. Production and use of these type of mutant host cell strains are described in commonly owned U.S. Appl. No. 60/122,392, filed Mar. 2, 1999, Ser. No. 09/518,188, filed Mar. 2, 2000 (now abandoned), Ser. No. 10/396,696, filed Mar. 20, 2003, and 60/475,004, filed Jun. 3, 2003, the disclosures of which are incorporated herein by reference in their entireties.

Methods for introducing the cloned product nucleic acid molecules and/or vectors of the invention into the host cells described herein, to produce host cells comprising one or more of the cloned nucleic acid molecules and/or vectors of the invention, will be familiar to those of ordinary skill in the art. For instance, the nucleic acid molecules and/or vectors of the invention may be introduced into host cells using well known techniques of infection, transduction, electroporation, transfection, and transformation. The nucleic acid molecules and/or vectors of the invention may be introduced alone or in conjunction with other the nucleic acid molecules and/or vectors and/or proteins, peptides or RNAs. Alternatively, the nucleic acid molecules and/or vectors of the invention may be introduced into host cells as a precipitate, such as a calcium phosphate precipitate, or in a complex with a lipid. Electroporation also may be used to introduce the nucleic acid molecules and/or vectors of the invention into a host. Likewise, such molecules may be introduced into chemically competent cells such as *E. coli*. If the vector is a virus, it may be packaged in vitro or introduced into a packaging cell and the packaged virus may be transduced into cells. Hence, a wide variety of techniques suitable for introducing the nucleic acid molecules and/or vectors of the invention into cells in accordance with this aspect of the invention are well known and routine to those of skill in the art. Such techniques are reviewed at length, for example, in Sambrook, J., et al., Molecular Cloning, a Laboratory Manual, 2nd Ed., Cold Spring Harbor, N.Y.: Cold Spring Harbor Laboratory Press, pp. 16.30-16.55 (1989), Watson, J. D., et al., Recombinant DNA, 2nd Ed., New York: W.H. Freeman and Co., pp. 213-234 (1992), and Winnacker, E.-L., From Genes to Clones, New York: VCH Publishers (1987), which are illustrative of the many laboratory manuals that detail these techniques and which are incorporated by reference herein in their entireties for their relevant disclosures.

The present invention also encompasses producing a subsequent nucleic acid and/or a protein by introduction of a cloned product nucleic acid molecule of the invention and expression in a host cell. Methods and conditions by which to produce such product nucleic acid molecules and product proteins are well known in the art. See for example, Sambrook, J., et al., Molecular Cloning, a Laboratory Manual, 2nd Ed., Cold Spring Harbor, N.Y.: Cold Spring Harbor Laboratory Press (1989).

The present invention also encompasses the nucleic acid molecules and proteins produced from a host cell of the invention. An improvement of the present invention is that nucleic acid molecules produced using methods of the present invention, in many instances, will not contain extraneous nucleotides that are not associated with the desired nucleic acid, for example nucleotides encoded by the restriction sites (e.g. type IIs restriction enzyme recognition sites). In other words, the seamless cloning methods of the present invention allow for a product molecule that does not contain extraneous nucleotides from other sources, including the restriction sites. Similarly, the product protein molecules produced using the methods of the present invention are free of amino acids that are not associated with the desired native or mature product protein, for example the product protein molecules are free of amino acids encoded by the restriction sites (e.g. type IIs restriction sites). The proteins produced by the methods of the invention may be of any size, including for example, a short peptide from about 5 amino acids, about 10 amino acids, about 20 amino acids, about 30 amino acids, about 40 amino acids, about 50 amino acids. The present invention also encompasses the production of larger proteins, for example about 300 amino acids in length, or even a large protein of greater than about 600 amino acids in length.

In one embodiment of the present invention, the nucleic acid molecules produced from the host cells may be useful as interfering RNA molecules. In biological systems that are not amenable to gene targeting or homologous recombination, a process called RNA interference (RNAi) is one practical method of generating knockout (KO) phenotypes. Post transcriptional gene silencing (PTGS) in plants and quelling in *Neurospora* was described in the early 1990s. RNAi was originally described in the model organism *C. elegans* as double stranded RNA (dsRNA) that mediated sequence specific gene silencing (Fire et al., Nature 391:806-811 (1998)). RNAi has also been described in yeast, *Drosophila*, plants and trypanosomes. RNAi can be used for genetic analysis. For example, it can be used for genome wide RNAi screens. RNAi has been shown to be conserved in mammals. RNAi has been used in the identification of a short interfering RNA (siRNA) as an effector molecule and with microRNA (miRNA) regulation. Essentially, the process involves application of double stranded RNA (dsRNA) that represents a complementary sense and anti-sense strand of a portion of a target gene within the region that encodes mRNA. The presence of the interfering dsRNA causes a severe post-transcriptional down-regulation of the target gene. This versatile technique has been used as a tool in the study of eukaryotic biology (see Sharp, P. A., *Genes Dev.* 13:139-141 (1999)).

Figure 13:
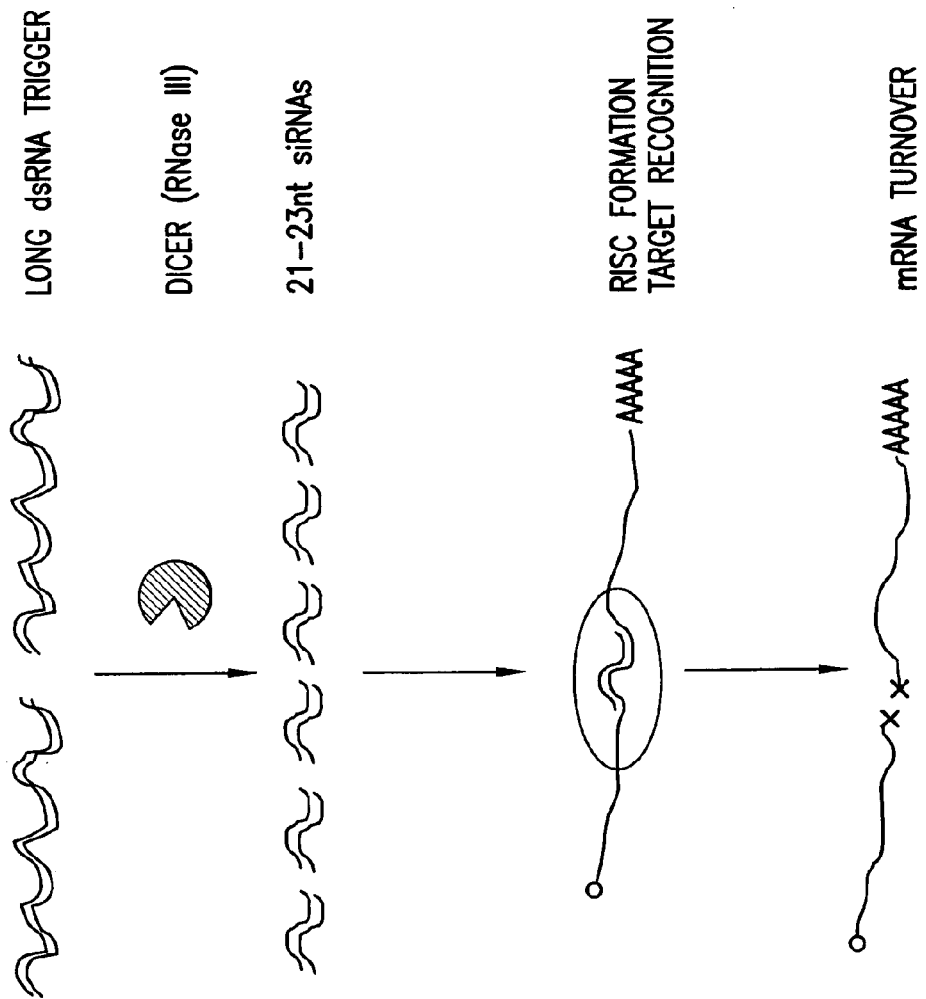
FIG. 13 depicts RNAi overview.
Figure 15:
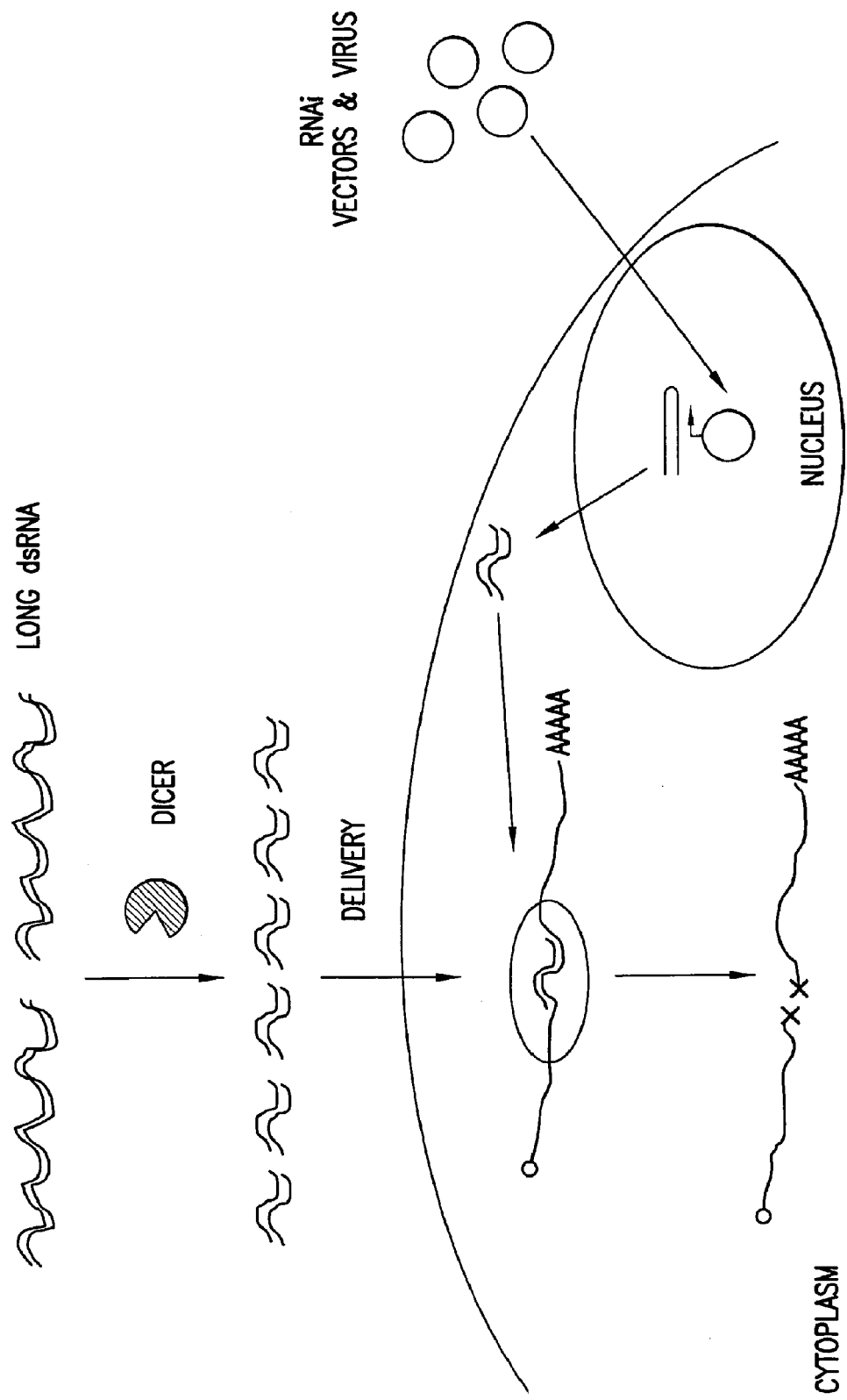
FIG. 15 depicts RNAi Methods.
Figure 17A:
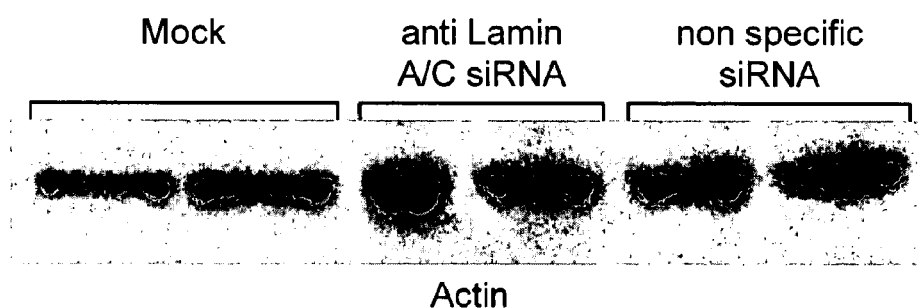
FIG. 17 depicts Transfection of siRNAs
Figure 17B:
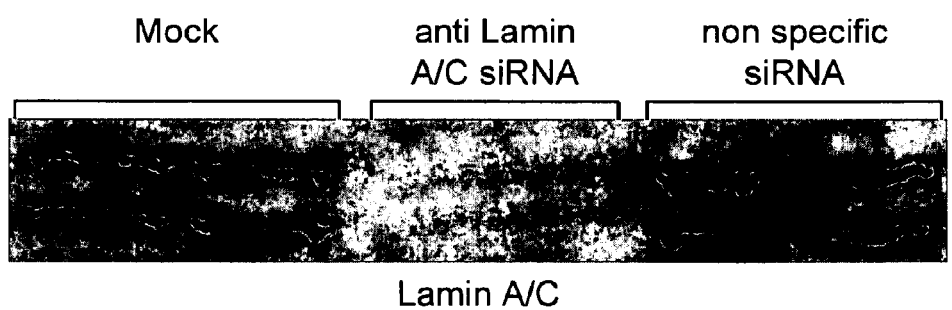
Figure 18C:
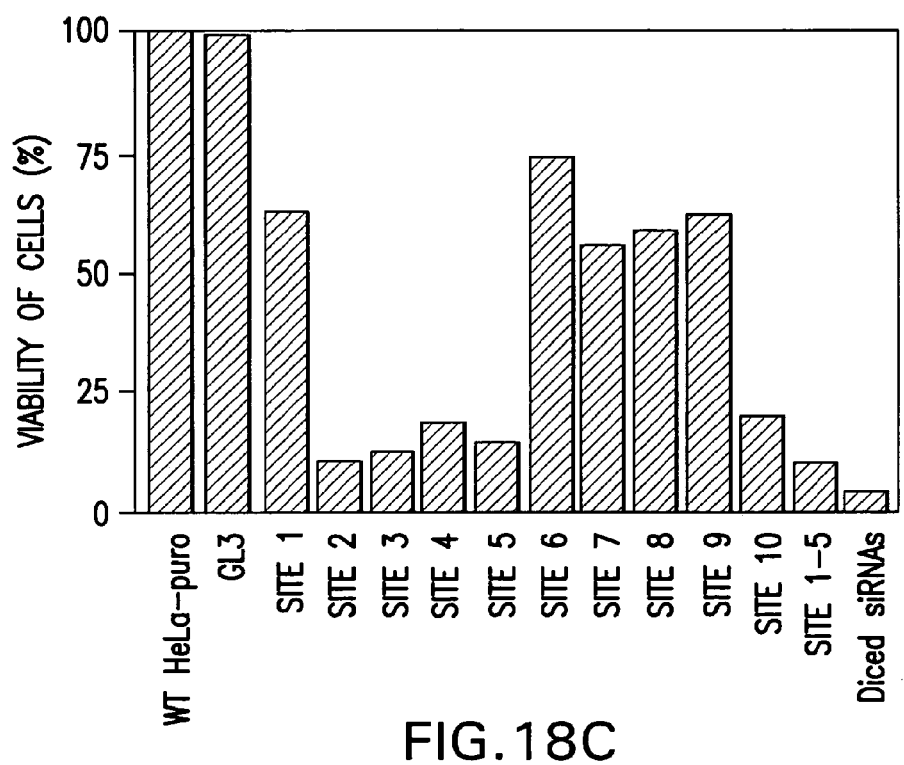
FIG. 18 depicts Variation in siRNA effectiveness.

RNAi is an evolutionarily conserved phenomenon and a multi-step process that involves generation of active small interfering RNA (siRNA) in vivo through the action of an RNase III endonuclease, DICER, which digests long double stranded RNA molecules (dsRNA) into shorter fragments (See FIG. 13). The 21- to 23-nucleotide base pair small interfering RNAs (siRNAs), produced through the action of DICER, mediate degradation of the complementary homologous RNA. One bottleneck to using RNAi as a tool has been mRNA target site selection. Yet another challenge has been delivery, either transient such as transfection of dsRNA (See FIGS. 16-18) (Kawasaki et. al, NAR, 31(3):981-987 (2003)) or stable expression using vectors or a virus (See FIGS. 15 and 19) (Dykxhoorn, Novina and Sharp, Nature Reviews, Vol. 4, (June 2003)). RNAi has successfully been reported in stable cell lines and transgenic mice. GFP shRNA block GFP expression in transgenic mice, decrease GFP in blastocytes and lower GFP fluorescence overall in a three day pup with two copies of the shRNA (Tiscornia et. al, PNAS, 2003).

RNAi is also powerful in reverse genetics. RNAi can be used as a loss of function tool, similar to antisense and ribozymes, but more potent. Natural cellular machinery use double stranded RNA to regulate cellular processes (e.g., miRNA). Some advantages of RNAi are that it is broadly conserved in eukaryotic organisms, is post transcriptional (effective in diploids) and is tunable (can adjust level of RNAi at several levels).

Until recently, RNAi technology did not appear to be applicable to mammalian systems. In mammals, dsRNA activates dsRNA-activated protein kinase (PKR) resulting in an apoptotic cascade and cell death (Der et al, *Proc. Natl. Acad. Sci. USA* 94:3279-3283 (1997)). In addition, it has long been known that dsRNA activates the interferon cascade in mammalian cells, which can also lead to altered cell physiology (Colby et al, *Annu. Rev. Microbiol.* 25:333 (1971); Kleinschmidt et al., *Annu. Rev. Biochem.* 41:517 (1972); Lampson et al., *Proc. Natl. Acad. Sci. USA* 58L782 (1967); Lomniczi et al., *J. Gen. Virol.* 8:55 (1970); Younger et al., *J. Bacteriol.* 92:862 (1966)). However, dsRNA-mediated activation of the PKR and interferon cascades typically require dsRNA longer than about 30 base pairs. Since the primary products of DICER are 21-23 base pair fragments of dsRNA, one can circumvent the adverse or undesired mammalian responses to dsRNA and still elicit an interfering RNA effect via siRNA (Elbashir et al., *Nature* 411:494-498 (2001)).

Thus, another aspect of the present invention provides methods of producing an RNA molecule for use as an interfering RNA comprising: (a) optionally, identifying one or more target nucleic acid sequences; (b) preparing one or more nucleic acid molecules which encode one or more interfering RNAs, wherein the interfering RNAs bind to the one or more target nucleic acid sequences; (c) combining in vitro or in vivo, (i) the one or more first nucleic acid molecules encoding one or more interfering RNAs that have one or more sticky ends that have been generated by one or more restriction enzymes (e.g. type IIs restriction enzymes); and (ii) one or more second nucleic acid molecules comprising one or more ends which are compatible with the one or more sticky ends on the first nucleic acid molecule(s), and optionally comprising one or more selectable markers; and (d) incubating the combination under conditions sufficient to join one or more of the nucleic acid molecules encoding the interfering RNAs and one or more of the second nucleic acid molecules, thereby producing one or more desired product nucleic acid molecules; (e) inserting the one or more product nucleic acid molecules into a host cell; and (f) expressing the one or more interfering RNAs in the host cell.

The present invention also provides methods of producing an RNA molecule for use as an interfering RNA comprising: (a) optionally, identifying one or more target nucleic acid sequences; (b) preparing one or more nucleic acid molecules which encode one or more interfering RNAs, wherein the interfering RNAs bind to the one or more target nucleic acid sequences; (c) combining in vitro or in vivo, (i) the one or more first nucleic acid molecules encoding one or more interfering RNAs flanked by one or more first restriction sites (e.g. one or more type IIs restriction enzyme recognition sites); (ii) one or more second nucleic acid molecules comprising one or more second restriction sites (e.g. one or more type IIs restriction enzyme recognition sites) and optionally comprising one or more selectable markers; and (iii) one or more site-specific restriction enzymes (e.g. one or more type IIs restriction enzymes); and (d) incubating the combination under conditions sufficient to join one or more of the nucleic acid molecules encoding the interfering RNAs and one or more of the second nucleic acid molecules, thereby producing one or more desired product nucleic acid molecules; (e) inserting the one or more product nucleic acid molecules into a host cell; and (f) expressing the one or more interfering RNAs in the host cell.

In yet another embodiment, the present invention provides methods of producing an RNA molecule for use as an interfering RNA comprising: (a) optionally, identifying one or more target nucleic acid sequences; (b) preparing one or more nucleic acid molecules which encode one or more interfering RNAs, wherein the interfering RNAs bind to the one or more target nucleic acid sequences; (c) combining in vitro or in vivo, (i) the one or more first nucleic acid molecules encoding one or more interfering RNAs that have one or more sticky ends that have been generated by one or more restriction enzymes (e.g. type IIs restriction enzymes); and (ii) one or more second nucleic acid molecules comprising one or more ends which are compatible with the one or more sticky ends on the first nucleic acid molecule(s), and optionally comprising one or more selectable markers; and (d) incubating the combination under conditions sufficient to join one or more of the nucleic acid molecules encoding the interfering RNAs and one or more of the second nucleic acid molecules, thereby producing one or more desired product nucleic acid molecules; and (e) expressing one or more interfering RNAs in vitro or in vivo. In a first further embodiment, the one or more interfering RNAs may be produced in vitro or isolated from a cell and then introduced into a second cell.

Another aspect of the present invention provides methods of producing an RNA molecule for use as an interfering RNA comprising: (a) optionally, identifying one or more target nucleic acid sequences; (b) preparing one or more nucleic acid molecules which encode one or more interfering RNAs, wherein the interfering RNAs bind to the one or more target nucleic acid sequences; (c) combining in vitro or in vivo, (i) the one or more first nucleic acid molecules encoding one or more interfering RNAs flanked by one or more first restriction sites (e.g. one or more type IIs restriction enzyme recognition sites); (ii) one or more second nucleic acid molecules comprising one or more second restriction sites (e.g. one or more type IIs restriction enzyme recognition sites) and optionally comprising one or more selectable markers; and (iii) one or more site-specific restriction enzymes (e.g. one or more type IIs restriction enzymes); and (d) incubating the combination under conditions sufficient to join one or more of the nucleic acid molecules encoding the interfering RNAs and one or more of the second nucleic acid molecules, thereby producing one or more desired product nucleic acid molecules; and (e) expressing one or more interfering RNAs in vitro or in vivo.

In a first further embodiment, the one or more interfering RNAs may be produced in vitro or isolated from a cell and then introduced into a second cell.

Another aspect of the present invention provides methods of producing an RNA molecule for use as an interfering RNA comprising: (a) optionally, identifying one or more target nucleic acid sequences; (b) preparing one or more interfering RNAs, wherein the interfering RNAs bind to the one or more target nucleic acid sequences; (c) combining in vitro or in vivo, (i) the one or more first nucleic acid molecules comprising one or more interfering RNAs that have one or more sticky ends that have been generated by one or more restriction enzymes (e.g. type IIs restriction enzymes); and (ii) one or more second nucleic acid molecules comprising one or more ends which are compatible with the one or more sticky ends on the first nucleic acid molecule(s), and optionally comprising one or more selectable markers; and (d) incubating the combination under conditions sufficient to join one or more interfering RNAs and one or more of the second nucleic acid molecules, thereby producing one or more desired product nucleic acid molecules; (e) inserting the one or more product nucleic acid molecules into a host cell; and (f) expressing the one or more interfering RNAs in the host cell.

The present invention also provides methods of producing an RNA molecule for use as an interfering RNA comprising: (a) optionally, identifying one or more target nucleic acid sequences; (b) preparing one or more nucleic acid molecules which comprise one or more interfering RNAs, wherein the interfering RNAs bind to the one or more target nucleic acid sequences; (c) combining in vitro or in vivo, (i) the one or more first nucleic acid molecules comprising one or more interfering RNAs flanked by one or more first restriction sites (e.g. one or more type IIs restriction enzyme recognition sites); (ii) one or more second nucleic acid molecules comprising one or more second restriction sites (e.g. one or more type IIs restriction enzyme recognition sites) and optionally comprising one or more selectable markers; and (iii) one or more site-specific restriction enzymes (e.g. one or more type IIs restriction enzymes); and (d) incubating the combination under conditions sufficient to join one or more interfering RNAs and one or more of the second nucleic acid molecules, thereby producing one or more desired product nucleic acid molecules; (e) inserting the one or more product nucleic acid molecules into a host cell; and (f) expressing the one or more interfering RNAs in the host cell.

Suitable nucleic acid molecules that can function as interfering RNA (iRNA) and that can be produced using the methods of the present invention may be either single- or double-stranded RNA (ssRNA or dsRNA, respectively). Examples of iRNA produced via methods of the present invention include, but are not limited to, antisense oligonucleotides, ribozymes, small interfering RNAs, double stranded RNAs, inverted repeats, short hairpin RNAs, small temporally regulated RNAs and the like.

Antisense Oligonucleotides

In general, antisense oligonucleotides comprise one or more nucleotide sequences sufficient in identity, number and size to effect specific hybridization with a preselected nucleic. Antisense oligonucleotides produced in accordance with the present invention typically have sequences that are selected to be sufficiently complementary to the target nucleic sequences (suitably mRNA in a target cell or organism) so that the antisense oligonucleotide forms a stable hybrid with the mRNA and inhibits the translation of the mRNA sequence, preferably under physiological conditions. It is preferred but not necessary that the antisense oligonucleotide be 100% complementary to a portion of the target gene sequence. However, the present invention also encompasses the production of antisense oligonucleotides with a different level of complementarity to the target gene sequence, e.g., antisense oligonucleotides that are at least about 50% complementary, at least about 55% complementary, at least about 60% complementary, at least about 65% complementary, at least about 70% complementary, at least about 75% complementary, at least about 80% complementary, at least about 85% complementary, at least about 90% complementary, at least about 91% complementary, at least about 92% complementary, at least about 93% complementary, at least about 94% complementary, at least about 95% complementary, at least about 96% complementary, at least about 97% complementary, at least about 98% complementary, or at least about 99% complementary, to the target gene sequence.

Antisense oligonucleotides that may be produced in accordance with the present invention are well known in the art and that will be familiar to the ordinarily skilled artisan. Representative teachings regarding the synthesis, design, selection and use of antisense oligonucleotides include without limitation U.S. Pat. Nos. 5,789,573, 6,197,584, and Ellington, "Current Protocols in Molecular Biology," 2nd Ed., Ausubel et al., eds., Wiley Interscience, New York (1992), the disclosures of which are incorporated by reference herein in their entireties.

Ribozymes

In general, ribozymes are RNA molecules having enzymatic activities usually associated with cleavage, splicing or ligation of nucleic acid sequences to which the ribozyme binds. Typical substrates for ribozymes include RNA molecules, although ribozymes may also catalyze reactions in which DNA molecules serve as substrates. Two distinct regions can be identified in a ribozyme: the binding region which gives the ribozyme its specificity through hybridization to a specific nucleic acid sequence, and a catalytic region which gives the ribozyme the activity of cleavage, ligation or splicing. Ribozymes which are active intracellularly work in cis, catalyzing only a single turnover, and are usually self-modified during the reaction. However, ribozymes can be engineered to act in trans, in a truly catalytic manner, with a turnover greater than one and without being self-modified. Owing to the catalytic nature of the ribozyme, a single ribozyme molecule cleaves many molecules of target nucleic acids and therefore therapeutic activity is achieved in relatively lower concentrations than those required in an antisense treatment (WO 96/23569).

Ribozymes that may be produced in accordance with the present invention are well known in the art and that will be familiar to the ordinarily skilled artisan. Representative teachings regarding the synthesis, design, selection and use of ribozymes include without limitation U.S. Pat. Nos. 4,987,071, and 5,877,021, the disclosures of all of which are incorporated herein by reference in their entireties.

Small Interfering RNAs (siRNA)

RNAi is mediated by double stranded RNA (dsRNA) molecules that have sequence-specific homology to their "target" nucleic acid sequences (Caplen, N. J., et al., Proc. Natl. Acad. Sci. USA 98:9742-9747 (2001)). Biochemical studies in *Drosophila* cell-free lysates indicate that, in certain embodiments of the present invention, the mediators of RNA-dependent gene silencing are 21-25 nucleotide "small interfering" RNA duplexes (siRNAs). Accordingly, siRNA molecules are suitably used in methods of the present invention. The siRNAs are derived from the processing of dsRNA by an RNase known as Dicer (Bernstein, E., et al., Nature 409:363-366 (2001)). It appears that siRNA duplex products are recruited into a multi-protein siRNA complex termed RISC(RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion (Bernstein, E., et al., Nature 409: 363-366 (2001); Boutla, A., et al., Curr. Biol. 11:1776-1780 (2001)).

Small interfering RNAs that may be produced in accordance with the present invention are well known in the art and that will be familiar to the ordinarily skilled artisan. Small interfering RNAs that may be produced via the methods of the present invention suitably comprise between about 1 to about 50 nucleotides (nt). For example, siRNAs may comprise about 5 to about 40 nt, about 5 to about 30 nt, about 10 to about 30 nt, or about 15 to about 30 nt. Longer siRNAs (greater than about 30 nucleotides in length) may be useful in some non-human animal systems, and may suitably be produced by the methods of the present invention. Most reports describe the use of U6 or H1 pol III promoters to drive production of siRNA (Lee et al., Nat. Biotechnol. 20:500-505 (2002); Paddison et al., Genes Dev. 16:948-958 (2002); Brummelkamp et al., Science 296:550-553 (2002)). Pol III promoters have all the elements required for initiation of transcription upstream of a defined transcription start site and terminate transcription at 4 or more Ts (incorporating only 1 or 2 Us into the 3' end of the nascent RNA). These attributes allow the production of short RNA molecules with defined ends.

Inverted Repeats

Inverted repeats comprise single stranded nucleic acid molecules that contain two sequences complementary to each other, oriented such that one of the sequences is inverted relative to the other. This orientation allows the two complementary sequences to base pair with each other, thereby forming a hairpin structure. The two copies of the inverted repeat need not be contiguous. There may be "n" additional nucleotides between the hairpin forming sequences, wherein "n" is any number of nucleotides. For example, n can be about 1, about 5, about 10, about 50, or about 100 nucleotide, or more, and can be any number of nucleotides falling within these discrete values.

Inverted repeats suitable that may be produced in accordance with the present invention can be synthesized and used according to procedures that are well known in the art and that will be familiar to the ordinarily skilled artisan. The production and use of inverted repeats for RNA interference can be found in, without limitation, Kirby, K., et al., Proc. Natl. Acad. Sci. USA 99:16162-16167 (2002), Adelman, Z. N., et al., J. Virol. 76:12925-12933 (2002), Yi, C. E., et al., J. Biol. Chem. 278:934-939 (2003), Yang, S., et al., Mol. Cell. Biol. 21:7807-7816 (2001), Svoboda, P., et al., Biochem. Biophys. Res. Commun. 287:1099-1104 (2001), and Martinek, S, and Young, M. W., Genetics 156:171-1725 (2000).

Short Hairpin RNA (shRNA)

Paddison, P. J., et al., Genes & Dev. 16:948-958 (2002) have used small RNA molecules folded into hairpins as a means to effect RNAi. Accordingly, such short hairpin RNA (shRNA) molecules that may be produced via the methods of the present invention. Functionally identical to the inverted repeats described herein, the length of the stem and loop of functional shRNAs distinguishes them from inverted repeats. Stem lengths can range from about 1 to about 30 nt, and loop size can range between 1 to about 25 nt without affecting silencing activity. While not wishing to be bound by any particular theory, it is believed that these shRNAs resemble the dsRNA products of the Dicer RNase and, in any event, have the same capacity for inhibiting expression of a specific gene.

Transcription of shRNAs is initiated at a polymerase III (pol III) promoter (e.g. U6 and H1 promoters) and is believed to be terminated at position 2 of a 4-5-thymine transcription termination site. Upon expression, shRNAs are thought to fold into a stem-loop structure with 3' UU-overhangs. Subsequently, the ends of these shRNAs are processed, converting the shRNAs into ~21 nt siRNA-like molecules.

Short hairpin RNAs that may be produced in accordance with the present invention are well known in the art and that will be familiar to the ordinarily skilled artisan. The production and use of inverted repeats for RNA interference can be found in, without limitation, Paddison, P. J., et al., *Genes & Dev.* 16:948-958 (2002), Yu, J-Y., et al. *Proc. Natl. Acad. Sci. USA* 99:6047-6052 (2002), and Paul, C. P. et al. *Nature Biotechnol.* 20:505-508 (2002).

MicroRNAs (miRNAs)

The invention may further be used to produce microRNA molecules.

Figure 14:
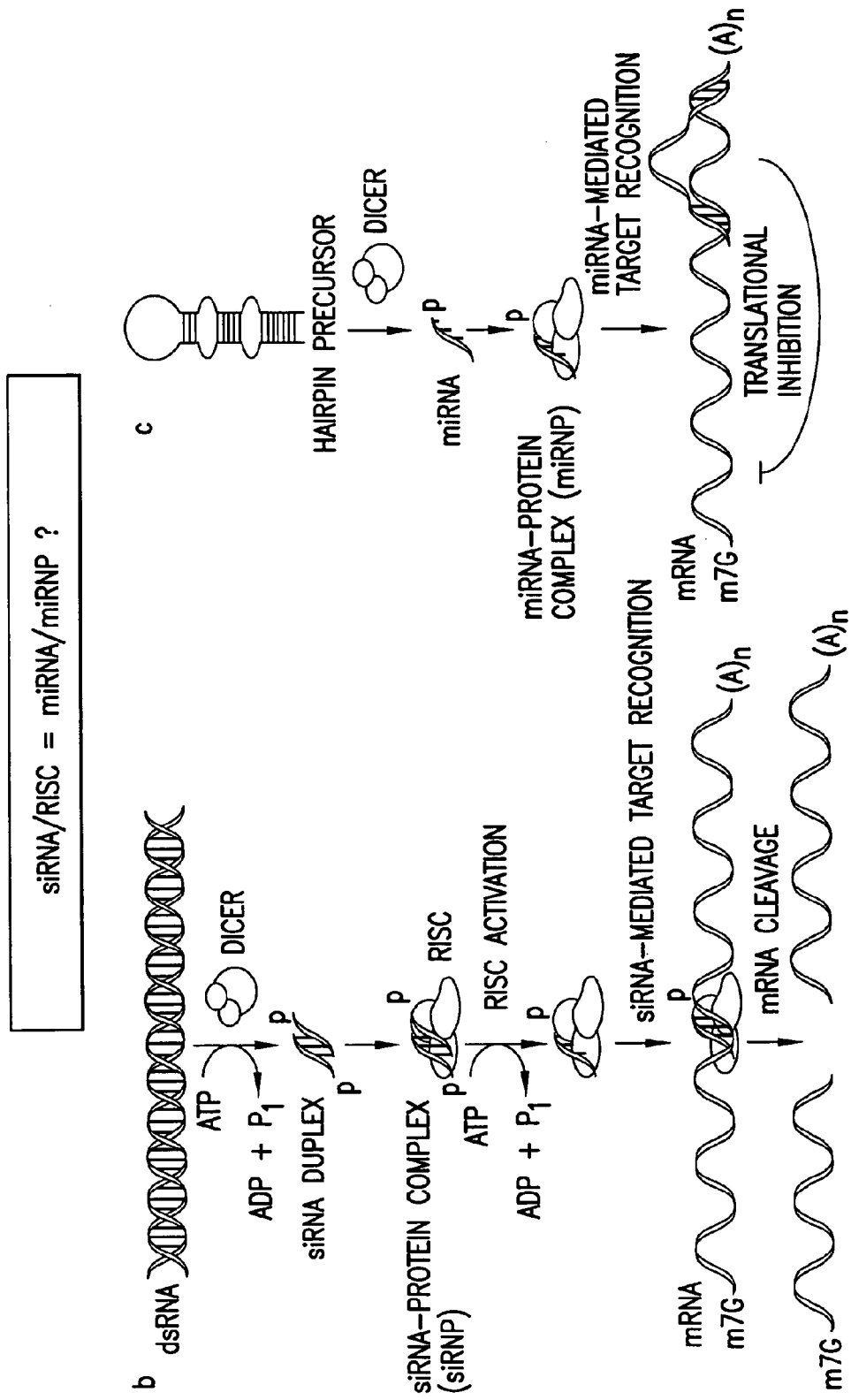
FIG. 14 depicts RNAi Mechanistic Model.
Figure 25:
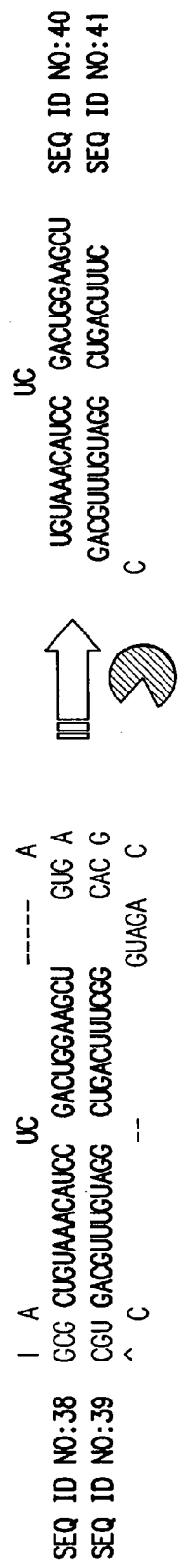
FIG. 25 depicts Micro RNA (miRNA).
Figure 26:
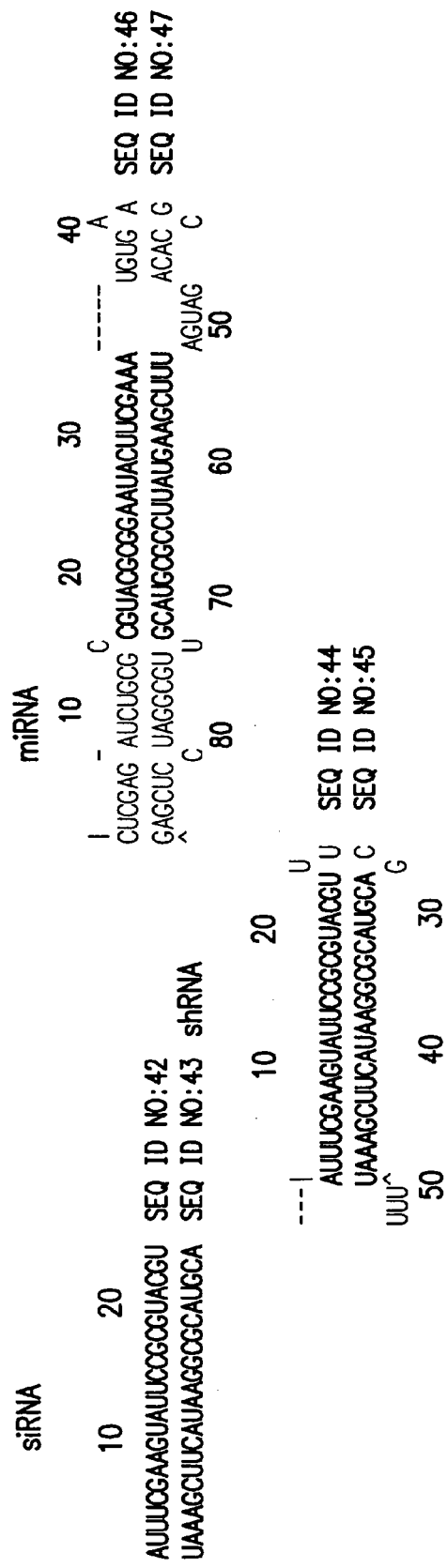
FIG. 26 depicts RNAi Vectors.
Figure 27:
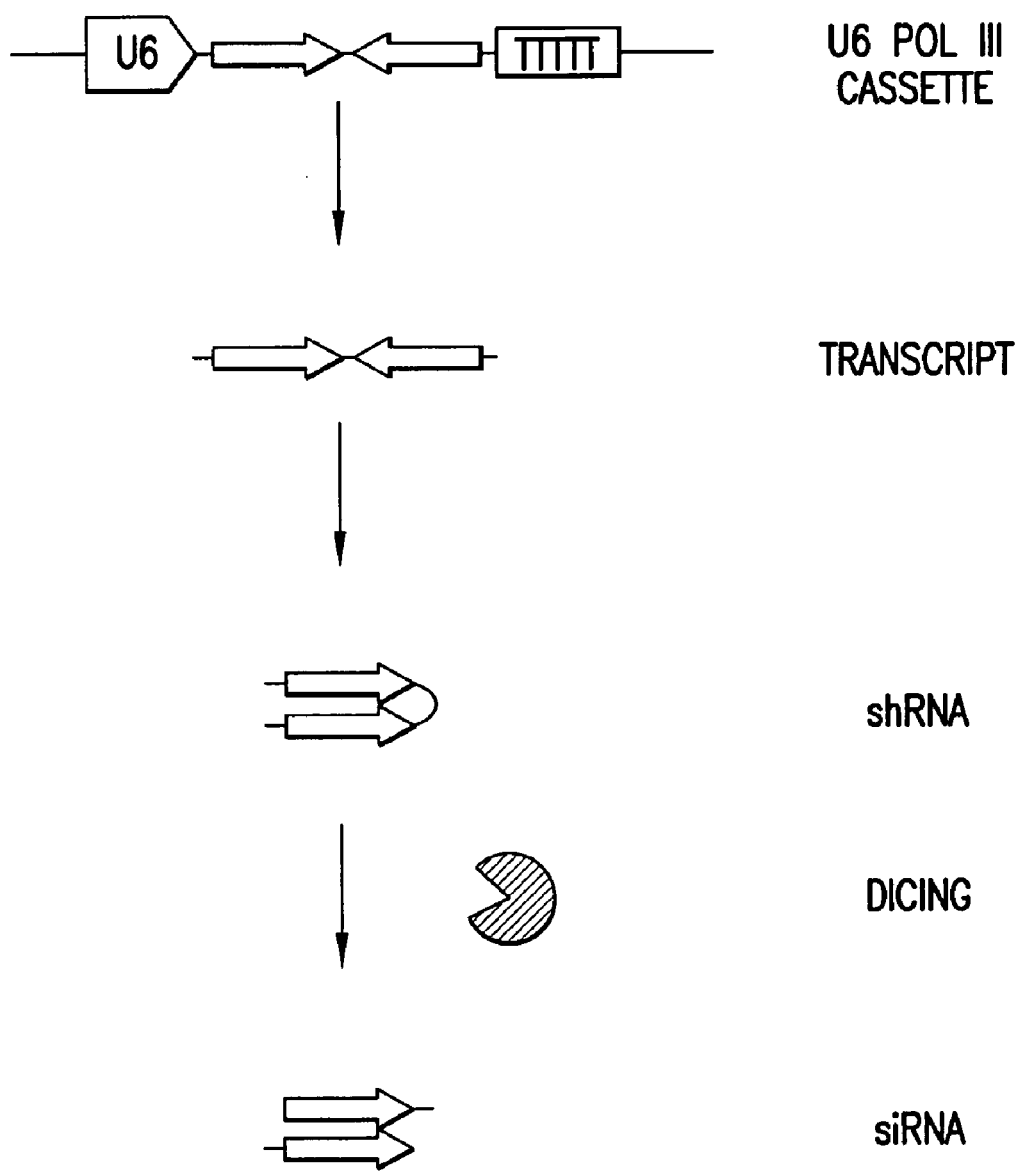
FIG. 27 depicts U6 RNAi.

MicroRNA molecules are molecules which are structurally similar to shRNA molecules but, typically, contain one or more mismatches or insertion/deletions in their regions of sequence complementary. Hundreds of miRNAs have been identified in *C. elegans*, flies and humans. *C. elegans* miRNA, lin-4 and let-7, have been identified to regulate developmental timing and inhibit expression of targeted genes. Examples of miRNA regulation from yeast to humans includes regulation of chromatin structure in yeast and tumor suppressor genes in humans. At least some microRNA molecules are transcribed as polycistrons of about 400, which are then processed to RNA molecules of about 70 nucleotides. These double stranded 70 mers are then processed again, presumably by the enzyme Dicer, to two RNA molecules which are about 22 nucleotides in length and often have one or more (e.g., one, two, three, four, five, etc.) internal mismatches in their regions of sequence complementarity. (See FIG. 25) (Lee et al., *EMBO* 21:4663-4670 (2002). The miRNA can enter a miRNA ribonucleoprotein particle (miRNP) similar to siRNA entering into the RISC protein complex (FIG. 14) (Dykxhoorn, Novina and Sharp, Nature Reviews, Vol. 4, (June 2003)). The binding of miRNA/siRNAs of perfect complementarity to a target results in mRNA degradation; single base mismatches can block translation. The invention also includes, for example, uses of microRNA molecules and nucleic acid molecules which encode microRNA molecules which are similar to the uses described herein for shRNA and non-hairpin double stranded RNA molecules.

Small Temporally Regulated RNAs (stRNAs)

Another group of small RNAs that may be produced via the methods of the present invention are the small temporally regulated RNAs (stRNAs). In general, stRNAs comprise from about 20 to about 30 nt (Banerjee and Slack, *Bioessays* 24:119-129 (2002)), although stRNAs of any size are also suitable for use in accordance with the invention. Unlike siRNAs, stRNAs downregulate expression of a target mRNA after the initiation of translation without degrading the mRNA.

The nucleic acids used in accordance with the present invention can be conveniently and routinely made through the well-known technique of solid-phase synthesis. Equipment for such synthesis is sold by several vendors including, for example, Applied Biosystems (Foster City, Calif.). Other methods for such synthesis that are known in the art may additionally or alternatively be employed. It is well-known to use similar techniques to prepare oligonucleotides such as the phosphorothioates and alkylated derivatives. By way of non-limiting example, see, e.g., U.S. Pat. Nos. 4,517,338, and 4,458,066; Lyer R P, et al., *Curr. Opin. Mol. Ther.* 1:344-358 (1999); and Verma S, and Eckstein F., *Annual Rev. Biochem.* 67:99-134 (1998), the disclosures of all of which are incorporated herein by reference in their entireties.

The present invention also provides methods for the production of gene knockout/knockdown cells and cells lines, as well as genetically modified transgenic animals.

In such suitable embodiments, the present invention provides methods of regulating the expression of one or more genes in a cell or an animal using interfering RNA, comprising: (a) identifying one or more target nucleic acid sequences; (b) preparing one or more nucleic acid molecules which encode one or more interfering RNAs, wherein the interfering RNAs bind to the one or more target nucleic acid sequences; (c) combining in vitro or in vivo, (i) the one or more first nucleic acid molecules encoding one or more interfering RNAs that have one or more sticky ends that have been generated by one or more restriction enzymes (e.g. type IIs restriction enzymes); and (ii) one or more second nucleic acid molecules comprising one or more ends which are compatible with the one or more sticky ends on the first nucleic acid molecule(s), and optionally comprising one or more selectable markers; (d) incubating the combination under conditions sufficient to join one or more of the nucleic acid molecules encoding the interfering RNAs and one or more of the second nucleic acid molecules, thereby producing one or more desired product nucleic acid molecules; and (e) inserting the one or more interfering RNA expression vectors into the cell or one or more cells of the animal, under conditions such that the one or more interfering RNAs bind to the one or more target nucleic acid sequences, thereby regulating expression of the one or more targeted genes.

The related embodiments, the present invention also provides methods of regulating the expression of one or more genes in a cell or an animal using interfering RNA, comprising: (a) identifying one or more target nucleic acid sequences; (b) preparing one or more nucleic acid molecules which comprise one or more interfering RNAs, wherein the interfering RNAs bind to the one or more target nucleic acid sequences; (c) combining in vitro or in vivo, (i) the one or more first nucleic acid molecules comprising one or more interfering RNAs flanked by one or more first restriction sites (e.g. one or more type IIs restriction enzyme recognition sites); (ii) one or more second nucleic acid molecules comprising one or more second restriction sites (e.g. one or more type IIs restriction enzyme recognition sites) and optionally comprising one or more selectable markers; and (iii) one or more site-specific restriction enzymes (e.g. one or more type IIs restriction enzymes); (d) incubating the combination under conditions sufficient to join one or more interfering RNAs and one or more of the second nucleic acid molecules, thereby producing one or more desired product nucleic acid molecules; and (e) inserting the one or more interfering RNA expression vectors into the cell or one or more cells of the animal, under conditions such that the one or more interfering RNAs bind to the one or more target nucleic acid sequences, thereby regulating expression of the one or more targeted genes.

The nucleic acid molecules of the invention can also be used to produce transgenic organisms (e.g., animals and plants). Animals of any species, including, but not limited to, mice, rats, rabbits, hamsters, guinea pigs, pigs, micro-pigs, goats, sheep, cows and non-human primates (e.g., baboons, monkeys, and chimpanzees) may be used to generate transgenic animals. Further, plants of any species, including but not limited to *Lepidium sativum, Brassica juncea, Brassica oleracea, Brassica rapa, Acena sativa, Triticum aestivum, Helianthus annuus,* Colonial bentgrass, Kentucky bluegrass, perennial ryegrass, creeping bentgrass, Bermudagrass, Buffalograss, centipedegrass, switch grass, Japanese lawngrass, coastal panicgrass, spinach, sorghum, tobacco and corn, may be used to generate transgenic plants.

Any technique known in the art may be used to introduce nucleic acid molecules of the invention into organisms to produce the founder lines of transgenic organisms. Such techniques include, but are not limited to, pronuclear microinjection (Paterson et al., *Appl. Microbiol. Biotechnol.* 40:691-698 (1994); Carver et al., *Biotechnology (NY)* 11:1263-1270 (1993); Wright et al., *Biotechnology (NY)* 9:830-834 (1991); and Hoppe et al., U.S. Pat. No. 4,873,191 (1989)); retrovirus mediated gene transfer into germ lines (Van der Putten et al., *Proc. Natl. Acad. Sci., USA* 82:6148-6152 (1985)), blastocysts or embryos; gene targeting in embryonic stem cells (Thompson et al., *Cell* 56:313-321 (1989)); electroporation of cells or embryos (Lo, *Mol. Cell. Biol.* 3:1803-1814 (1983)); introduction of the polynucleotides of the invention using a gene gun (see, e.g., Ulmer et al., *Science* 259:1745 (1993); introducing nucleic acid constructs into embryonic pluripotent stem cells and transferring the stem cells back into the blastocyst; and sperm-mediated gene transfer (Lavitrano et al., *Cell* 57:717-723 (1989); etc. For a review of such techniques, see Gordon, "Transgenic Animals," *Intl. Rev. Cytol.* 115:171-229 (1989), which is incorporated by reference herein in its entirety. Further, the contents of each of the documents recited in this paragraph is herein incorporated by reference in its entirety. See also, U.S. Pat. No. 5,464,764 (Capecchi et al., Positive-Negative Selection Methods and Vectors); U.S. Pat. No. 5,631,153 (Capecchi et al., Cells and Non-Human Organisms Containing Predetermined Genomic Modifications and Positive-Negative Selection Methods and Vectors for Making Same); U.S. Pat. No. 4,736,866 (Leder et al., Transgenic Non-Human Animals); and U.S. Pat. No. 4,873,191 (Wagner et al., Genetic Transformation of Zygotes); each of which is hereby incorporated by reference in its entirety.

Any technique known in the art may be used to produce transgenic clones containing nucleic acid molecules of the invention, for example, nuclear transfer into enucleated oocytes of nuclei from cultured embryonic, fetal, or adult cells induced to quiescence (Campell et al., *Nature* 380:64-66 (1996); Wilmut et al., *Nature* 385:810-813 (1997)), each of which is herein incorporated by reference in its entirety).

The present invention provides for transgenic organisms that carry nucleic acid molecules of the invention in all their cells, as well as organisms which carry these nucleic acid molecules, but not all their cells, i.e., mosaic organisms or chimeric. The nucleic acid molecules of the invention may be integrated as a single copy or as multiple copies such as in concatamers, e.g., head-to-head tandems or head-to-tail tandems. The nucleic acid molecules of the invention may also be selectively introduced into and activated in a particular cell type by following, for example, the teaching of Lasko et al. (Lasko et al., *Proc. Natl. Acad. Sci. USA* 89:6232-6236 (1992)). The regulatory sequences required for such a cell-type specific activation will depend upon the particular cell type of interest, and will be apparent to those of skill in the art. When it is desired that nucleic acid molecules of the invention be integrated into the chromosomal site of the endogenous gene, this will normally be done by gene targeting. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. Nucleic acid molecules of the invention may also be selectively introduced into a particular cell type, thus inactivating the endogenous gene in only that cell type, by following, for example, the teaching of Gu et al. (Gu et al., *Science* 265:103-106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic organisms have been generated, the expression of the recombinant gene may be assayed utilizing standard techniques. Initial screening may be accomplished by Southern blot analysis or PCR techniques to analyze organism tissues to verify that integration of nucleic acid molecules of the invention has taken place. The level of mRNA expression of nucleic acid molecules of the invention in the tissues of the transgenic organisms may also be assessed using techniques which include, but are not limited to, Northern blot analysis of tissue samples obtained from the organism, in situ hybridization analysis, and reverse transcriptase-PCR (rt-PCR). Samples of tissue may which express nucleic acid molecules of the invention also be evaluated immunocytochemically or immunohistochemically using antibodies specific for the expression product of these nucleic acid molecules.

Once the founder organisms are produced, they may be bred, inbred, outbred, or crossbred to produce colonies of the particular organism. Examples of such breeding strategies include, but are not limited to: outbreeding of founder organisms with more than one integration site in order to establish separate lines; inbreeding of separate lines in order to produce compound transgenic organisms that express nucleic acid molecules of the invention at higher levels because of the effects of additive expression of each copy of nucleic acid molecules of the invention; crossing of heterozygous transgenic organisms to produce organisms homozygous for a given integration site in order to both augment expression and eliminate the need for screening of organisms by DNA analysis; crossing of separate homozygous lines to produce compound heterozygous or homozygous lines; and breeding to place the nucleic acid molecules of the invention on a distinct background that is appropriate for an experimental model of interest.

Transgenic and "knock-out" organisms of the invention have uses which include, but are not limited to, model systems (e.g., animal model systems) useful in elaborating the biological function of expression products of nucleic acid molecules of the invention, studying conditions and/or disorders associated with aberrant expression of expression products of nucleic acid molecules of the invention, and in screening for compounds effective in ameliorating such conditions and/or disorders.

As one skilled in the art would recognize, in many instances when nucleic acid molecules of the invention are introduced into metazoan organisms, it will be desirable to operably link sequences which encode expression products to tissue-specific transcriptional regulatory sequences (e.g., tissue-specific promoters) where production of the expression product is desired. Such promoters can be used to facilitate production of these expression products in desired tissues. A considerable number of tissue-specific promoters are known in the art. Further, methods for identifying tissue-specific transcriptional regulatory sequences are described elsewhere herein.

The present invention also provides isolated nucleic acids comprising: (a) one or more sticky ends that have been generated by one or more restriction enzymes (e.g. one or more type IIs restriction enzymes); and (b) optionally one or more selectable markers. The present invention further provides isolated nucleic acids comprising: (a) one or more restriction sites (e.g. one or more type IIs restriction enzyme recognition sites); and (b) optionally one or more selectable markers. As noted above, selectable markers for use in the isolated nucleic acids of the present invention comprise antibiotic resistance genes and toxic genes. As also described above, the isolated nucleic acids molecules of the present invention may also comprise one or more recombination sites, and one or more topoisomerase recognition sites and/or one or more topoisomerases. In suitable embodiments, the topoisomerase recognition site, if present, may optionally be flanked by two or more recombination sites.

In another embodiment, the present invention provides isolated nucleic acids comprising: (a) one or more sticky ends that have been generated by one or more restriction enzymes (e.g. one or more type IIs restriction enzymes); and (b) one or more recombination sites. In yet another embodiment, the present invention provides isolated nucleic acids comprising: (a) one or more restriction sites (e.g. one or more type IIs restriction enzyme recognition sites); and (b) one or more recombination sites. Suitable recombination sites include, but are not limited to, attB sites, attP sites, attL sites, attR sites, lox sites, psi sites, tnpI sites, dif sites, cer sites, frt sites, and mutants, variants and derivatives thereof. In suitable embodiments, the isolated nucleic acid molecules of the present invention may optionally comprise one or more selectable markers, one or more topoisomerase recognition sites and/or one or more topoisomerases. In suitable embodiments, the topoisomerase recognition site, if present, may flanked by two or more recombination sites. In additional embodiments, the one or more recombination sites may flank one of more restriction sites (e.g. one or more type IIs sites) and/or the one or more selectable markers, if present.

The present invention also provides vectors comprising: (a) one or more desired nucleic acid segments; (b) optionally one or more toxic genes; and (c) one or more restriction sites (e.g. one or more type IIs restriction enzyme recognition sites). Desired nucleic acid segments include, but are not limited to one or more genes, and one or more promoters. Suitable restriction sites include type IIs restriction enzyme recognition sites, such as those sites described above. The vectors of the present invention may also comprise one or more recombination proteins, and one or more topoisomerase recognition sites and/or one or more topoisomerases. In suitable embodiments, the topoisomerase recognition site, if present, may flanked by two or more recombination sites. The vectors of the present invention optionally comprise suitable toxic genes, as described above. The vectors of the present invention may also optionally include one or more selectable marker as described throughout the specification. In another suitable embodiment, the vectors of the present invention may be "precut" by a restriction enzyme (e.g. a type IIs restriction enzyme). This precut vector may then be used to clone one more second nucleic acid molecules which may comprise sticky ends compatible with the vector, or optionally, may comprise on or more restriction sites (e.g. one or more type IIs restriction enzyme recognition sites).

The present invention also provides methods of expressing and isolating nucleic acid molecules and proteins comprising: (a) obtaining one or more isolated nucleic acid molecules of the present invention; (b) introducing the isolated nucleic acid molecule into a host cell; (c) incubating the host cell under conditions sufficient to allow expression of a nucleic acid molecule or a protein encoded by the isolated nucleic acid molecule; and (d) isolating the expressed nucleic acid molecule or expressed protein. Host cells suitable for use in accordance with this aspect of the invention are described elsewhere herein. Suitable incubation conditions are well known in the art and are described in Freshney, R. I., "Culture of Animal Cells: A Manual of Basic Technique," Alan R. Liss, Inc, New York (1983) and Maniatis et al., Molecular Cloning: A Laboratory Manual, Cold Spring Harbor Laboratory, Cold Spring Harbor, N.Y. (1982) and comprise incubating a host cell in a suitable growth medium with sufficient nutrients (e.g. Eagle's Minimum Essential Medium, DMEM: F12 Medium, RPMI-1640 Medium, Dulbecco's Modified Eagle's Medium, and the like) at an appropriate temperature (about 37° C.). Methods of isolation of nucleic acid molecules and expressed proteins from host cells are also well known in the art and described in Manitais id. and similar texts.

The expressed nucleic acid molecules may be suitable for use as interfering RNA as described above. As described throughout the specification, the expressed nucleic acid molecules will often not comprise extraneous, undesired nucleic acids, for example nucleic acids encoded by the one or more restriction sites (e.g. one or more type IIs recognition sites). Similarly, the proteins produced via the methods of the present invention may not comprise extraneous, undesired amino acids, for example amino acids encoded by the one or more restriction sites (e.g. one or more type IIs recognition sites).

The present invention also provides for methods of expressing desired nucleic acid segments comprising: obtaining a product nucleic acid molecule of the invention and incubating the nucleic acid molecule under conditions (in vitro or in vivo) such that the desired product nucleic acid molecule is transcribed and then translated. Incubation conditions for these methods of the invention are well known in the art as noted above.

The present invention also provides for methods of expressing desired nucleic acid segments comprising: (a) obtaining a vector of the present invention; (b) introducing the vector into a host cell; and (c) incubating the host cell under conditions sufficient to allow expression of a desired nucleic acid segment encoded by the vector. Incubation conditions for these methods of the invention are well known in the art as noted above.

Another embodiment of the present invention provides compositions comprising the elements described above that are involved in the various cloning methods of the invention. Such compositions comprise: (a) one or more first nucleic acid molecules comprising one or more sticky ends that have been generated by a restriction enzyme (e.g. one or more type IIs restriction enzymes); (b) one or more second nucleic acid molecules comprising one or more sticky ends which are compatible with the one more sticky ends one the first nucleic acid molecule and, optionally, one or more selectable markers. Suitable restriction enzymes include those described throughout the specification, including, type IIs restriction enzyme recognition sites. The nucleic acids comprised in any of the compositions of the present invention may optionally further comprise one or more selectable markers, one or more recombination sites, one or more topoisomerase recognition sites and/or one or more topoisomerases and described above. The compositions may comprise one or more recombination proteins. Suitable recombination proteins include, but are not limited to, those described throughout the specification.

Another embodiment of the present invention provides compositions comprising the elements described above that are involved in the various cloning methods of the invention. Such compositions comprise: (a) one or more first nucleic acid molecules comprising at least one nucleic acid segment flanked by one or more first restriction sites (e.g. one or more type IIs restriction enzyme recognition sites); (b) one or more second nucleic acid molecules comprising one or more second restriction sites (e.g. one or more type IIs restriction enzyme recognition sites) and optionally one or more selectable markers; and (c) one or more restriction enzymes (e.g. one or more type IIs restriction enzymes) that are specific for said first and/or second restriction enzyme recognition sites. Suitable restriction enzymes include those described throughout the specification, including, type IIs restriction enzyme recognition sites. The nucleic acids comprised in any of the compositions of the present invention may optionally further comprise one or more selectable markers, one or more recombination sites, one or more topoisomerase recognition sites and/or one or more topoisomerases and described above. The compositions may comprise one or more recombination proteins. Suitable recombination proteins include, but are not limited to, those described throughout the specification.

The present invention also provides kits comprising the isolated nucleic acids and/or vectors of the present invention. These kits are useful for practicing the various methods of the invention. Kits may comprise one or more first nucleic acid molecules and one or more second nucleic acid molecules. The first nucleic acid molecule may be an isolated nucleic acid molecule of the invention and the second nucleic acid molecule may be a vector of the present invention.

Kits of the invention may contain any number of components but typically will contain at least two components. Kits according to this aspect of the invention may comprise one or more containers, which may contain one or more components' selected from the group consisting of one or more nucleic acid molecules or vectors of the invention, one or more primers, one or more polymerases, one or more reverse transcriptases, one or more recombination proteins, one or more restriction enzymes (e.g. one or more type IIs restriction enzymes, or other enzymes for carrying out the methods of the invention), one or more topoisomerases, one or more buffers, one or more detergents, one or more restriction endonucleases, one or more nucleotides, one or more terminating agents (e.g., ddNTPs), one or more transfection reagents, pyrophosphatase, and the like. The kits of the invention may also comprise instructions for carrying out methods of the invention.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Expression of Interfering RNA Using a Seamless Cloning Vector

The expression of short interfering hairpin RNA molecules (shRNA) in vivo can decrease the expression of genes with complementary sequences by RNA interference (RNAi) as described previously. The seamless cloning vector described here (pENTR/U6) allows for rapid and efficient cloning of double-stranded oligonucleotide pairs (~47 bp) coding for a desired shRNA target sequence into a Pol III U6 expression cassette. The resulting shRNA vector contains an RNAi cassette flanked by attL sites. Therefore, the pENTR/U6 shRNA vectors can be used directly for transient transfection to test various shRNA target sequences, as well as to transfer the best shRNA cassettes to Lenti and Adenoviral DEST vectors for delivery into "hard to transfect" cells.

Kit Components.

Purified, BsaI-linearized pENTR/U6.2 (once it is cut with BsaI, i.e. the linear vector is called pENTR/U6) (Catalog No. K4945-00 and K4944-00, Invitrogen, Corp., Carlsbad, Calif.) Annealed lamin A/C control oligos: Top 5'-CACCGTGT-TCTTCTGGAAGTCCAGCGAACTGGACT-TCCAGAAGA ACA (SEQ ID NO:9), Bottom 5'-AAAAT-GTTCTTCTGGAAGTCCAGTTCGCTGGACTTCCAGA AGAACA C (SEQ ID NO:10), Sequencing primers: U6 forward 5'-GGACTATCATATGCTTACCG (SEQ ID NO:11), M13 reverse 5'-CAGGAAACAGCTATGAC (SEQ ID NO:12) (Catalog No. N530-2, Invitrogen, Corp., Carlsbad, Calif.), T4 DNA ligase (Catalog No. 15224-025, Invitrogen, Corp., Carlsbad, Calif.) 5×T4 DNA ligase buffer (Catalog No. Y90001, Invitrogen, Corp., Carlsbad, Calif.), OneShot Top10 cells (Catalog No. C4040-03, Invitrogen, Corp., Carlsbad, Calif.). Thus, exemplary kits of the invention may comprise one, more, or all of these components.

Vector Construction.

Entry vector. The nucleic acid sequence of pENTR U6.2 (BsaI-ccdB) is shown in Table 5, SEQ. ID. NO:1. The U6 promoter sequence was PCR amplified from genomic DNA (primers: 5'-AAGGTCGGG CAGGAAGAGGG-3' (SEQ ID NO:13); 5'-AGCGAGCACGGTGTTTCGTC-3' (SEQ ID NO:14)) and TOPO cloned into pCR2.1/TOPO (included in kits, Catalog Nos. K4500-01, K4500-40, K4550-01, K4550-40, K4560-01, K4560-40, K4520-01 and K4520-40, Invitrogen, Corp., Carlsbad, Calif.). The promoter sequence was subsequently PCR amplified with the same primer sequences but with Asp718 and NotI sites appended to the primer 5' ends (5'GTGGGTACCAAGGTCGGGCAGGAAG AGGG-3' (SEQ ID NO:15; 5'-GTGGCGGCCGCGGTGTTTCGTC-CTTTCCACAAG-3' (SEQ ID NO:16)). This PCR product was cloned by Asp718-NotI sticky end ligation into an Entry vector with the pENTR/1a polylinker (Catalog No. 11813, Invitrogen, Corp., Carlsbad, Calif.) and pDONR/221 backbone (Catalog No. 12536-017, and provided in kits 12537-023, 12538-013, 12535-019, Invitrogen, Corp., Carlsbad, Calif.). The ccdB gene was amplified from pLenti6N5/DEST (Catalog Nos. V496-10 and K4960-00, Invitrogen, Corp., Carlsbad, Calif.) (primers: 5'-GTGGCGGCCGCAAA-GATCCTCCAGTGGATCCGGCTTAC TAAAAG-3' (SEQ ID NO:17); 5'GTGCTCGAGAAAAAAGTCGACACG-GAGCCCTCC AGTTATATTCCCCAGAACATCAGG-3' (SEQ ID NO:18)) and cloned into the above vector at the NotI and XhoI sites. These primers introduced BpmI restriction enzyme sites in the proper position at the ends of the PCR product and a 6 bp polyT Pol III terminator.

To engineer the BsaI vector, a double stranded oligo containing a BsaI site and NotI site (5'GAGACCGCGGCCGCT-TCTCGAGGTCTCATT (SEQ ID NO:19)+5'TGAGAC-CTCGA GAAGCGGCCGCGGTCTCCG-3' (SEQ ID NO:20)) was cloned into BpmI-digested plasmid. The resulting plasmid was digested with NotI and XbaI and ligated to a new ccdB region PCR amplified (primers: 5'CACGCGGC-CGCTGGATCCGGCTTACTAAAAG-3' (SEQ ID NO:21); 5'CACTCTAGAA AAAATGAGACCTTATATTCCCCA-GAACATCAGG-3' (SEQ ID NO:22)) with a NotI site on one end and a BsaI site, 6 bp polyT Pol III terminator, and XbaI site at the other. The final construct is named pENTR/U6.2 (BsaI-ccdB).

LacZ expression control vector. The LacZ expression control plasmid, pcDNA2.2 MS/GW/LacZ was made using Multi-site Gateway (CMVlacZV5). pENTR5'-CMV, pENTR-LacZ and pENTR/V5TKpolyA were mixed with the DEST R4R3 plasmid using LR Plus Clonase. The three plasmids in the Multi-site reaction were all created by a standard Gateway recombination reaction: 1) the CMV promoter was amplified from pcDNA3.1 (Catalog No. V790-20 and V795-20, Invitrogen, Corp., Carlsbad, Calif.) using primers flanked with attB4 and attB1 sequences and recombined with pDonr 5'(P4-PIR) to form pENTR5"-CMV. 2) The LacZ gene was amplified from pcDNA3.1-LacZ using attB1 and attB2 flanking primers and recombined with pDonr 221 to create pENTR-LacZ, and, 3) the V5-TKpolyA element was amplified from pcDNA3.2 using attB2 and attB3 primers and recombined with pDonr3'(P2-P3R).

Preparation of linear pENTR/U6.2 ready for cloning. pENTR/U6.2 in DB3.1 cells was grown in LB media with 50 µg/ml kanamycin. Plasmid DNA was purified by SNAP midi prep with a yield of 67 µg/50 ml of culture. Ten µg of vector was digested with BsaI at 50° C. in 200 µl with 5 units of BsaI/µg of DNA for 2 hrs. After addition of 1.5 vol of SNAP miniprep binding buffer, the reaction was added to a SNAP miniprep column, washed according to the SNAP protocol for miniprep DNA, and eluted in 100 µl ddH2O and stored at −20° C.

ShRNA Oligonucleotide Annealing. DNA oligonucleotides of 46-53 nt were produced with desalt purification only. Individual oligos were diluted in ddH20 to a final concentration of 200 µM as verified by spectrophotometric analysis at $OD_{260}$. Complementary oligos were mixed to the final desired concentration with either: 1) TE (10 mM Tris pH 8.0, 1 mM EDTA), 2) 10× Annealing Buffer and ddH20 such that the final, 1× buffer was 10 mM Tris pH 8.0, 100 mM NaCl, 1 mM EDTA, or 3) the same buffer as in 2 but with a final concentration of 10 mM $MgCl_2$. (For example, to create a 50 µM stock of a ds-oligo in 200 µl, 5 µl of each 200 µM ss complementary oligo was mixed with 2 µl of 10× Annealing buffer and 8 µl of ddH20). Mixed oligo pairs were heated and cooled in either an MJ thermocycler (94° C. for 2 min, then decreased by 0.1° C. every second to 25° C., and stored at 4° C.) or incubation in a 95° C. bath for 4 min, then cooling to room temperature over 15 min before putting the sample on ice. Annealed ds-oligos were diluted to the desired concentration with TE at room temperature.

Cloning target site DNA oligos into pENTR/U6. BsaI cut pENTR/U6.2 and ds-oligos were incubated in a 20 µl reaction using 5 times ligase buffer and 1 µl ligase for 5 min at room temperature. Two microliters of the ligation reaction were added to chemically competent Top10 One Shot cells (Catalog Nos. C4040-10, C4040-03, C4040-06, Invitrogen, Corp., Carlsbad, Calif., ~50 µl), incubated on ice for 20 min, heat shocked at 42° C. for 30 sec., and placed back on ice, followed by the addition of 250 µl SOC and incubation at 37° C. (shaking) for 1 hr. Ten to one hundred microliters of this transformation reaction were plated on LB Kan (50 µg/ml) agarose plates.

The number of colonies per plate was determined after an overnight incubation at 37° C. A supercoiled pUC19 (2 µl of a 10 pg/µl stock) transformation control was performed with each set of cells transformed; in this case the transformation efficiency is reported as number of colony forming units per microgram.

Sequence analysis of pENTR/U6 shRNA target clones. Plasmid DNA was isolated from pENTR/U6 clones using the SNAP mini prep kit (Catalog No. K1900-01, Invitrogen, Corp., Carlsbad, Calif.) under standard conditions. Two different primers were used for sequence analysis:

1) U6 forward, 5'-GGACTATCATATGCTTACCG (forward primer, binds in U6 promoter 55 bp from the 3' end of the U6 promoter) (SEQ ID NO:11)

2) M13 R, 5'-CAGGAAACAGCTATGC (reverse primer, binds "downstream" from the AttL2 site, 146 bp from the pol III termination) (SEQ ID NO:12)

Gateway L×R recombination. 150 ng of each pENTR/U6 shRNA clone and 150 ng of pLenti6/PL-DEST or 300 ng of pAD/PL-DEST (FIG. 10) (Catalog No. V494-20, Invitrogen, Corp., Carlsbad, Calif.) were incubated in a 20 µl reaction using the 5× buffer and 5×LR Clonase enzyme mix, and incubated at 25° C. for 1 hr. Two microliters of this L×R reaction were transformed into chemically competent cells as described above except that selection plates had 50 ug/ml ampicillin instead of kanamycin.

ShRNA Transfections.

All transfections were carried out in 24-well plates. For luciferase and β-galactosidase (β-gal) knockdown experiments, 600 ng of pENTR/U6-shRNA vectors were cotransfected with 100 ng each pcDNA5/FRT/luc and the pcDNA1.2/V5-GW/lacZ positive control plasmid into GripTite™ 293 cells (Catalog No. R795-07, Invitrogen, Corp., Carlsbad, Calif.) using Lipofectamine 2000™. Briefly, cells were plated the day before transfection in 0.5 ml medium lacking antibiotics at $2\times10^5$ cells per well. On the day of transfection, cells were typically 90-95% confluent. For each well, 2 µl of Lipofectamine 2000™ were diluted with 48 µl OptiMEM, incubated 5 min at room temperature, then mixed with DNAs diluted with OptiMEM to 50 µl. Complexes were incubated an additional 20 min at room temperature before addition to cells. Medium was changed 3 hr after transfection to minimize toxicity.

Luciferase and β-gal Assays.

After 48 hr, GripTite™ 293 cells were lysed in 0.5 ml luciferase lysis buffer (25 mM Tris-HCl pH 8.0, 0.1 mM EDTA pH 8.0, 10% glycerol, 0.1% Triton X-100) and subjected to a −80° C. freeze-thaw. 50 µl of each lysate was used in a luciferase luminescence assay (Promega) while another 10 ul was used in a β-gal luminescence assay (Tropix) according to the manufacturers' instructions.

Results

The vector pENTR/U6 is designed to express shRNA in mammalian cells for use in RNAi. (pENTR/U6.2 is the supercoiled vector containing the ccdB gene; once linearized with BsaI, the vector will be referred to as pENTR/U6.) pENTR/U6 allows the cloning of shRNA target sequences between the human U6 pol III promoter and a 6 T termination signal in a Gateway Entry (ENTR) vector. In this case, the entire RNAi cassette (U6 promoter, cloning site, and termination signals) is between the attL1 and attL2 recombination sites. Therefore, U6 driven expression of an shRNA is possible directly from ENTR vector and does not require subsequent L×R transfer to a DEST vector.

Vector Preparation.

pENTR/U6.2 (BsaI-ccdB) is digested with the type IIS restriction enzyme BsaI in preparation for cloning ds-oligos (~47mers) containing shRNA target sequences. Type IIs restriction enzymes cut outside of their recognition sequence and can therefore be used to create sticky ends of any sequence in the vector. In this case, the BsaI digest leaves the 4 nt 5' ssDNA end 3'-GTGG-5' at the end of the U6 promoter and the single stranded 3'-TTTT-5' at the other vector end (the first four Ts of the termination signal).

Digestion of the pENTR/U6.2 by BsaI generates three fragments (2850, 577, and 91 bp). The linearized cloning vector is 2850 bp; smaller fragments derive from the ccdB gene (ccdB has a BsaI site). Removal of the smaller fragments from the final vector prep is not required; however, the amount of the 91 bp fragment recovered from the SNAP purification can vary. Uncut pENTR/U6.2 or clones that have reassembled the functional ccdB gene will not propagate in Top10 cells. The cloning efficiency of either small fragment alone is very low due to non-compatible ends.

Insert Annealing

A five-minute bench top ligation and subsequent transformation is highly efficient at cloning dsDNA oligo shRNA target sequences—if the oligo inserts are properly annealed. A typical 46 nt ss-oligo is made of a 4 nt 5' cloning overhang followed by 19 nt of "sense" and a complementary 19 nt "antisense" sequence connected by short 4 nt "loop." Thus the oligos can form a ~19 bp DNA intra-molecular hairpin. Therefore, conditions must be optimized to favor intermolecular annealing between two different complementary oligos rather than the production of single-strand intramolecular hairpins. The formation of intermolecular ds-oligos can be accomplished by melting (heating to 94° C.) and cooling complementary oligos at high concentrations in the appropriate buffer.

Intermolecular double-stranded molecules can be formed in annealing buffers containing either 20 or 100 mM NaCl when the oligo concentration is 50 µM during the heating and cooling cycle. The ds-molecules can be separated from the single-stranded hairpins in an E-gel. Additionally, no difference was noted between using the Thermocycler or water bath protocols to melt/cool the reaction.

Upon closer examination of the salt and oligo concentration, a buffer without any NaCl (TE) would not support formation of ds-47mers even at 100 µM concentrations, adding $MgCl_2$ to 100 mM NaCl had no effect, and oligo concentrations of less the 50 µM were compromised in the amount of ds-47mers created.

Once created, the dsDNA 47mer shRNA inserts can be diluted in TE for cloning. After the ds-47mers are diluted, they are stable at 4° C. overnight, but will form single strand hairpins if melted, i.e. incubated at temps above 42° C.

Heating and cooling of shRNA target oligos at concentrations of 50 µM or greater in 10 mM Tris pH 8.0, 100 mM NaCl, 1 mM EDTA creates a mixture of ~50:50 ds/hairpin molecules which can be effectively cloned into BsaI linearized pENTR/U6 (see pENTRJU6 cloning, below).

Gateway ENTR Vector Testing.

The supercoiled pENTR/U6.2 (BsaI-ccdB) vector, prior to linearization for cloning, passes the criteria set for Gateway ENTR vectors (>10$^4$ killing by ccdB). Supercoiled pENTR/U6.2 was transformed into E. coli cells it should kill (Top10 and HB101 cells) as well as the DB3.1 cell line designed to propagate plasmids with the ccdB gene. pENTR/U6.2 transforms DB3.1 cells $1.3 \times 10^4$ times better than Top10s cells once the number of colonies per plate are adjusted for the different transformation efficiencies of the different cell lines (the Top10 cells were ~200 times more competent than the DB3.1 cells and ~400 times more competent than the HB101 cells).

When BsaI digestion of pENTR/U6.2 is complete, most of the supercoiled vector is linearized. Transformation of BsaI cut, SNAP purified pENTR/U6 vector only generated a small number of "background" colonies per plate in Top10 or DB3.1 cells. Eight colonies were obtained in DB3.1 cells and all looked like the parent sc pENTR/U6.2 by RFLP analysis (data not shown) indicating the BsaI digest is efficient and only a small fraction of the plasmids are left uncut after the 2 hr incubation. In Top10 cells only 4 colonies were obtained; RFLP analysis of these indicated two classes, neither of which was the parent plasmid (possibly pENTR/U6 closed without the ccdB gene and one fragment of the ccdB gene re-cloned).

pENTR-U6 Cloning.

A five-minute bench-top ligation is an easy and efficient method to clone shRNA target sequences into pENTR/U6. The cloning process was optimized over a wide range of vector concentrations (20 pg-5 ng) and insert concentrations (0.4 pg-10 ng) with the shRNA target sequence lacZ-19. All the optimization of the cloning reaction was done with ds-oligos annealed at a concentration of 50 µM prior to dilution in TE and transformation into chemically competent Top10 cells. Sequence analysis of the shRNA clones demonstrate that >90% have inserts in the correct orientation.

Greater than 15 other ds-oligo inserts, each with a different shRNA target sequence, have been cloned into pENTR/U6 under comparable conditions. In all cases, the number of colonies generated was similar to the numbers of colonies generated with the lacZ-19 ds-oligo. No significant difference has been noted in how different inserts clone into the pENTR/U6 vector.

Sequence Analysis.

The efficiency of cloning shRNA target-sequence inserts was determined by sequence analysis through shRNA target sequences. Analysis of the lacZ-19 shRNA target inserts cloned in pENTR/U6 under the recommended conditions, demonstrated that 100% (38/38) of the randomly selected clones have an insert cloned in the correct orientation.

Sequence analysis with the U6 forward primer provides excellent sequence through the cloned shRNA target sequence. It is designed for ease of analysis of the cloned oligos, binds the U6 promoter inside the attL sites 55 bases from the cloning junction, and allows for the analysis of the entire cloned insert with a 100 base "read" before the "downstream" attL2 site.

RNAi by Transient Transfections.

Figure 3A:
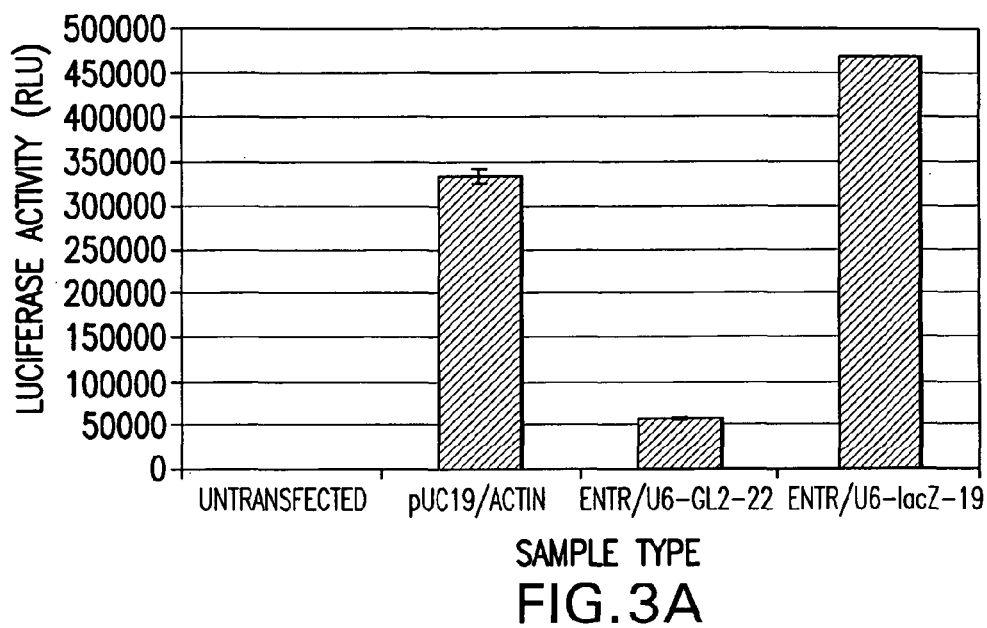
FIGS. 3A and 3B depict luciferase and β-gal suppression in GripTite™ 293 cells by transient cotransfection of reporters and pENTR/U6 vectors. A) Luciferase activities measured in lysates of cells: from left 1) untransfected, 2) cotransfected with luciferase and lacZ reporter genes plus a dummy plasmid (pUC19/actin), or 3-4) same as 2 except either pENTR/U6 targeting luciferase (GL2-22) or β-gal (lacZ-19) replace the pUC19/actin. B) β-gal activity measurements of the same lysates as in A. Activities are the average of duplicate wells. The standard error of the mean is indicated for each sample.
Figure 3B:
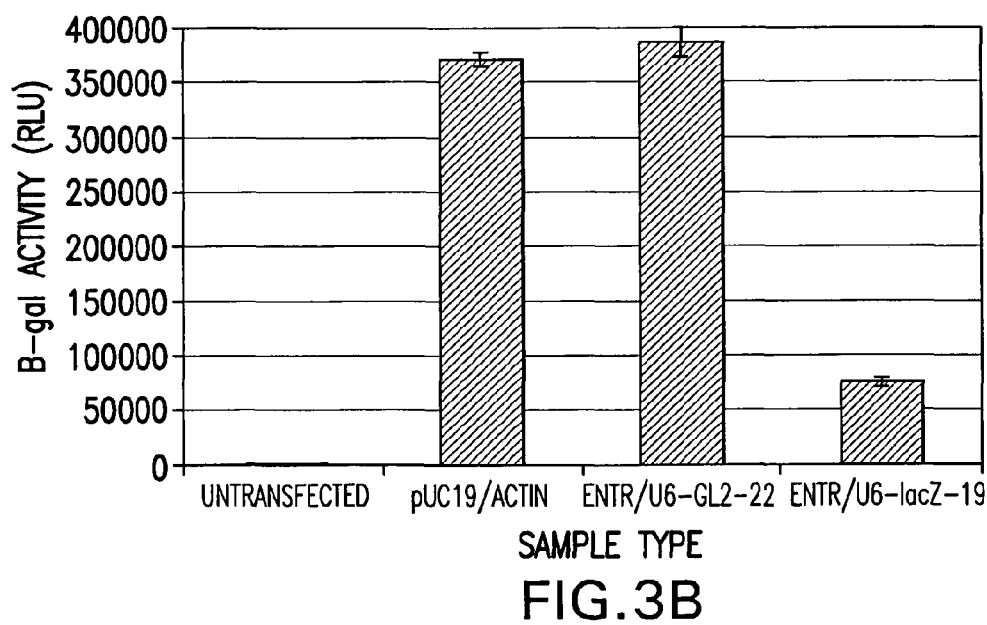

Post-transcriptional inhibition of luciferase (GL2) and lacZ expression was evident upon expression of shRNA targets from the pENTR/U6 vector (FIG. 3A). Specific inhibition is evident with pENTR/U6 shRNA clones targeting Luciferase and lacZ expression from co-transfected reporter constructs. The Luciferase pENTR/U6 GL2-22 construct inhibits expression of GL2 Luciferase but not lacZ (FIG. 3A); similarly, the pENTR/U6 with the lacZ-19 shRNA target sequence (the target provided as a control in this kit) inhibits lacZ expression from pcDNA1.21V5-GW/lacZ (the control expression vector for this kit)—but not Luciferase (FIG. 3B).

Figure 4A:
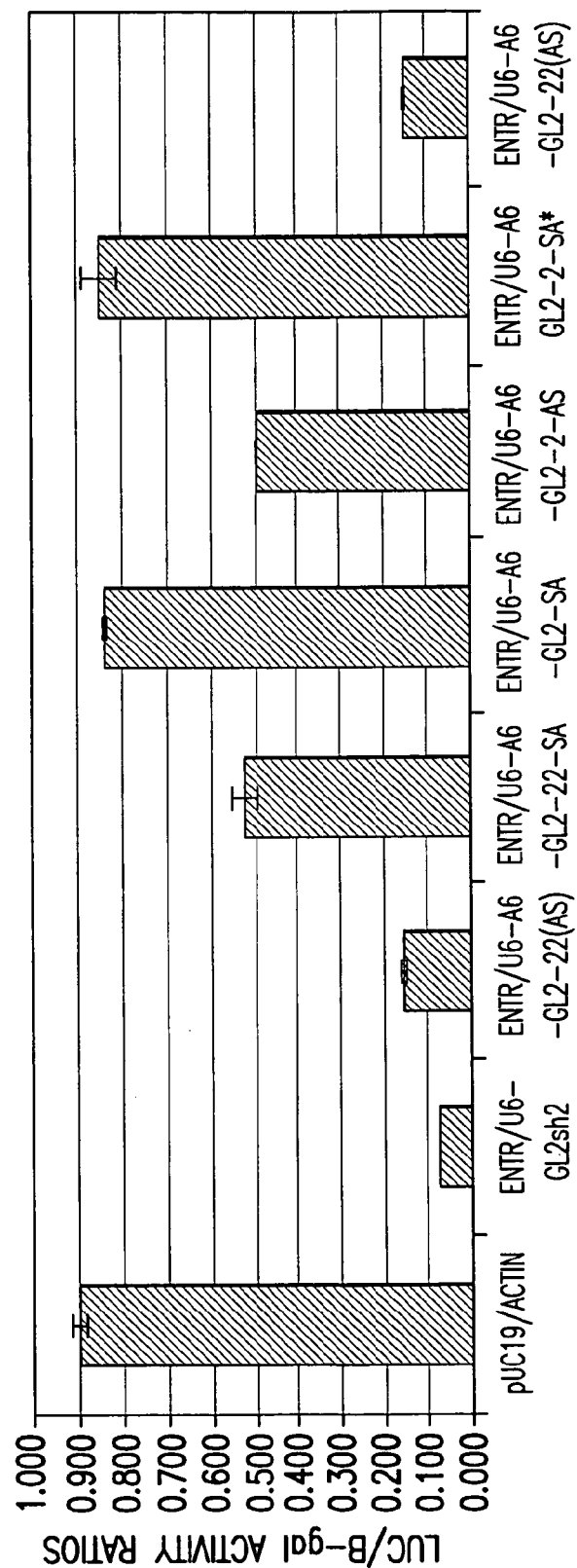
FIGS. 4A and 4B depicts RNAi of β-Gal and Luciferase activity from co-transfected reporter constructs by pENTR/U6 shRNA clones. Data are reported as the ratio of lacZ and Luciferase activity. Error bars are calculated from two independent samples. AS/SA indicates the orientation of the sense and anti-sense strand relative to the U6 promoter. A) Luciferase/β-gal activity after co-transfection with the indicated pENTR/U6 shRNA sequences targeting the Luciferase gene and a pUC19-actin control. pENTR/U6-A6-GL2-22 (AS) is the same construct used in FIG. 3. The asterisk (*) after ENTR/U6-A6-GL2-2-SA indicates a point mutation was identified in the shRNA target sequence clone used in this experiment. B) β-gal/Luciferase activity after co-transfection with various pENTR/U6 shRNA sequences targeting the LacZ gene. ENTR/U6-A6-lacZ-19 is the same construct used to generate the data presented in FIG. 3.
Figure 4B:
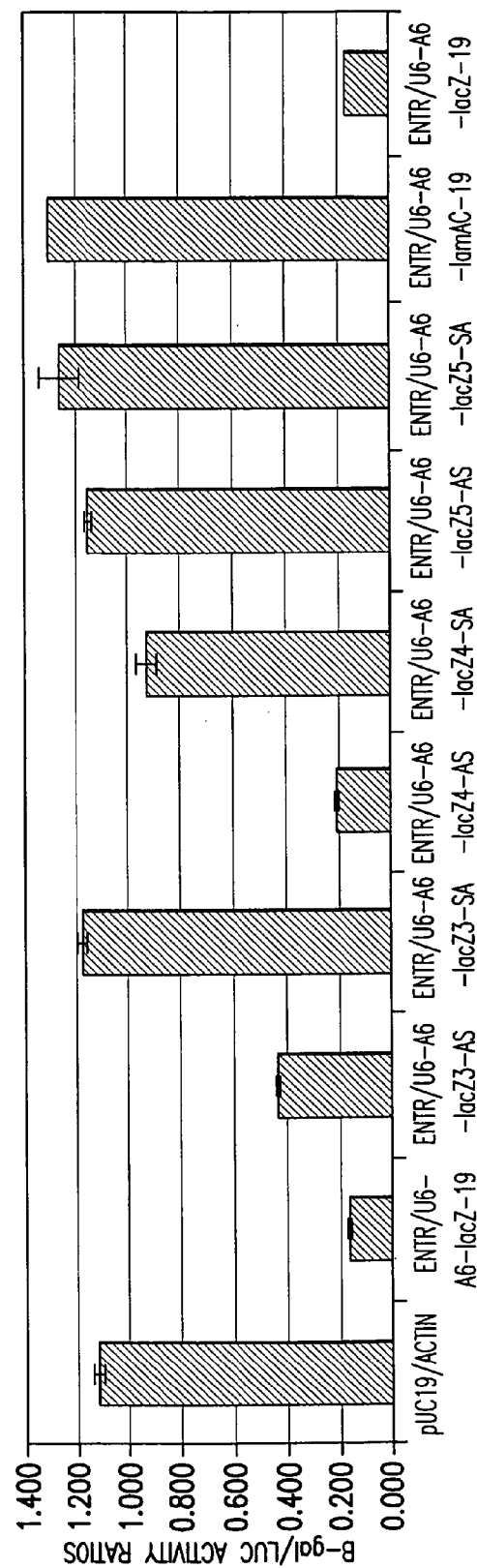

Similar inhibition of both lacZ and Luciferase is evident with shRNAs that target different sites, although not all shRNA sequences are effective (FIGS. 4A and 4B). The kit control lacZ-19 target site presented in FIG. 4B is the same shRNA target site used in FIG. 3B, and only the lacZ4-AS sequence inhibits expression to the same degree. The lacZ4-SA only moderately inhibits expression and the lacZ5 clones have little if any inhibitory effect. Similarly, the GL2sh2 and GL2-22 (AS) target sites are the most effective shRNA clones tested at inhibiting luciferase expression (FIGS. 4A and 4B). Interestingly, the sense to anti-sense orientation of the shRNA target sequence can make a considerable difference in the level of inhibition at a specific target (FIGS. 4A and 4B). However, the optimal orientation (sense-loop-antisense (SA) or antisense-loop-sense (AS)) is not clear; with Luciferase, the AS orientation was most effective, but with lacZ the SA orientation was most effective (FIG. 4A, ENTR/U6-A6-GL2-22 AS vs. SA, and FIG. 4B, ENTR/U6-A6-lacZ4-AS vs. SA).

Figure 5:
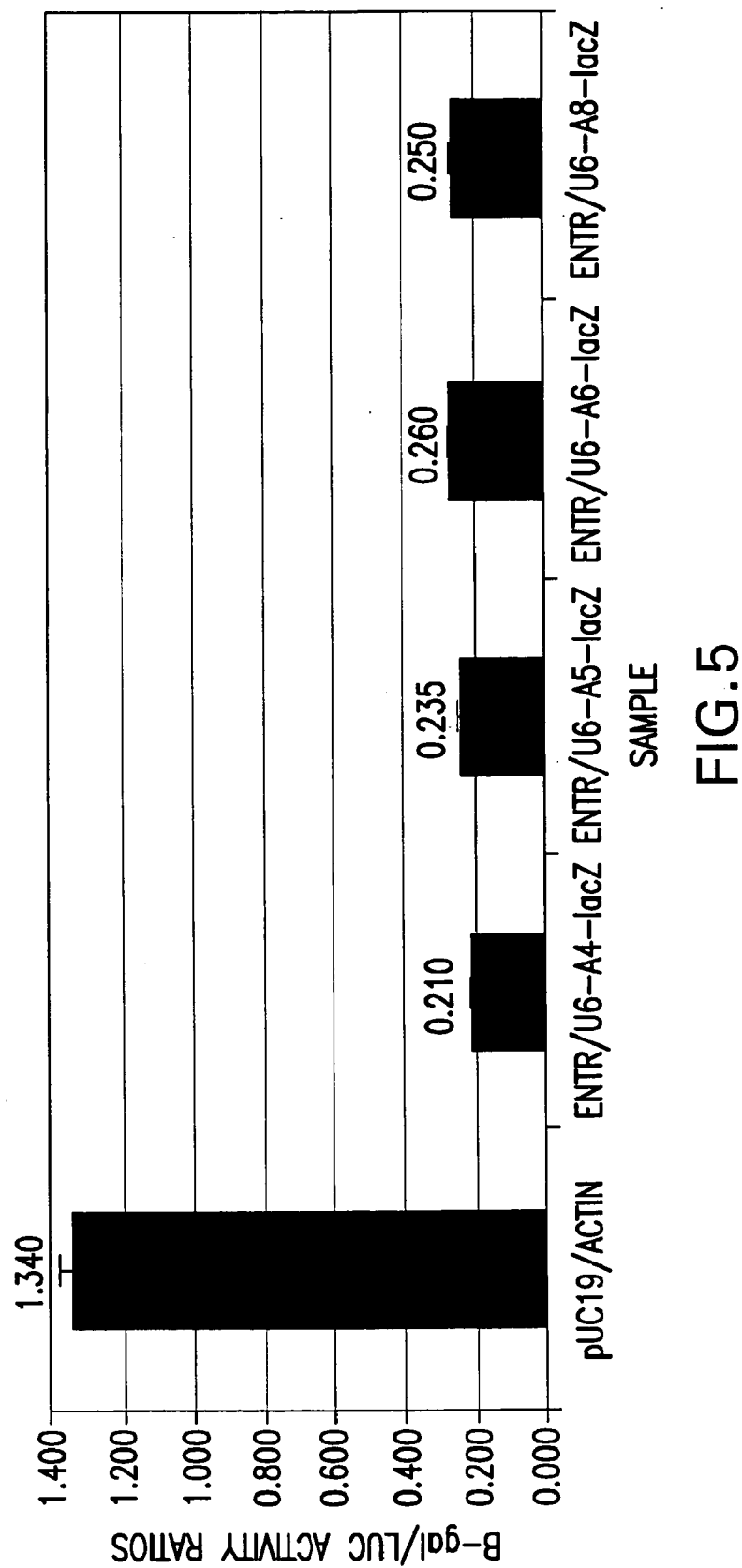
FIG. 5 depicts β-gal/Luciferase activity ratios after co-transfection reporter plasmids and pENTR/U6 LacZ-19 shRNA target clones with the indicated Terminator lengths. Terminators with 4, 5, 6 and 8 "Ts" were tested in the pENTR/U6.2 vector (A4-8).

Additionally, the lacZ-19 shRNA target sequence was tested in derivatives of the pENTR/U6 vector with terminators of 4-8 Ts. All the terminators behaved similarly (FIG. 5).

Gateway LxR Cross.

Figure 38:
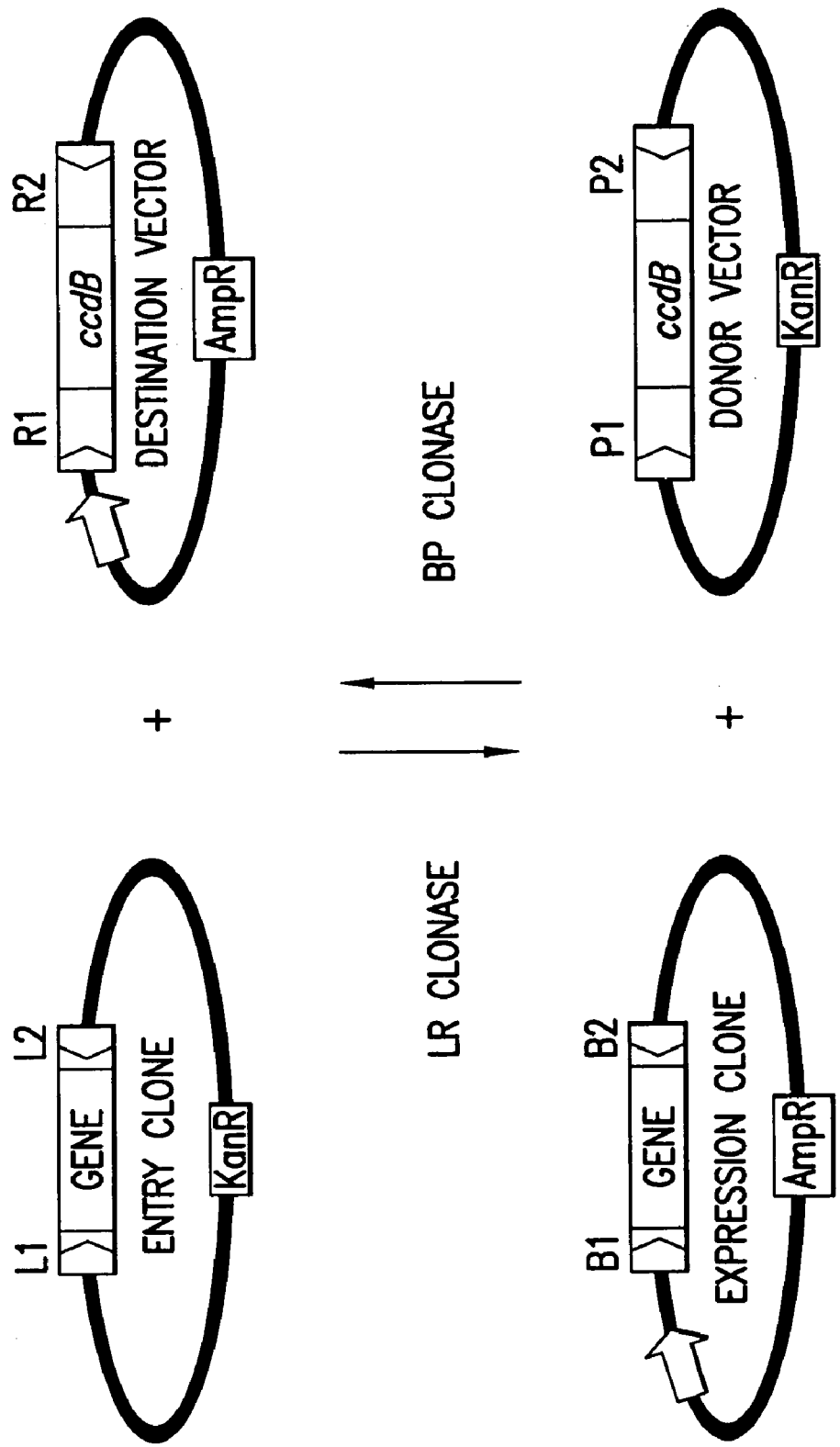
FIG. 38 depicts GATEWAY Cloning Technology.
Figure 39:
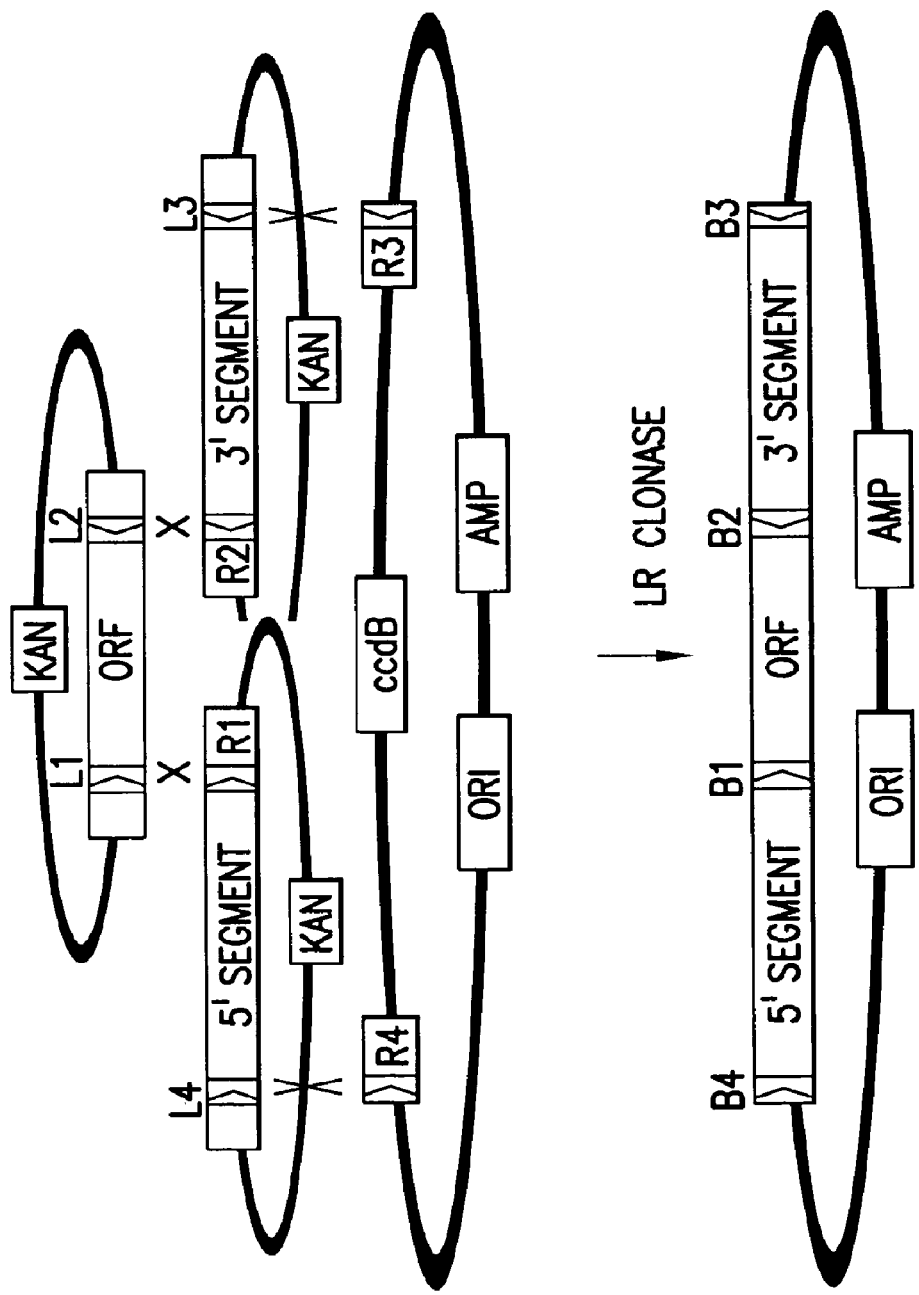
FIG. 39 depicts Assembly of Three DNA segments using Existing Entry Clones.

Any shRNA target sequence cloned into pENTR/U6 can easily be transferred as a U6 RNAi cassette to a Gateway DEST vector by attLxattR (LxR) recombination at the att sites. Following is a demonstration of the efficiency of LxR transfer. The lacZ-19 target sequence cloned into pENTR/U6 was transferred into pLenti6/PL-DEST and pAD/PL-DEST by a standard LxR Clonase catalyzed recombination reaction (See, e.g., FIGS. 38 and 39) as described previously (See U.S. Pat. Nos. 5,888,732; 6,143,577; 6,171,861; 6,277,608; and 6,720,140; the disclosures of which are incorporated by reference herein in their entireties). Additionally, 12 different pENTR/U6 shRNA target subclones, including target sequences to Lamin AC and Luciferase, were also recombined into these two DEST vectors. In all cases, the LxR crosses were efficient. When 2 µl/20 µl LxR reaction were transformed and 1/6th (50 µl of the transformation reaction plated, 300-800 colonies/plate were obtained in Top10 cells. Even in HB101 cells that were ~40 fold less competent to take up DNA than the Top 10 cells, 10-20 colonies/plate could be obtained by plating more of the transformation reaction (100 µl vs. 50 µl). Note that the number of clones obtained are similar between the Lenti DEST and the Adeno DEST vectors, even though the Adenoviral vector is almost 4 times the size of the Lentiviral vector (~36 kb vs. ~8.6 kb).

The LxR crosses were not only efficient but also effective. Ten out of ten of the Adeno DEST vector recombinants had the correct RNAi cassette as determined by RFLP analysis. pLenti DEST recombinants were transformed into both Top10 and HB101 E. coli cells because HB101 cells are known for reducing the recombination between the lentiviral LTR sequences. In this case, 10/10 recombinants were correct using HB101 cells.

shRNA Target Site Selection

The present invention may be used to create shRNAs with any desired stem length, orientation, and loop sequence. In general, target sequences should be complex (no runs of more than 3 of the same nucleotide), with low GC content (30-50%), and avoid known RNA-protein interaction sites. Target sites should be a minimum of 19 nt, and sites of up to 29 nt are effective.

DNA Oligo Insert Design

Once a candidate target site has been selected, it must be converted into an shRNA sequence, and the DNA oligos ordered for cloning into pENTR/U6. The shRNA sequence can be in two possible orientations. Either the sense target site or the antisense sequence of the target site can begin the shRNA, followed by a short loop sequence and then the opposite strand of the target site.

The fact that the polymerase (pol III) will terminate transcription after 4 thymidines (Ts) constrains the oligo design. Strings of more than 3 Ts should be avoided in the middle of a target site, or with any Ts in the connecting "loop", to prevent early termination. Additionally, Ts at the 3' end of the target will abut the polyT terminator and may cause slightly premature termination. Changing the sense/antisense orientation of the shRNA may be necessary for specific target sites to avoid early pol III termination by positioning different sequences next to the loop or polyT terminator.

Additionally, the native U6 snRNA initiates at a guanosine (G), and this +1 base is believed to be important. Although this system allows advanced users to choose any +1 base, we have designed all of our inserts to initiate at a G. In cases where the G is part of the target sequence, it is simply incorporated into the stem, with a complementary cytosine base placed just before the terminator. When G is not the first base in the sense or antisense target sequence, it is added to the 5' end of the shRNA with no complementary base at the 3' end. If use of a G is not desired, an A is believed to be better than an C or T.

Functional loops of anywhere from 4 to 1int have been reported in the literature. Short loops are preferred as they reduce the lengths of the oligos needed for cloning. 5'-TTCG, 5'-AACG, and 5'CGAA have been used as the loop sequences in successful RNAi constructs. However, loops containing thymidines must be avoided in some cases as they may cause early termination, as discussed above.

Finally, to convert an shRNA sequence into an oligo pair for insertion, 5'CACC-3' was added to the 5' end of the shRNA sequence to create the "top" oligo. The "bottom" oligo is the complimentary sequence of the top oligo with the 5'CACC-3' removed and 5'AAAA-3' appended to the 5' end.

Conclusion

Figure 28:
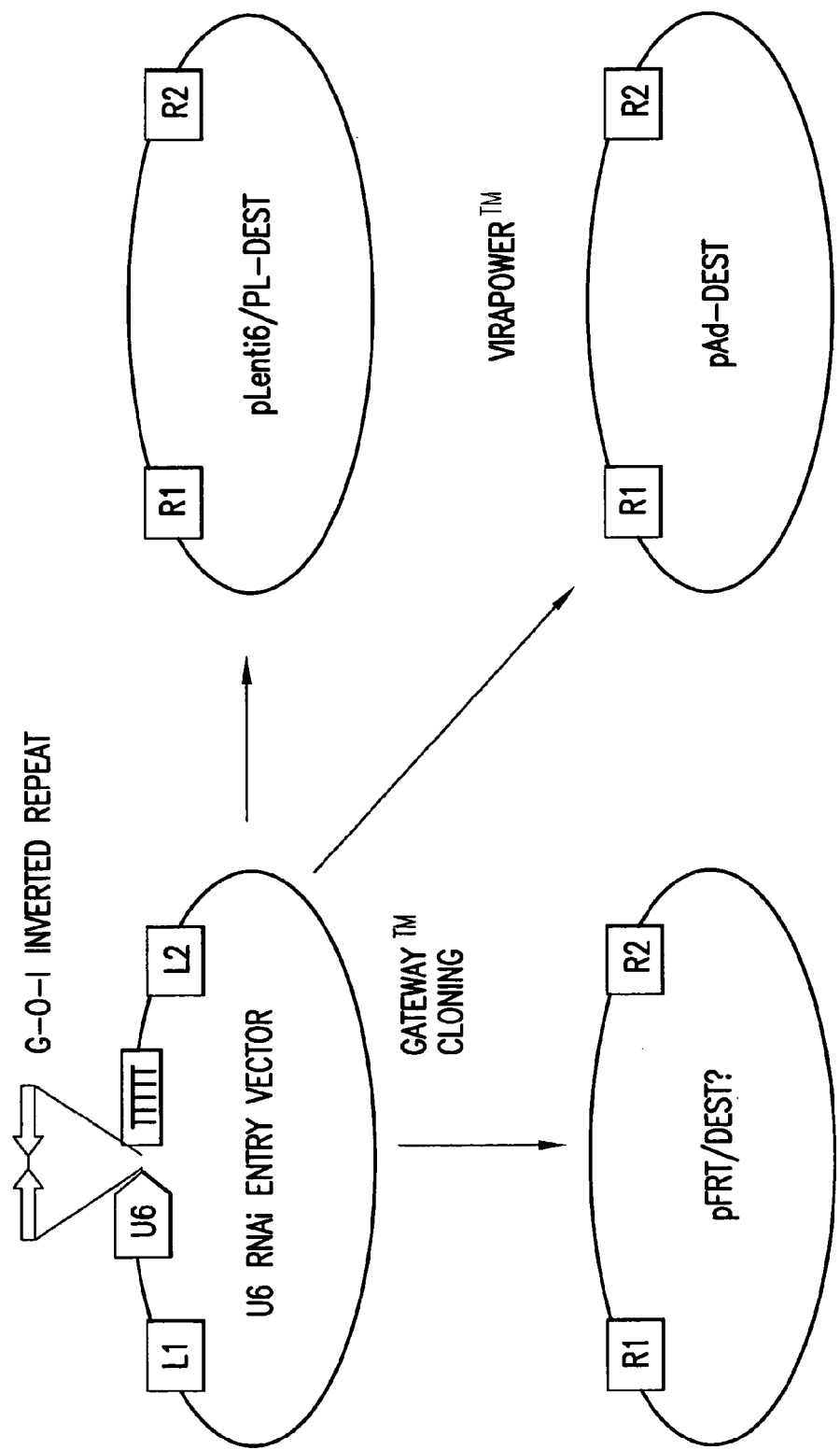
FIG. 28 depicts Gateway™ Cloning and ViraPower™ RNAI cassettes.

The pENTR/U6 and Gateway DEST vectors are the cornerstones of a superior system to clone shRNA target sequences into an RNAi expression cassette and deliver it to cells (FIG. 28). Two other commercial sources with similar pol III vectors (Ambion with pSilencer, and OligoEngines with pSuper) require the synthesis of longer insert oligos (~70 nt and 55 nt respectively) because their cloning schemes need the end of the U6 promoter and termination signals to be "built-back" with the insert. Additionally, their cloning protocols call for ligation incubations of 1 hr or greater compared to the 5 min bench-top reaction described here. This is likely due to the PEG present in the present ligation buffer, as well as the present vector design features that eliminate background (the ccdB negative selection and the non-compatible ends left after BsaI digestion). The present invention also has the Gateway Advantage; any insert cloned and sequence verified in pENTR/U6 is then available for any application made possible by the DEST vectors—such as viral delivery of shRNA by Virapower™.

The demonstrations of RNAi in transient transfections reported here, as well as examples of successful RNAi by transduction indicate the U6 promoter can generate sufficient shRNA for RNAi. Experiments that define the rules required for efficient RNAi will make this vector all the more valuable.

Example 2

Expression of Interfering RNA Using a Seamless Cloning Vector

Abstract and Introduction

Short hairpin RNA (shRNA) expression cassettes built into the U6 RNAi Entry Vector can be used to transiently knockdown genes of interest in cell culture. However, the Entry Vector carries no marker for selection in mammalian cells, and the plasmids must be introduced into cells by transfection. Transfection efficiency varies widely between cell lines and is ineffective in primary and terminally differentiated cells. In contrast to plasmid transfection, lentiviral delivery allows simple, stable transduction of a wide variety of cell types including primary and terminally differentiated cells. A number of recent publications describe the use of lentiviruses to deliver shRNAs to mammalian cells (Abbas-Terki et al. 2002, Dirac & Bernards 2003, Matta et al. 2003, Qin et al 2003, Rubinson et al 2003, Stewart et al 2003, Tiscornia et al. 2003), demonstrating an existing interest in this technique.

Figures 6A, 6B:
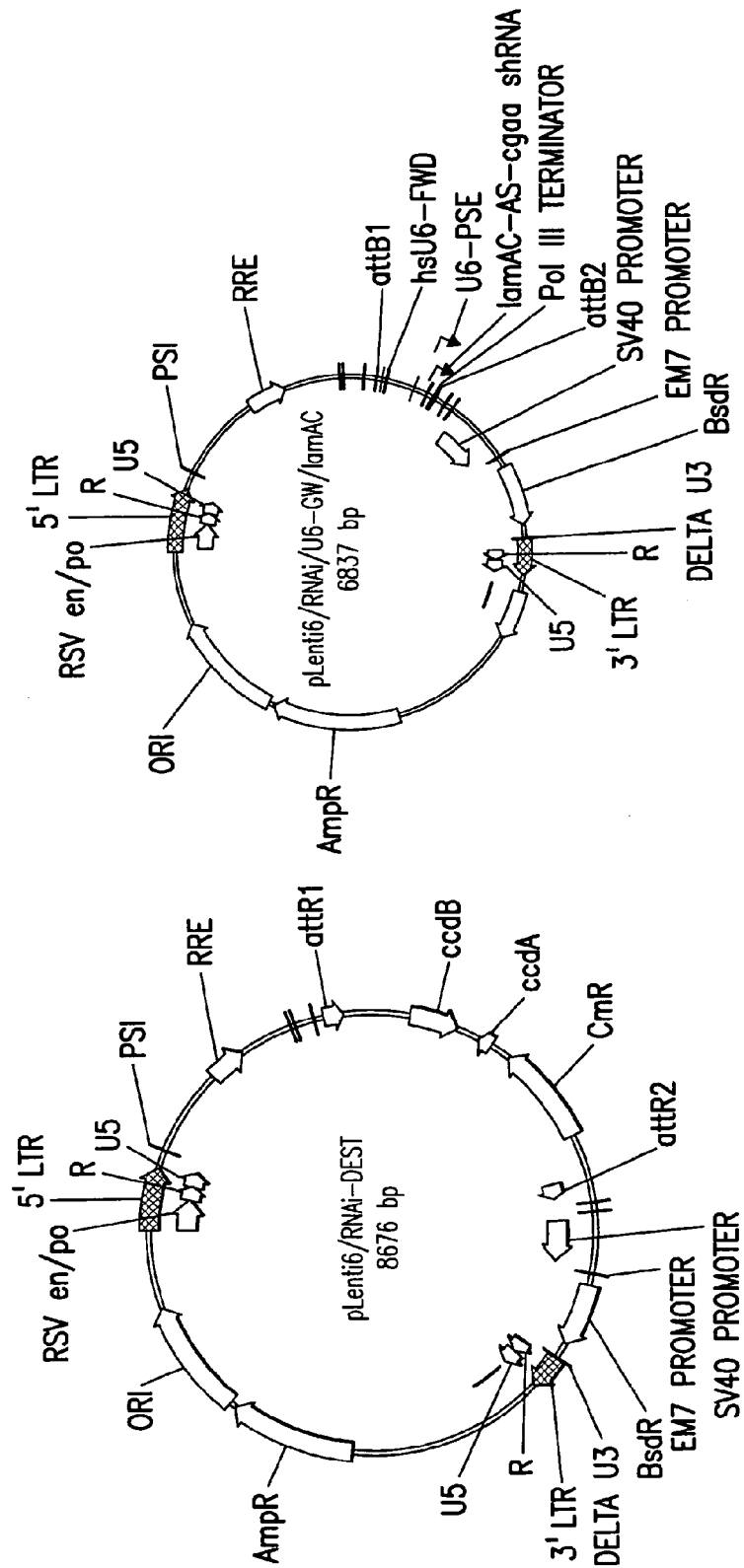
FIG. 6A is a schematic of the lentiviral RNAi shRNA transfer vector: pLenti6/RNAi-DEST which is a promoterless Gateway-adapted lenti vector which may be used to clone, for example an shRNA cassette of interest via Gateway LxR reaction with pENTR U6 vectors. The shRNA cassette will often contain an RNA pol III—or other—promoter of choice to drive hairpin expression. The vector confers blasticidin resistance to transduced cells.
FIG. 6B is a schematic of the lentiviral RNAi Kit control vector: Kit control plasmid pLenti6/RNAi/U6-GW/lamAC which results from LxR reaction between pLenti6/RNAi-DEST and pENTR/U6-lamAC-AS-cgaa. pLenti6/RNAi/U6-GW/lamAC expresses lamAC-AS-cgaa hairpin to specifically knockdown lamin A/C expression.

Invitrogen offers several Gateway-adapted lentiviral vectors for cloning of coding sequences downstream of a Pol II promoter. However, the presence of such an upstream promoter may interfere with Pol III expression from a U6 cassette. A promoterless Destination vector, pLenti6/RNAi-DEST has been created with attR1 and attR2 sites compatible with the U6 RNAi Entry Vector. A map of pLenti6/RNAi-DEST is shown in FIG. 6A. pLenti6/RNAi-DEST allows simple and reliable transfer of shRNA expression cassettes into the lentiviral backbone. The viral vector confers blasticidin resistance for selection of stably transduced cells. Transduction by lentiviruses expressing lamin A/C shRNAs is demonstrated to efficiently and specifically knock down endogenous protein levels. pLenti6/RNAi-DEST complements the ViraPower™ product line and provides a powerful new application for the U6 RNAi Entry Vector.

Key Performance Criteria for Lenti6/RNAi-DEST include: (1) pLenti6/RNAi-DEST passing standard manufacturing QC specs for Destination vectors. (2) Gateway cloning shRNAs into pLenti6/RNAi-DEST and packaging virus at levels comparable with regular vectors. (3) Showing specific knockdown of endogenous lamin A/C gene.

Materials and Methods

Construction of pLenti6/RNAi-DEST Vector pLenti6/RNAi-DEST is the product of a Gateway B×P reaction between pLenti6/PL/attB4/V5/GW-GFP and pDONR 221. The B×P reaction was transformed into DB3.1 and selected on LB media containing Ampicillin (100 µg/ml) and chloramphenicol (15 µg/ml). Colonies of the transformants were analyzed by restriction digest. A map of pLenti6/RNAi DEST is shown in FIG. 6A.

ShRNA-Containing Entry Clones

The various shRNA-containing Entry clones used are set out in Table 1. The hairpins are targeted to sites on the lamin A/C or luciferase genes as indicated. All entry clones were created by oligo cloning into pENTR/U6.2. Loops and stems choices are described in Example 1.

Cell Culture

293FT cells were cultured in DMEM/10% FBS/L-glutamine/non-essential amino acids/penicillin/streptomycin containing 500 µg/ml G418. HeLa cells were cultured in DMEM/10% FBS/L-glutamine/non-essential amino acids/penicillin/streptomycin.

Virus Production

For virus production, $1 \times 10^7$ 293FT cells were plated per T175 flask. Twenty-four hours later, culture medium was replaced with 20 ml OptiMem/10% FBS, and shRNA-encoding viruses were packaged by co-transfecting the 293FT cells with the respective lentiviral vector and pLP1, pLP2 and pLP/VSVG (at a mass ratio of 1:1:1:1, 24 µg of total DNA) as follows: The 24 µg DNA was mixed with 3 ml of OptiMem media. In a separate tube, 72 µl of Lipofectamine 2000 was also mixed with 3 ml of OptiMem media. After a 5-minute incubation period at room temperature, the two mixtures were combined and incubated at room temperature for an additional 20 minutes. At the completion of the incubation period, the transfection mixture was added to the cells dropwise and the flask was gently rocked to mix. The following day the transfection complex was replaced with 30 ml complete media (DMEM, 10% FBS, 1% penicillin/streptomycin, L-glutamine and non-essential amino acids). Virus-containing media were harvested at day 2 and day 3 post-transfection, centrifuged at 3000 rpm for 5 minutes to remove dead cells, and filtered through sterile 0.45 micron cellulose acetate filters to remove fine debris. Viruses in the filtrates were concentrated by ultracentrifugation (90 minutes, 23000×g, 4° C.). Viral pellets from ultra-centrifugation were resuspended in 500-600 µl growth media. One hundred-microliter aliquots of concentrated virus were stored in −80° C. freezer until use.

Viral Titering and Transduction

All applications of virus to cells were performed in the presence of 6 µg/ml polybrene (Sigma, hexadimethrin bromide, #H9268) and media changes were performed 12-24

TABLE 1 pENTR/U6 Entry Clones

| Clone name | Target gene | Orientation[a] | Loop sequence | Stem length[b] (bp) | Target position[c] (nt) |
|---|---|---|---|---|---|
| pENTR/U6-lamAC-SA-uucg | lamin A/C | SA | UUCG | 19 | 610-628 |
| pENTR/U6-lamAC-AS-uucg | lamin A/C | AS | UUCG | 19 | 610-628 |
| pENTR/U6-lamAC-AS-cgaa | lamin A/C | AS | CGAA | 19 | 610-628 |
| pENTR/U6-lamAC-SA-cgaa | lamin A/C | SA | CGAA | 19 | 610-628 |
| pENTR/U6-GL2-22 | luciferase | AS | UUCG | 22 | 153-174 |
| pENTR/U6-GL2sh2[d] | luciferase | AS | GAACGTTG | 29 | 1355-1383 |

[a]Orientations are either sense-loop-antisense (SA) or antisense-loop-sense (AS).
[b]Stem length does not include +1 G base if it is not also part of the target site.
[c]Target position is relative to start codon.
[d]Hairpin design based on a previously assessed technology from Cold Spring Harbor Laboratories.

Destination Vector QC and Generation of Expression Control Vector pLenti6/RNAi-DEST was monitored for quality using the official "Dest Vector QC Procedure" established by manufacturing. The expression control plasmid, pLenti6/RNAi/U6-GW/lamAC was generated by a standard Gateway L×R reaction between pLenti6/RNAi-DEST and pENTR/U6-lamAC-AS-cgaa. Clones of pLenti6/RNAi/U6-GW/lamAC were confirmed by restriction analyses. A map of pLenti6/RNAi/U6-GW/lamAC is shown in FIG. 6B.

hours post transduction. For titering virus, 6-well plates were seeded with $2 \times 10^5$ HT1080 cells per well the day before transduction. One milliliter each of ten-fold serial dilutions of viral supernatant ranging from $10^{-2}$ to $10^{-8}$ was prepared. All dilutions were mixed by gentle inversion prior to adding to cells. Mock-transduced cells had no virus added to them. Plates were gently swirled to mix. The following day, the media was replaced with complete media. Forty-eight hours post-transduction, the cells were placed under 10 µg/ml blasticidin selection. After 7 to 10 days of blasticidin selection the resulting colonies were stained with crystal violet: A 1% crystal violet solution was prepared in 10% ethanol. Each well was washed with 2 ml PBS followed by 1 ml of crystal violet solution for 10 minutes at room temperature. Excess stain was removed by two 2 ml PBS washes and colonies visible to the naked eye were counted to determine the viral titer of the original supernatants.

Transductions to test shRNA activities were performed in the appropriate cells in 12-well plates. Cells were plated at 1×10⁵/well twenty-four hours before transduction. The next day, the media was replaced with complete media. Transduction was conducted in a final volume of 500 µl and contained the appropriate volumes of virus supernatant to achieve a range of MOIs.

Cell Lysis and Western Blot

Cell lysis for lamin A/C and beta-actin western blots were performed as follows: Forty-eight or 120 hours post-transduction, cells were harvested with Versene (Invitrogen), transferred to microfuge tubes, and centrifuged at 3000 RPM for 4 min. Pellets were lysed in 2× NuPAGE® LDS Sample Buffer with 1× Sample Reducing Agent and denatured at 95° C. for 5 min prior to electrophoresis. Protein samples were electrophoresed on NuPAGE® Novex 4-12% Tris-Bis Gels in 1×MOPS-SDS buffer with NuPAGE® Antioxidant in the upper chamber. Western blot analyses were performed using the Western Breeze Immunodetection Kit (Invitrogen) according to the manufacturer's protocol. Lamin A/C and beta-actin proteins were detected using 1:1000 monoclonal anti-lamin A/C (BD Biosciences) and 1:5000 monoclonal anti-beta-actin (Abcam) antibodies, respectively.

Results and Discussion

Destination Vector QC pLenti6/RNAi-DEST passed the standard manufacturing QC specs for Destination vectors with respect to total colony count (Table 2) and ccdB assay (Table 3).

Virus Titers

ShRNA-encoding lentiviral vectors were used to produce virus in 293FT cells. The vectors produced viral titers comparable to titers attained with regular lentiviral vectors that do not contain shRNA (Table 4). This indicated that introduction of shRNAs into the lentiviral backbone does not compromise virus packaging or transduction efficiency.

TABLE 4

Lenti6/RNAi Virus Titers

| Virus | Crude Virus Titer (cfu/ml) | Concentrated Virus Titer (cfu/ml)[a] |
|---|---|---|
| Lenti6/RNAi/U6-GW/lamAC-SA-uucg | 1.00E+6 | 4.30E+08 |
| Lenti6/RNAi/U6.2-GW/lamAC-AS-uucg | 2.10E+6 | 5.85E+08 |
| Lenti6/RNAi/U6.2-GW/amAC-AS-cgaa | 8.00E+5 | 1.35E+08 |
| Lenti6/RNAi/U6.2-GW/lamAC-SA-cgaa | 1.20E+6 | 4.45E+08 |
| Lenti6/RNAi/U6-GW/GL2-22 | 6.00E+5 | 4.50E+08 |
| Lenti6RNAi/U6-GW/GL2sh2 | 1.30E+6 | 5.20E+08 |
| Lenti6/V5-GW/GFP(non-RNAi virus) | 4.00E+5 | 8.0E+07 |

[a]Concentrated from two 175 cm² flasks each.

Knockdown of Lamin A/C

Figure 7:
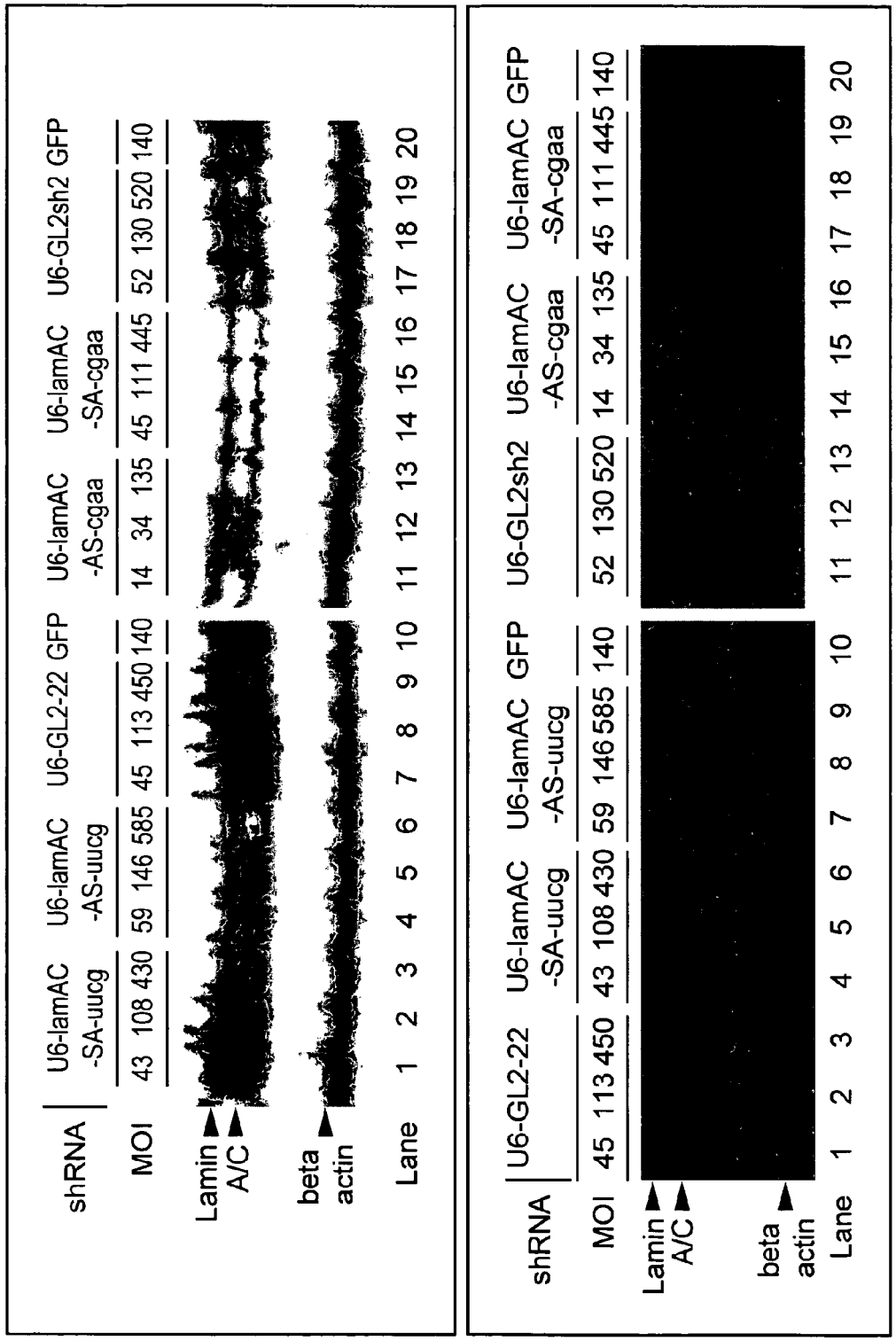
FIG. 7 depicts the inhibition of lamin A/C expression. Lenti6/RNAi viruses encoding anti-lamin A/C shRNAs (U6-lamAC) were transduced into HeLa cells to test inhibition of lamin A/C expression. Control viruses encoded GFP gene (GFP) or anti-luciferase shRNAs (U6-GL2). Western blots for lamin A/C or beta-actin were conducted on lysates from transduced cells. Top panel: Lysates were prepared 48 hrs post-transduction. Bottom panel: Lysates were prepared from transduced, shRNA-producing, blasticidin-resistant cells 5 days post-transduction.

Lentiviruses were tested for their ability to deliver shRNAs to specifically knock down lamin A/C expression in HeLa cells. Lentiviruses expressing luciferase-targeted shRNAs served as negative controls. Inhibition of lamin A/C expression was analyzed by western blot. ShRNAs targeted to lamin inhibited expression of both lamin A and C isoforms 48 hr and 5 days post-transduction (FIG. 7). The extent of inhibition depended on transduced MOI, indicating knockdown was dose-dependent. Lentiviruses encoding shRNAs lamAC-AS-cgaa and lamAC-SA-cgaa provided the best lamin knock-downs (FIG. 7, top panel lanes 11-16; bottom panel lanes 14-19). Of the two shRNAs, lamAC-AS-cgaa mediated robust inhibition even at the relatively low MOI of 14 (FIG. 7, top panel lane 11 and bottom panel lane 14). The lamin A/C shRNAs had no effect on beta-actin expression irrespective of transduced MOI (FIG. 7, beta-actin blots). Control luciferase shRNAs had no effect on beta-actin expression (FIG. 7, top panel lanes 7-9 and 17-19; bottom panel lanes 1-3 and 11-13) and minor effect on lamin A/C expression even at the very high MOI of 520 (FIG. 7, top panel lane 19; bottom panel lane 13). These results show specific inhibition of lamin expression with lamin-targeted shRNAs. The inhibition is not the effect of general inhibition of gene expression. Results of the control shRNA transduction provide further evidence of the specific activity of the lamin-directed shRNAs.

pLenti6/RNAi has also been used to specifically knock down luciferase (75% inhibition, 48 hrs post-transduction in Flp-In 293 luc cell line; data not shown) and lacZ at high MOIs (55% inhibition, 96 hrs post-transduction in HT1080LacZ cells; data not shown). These provide further evidence that pLenti6/RNAi-DEST vector will function with other RNAi cassettes.

Summary

Gateway-adapted lentiviral vector pLenti6/RNAi-DEST has been developed for RNAi analyses. pLenti6/RNAi-DEST is designed to be used in L×R reactions with pENTR/U6. pLenti6/RNAi-DEST meets the performance criteria for all DEST vectors as well as criteria for packaging and transducing lentiviruses. Viruses Lenti6/RNAi/U6-GW/lamAC-AS-cgaa and Lenti6/RNAi/U6-GW/lamAC-SA-cgaa transduce shRNAs that specifically knock down lamin A/C expression. The lamAC-AS-cgaa hairpin was chosen as the positive control for the U6 RNAi Entry and pLenti6/RNAi Kits. The sequence of lamAC-AS-cgaa hairpin is shown in the Kit Components and Configuration below.

Example 3

RNAi Using Block-iT™ Dicer Kit

Figure 21:
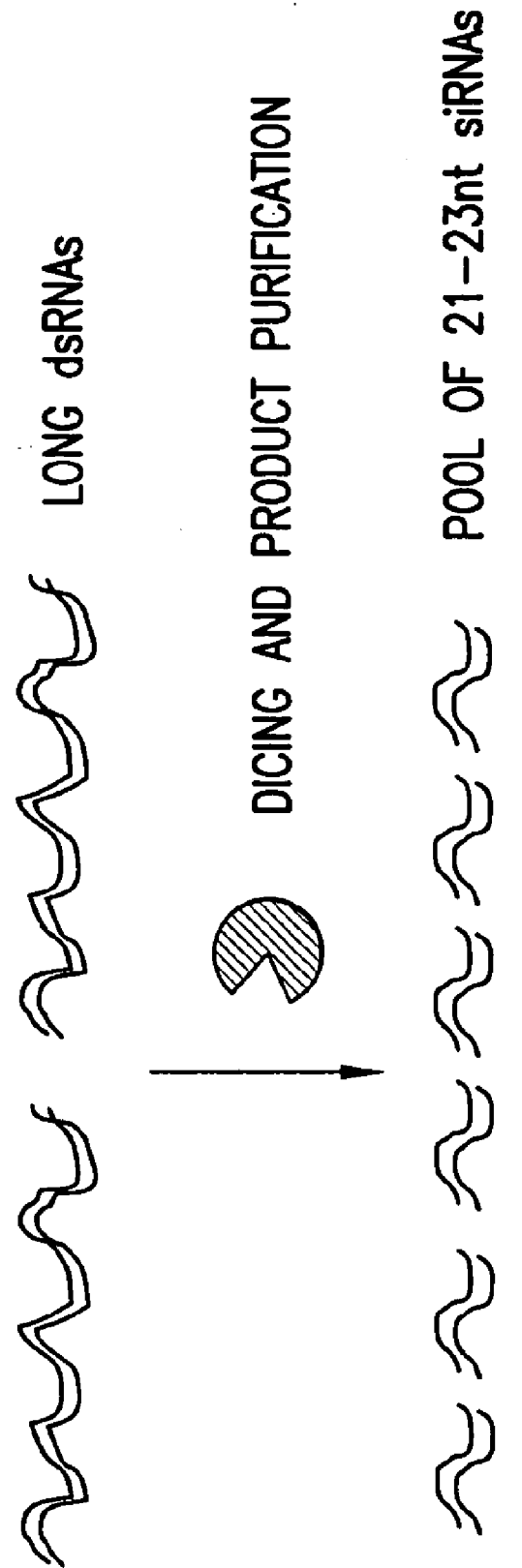
FIG. 21 depicts BLOCK-iT™ Dicer RNAi Kit
Figure 22A:
FIG. 22 depicts d-siRNA knockdown.
Figure 22B:
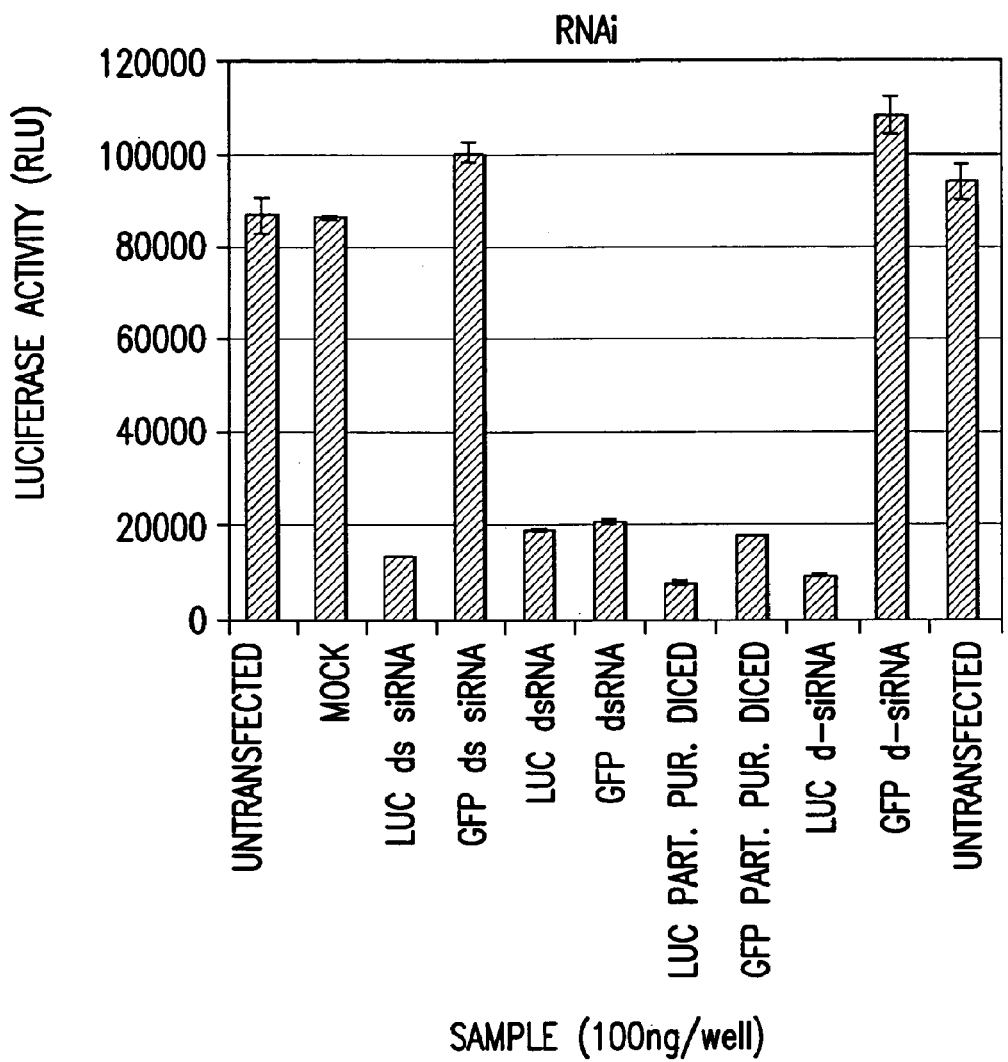

BLOCK-iT™ Kits (Invitrogen Corporation; Carlsbad, Calif.) can be used for fast and efficient RNAi applications. Eukaryotic cells naturally regulate gene expression with dsRNA. A BLOCK-iT™ Dicer Kit can be used to generate dsRNA that are then diced into siRNA, purified and transfected into cells. The BLOCK-iT™ Dicer Kit requires no expensive synthetic siRNAs. It also produces a pool of many siRNAs per gene, not just one or a few, which means a higher probability of knockdown (FIGS. 21, 22, and 23). A purification procedure gives a high yield of siRNAs in a transfection-ready buffer and virtually eliminates remaining long dsRNA and cleave intermediates.

Figure 20:
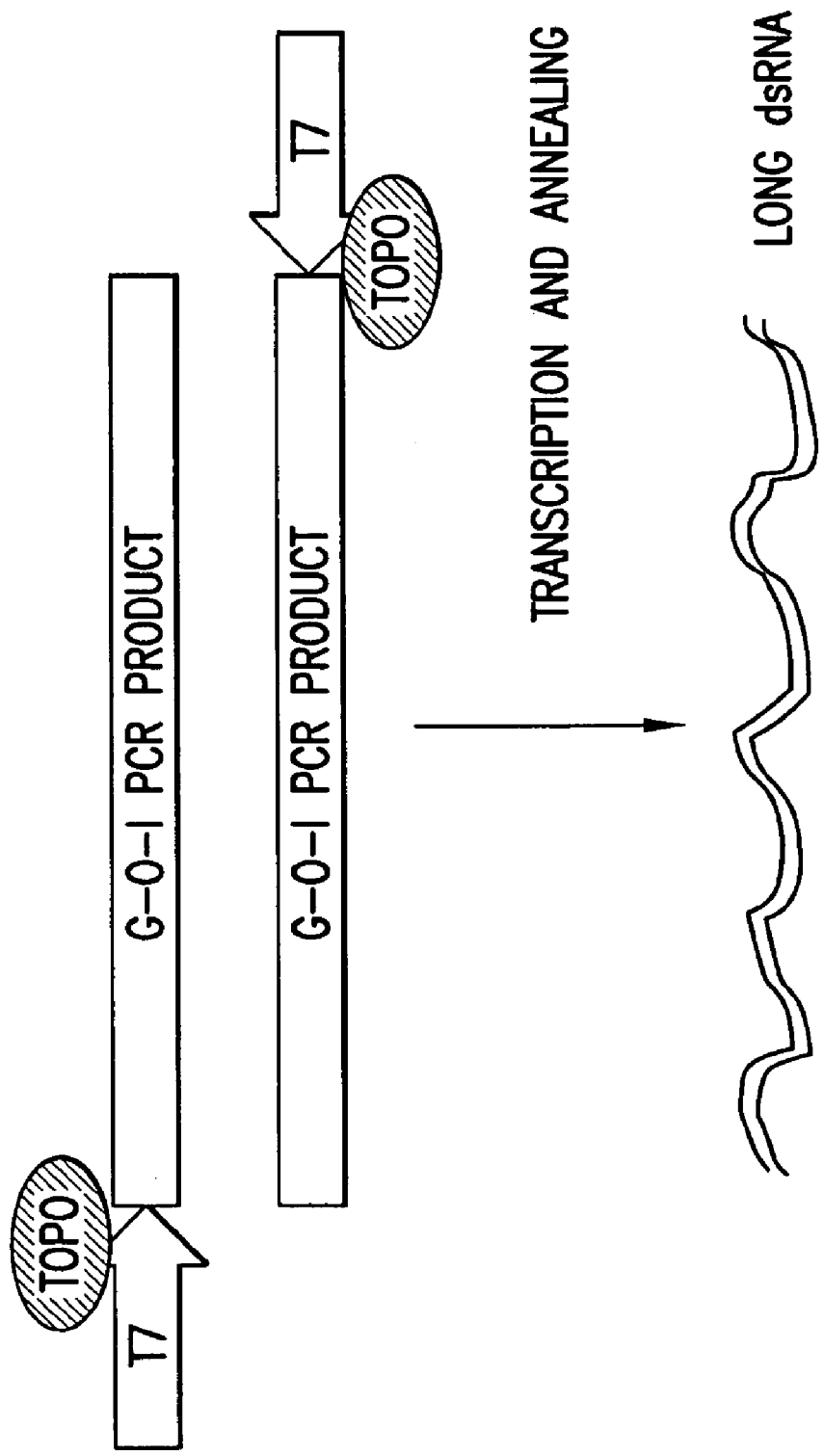
FIG. 20 depicts BLOCK-iT™ Long RNAi Transcription Kit.
Figure 24:
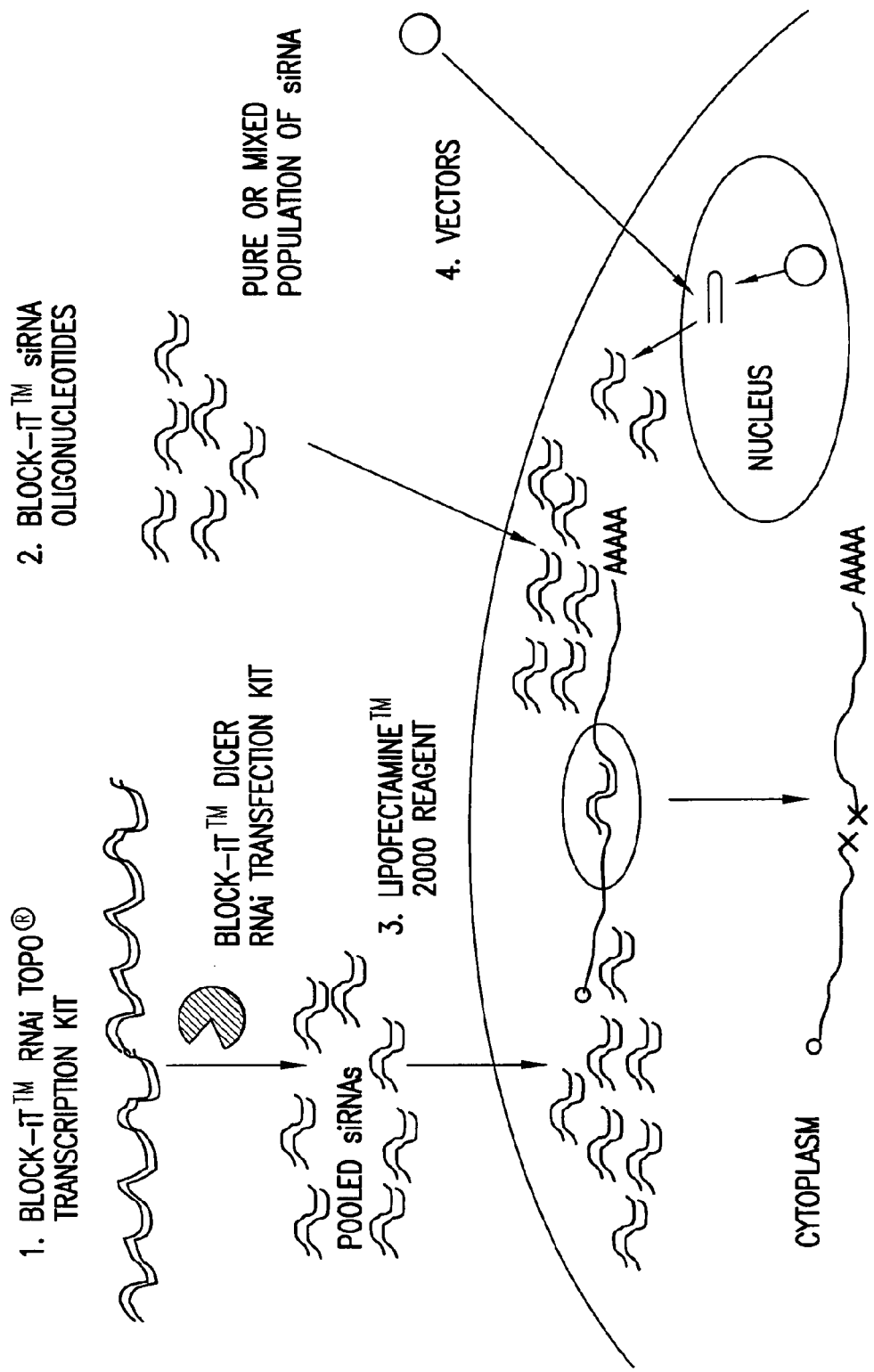
FIG. 24 depicts BLOCK-iT™ RNAi.

BLOCK-iT™ Long RNAi Transcription Kits use a T7 TOPO linker which allows any polymerase chain reaction (PCR) product to become a template for transcription (FIG. 20). This mediates RNAi in invertebrates (e.g., insects, nematodes and protozoans), some mammalian embryonic cells (undifferentiated ES cells) and many mammalian cell lines after treatment with Dicer/RNase III. BLOCK-iT™ Kits allows for an inexpensive alternative to siRNA oligos. Exemplary uses of BLOCK-iT™ Kits are summarized in FIG. 24.

Kit Components and Configurations

Complete Lentiviral RNAi Kit:

Components of the U6 RNAi Entry Vector Kit:

Purified, BsaI-linearized pENTR/U6.2; Annealed lamin A/C control oligos: Top 5'-CACCGTGTTCTTCTG- GAAGTCCAGCGAACT GGACTTCCAGAAGAACA (SEQ ID NO:9), Bottom 5'-AAAATGTTCTTCTGGA AGTCCAGTTCGCTGGACTTCCAGAAGAACAC (SEQ ID NO:10); Sequencing primers: U6 forward 5'-GGACTAT-CATATGCTTACCG (SEQ ID NO:11), M13 reverse 5'-CAG-GAAACAGCTATGAC (SEQ ID NO:12)(Catalog No. N530-02, Invitrogen Corp., Carlsbad, Calif.); T4 DNA ligase (Catalog No. 15224-025, Invitrogen Corp., Carlsbad, Calif.); 5×T4 DNA ligase buffer (Catalog No. Y90001, Invitrogen Corp., Carlsbad, Calif. Y90001); OneShot Top10 cells (Catalog No. C4040-03, Invitrogen Corp., Carlsbad, Calif.); pLenti6/RNAi/DEST; pLenti6/RNAi/U6-GW/lamAC; One-Shot STBL3 cells; Virapower Bsd Lentiviral Support Kit (Catalog No. K4970-00, Invitrogen Corp., Carlsbad, Calif.); Gateway LR Clonase enzyme mix (Catalog No. 11791-091, Invitrogen Corp., Carlsbad, Calif.).

Lentiviral RNAi DEST Kit:
pLenti6/RNAi/DEST; pLenti6/RNAi/U6-GW/lamAC; OneShot STBL3 cells; Gateway LR Clonase enzyme mix (Catalog No. 11791-019, Invitrogen Corp., Carlsbad, Calif.)

REFERENCES

Abbas-Terki et al., Lentiviral-mediated RNA interference. *Hum Gene Ther.* 13:2197-2201 (2002)

Dirac & Bernards, Reversal of senescence in mouse fibroblasts through lentiviral suppression of p53. *J. Biol. Chem.* 278:11731-11734 (2003)

Matta et al., Use of lentiviral vectors for delivery of small interfering RNA. *Cancer Biol. Ther.* 2:206-210 (2003)

Qin et al., Inhibiting HIV-1 infection in human T cells by lentiviral-mediated delivery of small interfering RNA against CCR5. *Proc. Natl. Acad. Sci. (USA)* 100:183-188 (2003)

Rubinson et al., A lentivirus-based system to functionally silence genes in primary mammalian cells, stem cells and transgenic mice by RNA interference. *Nat. Genet.* 33:401-406 (2003)

Stewart et al., Lentivirus-delivered stable gene silencing by RNAi in primary cells. *RNA.* 9:493-501 (2003)

Tiscornia et al., A general method for gene knockdown in mice by using lentiviral vectors expressing small interfering RNA. *Proc. Natl. Acad. Sci. (USA)* 100:1844-1848 (2003)

TABLE 2

L × R Assay

| Sample | Criteria | Values | Pass/Fail |
|---|---|---|---|
| Cells only | 0 cfu/μg DNA | 0 cfu/μg DNA | Pass |
| No DNA | 0 cfu/μg DNA | 0 cfu/μg DNA | Pass |
| DEST vector only | <1100 cfu/μg DNA | 660 cfu/μg DNA | Pass |
| L × R Reaction (n = 2) | ≧1.65 × $10^6$ cfu/μg DNA | 2.31 × $10^6$ cfu/μg DNA | Pass |
| pUC19 only (n = 2) | ≧7.5 × $10^8$ cfu/μg DNA | 2.53 × $10^{10}$ cfu/μg DNA | Pass |

TABLE 3 ccdB Assay

| Sample | Cell Type | Antibiotic | Transformation Efficiency |
|---|---|---|---|
| Cells Only | DB3.1 | Amp | 0 cfu/μg DNA |
|  |  | Kan | 0 cfu/μg DNA |
| pUC19 only (n = 4) | DB3.1 | Amp | 7.0 × $10^6$ cfu/μg DNA |
| DEST vector only (n = 4) | DB3.1 | Amp | 3.0 × $10^6$ cfu/μg DNA |
| Cells Only | TOP10 | Amp | 0 cfu/μg DNA |
|  |  | Kan | 0 cfu/μg DNA |
| pUC19 only (n = 4) | TOP10 | Amp | 2.65 × $10^8$ cfu/μg DNA |
| DEST vector only (n = 4) | TOP10 | Amp | 5.75 × $10^3$ cfu/μg DNA |
|  |  | Kan | 0 cfu/μg DNA |
| Fold-killing (criteria = 1 × $10^4$) |  |  | 2 × $10^4$ Pass |

The invention illustratively described herein suitably may be practiced in the absence of any element or elements, limitation or limitations which is not specifically disclosed herein. Thus, for example, in each instance herein any of the terms "comprising," "consisting essentially of," and "consisting of" may be replaced with either of the other two terms. The terms and expressions that have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed herein, optional features, modification and variation of the concepts herein disclosed may be resorted to by those skilled in the art, and that such modifications and variations are considered to be within the scope of this invention as defined by the appended claims. In addition, where features or aspects of the invention are described in terms of Markush groups, those skilled in the art will recognize that the invention is also thereby described in terms of any individual member or subgroup of members of the Markush group.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other aspects of the invention are within the following claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

TABLE 5 pENTRU6 Vector Nucleic Acid Sequence

CTTTCCTGCGTTATCCCCTGATTCTGTGGATAACCGTATTACCGCCT
TTGAGTGAGCTGATACCGCTCGCCGCAGCCGAACGACCGAGCGCA
GCGAGTCAGTGAGCGAGGAAGCGGAAGAGCGCCCAATACGCAAAC
CGCCTCTCCCCGCGCGTTGGCCGATTCATTAATGCAGCTGGCACGA
CAGGTTTCCCGACTGGAAAGCGGGCAGTGAGCGCAACGCAATTAA
TACGCGTACCGCTAGCCAGGAAGAGTTTGTAGAAACGCAAAAAGG
CCATCCGTCAGGATGGCCTTCTGCTTAGTTTGATGCCTGGCAGTTTA
TGGCGGGCGTCCTGCCCGCCACCCTCCGGGCCGTTGCTTCACAACG
TTCAAATCCGCTCCCGGCGGATTTGTCCTACTCAGGAGAGCGTTCA
CCGACAAACAACAGATAAAACGAAAGGCCCAGTCTTCCGACTGAG
CCTTTCGTTTTATTTGATGCCTGGCAGTTCCCTACTCTCGCGTTAAC
GCTAGCATGGATGTTTTCCCAGTCACGACGTTGTAAAACGACGGCC
AGTCTTAAGCTCGGGCCCCAAATAATGATTTTATTTTGACTGATAGT
GACCTGTTCGTTGCAACAAATTGATGAGCAATGCTTTTTTATAATGC
CAACTTTGTACAAAAAAGCAGGCTTTAAAGGAACCAATTCAGTCGA
CTGGATCCGGTACCAAGGTCGGGCAGGAAGAGGGCCTATTTCCCAT
GATTCCTTCATATTTGCATATACGATACAAGGCTGTTAGAGAGATA
ATTAGAATTAATTTGACTGTAAACACAAAGATATTAGTACAAAATA
CGTGACGTAGAAAGTAATAATTTCTTGGGTAGTTTGCAGTTTTAAA
ATTATGTTTTAAAATGGACTATCATATGCTTACCGTAACTTGAAAGT
ATTTCGATTTCTTGGCTTTATATATCTTGTGGAAAGGACGAAACACC
GGAGACCGCGGCCGCTGGATCCGGCTTACTAAAAGCCAGATAACA
GTATGCGTATTTGCGCGCTGATTTTTGCGGTATAAGAATATATACTG
ATATGTATACCCGAAGTATGTCAAAAAGAGGTGTGCTATGAAGCA
GCGTATTACAGTGACAGTTGACAGCGACAGCTATCAGTTGCTCAAG
GCATATATGATGTCAATATCTCCGGTCTGGTAAGCACAACCATGCA
GAATGAAGCCCGTCGTCTGCGTGCCGAACGCTGGAAAGCGGAAAA
TCAGGAAGGGATGGCTGAGGTCGCCCGGTTTATTGAAATGAACGG
CTCTTTTGCTGACGAGAACAGGGACTGGTGAAATGCAGTTTAAGGT
TTACACCTATAAAGAGAGAGCCGTTATCGTCTGTTTGTGGATGTA
CAGAGTGATATTATTGACACGCCCGGGCGACGGATGGTGATCCCCC
TGGCCAGTCACGTCTGCTGTCAGATAAAGTCTCCCGTGAACTTTA
CCCGGTGGTGCATATCGGGGATGAAAGCTGGCGCATGATGACCAC
CGATATGGCCAGTGTGCCGGTCTCCGTTATCGGGAAGAAGTGGCT
GATCTCAGCCACCGCGAAAATGACATCAAAAACGCCATTAACCTG
ATGTTCTGGGGAATATAAGGTCTCATTTTTTTCTAGACCCAGCTTT
CTTGTACAAAGTTGGCATTATAAGAAAGCATTGCTTATCAATTTGTT
GCAACGAACAGGTCACTATCAGTCAAAATAAAATCATTATTTGCCA
TCCAGCTGATATCCCCTATAGTGAGTCGTATTACATGGTCATAGCT
GTTTCCTGGCAGCTCTGGCCCGTGTCTCAAAATCTCTGATGTTACAT
TGCACAAGATAAAAATATATCATCATGAACAATAAAACTGTCTGCT
TACATAAACAGTAA
TACAAGGGTGTTATGAGCCATATTCAACGGGAAACGTCGAGGCC
GCGATTAAATTCCAACATGGATGCTGATTTATATGGGTATAAATGG
GCTCGCGATAATGTCGGGCAATCAGGTGCGACAATCTATCGCTTGT
ATGGGAAGCCCGATGCGCCAGAGTTGTTTCTGAAACATGGCAAAG
GTAGCGTTGCCAATGATGTTACAGATGAGATGGTCAGACTAAACTG
GCTGACGGAATTTATGCCTCTTCCGACCATCAAGCATTTTATCCGTA
CTCCTGATGATGCATGGTTACTCACCACTGCGATCCCCGGAAAAAC
AGCATTCCAGGTATTAGAAGAATATCCTGATTCAGGTGAAAATATT
GTTGATGCGCTGGCAGTGTTCCTGCGCCGGTTGCATTCGATTCCTGT
TTGTAATTGTCCTTTTAACAGCGATCGCGTATTTCGTCTCGCTCAGG
CGCAATCACGAATGAATAACGGTTTGGTTGATGCGAGTGATTTGAT
GACGAGCGTAATGGCTGGCCTGTTGAACAAGTCTGGAAAGAAATG
CATAAACTTTTGCCATTCTCACCGGATTCAGTCGTCACTCATGGTGA
TTTCTCACTTGATAACCTTATTTTTGACGAGGGGAAATTAATAGGTT
GTATTGATGTTGGACGAGTCGGAATCGCAGACCGATACCAGGATCT
TGCCATCCTATGGAACTGCCTCGGTGAGTTTTCTCCTTCATTACAGA
AACGGCTTTTTCAAAAATATGGTATTGATAATCCTGATATGAATAA
ATTGCAGTTTCATTTGATGCTCGATGAGTTTTTCTAATCAGAATTGG
TTAATTGGTTGTAACACTGGCAGAGCATTACGCTGACTTGACGGGA
CGGCGCAAGCTCATGACCAAAATCCCTTAACGTGAGTTACGCGTCG
TTCCACTGAGCGTCAGACCCCGTAGAAAAGATCAAAGGATCTTCTT
GAGATCCTTTTTTTCTGCGCGTAATCTGCTGCTTGCAAACAAAAAA
ACCACCGCTACCAGCGGTGGTTTGTTTGCCGGATCAAGAGCTACCA
ACTCTTTTTCCGAAGGTAACTGGCTTCAGCAGAGCGCAGATACCAA
ATACTGTCCTTCTAGTGTAGCCGTAGTTAGGCCACCACTTCAAGAA
CTCTGTAGCACCGCCTACATACCTCGCTCTGCTAATCCTGTTACCAG
TGGCTGCTGCCAGTGGCGATAAGTCGTGTCTTACCGGGTTGGACTC
AAGACGATAGTTACCGGATAAGGCGCAGCGGTCGGGCTGAACGG
GGGGTTCGTGCACACAGCCCAGCTTGGAGCGAACGACCTACACCG
AACTGAGATACCTACAGCGTGAGCATTGAGAAAGCGCCACGCTTCC
CGAAGGGAGAAAGGCGGACAGGTATCCGGTAAGCGGCAGGGTCGG
AACAGGAGAGCGCACGAGGGAGCTTCCAGGGGGAAACGCCTGGTA
TCTTTATAGTCCTGTCGGGTTTCGCCACCTCTGACTTGAGCGTCGAT
TTTTGTGATGCTCGTCAGGGGGGCGGAGCCTATGGAAAAACGCCAG
CAACGCGGCCTTTTTACGGTTCCTGGCCTTTTGCTGGCCTTTTGCTC
ACATGTT SEQ ID NO: 1

TABLE 6

Nucleotide sequence of plasmid pLenti6/V5-DEST.

AATGTAGTCTTATGCAATACTCTTGTAGTCTTGCAACATGGTAACG
ATGAGTTAGCAACATGCCTTACAAGGAGAGAAAAAGCACCGTGCA
TGCCGATTGGTGGAAGTAAGGTGGTACGATCGTGCCTTATTAGGAA
GGCAACAGACGGGTCTGACATGGATTGGACGAACCACTGAATTGC
CGCATTGCAGAGATATTGTATTTAAGTGCCTAGCTCGATACATAAA
CGGGTCTCTCTGGTTAGACCAGATCTGAGCCTGGGAGCTCTCTGGC
TAACTAGGGAACCCACTGCTTAAGCCTCAATAAAGCTTGCCTTGAG
TGCTTCAAGTAGTGTGTGCCCGTCTGTTGTGTGACTCTGGTAACTAG
AGATCCCTCAGACCCTTTTAGTCAGTGTGGAAAATCTCTAGCAGTG
GCGCCCGAACAGGGACTTGAAAGCGAAAGGGAAACCAGAGGAGCT
CTCTCGACGCAGGACTCGGCTTGCTGAAGCGCGCACGGCAAGAGG
CGAGGGGCGGCGACTGGTGAGTACGCCAAAAATTTTGACTAGCGG
AGGCTAGAAGGAGAGAGATGGGTGCGAGAGCGTCAGTATTAAGCG
GGGGAGAATTAGATCGCGATGGGAAAAAATTCGGTTAAGGCCAGG
GGGAAAGAAAAAATATAAATTAAAACATATAGTATGGGCAAGCAG
GGAGCTAGAACGATTCGCAGTTAATCCTGGCCTGTTAGAAACATCA
GAAGGCTGTAGACAAATACTGGGACAGCTACAACCATCCCTTCAG
ACAGGATCAGAAGAACTTAGATCATTATATAATACAGTAGCAACCC
TCTATTGTGTGCATCAAAGGATAGAGATAAAAGACACCAAGGAAG
CTTTAGACAAGATAGAGGAAGAGCAAAACAAAAGTAAGACCACCG
CACAGCAAGCGGCCGCTGATCTTCAGACCTGGAGGAGGAGATATG
AGGGACAATTGGAGAAGTGAATTATATAAATATAAAGTAGTAAAA
ATTGAACCATTAGGAGTAGCACCCACCAAGGCAAAGAGAAGAGTG
GTGCAGAGAGAAAAAAGAGCAGTGGGAATAGGAGCTTTGTTCCTT
GGGTTCTTGGGAGCAGCAGGAAGCACTATGGGCGCAGCGTCAATG
ACGCTGACGGTACAGGCCAGACAATTATTGTCTGGTATAGTGCAGC
AGCAGAACAATTTGCTGAGGGCTATTGAGGCGCAACAGCATCTGTT
GCAACTCACAGTCTGGGGCATCAAGCAGCTCCAGGCAAGAATCCT
GGCTGTGGAAAGATACCTAAAGGATCAACAGCTCCTGGGGATTTG
GGGTTGCTCTGGAAAACTCATTTGCACCACTGCTGTGCCTTGGAAT
GCTAGTTGGAGTAATAAATCTCTGGAACAGATTTGGAATCACACGA
CCTGGATGGAGTGGGACAGAGAAATTAACAATTACACAAGCTTAA
TACACTCCTTAATTGAAGAATCGCAAAACCAGCAAGAAAAGAATG
AACAAGAATTATTGGAATTAGATAAATGGGCAAGTTTGTGGAATTG
GTTTAACATAACAAATTGGCTGTGGTATATAAAATTATTCATAATG
ATAGTAGGAGGCTTGGTAGGTTTAAGAATAGTTTTTGCTGTACTTTC
TATAGTGAATAGAGTTAGGCAGGGATATTCACCATTATCGTTTCAG
ACCCACCTCCCAACCCCGAGGGGACCCGACAGGCCCGAAGGAATA
GAAGAAGAAGGTGGAGAGAGAGACAGAGACAGATCCATTCGATTA

GTGAACGGATCTCGACGGTATCGATAAGCTTGGGAGTTCCGCGTTA
CATAACTTACGGTAAATGGCCCGCCTGGCTGACCGCCCAACGACCC
CCGCCCATTGACGTCAATAATGACGTATGTTCCCATAGTAACGCCA
ATAGGGACTTTCCATTGACGTCAATGGGTGGAGTATTTACGGTAAA
CTGCCCACTTGGCAGTACATCAAGTGTATCATATGCCAAGTACGCC
CCCTATTGACGTCAATGACGGTAAATGGCCCGCCTGGCATTATGCC
CAGTACATGACCTTATGGGACTTTCCTACTTGGCAGTACATCTACGT
ATTAGTCATCGCTATTACCATGGTGATGCGGTTTTGGCAGTACATC
AATGGGCGTGGATAGCGGTTTGACTCACGGGGATTTCCAAGTCTCC
ACCCCATTGACGTCAATGGGAGTTTGTTTTGGCACCAAAATCAACG
GGACTTTCCAAAATGTCGTAACAACTCCGCCCCATTGACGCAAATG
GGCGGTAGGCGTGTACGGTGGGAGGTCTATATAAGCAGAGCTCGTT
TAGTGAACCGTCAGATCGCCTGGAGACGCCATCCACGCTGTTTTGA
CCTCCATAGAAGACACCGACTCTAGAGGATCCACTAGTCCAGTGTG
GTGGAATTCTGCAGATATCAACAAGTTTGTACAAAAAAGCTGAACG
AGAAACGTAAAATGATATAAATATCAATATATTAAATTAGATTTTG
CATAAAAAACAGACTACATAATACTGTAAAACACAACATATCCAG
TCACTATGGCGGCCGCATTAGGCACCCCAGGCTTTACACTTTATGC
TTCCGGCTCGTATAATGTGTGGATTTTGAGTTAGGATCCGGCGAGA
TTTTCAGGAGCTAAGGAAGCTAAAATGGAGAAAAAAATCACTGGA
TATACCACCGTTGATATATCCCAATGGCATCGTAAAGAACATTTTG
AGGCATTTCAGTCAGTTGCTCAATGTACCTATAACCAGACCGTTCA
GCTGGATATTACGGCCTTTTTAAAGACCGTAAAGAAAAATAAGCAC
AAGTTTTATCCGGCCTTTATTCACATTCTTGCCCGCCTGATGAATGC
TCATCCGGAATTCCGTATGGCAATGAAAGACGGTGAGCTGGTGATA
TGGGATAGTGTTCACCCTTGTTACACCGTTTTCCATGAGCAAACTG
AAACGTTTTCATCGCTCTGGAGTGAATACCACGACGATTTCCGGCA
GTTTCTACACATATATTCGCAAGATGTGGCGTGTTACGGTGAAAAC
CTGGCCTATTTCCCTAAAGGGTTTATTGAGAATATGTTTTTCGTCTC
AGCCAATCCCTGGGTGAGTTTCACCAGTTTTGATTTAAACGTGGCC
AATATGGACAACTTCTTCGCCCCCGTTTTCACCATGGGCAAATATT
ATACGCAAGGCGACAAGGTGCTGATGCCGCTGGCGATTCAGGTTCA
TCATGCCGTCTGTGATGGCTTCCATGTCGGCAGAATGCTTAATGAA
TTACAACAGTACTGCGATGAGTGGCAGGGCGGGGCGTAAAGATCT
GGATCCGGCTTACTAAAAGCCAGATAACAGTATGCGTATTTGCGCG
CTGATTTTTGCGGTATAAGAATATATACTGATATGTATACCCGAAG
TATGTCAAAAAGAGGTGTGCTATGAAGCAGCGTATTACAGTGACA
GTTGACAGCGACAGCTATCAGTTGCTCAAGGCATATATGATGTCAA
TATCTCCGGTCTGGTAAGCACAACCATGCAGAATGAAGCCCGTCGT

TABLE 6-continued

Nucleotide sequence of plasmid pLenti6/V5-DEST.

CTGCGTGCCGAACGCTGGAAAGCGGAAAATCAGGAAGGGATGGCT
GAGGTCGCCCGGTTTATTGAAATGAACG
GCTCTTTTGCTGACGAGAACAGGGACTGGTGAAATGCAGTTTAAGG
TTTACACCTATAAAGAGAGAGCCGTTATCGTCTGTTTGTGGATGT
ACAGAGTGATATTATTGACACGCCCGGGCGACGGATGGTGATCCCC
CTGGCCAGTGCACGTCTGCTGTCAGATAAAGTCTCCCGTGAACTTT
ACCCGGTGGTGCATATCGGGGATGAAAGCTGGCGCATGATGACCA
CCGATATGGCCAGTGTGCCGGTCTCCGTTATCGGGGAAGAAGTGGC
TGATCTCAGCCACCGCGAAAATGACATCAAAAACGCCATTAACCTG
ATGTTCTGGGGAATATAAATGTCAGGCTCCGTTATACACAGCCAGT
CTGCAGGTCGACCATAGTGACTGGATATGTTGTGTTTTACAGTATT
ATGTAGTCTGTTTTTTATGCAAAATCTAATTTAATATATTGATATTT
ATATCATTTTACGTTTCTCGTTCAGCTTTCTTGTACAAAGTGGTTGA
TATCCAGCACAGTGGCGGCCGCTCGAGTCTAGAGGGCCCGCGGTTC
GAAGGTAAGCCTATCCCTAACCCTCTCCTCGGTCTCGATTCTACGC
GTACCGGTTAGTAATGAGTTTGGAATTAATTCTGTGGAATGTGTGT
CAGTTAGGGTGTGGAAAGTCCCCAGGCTCCCCAGGCAGGCAGAAG
TATGCAAAGCATGCATCTCAATTAGTCAGCAACCAGGTGTGGAAAG
TCCCCAGGCTCCCCAGCAGGCAGAAGTATGCAAAGCATGCATCTCA
ATTAGTCAGCAACCATAGTCCCGCCCCTAACTCCGCCCATCCCGCC
CCTAACTCCGCCCAGTTCCGCCCATTCTCCGCCCCATGGCTGACTAA
TTTTTTTTATTTATGCAGAGGCCGAGGCCGCCTCTGCCTCTGAGCTA
TTCCAGAAGTAGTGAGGAGGCTTTTTTGGAGGCCTAGGCTTTTGCA
AAAAGCTCCCGGGAGCTTGTATATCCATTTTCGGATCTGATCAGCA
CGTGTTGACAATTAATCATCGGCATAGTATATCGGCATAGTATAAT
ACGACAAGGTGAGGAACTAAACCATGGCCAAGCCTTTGTCTCAAG
AAGAATCCACCCTCATTGAAAGAGCAACGGCTACAATCAACAGCA
TCCCCATCTCTGAAGACTACAGCGTCGCCAGCGCAGCTCTCTCTAG
CGACGGCCGCATCTTCACTGGTGTCAATGTATATCATTTTACTGGG
GGACCTTGTGCAGAACTCGTGGTGCTGGGCACTGCTGCTGCTGCGG
CAGCTGGCAACCTGACTTGTATCGTCGCGATCGGAAATGAGAACAG
GGGCATCTTGAGCCCCTGCGGACGGTGCCGACAGGTGCTTCTCGAT
CTGCATCCTGGGATCAAAGCCATAGTGAAGGACAGTGATGGACAG
CCGACGGCAGTTGGGATTCGTGAATTGCTGCCCTCTGGTTATGTGT
GGGAGGGCTAAGCACAATTCGAGCTCGGTACCTTTAAGACCAATG
ACTTACAAGGCAGCTGTAGATCTTAGCCACTTTTTAAAAGAAAAGG
GGGGACTGGAAGGGCTAATTCACTCCCAACGAAGACAAGATCTGC
TTTTTGCTTGTACTGGGTCTCTCTGGTTAGACCAGATCTGAGCCTGG
GAGCTCTCTGGCTAACTAGGGAACCCACTGCTTAAGCCTCAATAAA
GCTTGCCTTGAGTGCTTCAAGTAGTGTGTGCCCGTCTGTTGTGTGAC
TCT
GGTAACTAGAGATCCCTCAGACCCTTTTAGTCAGTGTGGAAAATCT
CTAGCAGTAGTAGTTCATGTCATCTTATTATTCAGTATTTATAACTT
GCAAAGAAATGAATATCAGAGAGTGAGAGGAACTTGTTTATTGCA
GCTTATAATGGTTACAAATAAAGCAATAGCATCACAAATTTCACAA
ATAAAGCATTTTTTTCACTGCATTCTAGTTGTGGTTTGTCCAAACTC
ATCAATGTATCTTATCATGTCTGGCTCTAGCTATCCCGCCCCTAACT
CCGCCCATCCCGCCCCTAACTCCGCCCAGTTCCGCCCATTCTCCGCC
CCATGGCTGACTAATTTTTTTTATTTATGCAGAGGCCGAGGCCGCCT
CGGCCTCTGAGCTATTCCAGAAGTAGTGAGGAGGCTTTTTTGGAGG
CCTAGGGACGTACCCAATTCGCCCTATAGTGAGTCGTATTACGCGC
GCTCACTGGCCGTCGTTTTACAACGTCGTGACTGGGAAAACCCTGG
CGTTACCCAACTTAATCGCCTTGCAGCACATCCCCCTTTCGCCAGCT
GGCGTAATAGCGAAGAGGCCCGCACCGATCGCCCTTCCCAACAGTT
GCGCAGCCTGAATGGCGAATGGGACGCGCCCTGTAGCGGCGCATT
AAGCGCGGCGGGTGTGGTGGTTACGCGCAGCGTGACCGCTACACTT
GCCAGCGCCCTAGCGCCCGCTCCTTTCGCTTTCTTCCCTTCCTTTCTC
GCCACGTTCGCCGGCTTTCCCCGTCAAGCTCTAAATCGGGGGCTCC
CTTTAGGGTTCCGATTTAGTGCTTTACGGCACCTCGACCCCAAAAA
ACTTGATTAGGGTGATGGTTCACGTAGTGGGCCATCGCCCTGATAG
ACGGTTTTTCGCCCTTTGACGTTGGAGTCCACGTTCTTTAATAGTGG
ACTCTTGTTCCAAACTGGAACAACACTCAACCCTATCTCGGTCTATT
CTTTTGATTTATAAGGGATTTTGCCGATTTCGGCCTATTGGTTAAAA
AATGAGCTGATTTAACAAAAATTTAACGCGAATTTTAACAAAATAT
TAACGCTTACAATTTAGGTGGCACTTTTCGGGGAAATGTGCGCGGA
ACCCCTATTTGTTTATTTTTCTAAATACATTCAAATATGTATCCGCT
CATGAGACAATAACCCTGATAAATGCTTCAATAATATTGAAAAAGG
AAGAGTATGAGTATTCAACATTTCCGTGTCGCCCTTATTCCCTTTTT
TGCGGCATTTTGCCTTCCTGTTTTTGCTCACCCAGAAACGCTGGTGA
AAGTAAAAGATGCTGAAGATCAGTTGGGTGCACGAGTGGGTTACA
TCGAACTGGATCTCAACAGCGGTAAGATCCTTGAGAGTTTTCGCCC
CGAAGAACGTTTTCCAATGATGAGCACTTTTAAAGTTCTGCTATGT
GGCGCGGTATTATCCCGTATTGACGCCGGGCAAGAGCAACTCGGTC
GCCGCATACACTATTCTCAGAATGACTTGGTTGAGTACTCACCAGT
CACAGAAAAGCATCTTACGGATGGCATGACAGTAAGAGAATTATG
CAGTGCTGCCATAACCATGAGTGATAACACTGCGGCCAACTTACTT
CTGACAACGATCGGAGGACCGAAGGAGCTAACCGCTTTTTTGCACA
ACATGGGGGATCATGTAACTCGCCTTGATCGTTGGGAACCGGAGCT

TABLE 6-continued

Nucleotide sequence of plasmid pLenti6/V5-DEST.

GAATGAAGCCATACCAAACGACGAGCGTGACACCACGATGCCTGT
AGCAATGGCAACAACGTTGCGCAAACTATTAACTGGCGAACTACTT
ACTCTAGCTTCCCGGCAACAATTAATAGACTGGATGGAGGCGGATA
AAGTTGCAGGACCACTTCTGCGCTCGGCCCTTCCGGCTGGCTGGTT
TATTGCTGATAAATCTGGAGCCGGTGAGCGTGGGTCTCGCGGTATC
ATTGCAGCACTGGGGCCAGATGGTAAGCCCTCCCGTATCGTAGTTA
TCTACACGACGGGGAGTCAGGCAACTATGGATGAACGAAATAGAC
AGATCGCTGAGATAGGTGCCTCACTGATTAAGCATTGGTAACTGTC
AGACCAAGTTTACTCATATATACTTTAGATTGATTTAAAACTTCATT
TTTAATTTAAAAGGATCTAGGTGAAGATCCTTTTTGATAATCTCATG
ACCAAAATCCCTTAACGTGAGTTTTCGTTCCACTGAGCGTCAGACC
CCGTAGAAAAGATCAAAGGATCTTCTTGAGATCCTTTTTTTCTGCGC
GTAATCTGCTGCTTGCAAACAAAAAAACCACCGCTACCAGCGGTGG
TTTGTTTGCCGGATCAAGAGCTACCAACTCTTTTTCCGAAGGTAACT
GGCTTCAGCAGAGCGCAGATACCAAATACTGTTCTTCTAGTGTAGC
CGTAGTTAGGCCACCACTTCAAGAACTCTGTAGCACCGCCTACATA
CCTCGCTCTGCTAATCCTGTTACCAGTGGCTGCTGCCAGTGGCGAT
AAGTCGTGTCTTACCGGGTTGGACTCAAGACGATAGTTACCGGATA
AGGCGCAGCGGTCGGGCTGAACGGGGGGTTCGTGCACACAGCCCA
GCTTGGAGCGAACGACCTACACCGAACTGAGATACCTACAGCGTG
AGCTATGAGAAAGCGCCACGCTTCCCGAAGGGAGAAAGGCGGACA
GGTATCCGGTAAGCGGCAGGGTCGGAACAGGAGAGCGCACGAGGG
AGCTTCCAGGGGGAAACGCCTGGTATCTTTATAGTCCTGTCGGGTT
TCGCCACCTCTGACTTGAGCGTCGATTTTTGTGATGCTCGTCAGGGG
GGCGGAGCCTATGGAAAAACGCCAGCAACGCGGCCTTTTTACGGTT
CCTGGCCTTTTGCTGGCCTTTTGCTCACATGTTCTTTCCTGCGTTATC
CCCTGATTCTGTGGATAACCGTATTACCGCCTTTGAGTGAGCTGAT
ACCGCTCGCCGCAGCCGAACGACCGAGCGCAGCGAGTCAGTGAGC
GAGGAAGCGGAAGAGCGCCCAATACGCAAACCGCCTCTCCCCGCG
CGTTGGCCGATTCATTAATGCAGCTGGCACGACAGGTTTCCCGACT
GGAAAGCGGGCAGTGAGCGCAACGCAATTAATGTGAGTTAGCTCA
CTCATTAGGCACCCCAGGCTTTACACTTTATGCTTCCGGCTCGTATG
TTGTGTGGAATTGTGAGCGGATAACAATTTCACACAGGAAACAGCT
ATGACCATGATTACGCCAAGCGCGCAATTAACCCTCACTAAAGGGA
ACAAAAGCTGGAGCTGCAAGCTT SEQ ID NO: 2

TABLE 7

Nucleotide sequence of plasmid pLenti6/V5-dTOPO™.

AATGTAGTCTTATGCAATACTCTTGTAGTCTTGCAACATGGTAACG
ATGAGTTAGCAACATGCCTTACAAGGAGAGAAAAAGCACCGTGCA
TGCCGATTGGTGGAAGTAAGGTGGTACGATCGTGCCTTATTAGGAA
GGCAACAGACGGGTCTGACATGGATTGGACGAACCACTGAATTGC
CGCATTGCAGAGATATTGTATTTAAGTGCCTAGCTCGATACATAAA
CGGGTCTCTCTGGTTAGACCAGATCTGAGCCTGGGAGCTCTCTGGC
TAACTAGGGAACCCACTGCTTAAGCCTCAATAAAGCTTGCCTTGAG
TGCTTCAAGTAGTGTGTGCCCGTCTGTTGTGTGACTCTGGTAACTAG
AGATCCCTCAGACCCTTTTAGTCAGTGTGGAAAATCTCTAGCAGTG
GCGCCCGAACAGGGACTTGAAAGCGAAAGGGAAACCAGAGGAGCT
CTCTCGACGCAGGACTCGGCTTGCTGAAGCGCGCACGGCAAGAGG
CGAGGGGCGGCGACTGGTGAGTACGCCAAAAATTTTGACTAGCGG
AGGCTAGAAGGAGAGAGATGGGTGCGAGAGCGTCAGTATTAAGCG
GGGGAGAATTAGATCGCGATGGGAAAAAATTCGGTTAAGGCCAGG
GGGAAAGAAAAAATATAAATTAAAACATATAGTATGGGCAAGCAG
GGAGCTAGAACGATTCGCAGTTAATCCTGGCCTGTTAGAAACATCA
GAAGGCTGTAGACAAATACTGGGACAGCTACAACCATCCCTTCAG
ACAGGATCAGAAGAACTTAGATCATTATATAATACAGTAGCAACCC
TCTATTGTGTGCATCAAAGGATAGAGATAAAAGACACCAAGGAAG
CTTTAGACAAGATAGAGGAAGAGCAAAACAAAAGTAAGACCACCG
CACAGCAAGCGGCCGCTGATCTTCAGACCTGGAGGAGGAGATATG
AGGGACAATTGGAGAAGTGAATTATATAAATATAAAGTAGTAAAA
ATTGAACCATTAGGAGTAGCACCCACCAAGGCAAAGAGAAGAGTG
GTGCAGAGAGAAAAAAGAGCAGTGGGAATAGGAGCTTTGTTCCTT
GGGTTCTTGGGAGCAGCAGGAAGCACTATGGGCGCAGCGTCAATG
ACGCTGACGGTACAGGCCAGACAATTATTGTCTGGTATAGTGCAGC
AGCAGAACAATTTGCTGAGGGCTATTGAGGCGCAACAGCATCTGTT
GCAACTCACAGTCTGGGGCATCAAGCAGCTCCAGGCAAGAATCCT
GGCTGTGGAAAGATACCTAAAGGATCAACAGCTCCTGGGGATTTG
GGGTTGCTCTGGAAAACTCATTTGCACCACTGCTGTGCCTTGGAAT
GCTAGTTGGAGTAATAAATCTCTGGAACAGATTTGGAATCACACGA
CCTGGATGGAGTGGGACAGAGAAATTAACAATTACACAAGCTTAA
TACACTCCTTAATTGAAGAATCGCAAAACCAGCAAGAAAAGAATG
AACAAGAATTATTGGAATTAGATAAATGGGCAAGTTTGTGGAATTG
GTTTAACATAACAAATTGGCTGTGGTATATAAAATTATTCATAATG
ATAGTAGGAGGCTTGGTAGGTTTAAGAATAGTTTTTGCTGTACTTTC
TATAGTGAATAGAGTTAGGCAGGGATATTCACCATTATCGTTTCAG
ACCCACCTCCCAACCCCGAGGGGACCCGACAGGCCCGAAGGAATA
GAAGAAGAAGGTGGAGAGAGAGACAGAGACAGATCCATTCGATTA

TABLE 7-continued

Nucleotide sequence of plasmid pLenti6/V5-dTOPO ™.

GTGAACGGATCTCGACGGTATCGATAAGCTTGGGAGTTCCGCGTTA
CATAACTTACGGTAAATGGCCCGCCTGGCTGACCGCCCAACGACCC
CCGCCCATTGACGTCAATAATGACGTATGTTCCCATAGTAACGCCA
ATAGGGACTTTCCATTGACGTCAATGGGTGGAGTATTTACGGTAAA
CTGCCCACTTGGCAGTACATCAAGTGTATCATATGCCAAGTACGCC
CCCTATTGACGTCAATGACGGTAAATGGCCCGCCTGGCATTATGCC
CAGTACATGACCTTATGGGACTTTCCTACTTGGCAGTACATCTACGT
ATTAGTCATCGCTATTACCATGGTGATGCGGTTTTGGCAGTACATC
AATGGGCGTGGATAGCGGTTTGACTCACGGGGATTTCCAAGTCTCC
ACCCCATTGACGTCAATGGGAGTTTGTTTTGGCACCAAAATCAACG
GGACTTTCCAAAATGTCGTAACAACTCCGCCCCATTGACGCAAATG
GGCGGTAGGCGTGTACGGTGGGAGGTCTATATAAGCAGAGCTCGTT
TAGTGAACCGTCAGATCGCCTGGAGACGCCATCCACGCTGTTTTGA
CCTCCATAGAAGACACCGACTCTAGAGGATCCACTAGTCCAGTGTG
GTGGAATTGATCCCTTCACCAAGGGCTCGAGTCTAGAGGGCCCGCG
GTTCGAAGGTAAGCCTATCCCTAACCCTCTCCTCGGTCTCGATTCTA
CGCGTACCGGTTAGTAATGAGTTTGGAATTAATTCTGTGGAATGTG
TGTCAGTTAGGGTGTGGAAAGTCCCCAGGCTCCCCAGGCAGGCAG
AAGTATGCAAAGCATGCATCTCAATTAGTCAGCAACCAGGTGTGGA
AAGTCCCCAGGCTCCCCAGCAGGCAGAAGTATGCAAAGCATGCAT
CTCAATTAGTCAGCAACCATAGTCCCGCCCCTAACTCCGCCCATCC
CGCCCCTAACTCCGCCCAGTTCCGCCCATTCTCCGCCCCATGGCTGA
CTAATTTTTTTTATTTATGCAGAGGCCGAGGCCGCCTCTGCCTCTGA
GCTATTCCAGAAGTAGTGAGGAGGCTTTTTTGGAGGCCTAGGCTTT
TGCAAAAAGCTCCCGGGAGCTTGTATATCCATTTTCGGATCTGATC
AGCACGTGTTGACAATTAATCATCGGCATAGTATATCGGCATAGTA
TAATACGACAAGGTGAGGAACTAAACCATGGCCAAGCCTTTGTCTC
AAGAAGAATCCACCCTCATTGAAAGAGCAACGGCTACAATCAACA
GCATCCCCATCTCTGAAGACTACAGCGTCGCCAGCGCAGCTCTCTC
TAGCGACGGCCGCATCTTCACTGGTGTCAATGTATATCATTTTACTG
GGGGACCTTGTGCAGAACTCGTGGTGCTGGGCACTGCTGCTGCTGC
GGCAGCTGGCAACCTGACTTGTATCGTCGCGATCGGAAATGAGAAC
AGGGGCATCTTGAGCCCCTGCGGACGGTGCCGACAGGTGCTTCTCG
ATCTGCATCCTGGGATCAAAGCCATAGTGAAGGACAGTGATGGAC
AGCCGACGGCAGTTGGGATTCGTGAATTGCTGCCCTCTGGTTATGT
GTGGGAGGGCTAAGCACAATTCGAGCTCGGTACCTTTAAGACCAAT
GACTTACAAGGCAGCTGTAGATCTTAGCCACTTTTTAAAAGAAAG
GGGGGACTGGAAGGGCTAATTCACTCCCAACGAAGACAAGATCTG
CTTTTTGCTTGTACTGGGTCTCTCTGGTTAGACCAGATCTGAGCCTGG

GAGCTCTCTGGCTAACTAGGGAACCCACTGCTTAAGCCTCAATAAA
GCTTGCCTTGAGTGCTTCAAGTAGTGTGTGCCCGTCTGTTGTGTGAC
TCTGGTAACTAGAGATCCCTCAGACCCTTTTAGTCAGTGTGGAAAA
TCTCTAGCAGTAGTAGTTCATGTCATCTTATTATTCAGTATTTATAA
CTTGCAAAGAAATGAATATCAGAGAGTGAGAGGAACTTGTTTATTG
CAGCTTATAATGGTTACAAATAAAGCAATAGCATCACAAATTTCAC
AAATAAAGCATTTTTTTCACTGCATTCTAGTTGTGGTTTGTCCAAAC
TCATCAATGTATCTTATCATGTCTGGCTCTAGCTATCCCGCCCCTAA
CTCCGCCCATCCCGCCCCTAACTCCGCCCAGTTCCGCCCATTCTCCG
CCCCATGGCTGACTAATTTTTTTTATTTATGCAGAGGCCGAGGCCGC
CTCGGCCTCTGAGCTATTCCAGAAGTAGTGAGGAGGCTTTTTTGGA
GGCCTAGGGACGTACCCAATTCGCCCTATAGTGAGTCGTATTACGC
GCGCTCACTGGCCGTCGTTTTACAACGTCGTGACTGGGAAAACCCT
GGCGTTACCCAACTTAATCGCCTTGCAGCACATCCCCCTTTCGCCA
GCTGGCGTAATAGCGAAGAGGCCCGCACCGATCGCCCTTCCCAACA
GTTGCGCAGCCTGAATGGCGAATGGGACGCGCCCTGTAGCGGCGC
ATTAAGCGCGGCGGGTGTGGTGGTTACGCGCAGCGTGACCGCTACA
CTTGCCAGCGCCCTAGCGCCCGCTCCTTTCGCTTTCTTCCCTTCCTTT
CTCGCCACGTTCGCCGGCTTTCCCCGTCAAGCTCTAAATCGGGGGC
TCCCTTTAGGGTTCCGATTTAGTGCTTTACGGCACCTCGACCCCAAA
AAACTTGATTAGGGTGATGGTTCACGTAGTGGGCCATCGCCCTGAT
AGACGGTTTTTCGCCCTTTGACGTTGGAGTCCACGTTCTTTAATAGT
GGACTCTTGTTCCAAACTGGAACAACACTCAACCCTATCTCGGTCT
ATTCTTTTGATTTATAAGGGATTTTGCCGATTTCGGCCTATTGGTTA
AAAAATGAGCTGATTTAACAAAAATTTAACGCGAATTTTAACAAAA
TATTAACGCTTACAATTTAGGTGGCACTTTTCGGGGAAATGTGCGC
GGAACCCCTATTTGTTTATTTTTCTAAATACATTCAAATATGTATCC
GCTCATGAGACAATAACCCTGATAAATGCTTCAATAATATTGAAAA
AGGAAGAGTATGAGTATTCAACATTTCCGTGTCGCCCTTATTCCCTT
TTTTGCGGCATTTTGCCTTCCTGTTTTTGCTCACCCAGAAACGCTGG
TGAAAGTAAAAGATGCTGAAGATCAGTTGGGTGCACGAGTGGGTT
ACATCGAACTGGATCTCAACAGCGGTAAGATCCTTGAGAGTTTTCG
CCCCGAAGAACGTTTTCCAATGATGAGCACTTTTAAAGTTCTGCTA
TGTGGCGCGGTATTATCCCGTATTGACGCCGGGCAAGAGCAACTCG
GTCGCCGCATACACTATTCTCAGAATGACTTGGTTGAGTACTCACC
AGTCACAGAAAAGCATCTTACGGATGGCATGACAGTAAGAGAATT
ATGCAGTGCTGCCATAACCATGAGTGATAACACTGCGGCCAACTTA
CTTCTGACAACGATCGGAGGACCGAAGGAGCTAACCGCTTTTTTGC
ACAACATGGGGGATCATGTAACTCGCCTTGATCGTTGGGAACCGGA

TABLE 7-continued

Nucleotide sequence of plasmid pLenti6/V5-dTOPO ™.

GCTGAATGAAGCCAT
ACCAAACGACGAGCGTGACACCACGATGCCTGTAGCAATGGCAAC
AACGTTGCGCAAACTATTAACTGGCGAACTACTTACTCTAGCTTCC
CGGCAACAATTAATAGACTGGATGGAGGCGGATAAAGTTGCAGGA
CCACTTCTGCGCTCGGCCCTTCCGGCTGGCTGGTTTATTGCTGATAA
ATCTGGAGCCGGTGAGCGTGGGTCTCGCGGTATCATTGCAGCACTG
GGGCCAGATGGTAAGCCCTCCCGTATCGTAGTTATCTACACGACGG
GGAGTCAGGCAACTATGGATGAACGAAATAGACAGATCGCTGAGA
TAGGTGCCTCACTGATTAAGCATTGGTAACTGTCAGACCAAGTTTA
CTCATATATACTTTAGATTGATTTAAAACTTCATTTTTAATTTAAAA
GGATCTAGGTGAAGATCCTTTTTGATAATCTCATGACCAAAATCCC
TTAACGTGAGTTTTCGTTCCACTGAGCGTCAGACCCCGTAGAAAAG
ATCAAAGGATCTTCTTGAGATCCTTTTTTTCTGCGCGTAATCTGCTG
CTTGCAAACAAAAAAACCACCGCTACCAGCGGTGGTTTGTTTGCCG
GATCAAGAGCTACCAACTCTTTTTCCGAAGGTAACTGGCTTCAGCA
GAGCGCAGATACCAAATACTGTTCTTCTAGTGTAGCCGTAGTTAGG
CCACCACTTCAAGAACTCTGTAGCACCGCCTACATACCTCGCTCTG
CTAATCCTGTTACCAGTGGCTGCTGCCAGTGGCGATAAGTCGTGTC
TTACCGGGTTGGACTCAAGACGATAGTTACCGGATAAGGCGCAGC
GGTCGGGCTGAACGGGGGGTTCGTGCACACAGCCCAGCTTGGAGC
GAACGACCTACACCGAACTGAGATACCTACAGCGTGAGCTATGAG
AAAGCGCCACGCTTCCCGAAGGGAGAAAGGCGGACAGGTATCCGG
TAAGCGGCAGGGTCGGAACAGGAGAGCGCACGAGGGAGCTTCCAG
GGGGAAACGCCTGGTATCTTTATAGTCCTGTCGGGTTTCGCCACCT
CTGACTTGAGCGTCGATTTTTGTGATGCTCGTCAGGGGGCGGAGC
CTATGGAAAAACGCCAGCAACGCGGCCTTTTTACGGTTCCTGGCCT
TTTGCTGGCCTTTTGCTCACATGTTCTTTCCTGCGTTATCCCCTGATT
CTGTGGATAACCGTATTACCGCCTTTGAGTGAGCTGATACCGCTCG
CCGCAGCCGAACGACCGAGCGCAGCGAGTCAGTGAGCGAGGAAGC
GGAAGAGCGCCCAATACGCAAACCGCCTCTCCCCGCGCGTTGGCCG
ATTCATTAATGCAGCTGGCACGACAGGTTTCCCGACTGGAAAGCGG
GCAGTGAGCGCAACGCAATTAATGTGAGTTAGCTCACTCATTAGGC
ACCCCAGGCTTTACACTTTATGCTTCCGGCTCGTATGTTGTGTGGAA
TTGTGAGCGGATAACAATTTCACACAGGAAACAGCTATGACCATGA
TTACGCCAAGCGCGCAATTAACCCTCACTAAAGGGAACAAAAGCT
GGAGCTGCAAGCTT SEQ ID NO: 3

TABLE 8

Nucleotide sequence of pLenti4/V5-DEST.

AATGTAGTCTTATGCAATACTCTTGTAGTCTTGCAACATGGTAACG
ATGAGTTAGCAACATGCCTTACAAGGAGAGAAAAAGCACCGTGCA
TGCCGATTGGTGGAAGTAAGGTGGTACGATCGTGCCTTATTAGGAA
GGCAACAGACGGGTCTGACATGGATTGGACGAACCACTGAATTGC
CGCATTGCAGAGATATTGTATTTAAGTGCCTAGCTCGATACATAAA
CGGGTCTCTCTGGTTAGACCAGATCTGAGCCTGGGAGCTCTCTGGC
TAACTAGGGAACCCACTGCTTAAGCCTCAATAAAGCTTGCCTTGAG
TGCTTCAAGTAGTGTGTGCCCGTCTGTTGTGTGACTCTGGTAACTAG
AGATCCCTCAGACCCTTTTAGTCAGTGTGGAAAATCTCTAGCAGTG
GCGCCCGAACAGGGACTTGAAAGCGAAAGGGAAACCAGAGGAGCT
CTCTCGACGCAGGACTCGGCTTGCTGAAGCGCGCACGGCAAGAGG
CGAGGGGCGGCGACTGGTGAGTACGCCAAAAATTTTGACTAGCGG
AGGCTAGAAGGAGAGAGATGGGTGCGAGAGCGTCAGTATTAAGCG
GGGGAGAATTAGATCGCGATGGGAAAAAATTCGGTTAAGGCCAGG
GGGAAAGAAAAAATATAAATTAAAACATATAGTATGGGCAAGCAG
GGAGCTAGAACGATTCGCAGTTAATCCTGGCCTGTTAGAAACATCA
GAAGGCTGTAGACAAATACTGGGACAGCTACAACCATCCCTTCAG
ACAGGATCAGAAGAACTTAGATCATTATATAATACAGTAGCAACCC
TCTATTGTGTGCATCAAAGGATAGAGATAAAAGACACCAAGGAAG
CTTTAGACAAGATAGAGGAAGAGCAAAACAAAAGTAAGACCACCG
CACAGCAAGCGGCCGCTGATCTTCAGACCTGGAGGAGGAGATATG
AGGGACAATTGGAGAAGTGAATTATATAAATATAAAGTAGTAAAA
ATTGAACCATTAGGAGTAGCACCCACCAAGGCAAAGAGAAGAGTG
GTGCAGAGAGAAAAAAGAGCAGTGGGAATAGGAGCTTTGTTCCTT
GGGTTCTTGGGAGCAGCAGGAAGCACTATGGGCGCAGCGTCAATG
ACGCTGACGGTACAGGCCAGACAATTATTGTCTGGTATAGTGCAGC
AGCAGAACAATTTGCTGAGGGCTATTGAGGCGCAACAGCATCTGTT
GCAACTCACAGTCTGGGGCATCAAGCAGCTCCAGGCAAGAATCCT
GGCTGTGGAAAGATACCTAAAGGATCAACAGCTCCTGGGGATTTG
GGGTTGCTCTGGAAAACTCATTTGCACCACTGCTGTGCCTTGGAAT
GCTAGTTGGAGTAATAAATCTCTGGAACAGATTTGGAATCACACGA
CCTGGATGGAGTGGGACAGAGAAATTAACAATTACACAAGCTTAA
TACACTCCTTAATTGAAGAATCGCAAAACCAGCAAGAAAAGAATG
AACAAGAATTATTGGAATTAGATAAATGGGCAAGTTTGTGGAATTG
GTTTAACATAACAAATTGGCTGTGGTATATAAAATTATTCATAATG
ATAGTAGGAGGCTTGGTAGGTTTAAGAATAGTTTTTGCTGTACTTTC
TATAGTGAATAGAGTTAGGCAGGGATATTCACCATTATCGTTTCAG
ACCCACCTCCCAACCCCGAGGGGACCCGACAGGCCCGAAGGAATA
GAAGAAGAAGGTGGAGAGAGA

TABLE 8-continued

Nucleotide sequence of pLenti4/V5-DEST.

GACAGAGACAGATCCATTCGATTAGTGAACGGATCTCGACGGTATC
GATAAGCTTGGGAGTTCCGCGTTACATAACTTACGGTAAATGGCCC
GCCTGGCTGACCGCCCAACGACCCCCGCCCATTGACGTCAATAATG
ACGTATGTTCCCATAGTAACGCCAATAGGGACTTTCCATTGACGTC
AATGGGTGGAGTATTTACGGTAAACTGCCCACTTGGCAGTACATCA
AGTGTATCATATGCCAAGTACGCCCCCTATTGACGTCAATGACGGT
AAATGGCCCGCCTGGCATTATGCCCAGTACATGACCTTATGGGACT
TTCCTACTTGGCAGTACATCTACGTATTAGTCATCGCTATTACCATG
GTGATGCGGTTTTGGCAGTACATCAATGGGCGTGGATAGCGGTTTG
ACTCACGGGGATTTCCAAGTCTCCACCCCATTGACGTCAATGGGAG
TTTGTTTTGGCACCAAAATCAACGGGACTTTCCAAAATGTCGTAAC
AACTCCGCCCCATTGACGCAAATGGGCGGTAGGCGTGTACGGTGG
GAGGTCTATATAAGCAGAGCTCGTTTAGTGAACCGTCAGATCGCCT
GGAGACGCCATCCACGCTGTTTTGACCTCCATAGAAGACACCGACT
CTAGAGGATCCACTAGTCCAGTGTGGTGGAATTCTGCAGATATCAA
CAAGTTTGTACAAAAAAGCTGAACGAGAAACGTAAAATGATATAA
ATATCAATATATTAAATTAGATTTGCATAAAAAACAGACTACATA
ATACTGTAAAACACAACATATCCAGTCACTATGGCGGCCGCATTAG
GCACCCCAGGCTTTACACTTTATGCTTCCGGCTCGTATAATGTGTGG
ATTTTGAGTTAGGATCCGGCGAGATTTTCAGGAGCTAAGGAAGCTA
AAATGGAGAAAAAATCACTGGATATACCACCGTTGATATATCCCA
ATGGCATCGTAAAGAACATTTTGAGGCATTTCAGTCAGTTGCTCAA
TGTACCTATAACCAGACCGTTCAGCTGGATATTACGGCCTTTTTAA
AGACCGTAAAGAAAAATAAGCACAAGTTTTATCCGGCCTTTATTCA
CATTCTTGCCCGCCTGATGAATGCTCATCCGGAATTCCGTATGGCA
ATGAAAGACGGTGAGCTGGTGATATGGGATAGTGTTCACCCTTGTT
ACACCGTTTTCCATGAGCAAACTGAAACGTTTTCATCGCTCTGGAG
TGAATACCACGACGATTTCCGGCAGTTTCTACACATATATTCGCAA
GATGTGGCGTGTTACGGTGAAAACCTGGCCTATTTCCCTAAAGGGT
TTATTGAGAATATGTTTTTCGTCTCAGCCAATCCCTGGGTGAGTTTC
ACCAGTTTTGATTTAAACGTGGCCAATATGGACAACTTCTTCGCCC
CCGTTTTCACCATGGGCAAATATTATACGCAAGGCGACAAGGTGCT
GATGCCGCTGGCGATTCAGGTTCATCATGCCGTCTGTGATGGCTTC
CATGTCGGCAGAATGCTTAATGAATTACAACAGTACTGCGATGAGT
GGCAGGGCGGGGCGTAAAGATCTGGATCCGGCTTACTAAAAGCCA
GATAACAGTATGCGTATTTGCGCGCTGATTTTTGCGGTATAAGAAT
ATATACTGATATGTATACCCGAAG
TATGTCAAAAAGAGGTGTGCTATGAAGCAGCGTATTACAGTGACA
GTTGACAGCGACAGCTATCAGTTGCTCAAGGCATATATGATGTCAA

TATCTCCGGTCTGGTAAGCACAACCATGCAGAATGAAGCCCGTCGT
CTGCGTGCCGAACGCTGGAAAGCGGAAAATCAGGAAGGGATGGCT
GAGGTCGCCCGGTTTATTGAAATGAACGGCTCTTTTGCTGACGAGA
ACAGGGACTGGTGAAATGCAGTTTAAGGTTTACACCTATAAAAGA
GAGAGCCGTTATCGTCTGTTTGTGGATGTACAGAGTGATATTATTG
ACACGCCCGGGCGACGGATGGTGATCCCCCTGGCCAGTGCACGTCT
GCTGTCAGATAAAGTCTCCCGTGAACTTTACCCGGTGGTGCATATC
GGGGATGAAAGCTGGCGCATGATGACCACCGATATGGCCAGTGTG
CCGGTCTCCGTTATCGGGGAAGAAGTGGCTGATCTCAGCCACCGCG
AAAATGACATCAAAAACGCCATTAACCTGATGTTCTGGGAATATA
AATGTCAGGCTCCGTTATACACAGCCAGTCTGCAGGTCGACCATAG
TGACTGGATATGTTGTGTTTTACAGTATTATGTAGTCTGTTTTTTAT
GCAAAATCTAATTTAATATATTGATATTTATATCATTTTACGTTTCT
CGTTCAGCTTTCTTGTACAAAGTGGTTGATATCCAGCACAGTGGCG
GCCGCTCGAGTCTAGAGGGCCCGCGGTTCGAAGGTAAGCCTATCCC
TAACCCTCTCCTCGGTCTCGATTCTACGCGTACCGGTTAGTAATGAG
TTTGGAATTAATTCTGTGGAATGTGTGTCAGTTAGGGTGTGGAAAG
TCCCCAGGCTCCCCAGGCAGGCAGAAGTATGCAAAGCATGCATCTC
AATTAGTCAGCAACCAGGTGTGGAAAGTCCCCAGGCTCCCCAGCA
GGCAGAAGTATGCAAAGCATGCATCTCAATTAGTCAGCAACCATA
GTCCCGCCCCTAACTCCGCCCATCCCGCCCCTAACTCCGCCCAGTTC
CGCCCATTCTCCGCCCCATGGCTGACTAATTTTTTTTATTTATGCAG
AGGCCGAGGCCGCCTCTGCCTCTGAGCTATTCCAGAAGTAGTGAGG
AGGCTTTTTTGGAGGCCTAGGCTTTTGCAAAAAGCTCCCCCTGTTG
ACAATTAATCATCGGCATAGTATATCGGCATAGTATAATACGACAA
GGTGAGGAACTAAACCATGGCCAAGTTGACCAGTGCCGTTCCGGTG
CTCACCGCGCGCGACGTCGCCGGAGCGGTCGAGTTCTGGACCGACC
GGCTCGGGTTCTCCCGGGACTTCGTGGAGGACGACTTCGCCGGTGT
GGTCCGGGACGACGTGACCCTGTTCATCAGCGCGGTCCAGGACCAG
GTGGTGCCGGACAACACCCTGGCCTGGGTGTGGGTGCGCGGCCTGG
ACGAGCTGTACGCCGAGTGGTCGGAGGTCGTGTCCACGAACTTCCG
GGACGCCTCCGGGCCGGCCATGACCGAGATCGGCGAGCAGCCGTG
GGGGCGGGAGTTCGCCCTGCGCGACCCGGCCGGCAACTGCGTGCA
CTTCGTGGCCGAGGAGCAGGACTGACACGTGCTACGAGATTTAAAT
GGTACCTTTAAGACCAATGACTTACAAGGCAGCTGTAGATCTTAGC
CACTTTTTAAAAGAAAAGGGGGGACTGGAAGGGCTAATTCACTCCC
AACGAAGACAAGATCTGCTTTTTGCTTGTACTGGGTCTCTCTGGTTA
GACCAGATCTGAGCCTGGGAGCTCTCTG
GCTAACTAGGGAACCCACTGCTTAAGCCTCAATAAAGCTTGCCTTG

TABLE 8-continued

Nucleotide sequence of pLenti4/V5-DEST.

AGTGCTTCAAGTAGTGTGTGCCCGTCTGTTGTGTGACTCTGGTAACT

AGAGATCCCTCAGACCCTTTTAGTCAGTGTGGAAAATCTCTAGCAG

TAGTAGTTCATGTCATCTTATTATTCAGTATTTATAACTTGCAAAGA

AATGAATATCAGAGAGTGAGAGGAACTTGTTTATTGCAGCTTATAA

TGGTTACAAATAAAGCAATAGCATCACAAATTTCACAAATAAAGC

ATTTTTTTCACTGCATTCTAGTTGTGGTTTGTCCAAACTCATCAATG

TATCTTATCATGTCTGGCTCTAGCTATCCCGCCCCTAACTCCGCCCA

TCCCGCCCCTAACTCCGCCCAGTTCCGCCCATTCTCCGCCCCATGGC

TGACTAATTTTTTTATTTATGCAGAGGCCGAGGCCGCCTCGGCCTC

TGAGCTATTCCAGAAGTAGTGAGGAGGCTTTTTTGGAGGCCTAGGG

ACGTACCCAATTCGCCCTATAGTGAGTCGTATTACGCGCGCTCACT

GGCCGTCGTTTTACAACGTCGTGACTGGGAAAACCCTGGCGTTACC

CAACTTAATCGCCTTGCAGCACATCCCCCTTTCGCCAGCTGGCGTA

ATAGCGAAGAGGCCCGCACCGATCGCCCTTCCCAACAGTTGCGCAG

CCTGAATGGCGAATGGGACGCGCCCTGTAGCGGCGCATTAAGCGC

GGCGGGTGTGGTGGTTACGCGCAGCGTGACCGCTACACTTGCCAGC

GCCCTAGCGCCCGCTCCTTTCGCTTTCTTCCCTTCCTTTCTCGCCACG

TTCGCCGGCTTTCCCCGTCAAGCTCTAAATCGGGGGCTCCCTTTAGG

GTTCCGATTTAGTGCTTTACGGCACCTCGACCCCAAAAAACTTGAT

TAGGGTGATGGTTCACGTAGTGGGCCATCGCCCTGATAGACGGTTT

TTCGCCCTTTGACGTTGGAGTCCACGTTCTTTAATAGTGGACTCTTG

TTCCAAACTGGAACAACACTCAACCCTATCTCGGTCTATTCTTTTGA

TTTATAAGGGATTTTGCCGATTTCGGCCTATTGGTTAAAAAATGAG

CTGATTTAACAAAAATTTAACGCGAATTTTAACAAAATATTAACGC

TTACAATTTAGGTGGCACTTTTCGGGGAAATGTGCGCGGAACCCCT

ATTTGTTTATTTTTCTAAATACATTCAAATATGTATCCGCTCATGAG

ACAATAACCCTGATAAATGCTTCAATAATATTGAAAAAGGAAGAG

TATGAGTATTCAACATTTCCGTGTCGCCCTTATTCCCTTTTTTGCGG

CATTTTGCCTTCCTGTTTTTGCTCACCCAGAAACGCTGGTGAAAGTA

AAAGATGCTGAAGATCAGTTGGGTGCACGAGTGGGTTACATCGAA

CTGGATCTCAACAGCGGTAAGATCCTTGAGAGTTTTCGCCCCGAAG

AACGTTTTCCAATGATGAGCACTTTTAAAGTTCTGCTATGTGGCGC

GGTATTATCCCGTATTGACGCCGGGCAAGAGCAACTCGGTCGCCGC

ATACACTATTCTCAGAATGACTTGGTTGAGTACTCACCAGTCACAG

AAAAGCATCTTACGGATGGCATGACAGTAAGAGAATTATGCAGTG

CTGCCATAACCATGAGTGATAACACTGCGGCCAACTTACTTCTGAC

AACGATCGGAGGACCGAAGGAGCTAACCGCTTTTTTGCACAACATG

GGGGATCATGTAACTCGCCTTGATCGTTGGGAACCGGAGCTGAATG

AAGCCATACCAAACGAC

TABLE 8-continued

Nucleotide sequence of pLenti4/V5-DEST.

GAGCGTGACACCACGATGCCTGTAGCAATGGCAACAACGTTGCGC

AAACTATTAACTGGCGAACTACTTACTCTAGCTTCCCGGCAACAAT

TAATAGACTGGATGGAGGCGGATAAAGTTGCAGGACCACTTCTGC

GCTCGGCCCTTCCGGCTGGCTGGTTTATTGCTGATAAATCTGGAGC

CGGTGAGCGTGGGTCTCGCGGTATCATTGCAGCACTGGGGCCAGAT

GGTAAGCCCTCCCGTATCGTAGTTATCTACACGACGGGGAGTCAGG

CAACTATGGATGAACGAAATAGACAGATCGCTGAGATAGGTGCCT

CACTGATTAAGCATTGGTAACTGTCAGACCAAGTTTACTCATATAT

ACTTTAGATTGATTTAAAACTTCATTTTTAATTTAAAAGGATCTAGG

TGAAGATCCTTTTTGATAATCTCATGACCAAAATCCCTTAACGTGA

GTTTTCGTTCCACTGAGCGTCAGACCCCGTAGAAAAGATCAAAGGA

TCTTCTTGAGATCCTTTTTTTCTGCGCGTAATCTGCTGCTTGCAAAC

AAAAAAACCACCGCTACCAGCGGTGGTTTGTTTGCCGGATCAAGAG

CTACCAACTCTTTTTCCGAAGGTAACTGGCTTCAGCAGAGCGCAGA

TACCAAATACTGTTCTTCTAGTGTAGCCGTAGTTAGGCCACCACTTC

AAGAACTCTGTAGCACCGCCTACATACCTCGCTCTGCTAATCCTGTT

ACCAGTGGCTGCTGCCAGTGGCGATAAGTCGTGTCTTACCGGGTTG

GACTCAAGACGATAGTTACCGGATAAGGCGCAGCGGTCGGGCTGA

ACGGGGGGTTCGTGCACACAGCCCAGCTTGGAGCGAACGACCTAC

ACCGAACTGAGATACCTACAGCGTGAGCTATGAGAAAGCGCCACG

CTTCCCGAAGGGAGAAAGGCGGACAGGTATCCGGTAAGCGGCAGG

GTCGGAACAGGAGAGCGCACGAGGGAGCTTCCAGGGGGAAACGCC

TGGTATCTTTATAGTCCTGTCGGGTTTCGCCACCTCTGACTTGAGCG

TCGATTTTTGTGATGCTCGTCAGGGGGGCGGAGCCTATGGAAAAAC

GCCAGCAACGCGGCCTTTTTACGGTTCCTGGCCTTTTGCTGGCCTTT

TGCTCACATGTTCTTTCCTGCGTTATCCCCTGATTCTGTGGATAACC

GTATTACCGCCTTTGAGTGAGCTGATACCGCTCGCCGCAGCCGAAC

GACCGAGCGCAGCGAGTCAGTGAGCGAGGAAGCGGAAGAGCGCCC

AATACGCAAACCGCCTCTCCCCGCGCGTTGGCCGATTCATTAATGC

AGCTGGCACGACAGGTTTCCCGACTGGAAAGCGGGCAGTGAGCGC

AACGCAATTAATGTGAGTTAGCTCACTCATTAGGCACCCCAGGCTT

TACACTTTATGCTTCCGGCTCGTATGTTGTGTGGAATTGTGAGCGGA

TAACAATTTCACACAGGAAACAGCTATGACCATGATTACGCCAAGC

GCGCAATTAACCCTCACTAAAGGGAACAAAAGCTGGAGCTGCAAG

CTT SEQ ID NO: 4

TABLE 9

Nucleotide sequence of pLenti6/UbC/V5-DEST.

AATGTAGTCTTATGCAATACTCTTGTAGTCTTGCAACATGGTAACG

ATGAGTTAGCAACATGCCTTACAAGGAGAGAAAAAGCACCGTGCA

TGCCGATTGGTGGAAGTAAGGTGGTACGATCGTGCCTTATTAGGA

GGCAACAGACGGGTCTGACATGGATTGGACGAACCACTGAATTGC

CGCATTGCAGAGATATTGTATTTAAGTGCCTAGCTCGATACATAAA

CGGGTCTCTCTGGTTAGACCAGATCTGAGCCTGGGAGCTCTCTGGC

TAACTAGGGAACCCACTGCTTAAGCCTCAATAAAGCTTGCCTTGAG

TGCTTCAAGTAGTGTGTGCCCGTCTGTTGTGTGACTCTGGTAACTAG

AGATCCCTCAGACCCTTTTAGTCAGTGTGGAAAATCTCTAGCAGTG

GCGCCCGAACAGGGACTTGAAAGCGAAAGGGAAACCAGAGGAGCT

CTCTCGACGCAGGACTCGGCTTGCTGAAGCGCGCACGGCAAGAGG

CGAGGGGCGGCGACTGGTGAGTACGCCAAAAATTTTGACTAGCGG

AGGCTAGAAGGAGAGATGGGTGCGAGAGCGTCAGTATTAAGCG

GGGGAGAATTAGATCGCGATGGGAAAAAATTCGGTTAAGGCCAGG

GGGAAAGAAAAAATATAAATTAAAACATATAGTATGGGCAAGCAG

GGAGCTAGAACGATTCGCAGTTAATCCTGGCCTGTTAGAAACATCA

GAAGGCTGTAGACAAATACTGGGACAGCTACAACCATCCCTTCAG

ACAGGATCAGAAGAACTTAGATCATTATATAATACAGTAGCAACCC

TCTATTGTGTGCATCAAAGGATAGAGATAAAAGACACCAAGGAAG

CTTTAGACAAGATAGAGGAAGAGCAAAACAAAAGTAAGACCACCG

CACAGCAAGCGGCCGCTGATCTTCAGACCTGGAGGAGGAGATATG

AGGGACAATTGGAGAAGTGAATTATATAAATATAAAGTAGTAAAA

ATTGAACCATTAGGAGTAGCACCCACCAAGGCAAAGAGAAGAGTG

GTGCAGAGAGAAAAAAGAGCAGTGGGAATAGGAGCTTTGTTCCTT

GGGTTCTTGGGAGCAGCAGGAAGCACTATGGGCGCAGCGTCAATG

ACGCTGACGGTACAGGCCAGACAATTATTGTCTGGTATAGTGCAGC

AGCAGAACAATTTGCTGAGGGCTATTGAGGCGCAACAGCATCTGTT

GCAACTCACAGTCTGGGGCATCAAGCAGCTCCAGGCAAGAATCCT

GGCTGTGGAAAGATACCTAAAGGATCAACAGCTCCTGGGGATTTG

GGGTTGCTCTGGAAAACTCATTTGCACCACTGCTGTGCCTTGGAAT

GCTAGTTGGAGTAATAAATCTCTGGAACAGATTTGGAATCACACGA

CCTGGATGGAGTGGGACAGAGAAATTAACAATTACACAAGCTTAA

TACACTCCTTAATTGAAGAATCGCAAAACCAGCAAGAAAAGAATG

AACAAGAATTATTGGAATTAGATAAATGGGCAAGTTTGTGGAATTG

GTTTAACATAACAAATTGGCTGTGGTATATAAAATTATTCATAATG

ATAGTAGGAGGCTTGGTAGGTTTAAGAATAGTTTTTGCTGTACTTTC

TATAGTGAATAGAGTTAGGCAGGGATATTCACCATTATCGTTTCAG

ACCCACCTCCCAACCCCGAGGGGACCCGACAGGCCCGAAGGAATA

GAAGAAGAAGGTGGAGAGAGA

GACAGAGACAGATCCATTCGATTAGTGAACGGATCTCGACGGTATC

GGATCTGGCCTCCGCGCCGGGTTTTGGCGCCTCCCGCGGGCGCCCC

CCTCCTCACGGCGAGCGCTGCCACGTCAGACGAAGGGCGCAGGAG

CGTCCTGATCCTTCCGCCCGGACGCTCAGGACAGCGGCCCGCTGCT

CATAAGACTCGGCCTTAGAACCCCAGTATCAGCAGAAGGACATTTT

AGGACGGGACTTGGGTGACTCTAGGGCACTGGTTTTCTTTCCAGAG

AGCGGAACAGGCGAGGAAAAGTAGTCCCTTCTCGGCGATTCTGCG

GAGGGATCTCCGTGGGGCGGTAACGCCGATGATTATATAAGGAC

GCGCCGGGTGTGGCACAGCTAGTTCCGTCGCAGCCGGGATTTGGGT

CGCGGTTCTTGTTTGTGGATCGCTGTGATCGTCACTTGGTGAGTAGC

GGGCTGCTGGGCTGGCCGGGGCTTTCGTGGCCGCCGGGCCGCTCGG

TGGGACGGAAGCGTGTGGAGAGACCGCCAAGGGCTGTAGTCTGGG

TCCGCGAGCAAGGTTGCCCTGAACTGGGGGTTGGGGGGAGCGCAG

CAAAATGGCGGCTGTTCCCGAGTCTTGAATGGAAGACGCTTGTGAG

GCGGGCTGTGAGGTCGTTGAAACAAGGTGGGGGGCATGGTGGGCG

GCAAGAACCCAAGGTCTTGAGGCCTTCGCTAATGCGGGAAAGCTCT

TATTCGGGTGAGATGGGCTGGGGCACCATCTGGGGACCCTGACGTG

AAGTTTGTCACTGACTGGAGAACTCGGTTTGTCGTCTGTTGCGGGG

GCGGCAGTTATGCGGTGCCGTTGGGCAGTGCACCCGTACCTTTGGG

AGCGCGCGCCCTCGTCGTGTCGTGACGTCACCCGTTCTGTTGGCTTA

TAATGCAGGGTGGGGCCACCTGCCGGTAGGTGTGCGGTAGGCTTTT

CTCCGTCGCAGGACGCAGGGTTCGGGCCTAGGGTAGGCTCTCCTGA

ATCGACAGGCGCCGGACCTCTGGTGAGGGGAGGGATAAGTGAGGC

GTCAGTTTCTTTGGTCGGTTTTATGTACCTATCTTCTTAAGTAGCTG

AAGCTCCGGTTTTGAACTATGCGCTCGGGGTTGGCGAGTGTGTTTT

GTGAAGTTTTTTAGGCACCTTTTGAAATGTAATCATTTGGGTCAATA

TGTAATTTTCAGTGTTAGACTAGTAAATTGTCCGCTAAATTCTGGCC

GTTTTTGGCTTTTTTGTTAGACGAAGCTTGGTACCGAGCTCGGATCC

ACTAGTCCAGTGTGGTGGAATTCTGCAGATATCAACAAGTTTGTAC

AAAAAAGCTGAACGAGAAACGTAAAATGATATAAATATCAATATA

TTAAATTAGATTTTGCATAAAAAACAGACTACATAATACTGTAAAA

CACAACATATCCAGTCACTATGGCGGCCGCATTAGGCACCCCAGGC

TTTACACTTTATGCTTCCGGCTCGTATAATGTGTGGATTTTGAGTTA

GGATCCGGCGAGATTTTCAGGAGCTAAGGAAGCTAAAATGGAGAA

AAAAATCACTGGATATACCACCGTTGATATATCCCAATGGCATCGT

AAAGAACATTTTGAGGCATTTCAGTCAGTTGCTCAATGTACCTATA

ACCAGACCGTTCAGCTGGATATTACGGCCTTTTTAAAGACCGTAAA

GAAAATAAGCACAAGTTTTATCCGGCCTTTATTCACATTCTTGCCC

GCC

TABLE 9-continued

Nucleotide sequence of pLenti6/UbC/V5-DEST.

TGATGAATGCTCATCCGGAATTCCGTATGGCAATGAAAGACGGTGA

GCTGGTGATATGGGATAGTGTTCACCCTTGTTACACCGTTTTCCATG

AGCAAACTGAAACGTTTTCATCGCTCTGGAGTGAATACCACGACGA

TTTCCGGCAGTTTCTACACATATATTCGCAAGATGTGGCGTGTTACG

GTGAAAACCTGGCCTATTTCCCTAAAGGGTTTATTGAGAATATGTT

TTTCGTCTCAGCCAATCCCTGGGTGAGTTTCACCAGTTTTGATTTAA

ACGTGGCCAATATGGACAACTTCTTCGCCCCCGTTTTCACCATGGG

CAAATATTATACGCAAGGCGACAAGGTGCTGATGCCGCTGGCGATT

CAGGTTCATCATGCCGTCTGTGATGGCTTCCATGTCGGCAGAATGC

TTAATGAATTACAACAGTACTGCGATGAGTGGCAGGGCGGGGCGT

AAAGATCTGGATCCGGCTTACTAAAAGCCAGATAACAGTATGCGTA

TTTGCGCGCTGATTTTTGCGGTATAAGAATATATACTGATATGTATA

CCCGAAGTATGTCAAAAAGAGGTGTGCTATGAAGCAGCGTATTAC

AGTGACAGTTGACAGCGACAGCTATCAGTTGCTCAAGGCATATATG

ATGTCAATATCTCCGGTCTGGTAAGCACAACCATGCAGAATGAAGC

CCGTCGTCTGCGTGCCGAACGCTGGAAAGCGGAAAATCAGGAAGG

GATGGCTGAGGTCGCCCGGTTTATTGAAATGAACGGCTCTTTTGCT

GACGAGAACAGGGACTGGTGAAATGCAGTTTAAGGTTTACACCTAT

AAAAGAGAGAGCCGTTATCGTCTGTTTGTGGATGTACAGAGTGATA

TTATTGACACGCCCGGGCGACGGATGGTGATCCCCCTGGCCAGTGC

ACGTCTGCTGTCAGATAAAGTCTCCCGTGAACTTTACCCGGTGGTG

CATATCGGGGATGAAAGCTGGCGCATGATGACCACCGATATGGCC

AGTGTGCCGGTCTCCGTTATCGGGGAAGAAGTGGCTGATCTCAGCC

ACCGCGAAAATGACATCAAAAACGCCATTAACCTGATGTTCTGGGG

AATATAAATGTCAGGCTCCGTTATACACAGCCAGTCTGCAGGTCGA

CCATAGTGACTGGATATGTTGTGTTTTACAGTATTATGTAGTCTGTT

TTTTATGCAAAATCTAATTTAATATATTGATATTTATATCATTTTAC

GTTTCTCGTTCAGCTTTCTTGTACAAAGTGGTTGATATCCAGCACAG

TGGCGGCCGCTCGAGTCTAGAGGGCCCGCGGTTCGAAGGTAAGCCT

ATCCCTAACCCTCTCCTCGGTCTCGATTCTACGCGTACCGGTTAGTA

ATGAGTTTGGAATTAATTCTGTGGAATGTGTGTCAGTTAGGGTGTG

GAAAGTCCCCAGGCTCCCCAGGCAGGCAGAAGTATGCAAAGCATG

CATCTCAATTAGTCAGCAACCAGGTGTGGAAAGTCCCCAGGCTCCC

CAGCAGGCAGAAGTATGCAAAGCATGCATCTCAATTAGTCAGCAA

CCATAGTCCCGCCCCTAACTCCGCCCATCCCGCCCCTAACTCCGCCC

AGTTCCGCCCATTCTCCGCCCCATGGCTGACTAATTTTTTTTATTTA

TGCAGAGGCCGAGGCCGCCT

CTGCCTCTGAGCTATTCCAGAAGTAGTGAGGAGGCTTTTTTGGAGG

CCTAGGCTTTTGCAAAAAGCTCCCGGGAGCTTGTATATCCATTTTCG

GATCTGATCAGCACGTGTTGACAATTAATCATCGGCATAGTATATC

GGCATAGTATAATACGACAAGGTGAGGAACTAAACCATGGCCAAG

CCTTTGTCTCAAGAAGAATCCACCCTCATTGAAAGAGCAACGGCTA

CAATCAACAGCATCCCCATCTCTGAAGACTACAGCGTCGCCAGCGC

AGCTCTCTCTAGCGACGGCCGCATCTTCACTGGTGTCAATGTATATC

ATTTTACTGGGGGACCTTGTGCAGAACTCGTGGTGCTGGGCACTGC

TGCTGCTGCGGCAGCTGGCAACCTGACTTGTATCGTCGCGATCGGA

AATGAGAACAGGGGCATCTTGAGCCCCTGCGGACGGTGCCGACAG

GTGCTTCTCGATCTGCATCCTGGGATCAAAGCCATAGTGAAGGACA

GTGATGGACAGCCGACGGCAGTTGGGATTCGTGAATTGCTGCCCTC

TGGTTATGTGTGGGAGGGCTAAGCACAATTCGAGCTCGGTACCTTT

AAGACCAATGACTTACAAGGCAGCTGTAGATCTTAGCCACTTTTTA

AAAGAAAGGGGGGACTGGAAGGGCTAATTCACTCCCAACGAAGA

CAAGATCTGCTTTTTGCTTGTACTGGGTCTCTCTGGTTAGACCAGAT

CTGAGCCTGGGAGCTCTCTGGCTAACTAGGGAACCCACTGCTTAAG

CCTCAATAAAGCTTGCCTTGAGTGCTTCAAGTAGTGTGTGCCCGTCT

GTTGTGTGACTCTGGTAACTAGAGATCCCTCAGACCCTTTTAGTCA

GTGTGGAAAATCTCTAGCAGTAGTAGTTCATGTCATCTTATTATTCA

GTATTTATAACTTGCAAAGAAATGAATATCAGAGAGTGAGAGGAA

CTTGTTTATTGCAGCTTATAATGGTTACAAATAAAGCAATAGCATC

ACAAATTTCACAAATAAAGCATTTTTTTCACTGCATTCTAGTTGTGG

TTTGTCCAAACTCATCAATGTATCTTATCATGTCTGGCTCTAGCTAT

CCCGCCCCTAACTCCGCCCATCCCGCCCCTAACTCCGCCCAGTTCCG

CCCATTCTCCGCCCCATGGCTGACTAATTTTTTTATTTATGCAGAG

GCCGAGGCCGCCTCGGCCTCTGAGCTATTCCAGAAGTAGTGAGGAG

GCTTTTTTGGAGGCCTAGGGACGTACCCAATTCGCCCTATAGTGAG

TCGTATTACGCGCGCTCACTGGCCGTCGTTTTACAACGTCGTGACTG

GGAAAACCCTGGCGTTACCCAACTTAATCGCCTTGCAGCACATCCC

CCTTTCGCCAGCTGGCGTAATAGCGAAGAGGCCCGCACCGATCGCC

CTTCCCAACAGTTGCGCAGCCTGAATGGCGAATGGGACGCGCCCTG

TAGCGGCGCATTAAGCGCGGCGGGTGTGGTGGTTACGCGCAGCGT

GACCGCTACACTTGCCAGCGCCCTAGCGCCCGCTCCTTTCGCTTTCT

TCCCTTCCTTTCTCGCCACGTTCGCCGGCTTTCCCCGTCA

AGCTCTAAATCGGGGCTCCCTTTAGGGTTCCGATTTAGTGCTTTAC

GGCACCTCGACCCCAAAAAACTTGATTAGGGTGATGGTTCACGTAG

TGGGCCATCGCCCTGATAGACGGTTTTTCGCCCTTTGACGTTGGAGT

CCACGTTCTTTAATAGTGGACTCTTGTTCCAAACTGGAACAACACT

CAACCCTATCTCGGTCTATTCTTTTGATTTATAAGGGATTTTGCCGA

TTTCGGCCTATTGGTTAAAAAATGAGCTGATTTAACAAAAATTTAA

TABLE 9-continued

Nucleotide sequence of pLenti6/UbC/V5-DEST.

CGCGAATTTTAACAAAATATTAACGCTTACAATTTAGGTGGCACTT

TTCGGGGAAATGTGCGCGGAACCCCTATTTGTTTATTTTTCTAAATA

CATTCAAATATGTATCCGCTCATGAGACAATAACCCTGATAAATGC

TTCAATAATATTGAAAAAGGAAGAGTATGAGTATTCAACATTTCCG

TGTCGCCCTTATTCCCTTTTTTGCGGCATTTTGCCTTCCTGTTTTTGC

TCACCCAGAAACGCTGGTGAAAGTAAAAGATGCTGAAGATCAGTT

GGGTGCACGAGTGGGTTACATCGAACTGGATCTCAACAGCGGTAA

GATCCTTGAGAGTTTTCGCCCCGAAGAACGTTTTCCAATGATGAGC

ACTTTTAAAGTTCTGCTATGTGGCGCGGTATTATCCCGTATTGACGC

CGGGCAAGAGCAACTCGGTCGCCGCATACACTATTCTCAGAATGAC

TTGGTTGAGTACTCACCAGTCACAGAAAAGCATCTTACGGATGGCA

TGACAGTAAGAGAATTATGCAGTGCTGCCATAACCATGAGTGATAA

CACTGCGGCCAACTTACTTCTGACAACGATCGGAGGACCGAAGGA

GCTAACCGCTTTTTTGCACAACATGGGGGATCATGTAACTCGCCTT

GATCGTTGGGAACCGGAGCTGAATGAAGCCATACCAAACGACGAG

CGTGACACCACGATGCCTGTAGCAATGGCAACAACGTTGCGCAAA

CTATTAACTGGCGAACTACTTACTCTAGCTTCCCGGCAACAATTAA

TAGACTGGATGGAGGCGGATAAAGTTGCAGGACCACTTCTGCGCTC

GGCCCTTCCGGCTGGCTGGTTTATTGCTGATAAATCTGGAGCCGGT

GAGCGTGGGTCTCGCGGTATCATTGCAGCACTGGGGCCAGATGGTA

AGCCCTCCCGTATCGTAGTTATCTACACGACGGGGAGTCAGGCAAC

TATGGATGAACGAAATAGACAGATCGCTGAGATAGGTGCCTCACT

GATTAAGCATTGGTAACTGTCAGACCAAGTTTACTCATATATACTTT

AGATTGATTTAAAACTTCATTTTTAATTTAAAAGGATCTAGGTGAA

GATCCTTTTTGATAATCTCATGACCAAAATCCCTTAACGTGAGTTTT

CGTTCCACTGAGCGTCAGACCCCGTAGAAAAGATCAAAGGATCTTC

TTGAGATCCTTTTTTTCTGCGCGTAATCTGCTGCTTGCAAACAAAAA

AACCACCGCTACCAGCGGTGGTTTGTTTGCCGGATCAAGAGCTACC

AACTCTTTTTCCGAAGGTAACTGGCTTCAGCAGAGCGCAGATACCA

AATACTGTTCTTCTAGTGTAGCCGTAGTTAGGCCACCACTTCAAGA

ACTCTGTAGCACCGCCTACATACCTCGCTCTGCTAATCCTGTTACCA

GTGGCTGCTGCCAGTGGCGATAAGTCGTGTCTTACCGGGTTGGACT

CAAGACGATAGTTACCGGATAAGGCGCAGCGGTCGGGCTGAACGG

GGGGTTCGTGCACACAGCCCAG

CTTGGAGCGAACGACCTACACCGAACTGAGATACCTACAGCGTGA

GCTATGAGAAAGCGCCACGCTTCCCGAAGGGAGAAAGGCGGACAG

GTATCCGGTAAGCGGCAGGGTCGGAACAGGAGAGCGCACGAGGGA

GCTTCCAGGGGGAAACGCCTGGTATCTTTATAGTCCTGTCGGGTTT

CGCCACCTCTGACTTGAGCGTCGATTTTTGTGATGCTCGTCAGGGG

TABLE 9-continued

Nucleotide sequence of pLenti6/UbC/V5-DEST.

GGCGGAGCCTATGGAAAAACGCCAGCAACGCGGCCTTTTTACGGTT

CCTGGCCTTTTGCTGGCCTTTTGCTCACATGTTCTTTCCTGCGTTATC

CCCTGATTCTGTGGATAACCGTATTACCGCCTTTGAGTGAGCTGAT

ACCGCTCGCCGCAGCCGAACGACCGAGCGCAGCGAGTCAGTGAGC

GAGGAAGCGGAAGAGCGCCCAATACGCAAACCGCCTCTCCCCGCG

CGTTGGCCGATTCATTAATGCAGCTGGCACGACAGGTTTCCCGACT

GGAAAGCGGGCAGTGAGCGCAACGCAATTAATGTGAGTTAGCTCA

CTCATTAGGCACCCCAGGCTTTACACTTTATGCTTCCGGCTCGTATG

TTGTGTGGAATTGTGAGCGGATAACAATTTCACACAGGAAACAGCT

ATGACCATGATTACGCCAAGCGCGCAATTAACCCTCACTAAAGGGA

ACAAAAGCTGGAGCTGCAAGCTT SEQ ID NO: 5

TABLE 10

Nucleotide sequence of plasmid pLP1.

TTGGCCCATTGCATACGTTGTATCCATATCATAATATGTACATTTAT

ATTGGCTCATGTCCAACATTACCGCCATGTTGACATTGATTATTGAC

TAGTTATTAATAGTAATCAATTACGGGGTCATTAGTTCATAGCCCA

TATATGGAGTTCCGCGTTACATAACTTACGGTAAATGGCCCGCCTG

GCTGACCGCCCAACGACCCCCGCCCATTGACGTCAATAATGACGTA

TGTTCCCATAGTAACGCCAATAGGGACTTTCCATTGACGTCAATGG

GTGGAGTATTTACGGTAAACTGCCCACTTGGCAGTACATCAAGTGT

ATCATATGCCAAGTACGCCCCCTATTGACGTCAATGACGGTAAATG

GCCCGCCTGGCATTATGCCCAGTACATGACCTTATGGGACTTTCCT

ACTTGGCAGTACATCTACGTATTAGTCATCGCTATTACCATGGTGAT

GCGGTTTTGGCAGTACATCAATGGGCGTGGATAGCGGTTTGACTCA

CGGGGATTTCCAAGTCTCCACCCCATTGACGTCAATGGGAGTTTGT

TTTGGCACCAAAATCAACGGGACTTTCCAAAATGTCGTAACAACTC

CGCCCCATTGACGCAAATGGGCGGTAGGCGTGTACGGTGGGAGGT

CTATATAAGCAGAGCTCGTTTAGTGAACCGTCAGATCGCCTGGAGA

CGCCATCCACGCTGTTTTGACCTCCATAGAAGACACCGGGACCGAT

CCAGCCTCCCCTCGAAGCTTACATGTGGTACCGAGCTCGGATCCTG

AGAACTTCAGGGTGAGTCTATGGGACCCTTGATGTTTTCTTTCCCCT

TCTTTTCTATGGTTAAGTTCATGTCATAGGAAGGGGAGAAGTAACA

GGGTACACATATTGACCAAATCAGGGTAATTTTGCATTTGTAATTTT

AAAAAATGCTTTCTTCTTTTAATATACTTTTTTGTTTATCTTATTTCT

AATACTTTCCCTAATCTCTTTCTTTCAGGGCAATAATGATACAATGT

ATCATGCCTCTTTGCACCATTCTAAAGAATAACAGTGATAATTTCTG

GGTTAAGGCAATAGCAATATTTCTGCATATAAATATTTCTGCATAT

AAATTGTAACTGATGTAAGAGGTTTCATATTGCTAATAGCAGCTAC

TABLE 10-continued

Nucleotide sequence of plasmid pLP1.

AATCCAGCTACCATTCTGCTTTTATTTTATGGTTGGGATAAGGCTGG

ATTATTCTGAGTCCAAGCTAGGCCCTTTTGCTAATCATGTTCATACC

TCTTATCTTCCTCCCACAGCTCCTGGGCAACGTGCTGGTCTGTGTGC

TGGCCCATCACTTTGGCAAAGCACGTGAGATCTGAATTCAGATCT

GCCGCCGCCATGGGTGCGAGAGCGTCAGTATTAAGCGGGGAGAA

TTAGATCGATGGGAAAAATTCGGTTAAGGCCAGGGGGAAAGAAA

AAATATAAATTAAAACATATAGTATGGGCAAGCAGGGAGCTAGAA

CGATTCGCAGTTAATCCTGGCCTGTTAGAAACATCAGAAGGCTGTA

GACAAATACTGGGACAGCTACAACCATCCCTTCAGACAGGATCAG

AAGAACTTAGATCATTATATAATACAGTAGCAACCCTCTATTGTGT

GCATCAAAGGATAGAGATAAAAGACACCAAGGAAGCTTTAGACAA

GATAGAGGAAGAGCAAAACAAAAGTAAGAAAAAAGCACAGCAAG

CAGCAGCTGACACAGGACACAGCAATCAGGTCAGCCAAAATTACC

CTATAGTGCAGAACATCCAGGGGCAAATGGTACATCAGGCCATATC

ACCTAGAACTTTAAATGCATGGG

TAAAAGTAGTAGAAGAGAAGGCTTTCAGCCCAGAAGTGATACCCA

TGTTTTCAGCATTATCAGAAGGAGCCACCCCACAAGATTTAAACAC

CATGCTAAACACAGTGGGGGGACATCAAGCAGCCATGCAAATGTT

AAAAGAGACCATCAATGAGGAAGCTGCAGAATGGGATAGAGTGCA

TCCAGTGCATGCAGGGCCTATTGCACCAGGCCAGATGAGAGAACC

AAGGGGAAGTGACATAGCAGGAACTACTAGTACCCTTCAGGAACA

AATAGGATGGATGACACATAATCCACCTATCCCAGTAGGAGAAAT

CTATAAAAGATGGATAATCCTGGGATTAAATAAAATAGTAAGAAT

GTATAGCCCTACCAGCATTCTGGACATAAGACAAGGACCAAAGGA

ACCCTTTAGAGACTATGTAGACCGATTCTATAAAACTCTAAGAGCC

GAGCAAGCTTCACAAGAGGTAAAAAATTGGATGACAGAAACCTTG

TTGGTCCAAAATGCGAACCCAGATTGTAAGACTATTTTAAAAGCAT

TGGGACCAGGAGCGACACTAGAAGAAATGATGACAGCATGTCAGG

GAGTGGGGGGACCCGGCCATAAAGCAAGAGTTTTGGCTGAAGCAA

TGAGCCAAGTAACAAATCCAGCTACCATAATGATACAGAAAGGCA

ATTTTAGGAACCAAAGAAAGACTGTTAAGTGTTTCAATTGTGGCAA

AGAAGGGCACATAGCCAAAAATTGCAGGGCCCCTAGGAAAAAGGG

CTGTTGGAAATGTGGAAAGGAAGGACACCAAATGAAAGATTGTAC

TGAGAGACAGGCTAATTTTTTAGGGAAGATCTGGCCTTCCCACAAG

GGAAGGCCAGGGAATTTTCTTCAGAGCAGACCAGAGCCAACAGCC

CCACCAGAAGAGAGCTTCAGGTTTGGGGAAGAGACAACAACTCCC

TCTCAGAAGCAGGAGCCGATAGACAAGGAACTGTATCCTTTAGCTT

CCCTCAGATCACTCTTTGGCAGCGACCCCTCGTCACAATAAAGATA

GGGGGGCAATTAAAGGAAGCTCTATTAGATACAGGAGCAGATGAT

ACAGTATTAGAAGAAATGAATTTGCCAGGAAGATGGAAACCAAAA

ATGATAGGGGGAATTGGAGGTTTTATCAAAGTAAGACAGTATGATC

AGATACTCATAGAAATCTGCGGACATAAAGCTATAGGTACAGTATT

AGTAGGACCTACACCTGTCAACATAATTGGAAGAAATCTGTTGACT

CAGATTGGCTGCACTTTAAATTTTCCCATTAGTCCTATTGAGACTGT

ACCAGTAAAATTAAAGCCAGGAATGGATGGCCCAAAAGTTAAACA

ATGGCCATTGACAGAAGAAAAAATAAAAGCATTAGTAGAAATTTG

TACAGAAATGGAAAAGGAAGGAAAAATTTCAAAAATTGGGCCTGA

AAATCCATACAATACTCCAGTATTTGCCATAAAGAAAAAAGACAGT

ACTAAATGGAGAAAATTAGTAGATTTCAGAGAACTTAATAAGAGA

ACTCAAGATTTCTGGGAAGTTCAATTAGGAATACCACATCCTGCAG

GGTTAAAACAGAAAAAATCAGTAACAGTACTGGATGTGGGCGATG

CATATTTTTCAGTTCCCTTAGATAAAGACTTCAGGAAGTATACTGC

ATTTACCATACCTAGTATAAACAATGAGACACCAGGGATTAGATAT

CAGTACAATGTGCTTCCACAGGGA

TGGAAAGGATCACCAGCAATATTCCAGTGTAGCATGACAAAAATCT

TAGAGCCTTTTAGAAAACAAAATCCAGACATAGTCATCTATCAATA

CATGGATGATTTGTATGTAGGATCTGACTTAGAAATAGGGCAGCAT

AGAACAAAAATAGAGGAACTGAGACAACATCTGTTGAGGTGGGGA

TTTACCACACCAGACAAAAAACATCAGAAAGAACCTCCATTCCTTT

GGATGGGTTATGAACTCCATCCTGATAAATGGACAGTACAGCCTAT

AGTGCTGCCAGAAAAGGACAGCTGGACTGTCAATGACATACAGAA

ATTAGTGGGAAAATTGAATTGGGCAAGTCAGATTTATGCAGGGATT

AAAGTAAGGCAATTATGTAAACTTCTTAGGGGAACCAAAGCACTA

ACAGAAGTAGTACCACTAACAGAAGAAGCAGAGCTAGAACTGGCA

GAAAACAGGGAGATTCTAAAAGAACCGGTACATGGAGTGTATTAT

GACCCATCAAAAGACTTAATAGCAGAAATACAGAAGCAGGGGCAA

GGCCAATGGACATATCAAATTTATCAAGAGCCATTTAAAAATCTGA

AAACAGGAAAGTATGCAAGAATGAAGGGTGCCCACACTAATGATG

TGAAACAATTAACAGAGGCAGTACAAAAAATAGCCACAGAAAGCA

TAGTAATATGGGGAAAGACTCCTAAATTTAAATTACCCATACAAAA

GGAAACATGGGAAGCATGGTGGACAGAGTATTGGCAAGCCACCTG

GATTCCTGAGTGGGAGTTTGTCAATACCCCTCCCTTAGTGAAGTTAT

GGTACCAGTTAGAGAAAGAACCCATAATAGGAGCAGAAACTTTCT

ATGTAGATGGGGCAGCCAATAGGGAAACTAAATTAGGAAAAGCAG

GATATGTAACTGACAGAGGAAGACAAAAAGTTGTCCCCCTAACGG

ACACAACAAATCAGAAGACTGAGTTACAAGCAATTCATCTAGCTTT

GCAGGATTCGGGATTAGAAGTAAACATAGTGACAGACTCACAATA

TGCATTGGGAATCATTCAAGCACAACCAGATAAGAGTGAATCAGA

TABLE 10-continued

Nucleotide sequence of plasmid pLP1.

```
GTTAGTCAGTCAAATAATAGAGCAGTTAATAAAAAAGGAAAAAGT
CTACCTGGCATGGGTACCAGCACACAAAGGAATTGGAGGAAATGA
ACAAGTAGATAAATTGGTCAGTGCTGGAATCAGGAAAGTACTATTT
TTAGATGGAATAGATAAGGCCCAAGAAGAACATGAGAAATATCAC
AGTAATTGGAGAGCAATGGCTAGTGATTTTAACCTACCACCTGTAG
TAGCAAAAGAAATAGTAGCCAGCTGTGATAAATGTCAGCTAAAAG
GGGAAGCCATGCATGGACAAGTAGACTGTAGCCCAGGAATATGGC
AGCTAGATTGTACACATTTAGAAGGAAAAGTTATCTTGGTAGCAGT
TCATGTAGCCAGTGGATATATAGAAGCAGAAGTAATTCCAGCAGA
GACAGGGCAAGAAACAGCATACTTCCTCTTAAAATTAGCAGGAAG
ATGGCCAGTAAAAACAGTACATACAGACAATGGCAGCAATTTCAC
CAGTACTACAGTTAAGGCCGCCTGTTGGTGGGCGGGGATCAAGCA
GGAATTTGGCATTCCCTACAATCCCCAAAGTCAAGGAGTAATAGAA
TCTATGAATAAAGAATTAAAGAAAATTATAGGACAGGTAAGAGAT
CAGGCTGAACATCTTAAGACAGCAGTACAAATGGCAGTATTCATCC
ACAATTTTAAAAGAAAAGGGGGGATTGGGGGGTACAGTGCAGGGG
AAAGAATAGTAGACATAATAGCAACAGACATACAAACTAAAGAAT
TACAAAAACAAATTACAAAAATTCAAAATTTTCGGGTTTATTACAG
GGACAGCAGAGATCCAGTTTGGAAAGGACCAGCAAAGCTCCTCTG
GAAAGGTGAAGGGGCAGTAGTAATACAAGATAATAGTGACATAAA
AGTAGTGCCAAGAAGAAAAGCAAAGATCATCAGGGATTATGGAAA
ACAGATGGCAGGTGATGATTGTGTGGCAAGTAGACAGGATGAGGA
TTAACACATGGAATTCCGGAGCGGCCGCAGGAGCTTTGTTCCTTGG
GTTCTTGGGAGCAGCAGGAAGCACTATGGGCGCAGCGTCAATGAC
GCTGACGGTACAGGCCAGACAATTATTGTCTGGTATAGTGCAGCAG
CAGAACAATTTGCTGAGGGCTATTGAGGCGCAACAGCATCTGTTGC
AACTCACAGTCTGGGGCATCAAGCAGCTCCAGGCAAGAATCCTGG
CTGTGGAAAGATACCTAAAGGATCAACAGCTCCTGGGGATTTGGG
GTTGCTCTGGAAAACTCATTTGCACCACTGCTGTGCCTTGGAATGCT
AGTTGGAGTAATAAATCTCTGGAACAGATTTGGAATCACACGACCT
GGATGGAGTGGGACAGAGAAATTAACAATTACACAAGCTTCCGCG
GAATTCACCCCACCAGTGCAGGCTGCCTATCAGAAAGTGGTGGCTG
GTGTGGCTAATGCCCTGGCCCACAAGTATCACTAAGCTCGCTTTCTT
GCTGTCCAATTTCTATTAAAGGTTCCTTTGTTCCCTAAGTCCAACTA
CTAAACTGGGGGATATTATGAAGGGCCTTGAGCATCTGGATTCTGC
CTAATAAAAAACATTTATTTTCATTGCAATGATGTATTTAAATTATT
TCTGAATATTTTACTAAAAAGGGAATGTGGGAGGTCAGTGCATTTA
AAACATAAAGAAATGAAGAGCTAGTTCAAACCTTGGGAAAATACA
CTATATCTTAAACTCCATGAAAGAAGGTGAGGCTGCAAACAGCTAA
TGCACATTGGCAACAGCCCCTGATGCCTATGCCTTATTCATCCCTCA
GAAAAGGATTCAAGTAGAGGCTTGATTTGGAGGTTAAAGTTTTGCT
ATGCTGTATTTTACATTACTTATTGTTTTAGCTGTCCTCATGAATGT
CTTTTCACTACCCATTTGCTTATCCTGCATCTCTCAGCCTTGACTCC
ACTCAGTTCTCTTGCTTAGAGATACCACCTTTCCCCTGAAGTGTTCC
TTCCATGTTTTACGGCGAGATGGTTTCTCCTCGCCTGGCCACTCAGC
CTTAGTTGTCTCTGTTGTCTTATAGAGGTCTACTTGAAGAAGGAAA
AACAGGGGCATGGTTTGACTGTCCTGTGAGCCCTTCTTCCCTGCCT
CCCCCACTCACAGTGACCCGGAATCCCTCGACATGGCAGTCTAGCA
CTAGTGCGGCCGCAGATCTGCTTCCTCGCTCACTGACTCGCTGCGCT
CGGTCGTTCGGCTGCGGCGAGCGGTATCAGCTCACTCAAAGGCGGT
AATACGGTTATCCACAGAATCAGGGGATAACGCAGGAAAGAACAT
GTGAGCAAAAGGCCAGCAAAAGGCCAGGAACCGTAAAAAGGCCG
CGTTGCTGGCGTTTTTCCATAGGCTCCGCC
CCCCTGACGAGCATCACAAAAATCGACGCTCAAGTCAGAGGTGGC
GAAACCCGACAGGACTATAAAGATACCAGGCGTTTCCCCCTGGAA
GCTCCCTCGTGCGCTCTCCTGTTCCGACCCTGCCGCTTACCGGATAC
CTGTCCGCCTTTCTCCCTTCGGGAAGCGTGGCGCTTTCTCATAGCTC
ACGCTGTAGGTATCTCAGTTCGGTGTAGGTCGTTCGCTCCAAGCTG
GGCTGTGTGCACGAACCCCCCGTTCAGCCCGACCGCTGCGCCTTAT
CCGGTAACTATCGTCTTGAGTCCAACCCGGTAAGACACGACTTATC
GCCACTGGCAGCAGCCACTGGTAACAGGATTAGCAGAGCGAGGTA
TGTAGGCGGTGCTACAGAGTTCTTGAAGTGGTGGCCTAACTACGGC
TACACTAGAAGAACAGTATTTGGTATCTGCGCTCTGCTGAAGCCAG
TTACCTTCGGAAAAAGAGTTGGTAGCTCTTGATCCGGCAAACAAAC
CACCGCTGGTAGCGGTGGTTTTTTTGTTTGCAAGCAGCAGATTACG
CGCAGAAAAAAAGGATCTCAAGAAGATCCTTTGATCTTTTCTACGG
GGTCTGACGCTCAGTGGAACGAAAACTCACGTTAAGGGATTTTGGT
CATGAGATTATCAAAAAGGATCTTCACCTAGATCCTTTTAAATTAA
AAATGAAGTTTTAAATCAATCTAAAGTATATATGAGTAAACTTGGT
CTGACAGTTACCAATGCTTAATCAGTGAGGCACCTATCTCAGCGAT
CTGTCTATTTCGTTCATCCATAGTTGCCTGACTCCCCGTCGTGTAGA
TAACTACGATACGGGAGGGCTTACCATCTGGCCCCAGTGCTGCAAT
GATACCGCGAGACCCACGCTCACCGGCTCCAGATTTATCAGCAATA
AACCAGCCAGCCGGAAGGGCCGAGCGCAGAAGTGGTCCTGCAACT
TTATCCGCCTCCATCCAGTCTATTAATTGTTGCCGGGAAGCTAGAGT
AAGTAGTTCGCCAGTTAATAGTTTGCGCAACGTTGTTGCCATTGCT
ACAGGCATCGTGGTGTCACGCTCGTCGTTTGGTATGGCTTCATTCA
GCTCCGGTTCCCAACGATCAAGGCGAGTTACATGATCCCCCATGTT
```

TABLE 10-continued

Nucleotide sequence of plasmid pLP1.

GTGCAAAAAAGCGGTTAGCTCCTTCGGTCCTCCGATCGTTGTCAGA
AGTAAGTTGGCCGCAGTGTTATCACTCATGGTTATGGCAGCACTGC
ATAATTCTCTTACTGTCATGCCATCCGTAAGATGCTTTTCTGTGACT
GGTGAGTACTCAACCAAGTCATTCTGAGAATAGTGTATGCGGCGAC
CGAGTTGCTCTTGCCCGGCGTCAATACGGGATAATACCGCGCCACA
TAGCAGAACTTTAAAAGTGCTCATCATTGGAAAACGTTCTTCGGGG
CGAAAACTCTCAAGGATCTTACCGCTGTTGAGATCCAGTTCGATGT
AACCCACTCGTGCACCCAACTGATCTTCAGCATCTTTTACTTTCACC
AGCGTTTCTGGGTGAGCAAAAACAGGAAGGCAAAATGCCGCAAAA
AAGGGAATAAGGGCGACACGGAAATGTTGAATACTCATACTCTTCC
TTTTTCAATATTATTGAAGCATTTATCAGGGTTATTGTCTCATGAGC
GGATACATATTTGAATGTATTTAGAAAAATAAACAAATAGGGGTTC
CGCGCACATTTCCCCGAAAAGTGCCACCTGACGGGATCCCCTGAGG
GGGCCCCCATGGGCTAGAGGATCCGGCCTCGGCCTCTGCATAAATA
AAAAAAAATTAGTCAGCCATGAGC SEQ ID NO: 6

TABLE 11

Nucleotide sequence of plasmid pLP2.

AATGTAGTCTTATGCAATACTCTTGTAGTCTTGCAACATGGTAACG
ATGAGTTAGCAACATGCCTTACAAGGAGAGAAAAAGCACCGTGCA
TGCCGATTGGTGGAAGTAAGGTGGTACGATCGTGCCTTATTAGGAA
GGCAACAGACGGGTCTGACATGGATTGGACGAACCACTGAATTCC
GCATTGCAGAGATATTGTATTTAAGTGCCTAGCTCGATACAATAAA
CGCCATTTGACCATTCACCACATTGGTGTGCACCTCCAAGCTCGAG
CTCGTTTAGTGAACCGTCAGATCGCCTGGAGACGCCATCCACGCTG
TTTTGACCTCCATAGAAGACACCGGGACCGATCCAGCCTCCCCTCG
AAGCTAGTCGATTAGGCATCTCCTATGGCAGGAAGAAGCGGAGAC
AGCGACGAAGACCTCCTCAAGGCAGTCAGACTCATCAAGTTTCTCT
ATCAAAGCAACCCACCTCCCAATCCCGAGGGGACCCGACAGGCCC
GAAGGAATAGAAGAAGAAGGTGGAGAGAGAGACAGAGACAGATC
CATTCGATTAGTGAACGGATCCTTAGCACTTATCTGGGACGATCTG
CGGAGCCTGTGCCTCTTCAGCTACCACCGCTTGAGAGACTTACTCTT
GATTGTAACGAGGATTGTGGAACTTCTGGGACGCAGGGGTGGGA
AGCCCTCAAATATTGGTGGAATCTCCTACAATATTGGAGTCAGGAG
CTAAAGAATAGTGCTGTTAGCTTGCTCAATGCCACAGCTATAGCAG
TAGCTGAGGGGACAGATAGGGTTATAGAAGTAGTACAAGAAGCTT
GGCACTGGCCGTCGTTTTACAACGTCGTGATCTGAGCCTGGGAGAT
CTCTGGCTAACTAGGGAACCCACTGCTTAAGCCTCAATAAAGCTTG

TABLE 11-continued

Nucleotide sequence of plasmid pLP2.

CCTTGAGTGCTTCAAGTAGTGTGTGCCCGTCTGTTGTGTGACTCTGG
TAACTAGAGATCAGGAAAACCCTGGCGTTACCCAACTTAATCGCCT
TGCAGCACATCCCCCTTTCGCCAGCTGGCGTAATAGCGAAGAGGCC
CGCACCGATCGCCCTTCCCAACAGTTGCGCAGCCTGAATGGCGAAT
GGCGCCTGATGCGGTATTTTCTCCTTACGCATCTGTGCGGTATTTCA
CACCGCATACGTCAAAGCAACCATAGTACGCGCCCTGTAGCGGCGC
ATTAAGCGCGGCGGGTGTGGTGGTTACGCGCAGCGTGACCGCTACA
CTTGCCAGCGCCCTAGCGCCCGCTCCTTTCGCTTTCTTCCCTTCCTTT
CTCGCCACGTTCGCCGGCTTTCCCCGTCAAGCTCTAAATCGGGGGC
TCCCTTTAGGGTTCCGATTTAGTGCTTTACGGCACCTCGACCCCAAA
AAACTTGATTTGGGTGATGGTTCACGTAGTGGGCCATCGCCCTGAT
AGACGGTTTTTCGCCCTTTGACGTTGGAGTCCACGTTCTTTAATAGT
GGACTCTTGTTCCAAACTGGAACAACACTCAACCCTATCTCGGGCT
ATTCTTTTGATTTATAAGGGATTTTGCCGATTTCGGCCTATTGGTTA
AAAAATGAGCTGATTTAACAAAAATTTAACGCGAATTTTAACAAAA
TATTAACGTTTACAATTTTATGGTGCACTCTCAGTACAATCTGCTCT
GATGCCGCATAGTTAAGCCAGCCCCGACACCCGCCAACACCCGCTG
ACGCGCCCTGACGGGCTTGTCTGCTCCCGGCATCCGCTTACAGACAA
GCTGTGACCGTCTCCGGGAGCTGCATGTGTCAGAGGTTTTCACCGT
CATCACCGAAACGCGCGAGACGAAAGGGCCTCGTGATACGCCTAT
TTTTATAGGTTAATGTCATGATAATAATGGTTTCTTAGACGTCAGGT
GGCACTTTTCGGGGAAATGTGCGCGGAACCCCTATTTGTTTATTTTT
CTAAATACATTCAAATATGTATCCGCTCATGAGACAATAACCCTGA
TAAATGCTTCAATAATATTGAAAAAGGAAGAGTATGAGTATTCAAC
ATTTCCGTGTCGCCCTTATTCCCTTTTTTGCGGCATTTTGCCTTCCTG
TTTTTGCTCACCCAGAAACGCTGGTGAAAGTAAAAGATGCTGAAGA
TCAGTTGGGTGCACGAGTGGGTTACATCGAACTGGATCTCAACAGC
GGTAAGATCCTTGAGAGTTTTCGCCCCGAAGAACGTTTTCCAATGA
TGAGCACTTTTAAAGTTCTGCTATGTGGCGCGGTATTATCCCGTATT
GACGCCGGGCAAGAGCAACTCGGTCGCCGCATACACTATTCTCAGA
ATGACTTGGTTGAGTACTCACCAGTCACAGAAAAGCATCTTACGGA
TGGCATGACAGTAAGAGAATTATGCAGTGCTGCCATAACCATGAGT
GATAACACTGCGGCCAACTTACTTCTGACAACGATCGGAGGACCGA
AGGAGCTAACCGCTTTTTTGCACAACATGGGGGATCATGTAACTCG
CCTTGATCGTTGGGAACCGGAGCTGAATGAAGCCATACCAAACGA
CGAGCGTGACACCACGATGCCTGTAGCAATGGCAACAACGTTGCG
CAAACTATTAACTGGCGAACTACTTACTCTAGCTTCCCGGCAACAA
TTAATAGACTGGATGGAGGCGGATAAAGTTGCAGGACCACTTCTGC
GCTCGGCCCTTCCGGCTGGCTGGTTTATTGCTGATAAATCTGGAGC

TABLE 11-continued

Nucleotide sequence of plasmid pLP2.

CGGTGAGCGTGGGTCTCGCGGTATCATTGCAGCACTGGGGCCAGAT
GGTAAGCCCTCCCGTATCGTAGTTATCTACACGACGGGGAGTCAGG
CAACTATGGATGAACGAAATAGACAGATCGCTGAGATAGGTGCCT
CACTGATTAAGCATTGGTAACTGTCAGACCAAGTTTACTCATATAT
ACTTTAGATTGATTTAAAACTTCATTTTTAATTTAAAAGGATCTAGG
TGAAGATCCTTTTTGATAATCTCATGACCAAAATCCCTTAACGTGA
GTTTTCGTTCCACTGAGCGTCAGACCCCGTAGAAAAGATCAAAGGA
TCTTCTTGAGATCCTTTTTTTCTGCGCGTAATCTGCTGCTTGCAAAC
AAAAAAACCACCGCTACCAGCGGTGGTTTGTTTGCCGGATCAAGAG
CTACCAACTCTTTTTCCGAAGGTAACTGGCTTCAGCAGAGCGCAGA
TACCAAATACTGTTCTTCTAGTGTAGCCGTAGTTAGGCCACCACTTC
AAGAACTCTGTAGCACCGCCTACATACCTCGCTCTGCTAATCCTGTT
ACCAGTGGCTGCTGCCAGTGGCGATAAGTCGTGTCTTACCGGGTTG
GACTCAAGACGATAGTTACCGGATAAGGCGCAGCGGTCGGGCTGA
ACGGGGGGTTCGTGCACACAGCCCAGCTTGGAGCGAACGACCTAC
ACCGAACTGAGATACCTACAGCGTGAGCTATGAGAAAGCGCCACG
CTTCCCGAAGGGAGAAAGGCGGACAGGTATCCGGTAAGCGGCAGGG
TCGGAACAGGAGAGCGCACGAGGGAGCTTCCAGGGGGAAACGCCT
GGTATCTTTATAGTCCTGTCGGGTTTCGCCACCTCTGACTTGAGCGT
CGATTTTTGTGATGCTCGTCAGGGGGGCGGAGCCTATGGAAAAACG
CCAGCAACGCGGCCTTTTTACGGTTCCTGGCCTTTTGCTGGCCTTTT
GCTCACATGTTCTTTCCTGCGTTATCCCCTGATTCTGTGGATAACCG
TATTACCGCCTTTGAGTGAGCTGATACCGCTCGCCGCAGCCGAACG
ACCGAGCGCAGCGAGTCAGTGAGCGAGGAAGCGGAAGAGCGCCCA
ATACGCAAACCGCCTCTCCCCGCGCGTTGGCCGATTCATTAATGCA
GCTGGCACGACAGGTTTCCCGACTGGAAAGCGGGCAGTGAGCGCA
ACGCAATTAATGTGAGTTAGCTCACTCATTAGGCACCCCAGGCTTT
ACACTTTATGCTTCCGGCTCGTATGTTGTGTGGAATTGTGAGCGGAT
AACAATTTCACACAGGAAACAGCTATGACATGATTACGAATTCGAT
GTACGGGCCAGATATACGCGTATCTGAGGGGACTAGGGTGTGTTTA
GGCGAAAAGCGGGGCTTCGGTTGTACGCGGTTAGGAGTCCCCTCAG
GATATAGTAGTTTCGCTTTTGCATAGGGAGGGGA SEQ ID NO: 7

TABLE 12

Nucleotide sequence of plasmid pLP/VSVG.

TTGGCCCATTGCATACGTTGTATCCATATCATAATATGTACATTTAT
ATTGGCTCATGTCCAACATTACCGCCATGTTGACATTGATTATTGAC
TAGTTATTAATAGTAATCAATTACGGGGTCATTAGTTCATAGCCCA
TATATGGAGTTCCGCGTTACATAACTTACGGTAAATGGCCCGCCTG

TABLE 12-continued

Nucleotide sequence of plasmid pLP/VSVG.

GCTGACCGCCCAACGACCCCCGCCCATTGACGTCAATAATGACGTA
TGTTCCCATAGTAACGCCAATAGGGACTTTCCATTGACGTCAATGG
GTGGAGTATTTACGGTAAACTGCCCACTTGGCAGTACATCAAGTGT
ATCATATGCCAAGTACGCCCCCTATTGACGTCAATGACGGTAAATG
GCCCGCCTGGCATTATGCCCAGTACATGACCTTATGGGACTTTCCT
ACTTGGCAGTACATCTACGTATTAGTCATCGCTATTACCATGGTGAT
GCGGTTTTGGCAGTACATCAATGGGCGTGGATAGCGGTTTGACTCA
CGGGGATTTCCAAGTCTCCACCCCATTGACGTCAATGGGAGTTTGT
TTTGGCACCAAAATCAACGGGACTTTCCAAAATGTCGTAACAACTC
CGCCCCATTGACGCAAATGGGCGGTAGGCGTGTACGGTGGGAGGT
CTATATAAGCAGAGCTCGTTTAGTGAACCGTCAGATCGCCTGGAGA
CGCCATCCACGCTGTTTTGACCTCCATAGAAGACACCGGGACCGAT
CCAGCCTCCCCTCGAAGCTTACATGTGGTACCGAGCTCGGATCCTG
AGAACTTCAGGGTGAGTCTATGGGACCCTTGATGTTTTCTTTCCCCT
TCTTTTCTATGGTTAAGTTCATGTCATAGGAAGGGGAGAAGTAACA
GGGTACACATATTGACCAAATCAGGGTAATTTTGCATTTGTAATTTT
AAAAAATGCTTTCTTCTTTTAATATACTTTTTTGTTTATCTTATTTCT
AATACTTTCCCTAATCTCTTTCTTTCAGGGCAATAATGATACAATGT
ATCATGCCTCTTTGCACCATTCTAAAGAATAACAGTGATAATTTCTG
GGTTAAGGCAATAGCAATATTTCTGCATATAAATATTTCTGCATAT
AAATTGTAACTGATGTAAGAGGTTTCATATTGCTAATAGCAGCTAC
AATCCAGCTACCATTCTGCTTTTATTTTATGGTTGGGATAAGGCTGG
ATTATTCTGAGTCCAAGCTAGGCCCTTTTGCTAATCATGTTCATACC
TCTTATCTTCCTCCCACAGCTCCTGGGCAACGTGCTGGTCTGTGTGC
TGGCCCATCACTTTGGCAAAGCACGTGAGATCTGAATTCTGACACT
ATGAAGTGCCTTTTGTACTTAGCCTTTTTATTCATTGGGGTGAATTG
CAAGTTCACCATAGTTTTTCCACACAACCAAAAAGGAAACTGGAAA
AATGTTCCTTCTAATTACCATTATTGCCCGTCAAGCTCAGATTTAAA
TTGGCATAATGACTTAATAGGCACAGCCTTACAAGTCAAAATGCCC
AAGAGTCACAAGGCTATTCAAGCAGACGGTTGGATGTGTCATGCTT
CCAAATGGGTCACTACTTGTGATTTCCGCTGGTATGGACCGAAGTA
TATAACACATTCCATCCGATCCTTCACTCCATCTGTAGAACAATGC
AAGGAAAGCATTGAACAAACGAAACAAGGAACTTGGCTGAATCCA
GGCTTCCCTCCTCAAAGTTGTGGATATGCAACTGTGACGGATGCCG
AAGCAGTGATTGTCCAGGTGACTCCTCACCATGTGCTGGTTGATGA
ATACACAGGAGAATGGGTTGATTCACAGTTCATCAACGGAAAATG
CAGCAATTACATATGCCCCACTGTCCATAACTCTACAACCTGGCAT
TCTGACTATAAGGTCAAAGGGTATGTGATTCTAACCTCATTTCCAT
GGACATCACCTTCTTCTCAGAGGACGGAGAGCTATCATCCCTGGA

TABLE 12-continued

Nucleotide sequence of plasmid pLP/VSVG.

AAGGAGGGCACAGGGTTCAGAAGTAACTACTTTGCTTATGAAACTG
GAGGCAAGGCCTGCAAAATGCAATACTGCAAGCATTGGGGAGTCA
GACTCCCATCAGGTGTCTGGTTCGAGATGGCTGATAAGGATCTCTT
TGCTGCAGCCAGATTCCCTGAATGCCCAGAAGGGTCAAGTATCTCT
GCTCCATCTCAGACCTCAGTGGATGTAAGTCTAATTCAGGACGTTG
AGAGGATCTTGGATTATTCCCTCTGCCAAGAAACCTGGAGCAAAAT
CAGAGCGGGTCTTCCAATCTCTCCAGTGGATCTCAGCTATCTTGCTC
CTAAAAACCCAGGAACCGGTCCTGCTTTCACCATAATCAATGGTAC
CCTAAAATACTTTGAGACCAGATACATCAGAGTCGATATTGCTGCT
CCAATCCTCTCAAGAATGGTCGGAATGATCAGTGGAACTACCACAG
AAAGGGAACTGTGGGATGACTGGGCACCATATGAAGACGTGGAAA
TTGGACCCAATGGAGTTCTGAGGACCAGTTCAGGATATAAGTTTCC
TTTATACATGATTGGACATGGTATGTTGGACTCCGATCTTCATCTTA
GCTCAAAGGCTCAGGTGTTCGAACATCCTCACATTCAAGACGCTGC
TTCGCAACTTCCTGATGATGAGAGTTTATTTTTTGGTGATACTGGGC
TATCCAAAAATCCAATCGAGCTTGTAGAAGGTTGGTTCAGTAGTTG
GAAAAGCTCTATTGCCTCTTTTTTCTTTATCATAGGGTTAATCATTG
GACTATTCTTGGTTCTCCGAGTTGGTATCCATCTTTGCATTAAATTA
AAGCACACCAAGAAAAGACAGATTTATACAGACATAGAGATGAAC
CGACTTGGAAAGTAACTCAAATCCTGCACAACAGATTCTTCATGTT
TGGACCAAATCAACTTGTGATACCATGCTCAAAGAGGCCTCAATTA
TATTTGAGTTTTAATTTTATGAAAAAAAAAAAAAAAACGGAAT
TCACCCCACCAGTGCAGGCTGCCTATCAGAAAGTGGTGGCTGGTGT
GGCTAATGCCCTGGCCCACAAGTATCACTAAGCTCGCTTTCTTGCT
GTCCAATTTCTATTAAAGGTTCCTTTGTTCCCTAAGTCCAACTACTA
AACTGGGGGATATTATGAAGGGCCTTGAGCATCTGGATTCTGCCTA
ATAAAAAACATTTATTTTCATTGCAATGATGTATTTAAATTATTTCT
GAATATTTTACTAAAAAGGGAATGTGGGAGGTCAGTGCATTTAAAA
CATAAAGAAATGAAGAGCTAGTTCAAACCTTGGGAAAATACACTA
TATCTTAAACTCCATGAAAGAAGGTGAGGCTGCAAACAGCTAATGC
ACATTGGCAACAGCCCCTGATGCCTATGCCTTATTCATCCCTCAGA
AAAGGATTCAAGTAGAGGCTTGATTTGGAGGTTAAAGTTTTGCTAT
GCTGTATTTTACATTACTTATTGTTTAGCTGTCCTCATGAATGTCTT
TTCACTACCCATTTGCTTATCCTGCATCTCTCAGCCTTGACTCCACT
CAGTTCTCTTGCTTAGAGATACCACCTTTCCCCTGAAGTGTTCCTTC
CATGTTTTACGCGAGATGGTTTCTCCTCGCCT
GGCCACTCAGCCTTAGTTGTCTCTGTTGTCTTATAGAGGTCTACTTG
AAGAAGGAAAAACAGGGGGCATGGTTTGACTGTCCTGTGAGCCCT
TCTTCCCTGCCTCCCCCACTCACAGTGACCCGGAATCCCTCGACATG

TABLE 12-continued

Nucleotide sequence of plasmid pLP/VSVG.

GCAGTCTAGCACTAGTGCGGCCGCAGATCTGCTTCCTCGCTCACTG
ACTCGCTGCGCTCGGTCGTTCGGCTGCGGCGAGCGGTATCAGCTCA
CTCAAAGGCGGTAATACGGTTATCCACAGAATCAGGGGATAACGC
AGGAAAGAACATGTGAGCAAAAGGCCAGCAAAAGGCCAGGAACC
GTAAAAAGGCCGCGTTGCTGGCGTTTTTCCATAGGCTCCGCCCCCC
TGACGAGCATCACAAAAATCGACGCTCAAGTCAGAGGTGGCGAAA
CCCGACAGGACTATAAAGATACCAGGCGTTTCCCCCTGGAAGCTCC
CTCGTGCGCTCTCCTGTTCCGACCCTGCCGCTTACCGGATACCTGTC
CGCCTTTCTCCCTTCGGGAAGCGTGGCGCTTTCTCATAGCTCACGCT
GTAGGTATCTCAGTTCGGTGTAGGTCGTTCGCTCCAAGCTGGGCTG
TGTGCACGAACCCCCCGTTCAGCCCGACCGCTGCGCCTTATCCGGT
AACTATCGTCTTGAGTCCAACCCGGTAAGACACGACTTATCGCCAC
TGGCAGCAGCCACTGGTAACAGGATTAGCAGAGCGAGGTATGTAG
GCGGTGCTACAGAGTTCTTGAAGTGGTGGCCTAACTACGGCTACAC
TAGAAGAACAGTATTTGGTATCTGCGCTCTGCTGAAGCCAGTTACC
TTCGGAAAAAGAGTTGGTAGCTCTTGATCCGGCAAACAAACCACCG
CTGGTAGCGGTGGTTTTTTTGTTTGCAAGCAGCAGATTACGCGCAG
AAAAAAAGGATCTCAAGAAGATCCTTTGATCTTTTCTACGGGGTCT
GACGCTCAGTGGAACGAAAACTCACGTTAAGGGATTTTGGTCATGA
GATTATCAAAAAGGATCTTCACCTAGATCCTTTTAAATTAAAAATG
AAGTTTTAAATCAATCTAAAGTATATATGAGTAAACTTGGTCTGAC
AGTTACCAATGCTTAATCAGTGAGGCACCTATCTCAGCGATCTGTC
TATTTCGTTCATCCATAGTTGCCTGACTCCCCGTCGTGTAGATAACT
ACGATACGGGAGGGCTTACCATCTGGCCCCAGTGCTGCAATGATAC
CGCGAGACCCACGCTCACCGGCTCCAGATTTATCAGCAATAAACCA
GCCAGCCGGAAGGGCCGAGCGCAGAAGTGGTCCTGCAACTTTATC
CGCCTCCATCCAGTCTATTAATTGTTGCCGGGAAGCTAGAGTAAGT
AGTTCGCCAGTTAATAGTTTGCGCAACGTTGTTGCCATTGCTACAG
GCATCGTGGTGTCACGCTCGTCGTTTGGTATGGCTTCATTCAGCTCC
GGTTCCCAACGATCAAGGCGAGTTACATGATCCCCCATGTTGTGCA
AAAAAGCGGTTAGCTCCTTCGGTCCTCCGATCGTTGTCAGAAGTAA
GTTGGCCGCAGTGTTATCACTCATGGTTATGGCAGCACTGCATAAT
TCTCTTACTGTCATGCCATCCGTAAGATGCTTTTCTGTGACTGGTGA
GTACTCAACCAAGTCATTCTGAGAATAGTGTATGCGGCGACCGAGT
TGCTCTTGCCCGGCGTCAATACGGGATAATACCGCGCCACATAGCA
GAACTTTAAAAGTGCTCATCATTGGAAAACGTTCTTCGGGGCGAAA
ACTCTCAAGGATCTTACCGCTGTTGA
GATCCAGTTCGATGTAACCCACTCGTGCACCCAACTGATCTTCAGC
ATCTTTTACTTTCACCAGCGTTTCTGGGTGAGCAAAAACAGGAAGG

TABLE 12-continued

Nucleotide sequence of plasmid pLP/VSVG.

CAAAATGCCGCAAAAAAGGGAATAAGGGCGACACGGAAATGTTGA

ATACTCATACTCTTCCTTTTTCAATATTATTGAAGCATTTATCAGGG

TTATTGTCTCATGAGCGGATACATATTTGAATGTATTTAGAAAAAT

AAACAAATAGGGGTTCCGCGCACATTTCCCCGAAAAGTGCCACCTG

TABLE 12-continued

Nucleotide sequence of plasmid pLP/VSVG.

ACGGGATCCCCTGAGGGGGCCCCCATGGGCTAGAGGATCCGGCCT

CGGCCTCTGCATAAATAAAAAAAATTAGTCAGCCATGAGC

SEQ ID NO: 8

What is claimed is:

1. A method for preparing a recombinant nucleic acid molecule, the method comprising:
   (a) contacting two or more nucleic acid molecules, each nucleic acid molecule comprising two type IIs restriction enzyme recognition sites, with one or more type IIs restriction enzymes under conditions which allow for the generation of overhanging ends, to generate two or more digested nucleic acid molecules;
   (b) contacting a nucleic acid vector comprising two type IIs restriction enzyme recognition sites with one or more type IIs restriction enzyme under conditions which allow for the generation of overhanging ends and excision of a segment of the nucleic acid vector, to generate a digested nucleic acid vector, wherein the overhanging ends of the digested nucleic acid vector are each capable of hybridizing with at least one overhanging end of at least one of the two or more digested nucleic acid molecules; and
   (c) contacting the two or more digested nucleic acid molecules and the digested nucleic acid vector under conditions which allow for (i) hybridization of overhanging ends and (ii) covalent joining digested nucleic acid molecules to the digested nucleic acid molecule vector to form the recombinant nucleic acid molecule.

2. The method of claim 1, wherein the recombinant nucleic acid molecule is circular.

3. The method of claim 1, wherein the two or more nucleic acid molecules encode an expression product.

4. The method of claim 3, wherein the expression product is a protein.

5. The method of claim 1, wherein the excised segment of the nucleic acid vector contains an open reading frame.

6. The method of claims 5, wherein the open reading frame encodes a selectable marker.

7. The method of claim 6, wherein the selectable marker is a negative selectable marker.

8. The method of claim 7, wherein the negative selectable marker is ccdB.

9. The method of claim 6, wherein the selectable marker is a marker selected from the group consisting of:
   (a) ccdB,
   (b) β-galactosidase, and
   (c) a green fluorescent protein.

10. The method of claim 2, wherein selective pressure is applied against circularized nucleic acid vectors not containing an insert.

11. The method of claim 1, wherein the excised segment of the nucleic acid vector is flanked by type IIs restriction enzyme recognition sites which are recognized by the same type IIs restriction enzyme.

12. The method of claim 11, wherein the restriction enzyme is BsaI.

13. The method of claim 1, wherein the digested nucleic acid vector contains two or more recombination sites.

14. The method of claim 13, wherein the recombination sites are att sites or lox sites.

15. A method for preparing a recombinant nucleic acid molecule, the method comprising:
   (a) forming a mixture comprising:
      (i) two or more nucleic acid molecules, each comprising two type IIs restriction enzyme recognition sites;
      (ii) a nucleic acid vector comprising two type IIs restriction enzyme recognition sites; and
      (iii) one or more type IIs restriction enzymes that are specific for the type IIs restriction enzyme recognition sites of the two or more nucleic acid molecules and the nucleic acid vector;
      wherein the mixture is incubated under conditions which allow for digestion of the two or more nucleic acid molecules and the nucleic acid vector to generate overhanging ends, and
   (b) incubating the digestion products generated in (a) under conditions which allow for hybridization of compatible overhanging ends and covalent joining of the hybridized ends.

16. The method of claim 15, wherein steps (a) and (b) occur in the same container.

17. A method for preparing a recombinant nucleic acid molecule, the method comprising:
   (a) forming a mixture comprising:
      (i) two or more nucleic acid molecules, each comprising two type IIs restriction enzyme recognition sites;
      (ii) a linear nucleic acid vector comprising at least one overhanging end; and
      (iii) one or more type IIs restriction enzymes that are specific for the type IIs restriction enzyme recognition sites of the two or more nucleic acid molecules and the nucleic acid vector;
      wherein the mixture is incubated under conditions which allow for digestion of the two or more nucleic acid molecules to generate overhanging ends, and
   (b) incubating the digestion products generated in (a) under conditions which allow for hybridization of compatible overhanging ends and covalent joining of the hybridized ends.

18. The method of claim 17, wherein the linear nucleic acid vector contains topoisomerase covalently bound to at least one end.

19. The method of claim 18, wherein the topoisomerase is a type 1B topoisomerase.

20. The method of claim 17, wherein the linear nucleic acid vector comprises at least one site specific recombination site.

* * * * *

SEQUENCE LISTING

<160> NUMBER OF SEQ ID NOS: 51

<210> SEQ ID NO 1
<211> LENGTH: 3519
<212> TYPE: DNA
<213> ORGANISM: Artificial
<220> FEATURE:
<223> OTHER INFORMATION: pENTR U6 Vector

<400> SEQUENCE: 1

```
ctttcctgcg ttatcccctg attctgtgga taaccgtatt accgcctttg agtgagctga      60
taccgctcgc cgcagccgaa cgaccgagcg cagcgagtca gtgagcgagg aagcggaaga     120
gcgcccaata cgcaaaccgc ctctccccgc gcgttggccg attcattaat gcagctggca     180
cgacaggttt cccgactgga aagcgggcag tgagcgcaac gcaattaata cgcgtaccgc     240
tagccaggaa gagtttgtag aaacgcaaaa aggccatccg tcaggatggc cttctgctta     300
gtttgatgcc tggcagttta tggcgggcgt cctgcccgcc accctccggg ccgttgcttc     360
acaacgttca atccgctcc cggcggattt gtcctactca ggagagcgtt caccgacaaa     420
caacagataa aacgaaaggc ccagtcttcc gactgagcct ttcgttttat ttgatgcctg     480
gcagttccct actctcgcgt taacgctagc atggatgttt cccagtcac gacgttgtaa     540 aacgacggcc agtcttaagc tcgggcccca ataatgatt ttattttgac tgatagtgac     600
ctgttcgttg caacaaattg atgagcaatg cttttttata atgccaactt tgtacaaaaa     660
agcaggcttt aaaggaacca attcagtcga ctggatccgg taccaaggtc gggcaggaag     720
agggcctatt tcccatgatt ccttcatatt tgcatatacg atacaaggct gttagagaga     780
taattagaat taatttgact gtaaacacaa agatattagt acaaaatacg tgacgtagaa     840
agtaataatt tcttgggtag tttgcagttt taaaattatg ttttaaaatg gactatcata     900
tgcttaccgt aacttgaaag tatttcgatt tcttggcttt atatatcttg tggaaaggac     960
gaaacaccgg agaccgcggc cgctggatcc ggcttactaa aagccagata acagtatgcg    1020
tatttgcgcg ctgattttg cggtataaga atatatactg atatgtatac cgaagtatg     1080 tcaaaaagag gtgtgctatg aagcagcgta ttacagtgac agttgacagc gacagctatc    1140
agttgctcaa ggcatatatg atgtcaatat ctccggtctg gtaagcacaa ccatgcagaa    1200
tgaagcccgt cgtctgcgtg ccgaacgctg gaaagcggaa atcaggaag ggatggctga    1260 ggtcgcccgg tttattgaaa tgaacggctc ttttgctgac gagaacaggg actggtgaaa    1320
tgcagtttaa ggtttacacc tataaaagag agagccgtta tcgtctgttt gtggatgtac    1380
agagtgatat tattgacacg cccgggcgac ggatggtgat ccccctggcc agtgcacgtc    1440
tgctgtcaga taaagtctcc cgtgaacttt acccggtggt gcatatcggg gatgaaagct    1500
ggcgcatgat gaccaccgat atggccagtg tgccggtctc cgttatcggg gaagaagtgg    1560
```

| | |
|---|---|
| ctgatctcag ccaccgcgaa aatgacatca aaaacgccat taacctgatg ttctggggaa | 1620 |
| tataaggtct catttttttt ctagacccag ctttcttgta caaagttggc attataagaa | 1680 |
| agcattgctt atcaatttgt tgcaacgaac aggtcactat cagtcaaaat aaaatcatta | 1740 |
| tttgccatcc agctgatatc ccctatagtg agtcgtatta catggtcata gctgtttcct | 1800 |
| ggcagctctg gcccgtgtct caaaatctct gatgttacat tgcacaagat aaaaatatat | 1860 |
| catcatgaac aataaaactg tctgcttaca taaacagtaa tacaaggggt gttatgagcc | 1920 |
| atattcaacg ggaaacgtcg aggccgcgat taaattccaa catggatgct gatttatatg | 1980 |
| ggtataaatg ggctcgcgat aatgtcgggc aatcaggtgc gacaatctat cgcttgtatg | 2040 |
| ggaagcccga tgcgccagag ttgtttctga acatggcaa aggtagcgtt gccaatgatg | 2100 |
| ttacagatga gatggtcaga ctaaactggc tgacggaatt tatgcctctt ccgaccatca | 2160 |
| agcattttat ccgtactcct gatgatgcat ggttactcac cactgcgatc cccggaaaaa | 2220 |
| cagcattcca ggtattagaa gaatatcctg attcaggtga aaatattgtt gatgcgctgg | 2280 |
| cagtgttcct gcgccggttg cattcgattc ctgtttgtaa ttgtcctttt aacagcgatc | 2340 |
| gcgtatttcg tctcgctcag gcgcaatcac gaatgaataa cggtttggtt gatgcgagtg | 2400 |
| atttgatgac gagcgtaatg gctggcctgt tgaacaagtc tggaaagaaa tgcataaact | 2460 |
| tttgccattc tcaccggatt cagtcgtcac tcatggtgat ttctcacttg ataaccttat | 2520 |
| ttttgacgag gggaaattaa taggttgtat tgatgttgga cgagtcggaa tcgcagaccg | 2580 |
| ataccaggat cttgccatcc tatggaactg cctcggtgag ttttctcctt cattacagaa | 2640 |
| acggcttttt caaaaatatg gtattgataa tcctgatatg aataaattgc agtttcattt | 2700 |
| gatgctcgat gagttttct aatcagaatt ggttaattgg ttgtaacact ggcagagcat | 2760 |
| tacgctgact tgacgggacg gcgcaagctc atgaccaaaa tcccttaacg tgagttacgc | 2820 |
| gtcgttccac tgagcgtcag accccgtaga aaagatcaaa ggatcttctt gagatccttt | 2880 |
| ttttctgcgc gtaatctgct gcttgcaaac aaaaaaacca ccgctaccag cggtggtttg | 2940 |
| tttgccggat caagagctac caactctttt tccgaaggta actggcttca gcagagcgca | 3000 |
| gataccaaat actgtccttc tagtgtagcc gtagttaggc caccacttca agaactctgt | 3060 |
| agcaccgcct acatacctcg ctctgctaat cctgttacca gtggctgctg ccagtggcga | 3120 |
| taagtcgtgt cttaccgggt tggactcaag acgatagtta ccggataagg cgcagcggtc | 3180 |
| gggctgaacg gggggttcgt gcacacagcc cagcttggag cgaacgacct acaccgaact | 3240 |
| gagataccta cagcgtgagc attgagaaag cgccacgctt cccgaaggga gaaaggcgga | 3300 |
| caggtatccg gtaagcggca gggtcggaac aggagagcgc acgagggagc ttccaggggg | 3360 |
| aaacgcctgg tatctttata gtcctgtcgg gtttcgccac ctctgacttg agcgtcgatt | 3420 |
| tttgtgatgc tcgtcagggg ggcggagcct atgaaaaac gccagcaacg cggccttttt | 3480 |
| acggttcctg gccttttgct ggccttttgc tcacatgtt | 3519 |

<210> SEQ ID NO 2
<211> LENGTH: 8688
<212> TYPE: DNA
<213> ORGANISM: Artificial
<220> FEATURE:
<223> OTHER INFORMATION: pLenti6/V5-DEST

<400> SEQUENCE: 2

| | |
|---|---|
| aatgtagtct tatgcaatac tcttgtagtc ttgcaacatg gtaacgatga gttagcaaca | 60 |
| tgccttacaa ggagagaaaa agcaccgtgc atgccgattg gtggaagtaa ggtggtacga | 120 |

| | |
|---|---|
| tcgtgcctta ttaggaaggc aacagacggg tctgacatgg attggacgaa ccactgaatt | 180 |
| gccgcattgc agagatattg tatttaagtg cctagctcga tacataaacg ggtctctctg | 240 |
| gttagaccag atctgagcct gggagctctc tggctaacta gggaacccac tgcttaagcc | 300 |
| tcaataaagc ttgccttgag tgcttcaagt agtgtgtgcc cgtctgttgt gtgactctgg | 360 |
| taactagaga tccctcagac ccttttagtc agtgtggaaa atctctagca gtggcgcccg | 420 |
| aacagggact tgaaagcgaa agggaaacca gaggagctct ctcgacgcag gactcggctt | 480 |
| gctgaagcgc gcacggcaag aggcgagggg cggcgactgg tgagtacgcc aaaaattttg | 540 |
| actagcggag gctagaagga gagagatggg tgcgagagcg tcagtattaa gcggggggaga | 600 |
| attagatcgc gatgggaaaa aattcggtta aggccagggg gaagaaaaaa atataaatta | 660 |
| aaacatatag tatgggcaag cagggagcta gaacgattcg cagttaatcc tggcctgtta | 720 |
| gaaacatcag aaggctgtag acaaatactg ggacagctac aaccatccct tcagacagga | 780 |
| tcagaagaac ttagatcatt atataataca gtagcaaccc tctattgtgt gcatcaaagg | 840 |
| atagagataa aagacaccaa ggaagcttta gacaagatag aggaagagca aaacaaaagt | 900 |
| aagaccaccg cacagcaagc ggccgctgat cttcagacct ggaggaggag atatgaggga | 960 |
| caattggaga agtgaattat ataaatataa agtagtaaaa attgaaccat taggagtagc | 1020 |
| acccaccaag gcaaagagaa gagtggtgca gagagaaaaa agagcagtgg gaataggagc | 1080 |
| tttgttcctt gggttcttgg gagcagcagg aagcactatg ggcgcagcgt caatgacgct | 1140 |
| gacggtacag gccagacaat tattgtctgg tatagtgcag cagcagaaca atttgctgag | 1200 |
| ggctattgag gcgcaacagc atctgttgca actcacagtc tggggcatca agcagctcca | 1260 |
| ggcaagaatc ctggctgtgg aaagatacct aaaggatcaa cagctcctgg ggatttgggg | 1320 |
| ttgctctgga aaactcattt gcaccactgc tgtgccttgg aatgctagtt ggagtaataa | 1380 |
| atctctggaa cagatttgga atcacacgac ctggatggag tgggacagag aaattaacaa | 1440 |
| ttacacaagc ttaatacact ccttaattga agaatcgcaa aaccagcaag aaaagaatga | 1500 |
| acaagaatta ttggaattag ataaatgggc aagtttgtgg aattggttta acataacaaa | 1560 |
| ttggctgtgg tatataaaat tattcataat gatagtagga ggcttggtag gtttaagaat | 1620 |
| agtttttgct gtactttcta tagtgaatag agttaggcag ggatattcac cattatcgtt | 1680 |
| tcagacccac ctcccaaccc cgaggggacc cgacaggccc gaaggaatag aagaagaagg | 1740 |
| tggagagaga gacagagaca gatccattcg attagtgaac ggatctcgac ggtatcgata | 1800 |
| agcttgggag ttccgcgtta cataacttac ggtaaatggc ccgcctggct gaccgcccaa | 1860 |
| cgacccccgc ccattgacgt caataatgac gtatgttccc atagtaacgc caatagggac | 1920 |
| tttccattga cgtcaatggg tggagtattt acggtaaact gcccacttgg cagtacatca | 1980 |
| agtgtatcat atgccaagta cgccccctat tgacgtcaat gacggtaaat ggcccgcctg | 2040 |
| gcattatgcc cagtacatga ccttatggga ctttcctact ggcagtaca tctacgtatt | 2100 |
| agtcatcgct attaccatgg tgatgcggtt ttggcagtac atcaatgggc gtggatagcg | 2160 |
| gtttgactca cggggatttc caagtctcca ccccattgac gtcaatggga gtttgttttg | 2220 |
| gcaccaaaat caacgggact ttccaaaatg tcgtaacaac tccgccccat tgacgcaaat | 2280 |
| gggcggtagg cgtgtacggt gggaggtcta tataagcaga gctcgtttag tgaaccgtca | 2340 |
| gatcgcctgg agacgccatc cacgctgttt tgacctccat agaagacacc gactctagag | 2400 |
| gatccactag tccagtgtgg tggaattctg cagatatcaa caagtttgta caaaaaagct | 2460 |
| gaacgagaaa cgtaaaatga tataaatatc aatatattaa attagatttt gcataaaaaa | 2520 |

-continued

```
cagactacat aatactgtaa aacacaacat atccagtcac tatggcggcc gcattaggca   2580
ccccaggctt tacactttat gcttccggct cgtataatgt gtggattttg agttaggatc   2640
cggcgagatt ttcaggagct aaggaagcta aaatggagaa aaaaatcact ggatatacca   2700
ccgttgatat atcccaatgg catcgtaaag aacattttga ggcatttcag tcagttgctc   2760
aatgtaccta taaccagacc gttcagctgg atattacggc cttttttaaag accgtaaaga   2820 aaaataagca caagttttat ccggcccttta ttcacattct tgcccgcctg atgaatgctc   2880
atccggaatt ccgtatggca atgaaagacg gtgagctggt gatatgggat agtgttcacc   2940
cttgttacac cgttttccat gagcaaactg aaacgttttc atcgctctgg agtgaatacc   3000
acgacgattt ccggcagttt ctacacatat attcgcaaga tgtggcgtgt tacggtgaaa   3060
acctggccta tttccctaaa gggtttattg agaatatgtt tttcgtctca gccaatccct   3120
gggtgagttt caccagtttt gatttaaacg tggccaatat ggacaacttc ttcgcccccg   3180
ttttcaccat gggcaaatat tatacgcaag gcgacaaggt gctgatgccg ctggcgattc   3240
aggttcatca tgccgtctgt gatggcttcc atgtcggcag aatgcttaat gaattacaac   3300
agtactgcga tgagtggcag ggcggggcgt aaagatctgg atccggctta ctaaaagcca   3360
gataacagta tgcgtatttg cgcgctgatt tttgcggtat aagaatatat actgatatgt   3420
atacccgaag tatgtcaaaa agaggtgtgc tatgaagcag cgtattacag tgacagttga   3480
cagcgacagc tatcagttgc tcaaggcata tatgatgtca atatctccgg tctggtaagc   3540
acaaccatgc agaatgaagc ccgtcgtctg cgtgccgaac gctggaaagc ggaaaatcag   3600
gaagggatgg ctgaggtcgc ccggtttatt gaaatgaacg gctcttttgc tgacgagaac   3660
agggactggt gaaatgcagt ttaaggttta cacctataaa agagagagcc gttatcgtct   3720
gtttgtggat gtacagagtg atattattga cacgcccggg cgacggatgg tgatcccccct   3780 ggccagtgca cgtctgctgt cagataaagt ctcccgtgaa cttacccggg tggtgcatat   3840
cggggatgaa agctggcgca tgatgaccac cgatatggcc agtgtgccgg tctccgttat   3900
cggggaagaa gtggctgatc tcagccaccg cgaaaatgac atcaaaaacg ccattaacct   3960
gatgttctgg ggaatataaa tgtcaggctc cgttatacac agccagtctg caggtcgacc   4020
atagtgactg gatatgttgt gttttacagt attatgtagt ctgttttta tgcaaaatct   4080 aatttaatat attgatattt atatcatttt acgtttctcg ttcagctttc ttgtacaaag   4140
tggttgatat ccagcacagt ggcggccgct cgagtctaga gggcccgcgg ttcgaaggta   4200
agcctatccc taaccctctc ctcggtctcg attctacgcg taccggttag taatgagttt   4260
ggaattaatt ctgtggaatg tgtgtcagtt agggtgtgga agtccccag gctccccagg   4320 caggcagaag tatgcaaagc atgcatctca attagtcagc aaccaggtgt ggaaagtccc   4380
caggctcccc agcaggcaga gtatgcaaaa gcatgcatct caattagtca gcaaccatag   4440
tcccgcccct aactccgccc atcccgcccc taactccgcc cagttccgcc cattctccgc   4500
cccatggctg actaatttt tttatttatg cagaggccga ggccgcctct gcctctgagc   4560
tattccagaa gtagtgagga ggcttttttg gaggcctagg cttttgcaaa aagctcccgg   4620
gagcttgtat atccattttc ggatctgatc agcacgtgtt gacaattaat catcggcata   4680
gtatatcggc atagtataat acgacaaggt gaggaactaa accatggcca gcctttgtc   4740 tcaagaagaa tccacccctca ttgaaagagc aacggctaca atcaacagca tccccatctc   4800
tgaagactac agcgtcgcca gcgcagctct ctctagcgac ggccgcatct tcactggtgt   4860
caatgtatat cattttactg ggggaccttg tgcagaactc gtggtgctgg gcactgctgc   4920
```

```
tgctgcggca gctggcaacc tgacttgtat cgtcgcgatc ggaaatgaga acagggcat    4980
cttgagcccc tgcggacggt gccgacaggt gcttctcgat ctgcatcctg ggatcaaagc   5040
catagtgaag acagtgatg gacagccgac ggcagttggg attcgtgaat tgctgccctc    5100
tggttatgtg tgggagggct aagcacaatt cgagctcggt acctttaaga ccaatgactt   5160
acaaggcagc tgtagatctt agccactttt taaaagaaaa ggggggactg aagggctaa    5220
ttcactccca acgaagacaa gatctgcttt ttgcttgtac tgggtctctc tggttagacc   5280
agatctgagc ctgggagctc tctggctaac tagggaaccc actgcttaag cctcaataaa   5340
gcttgccttg agtgcttcaa gtagtgtgtg cccgtctgtt gtgtgactct ggtaactaga   5400
gatccctcag acccttttag tcagtgtgga aatctctag cagtagtagt tcatgtcatc     5460
ttattattca gtatttataa cttgcaaaga aatgaatatc agagagtgag aggaacttgt   5520
ttattgcagc ttataatggt tacaaataaa gcaatagcat cacaaatttc acaaataaag   5580
catttttttc actgcattct agttgtggtt tgtccaaact catcaatgta tcttatcatg   5640
tctggctcta gctatcccgc ccctaactcc gcccatcccg ccctaactc cgcccagttc    5700
cgcccattct ccgccccatg gctgactaat tttttttatt tatgcagagg ccgaggccgc   5760
ctcggcctct gagctattcc agaagtagtg aggaggcttt tttggaggcc tagggacgta   5820
cccaattcgc cctatagtga gtcgtattac gcgcgctcac tggccgtcgt tttacaacgt   5880
cgtgactggg aaaaccctgg cgttacccaa cttaatcgcc ttgcagcaca tccccctttc   5940
gccagctggg gtaatagcga agaggcccgc accgatcgcc cttcccaaca gttgcgcagc   6000
ctgaatggcg aatgggacgc gccctgtagc ggcgcattaa gcgcggcggg tgtggtggtt   6060
acgcgcagcg tgaccgctac acttgccagc gccctagcgc ccgctccttt cgctttcttc   6120
ccttcctttc tcgccacgtt cgccggcttt ccccgtcaag ctctaaatcg gggctccct   6180
ttagggttcc gatttagtgc tttacggcac ctcgacccca aaaaacttga ttagggtgat   6240
ggttcacgta gtgggccatc gccctgatag acggttttc gccctttgac gttggagtcc    6300
acgttcttta atagtggact cttgttccaa actggaacaa cactcaaccc tatctcggtc   6360
tattctttg atttataagg gattttgccg atttcggcct attggttaaa aaatgagctg    6420
atttaacaaa aatttaacgc gaattttaac aaaatattaa cgcttacaat ttaggtggca   6480
cttttcgggg aaatgtgcgc ggaaccccta tttgtttatt tttctaaata cattcaaata   6540
tgtatccgct catgagacaa taaccctgat aaatgcttca ataatattga aaaggaaga    6600
gtatgagtat tcaacatttc cgtgtcgccc ttattccctt ttttgcggca ttttgccttc   6660
ctgtttttgc tcacccagaa acgctggtga agtaaaaga tgctgaagat cagttgggtg    6720
cacgagtggg ttacatcgaa ctggatctca acagcggtaa gatccttgag agttttcgcc   6780
ccgaagaacg ttttccaatg atgagcactt ttaaagttct gctatgtggc gcggtattat   6840
cccgtattga cgccgggcaa gagcaactcg gtcgccgcat acactattct cagaatgact   6900
tggttgagta ctcaccagtc acagaaaagc atcttacgga tggcatgaca gtaagagaat   6960
tatgcagtgc tgccataacc atgagtgata acactgcggc caacttactt ctgacaacga   7020
tcggaggacc gaaggagcta accgcttttt tgcacaacat ggggggatcat gtaactcgcc   7080
ttgatcgttg gaaccggag ctgaatgaag ccataccaaa cgacgagcgt gacaccacga    7140
tgcctgtagc aatggcaaca acgttgcgca aactattaac tggcgaacta cttactctag   7200
cttcccggca acaattaata gactggatgg aggcggataa agttgcagga ccacttctgc   7260
gctcggccct tccggctggc tggtttattg ctgataaatc tggagccggt gagcgtgggt   7320
```

```
ctcgcggtat cattgcagca ctggggccag atggtaagcc ctcccgtatc gtagttatct    7380
acacgacggg gagtcaggca actatggatg aacgaaatag acagatcgct gagataggtg    7440
cctcactgat taagcattgg taactgtcag accaagttta ctcatatata ctttagattg    7500
atttaaaact tcattttaa tttaaaagga tctaggtgaa gatcctttt gataatctca     7560 tgaccaaaat cccttaacgt gagttttcgt tccactgagc gtcagacccc gtagaaaaga    7620
tcaaaggatc ttcttgagat cctttttttc tgcgcgtaat ctgctgcttg caaacaaaaa    7680
aaccaccgct accagcggtg gtttgtttgc cggatcaaga gctaccaact ctttttccga    7740
aggtaactgg cttcagcaga gcgcagatac caaatactgt tcttctagtg tagccgtagt    7800
taggccacca cttcaagaac tctgtagcac cgcctacata cctcgctctg ctaatcctgt    7860
taccagtggc tgctgccagt ggcgataagt cgtgtcttac cgggttggac tcaagacgat    7920
agttaccgga taaggcgcag cggtcgggct gaacggggg ttcgtgcaca cagcccagct    7980
tggagcgaac gacctacacc gaactgagat acctacagcg tgagctatga aaagcgcca    8040 cgcttcccga aggagaaag gcggacaggt atccggtaag cggcagggtc ggaacaggag    8100
agcgcacgag ggagcttcca gggggaaacg cctggtatct ttatagtcct gtcgggtttc    8160
gccacctctg acttgagcgt cgatttttgt gatgctcgtc aggggggcgg agcctatgga    8220
aaaacgccag caacgcggcc ttttacggt tcctggcctt ttgctggcct tttgctcaca    8280
tgttctttcc tgcgttatcc cctgattctg tggataaccg tattaccgcc tttgagtgag    8340
ctgataccgc tcgccgcagc cgaacgaccg agcgcagcga gtcagtgagc gaggaagcgg    8400
aagagcgccc aatacgcaaa ccgcctctcc ccgcgcgttg gccgattcat taatgcagct    8460
ggcacgacag gtttcccgac tggaaagcgg gcagtgagcg caacgcaatt aatgtgagtt    8520
agctcactca ttaggcaccc caggctttac actttatgct tccggctcgt atgttgtgtg    8580
gaattgtgag cggataacaa tttcacacag gaaacagcta tgaccatgat tacgccaagc    8640
gcgcaattaa ccctcactaa agggaacaaa agctggagct gcaagctt                 8688
```

<210> SEQ ID NO 3
<211> LENGTH: 6964
<212> TYPE: DNA
<213> ORGANISM: Artificial
<220> FEATURE:
<223> OTHER INFORMATION: pLenti6/V5-dTOPO

<400> SEQUENCE: 3

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga    120
tcgtgcctta ttaggaaggc aacagacggg tctgacatgg attggacgaa ccactgaatt    180
gccgcattgc agagatattg tatttaagtg cctagctcga tacataaacg ggtctctctg    240
gttagaccag atctgagcct gggagctctc tggctaacta gggaacccac tgcttaagcc    300
tcaataaagc ttgccttgag tgcttcaagt agtgtgtgcc cgtctgttgt gtgactctgg    360
taactagaga tccctcagac ccttttagtc agtgtggaaa atctctagca gtggcgcccg    420
aacagggact tgaaagcgaa agggaaacca ggagagctct ctcgacgcag gactcggctt    480
gctgaagcgc gcacggcaag aggcgagggg cggcgactgg tgagtacgcc aaaaattttg    540
actagcggag gctagaagga gagagatggg tgcgagagcg tcagtattaa gcggggagaa    600
attagatcgc gatgggaaaa aattcggtta aggccagggg gaaagaaaaa atataaatta    660
aaacatatag tatgggcaag cagggagcta gaacgattcg cagttaatcc tggcctgtta    720
```

```
gaaacatcag aaggctgtag acaaatactg ggacagctac aaccatccct tcagacagga   780
tcagaagaac ttagatcatt atataataca gtagcaaccc tctattgtgt gcatcaaagg   840
atagagataa aagacaccaa ggaagcttta gacaagatag aggaagagca aaacaaaagt   900
aagaccaccg cacagcaagc ggccgctgat cttcagacct ggaggaggag atatgaggga   960
caattggaga agtgaattat ataaatataa agtagtaaaa attgaaccat taggagtagc  1020
acccaccaag gcaaagagaa gagtggtgca gagagaaaaa agagcagtgg aataggagc   1080 tttgttcctt gggttcttgg agcagcagg aagcactatg ggcgcagcgt caatgacgct   1140
gacggtacag gccagacaat tattgtctgg tatagtgcag cagcagaaca atttgctgag  1200
ggctattgag gcgcaacagc atctgttgca actcacagtc tggggcatca agcagctcca  1260
ggcaagaatc ctggctgtgg aaagatacct aaaggatcaa cagctcctgg ggatttgggg  1320
ttgctctgga aaactcattt gcaccactgc tgtgccttgg aatgctagtt ggagtaataa  1380
atctctggaa cagatttgga atcacacgac ctggatggag tgggacagag aaattaacaa  1440
ttacacaagc ttaatacact ccttaattga agaatcgcaa aaccagcaag aaaagaatga  1500
acaagaatta ttggaattag ataaatgggc aagtttgtgg aattggttta acataacaaa  1560
ttggctgtgg tatataaaat tattcataat gatagtagga ggcttggtag gtttaagaat  1620
agtttttgct gtactttcta tagtgaatag agttaggcag ggatattcac cattatcgtt  1680
tcagacccac ctcccaaccc cgaggggacc cgacaggccc gaaggaatag aagaagaagg  1740
tggagagaga gacagagaca gatccattcg attagtgaac ggatctcgac ggtatcgata  1800
agcttgggag ttccgcgtta cataacttac ggtaaatggc ccgcctggct gaccgcccaa  1860
cgacccccgc ccattgacgt caataatgac gtatgttccc atagtaacgc caatagggac  1920
tttccattga cgtcaatggg tggagtattt acggtaaact gcccacttgg cagtacatca  1980
agtgtatcat atgccaagta cgccccctat tgacgtcaat gacggtaaat ggcccgcctg  2040
gcattatgcc cagtacatga ccttatggga ctttcctact tggcagtaca tctacgtatt  2100
agtcatcgct attaccatgg tgatgcggtt ttggcagtac atcaatgggc gtggatagcg  2160
gtttgactca cggggatttc caagtctcca ccccattgac gtcaatggga gtttgttttg  2220
gcaccaaaat caacgggact ttccaaaatg tcgtaacaac tccgccccat tgacgcaaat  2280
gggcggtagg cgtgtacggt gggaggtcta tataagcaga gctcgtttag tgaaccgtca  2340
gatcgcctgg agacgccatc cacgctgttt tgacctccat agaagacacc gactctagag  2400
gatccactag tccagtgtgg tggaattgat cccttcacca agggctcgag tctagagggc  2460
ccgcggttcg aaggtaagcc tatccctaac cctctcctcg gtctcgattc tacgcgtacc  2520
ggttagtaat gagtttggaa ttaattctgt ggaatgtgtg tcagttaggg tgtggaaagt  2580
ccccaggctc cccaggcagg cagaagtatg caaagcatgc atctcaatta gtcagcaacc  2640
aggtgtggaa agtccccagg ctccccagca ggcagaagta tgcaaagcat gcatctcaat  2700
tagtcagcaa ccatagtccc gcccctaact ccgcccatcc cgcccctaac tccgccagt   2760 tccgcccatt ctccgcccca tggctgacta atttttttta tttatgcaga ggccgaggcc  2820
gcctctgcct ctgagctatt ccagaagtag tgaggaggct tttttggagg cctaggcttt  2880
tgcaaaaagc tcccgggagc ttgtatatcc attttcggat ctgatcagca cgtgttgaca  2940
attaatcatc ggcatagtat atcggcatag tataatacga caaggtgagg aactaaacca  3000
tggccaagcc tttgtctcaa gaagaatcca ccctcattga aagagcaacg gctacaatca  3060
acagcatccc catctctgaa gactacagcg tcgccagcgc agctctctct agcgacggcc  3120
```

```
gcatcttcac tggtgtcaat gtatatcatt ttactggggg accttgtgca gaactcgtgg    3180
tgctgggcac tgctgctgct gcggcagctg gcaacctgac ttgtatcgtc gcgatcggaa    3240
atgagaacag gggcatcttg agccctgcg gacggtgccg acaggtgctt ctcgatctgc     3300
atcctgggat caaagccata gtgaaggaca gtgatggaca gccgacggca gttgggattc    3360
gtgaattgct gccctctggt tatgtgtggg agggctaagc acaattcgag ctcggtacct    3420
ttaagaccaa tgacttacaa ggcagctgta gatcttagcc acttttttaaa agaaaagggg   3480 ggactggaag ggctaattca ctcccaacga agacaagatc tgcttttttgc ttgtactggg   3540 tctctctggt tagaccagat ctgagcctgg gagctctctg gctaactagg gaacccactg    3600
cttaagcctc aataaagctt gccttgagtg cttcaagtag tgtgtgcccg tctgttgtgt    3660
gactctggta actagagatc cctcagaccc ttttagtcag tgtggaaaat ctctagcagt    3720
agtagttcat gtcatcttat tattcagtat ttataacttg caaagaaatg aatatcagag    3780
agtgagagga acttgtttat tgcagcttat aatggttaca aataaagcaa tagcatcaca    3840
aatttcacaa ataaagcatt ttttcactg cattctagtt gtggtttgtc caaactcatc     3900
aatgtatctt atcatgtctg gctctagcta tcccgcccct aactccgccc atcccgcccc    3960
taactccgcc cagttccgcc cattctccgc cccatggctg actaattttt tttatttatg    4020
cagaggccga ggccgcctcg gcctctgagc tattccagaa gtagtgagga ggcttttttg    4080
gaggcctagg gacgtaccca attcgcccta gtgagtcg tattacgcgc gctcactggc      4140 cgtcgttta  caacgtcgtg actgggaaaa ccctggcgtt acccaactta atcgccttgc    4200
agcacatccc cctttcgcca gctggcgtaa tagcgaagag gcccgcaccg atcgcccttc    4260 ccaacgttg  cgcagcctga atggcgaatg ggacgcgccc tgtagcggcg cattaagcgc    4320
ggcgggtgtg gtggttacgc gcagcgtgac cgctacactt gccagcgccc tagcgcccgc    4380
tcctttcgct ttcttccctt cctttctcgc cacgttcgcc ggctttcccc gtcaagctct    4440
aaatcggggg ctccctttag ggttccgatt tagtgcttta cggcacctcg accccaaaaa    4500
acttgattag ggtgatggtt cacgtagtgg gccatcgccc tgatagacgg ttttttcgccc   4560 tttgacgttg gagtccacgt tctttaatag tggactcttg ttccaaactg gaacaacact    4620
caaccctatc tcggtctatt cttttgattt ataagggatt ttgccgattt cggcctattg    4680
gttaaaaaat gagctgattt aacaaaaatt taacgcgaat tttaacaaaa tattaacgct    4740
tacaatttag gtggcacttt tcggggaaat gtgcgcggaa cccctatttg tttatttttc    4800
taaatacatt caaatatgta tccgctcatg agacaataac cctgataaat gcttcaataa    4860
tattgaaaaa ggaagagtat gagtattcaa catttccgtg tcgcccttat tcccttttt    4920 gcggcatttt gccttcctgt ttttgctcac ccagaaacgc tggtgaaagt aaaagatgct    4980
gaagatcagt tgggtgcacg agtgggttac atcgaactgg atctcaacag cggtaagatc    5040
cttgagagtt ttcgccccga agaacgtttt ccaatgatga gcacttttaa agttctgcta    5100
tgtggcgcgg tattatcccg tattgacgcc gggcaagagc aactcggtcg ccgcatacac    5160
tattctcaga atgacttggt tgagtactca ccagtcacag aaaagcatct tacggatggc    5220
atgacagtaa gagaattatg cagtgctgcc ataaccatga gtgataacac tgcggccaac    5280
ttacttctga caacgatcgg aggaccgaag gagctaaccg cttttttgca caacatggg    5340 gatcatgtaa ctcgccttga tcgttgggaa ccggagctga atgaagccat accaaacgac    5400
gagcgtgaca ccacgatgcc tgtagcaatg gcaacaacgt tgcgcaaact attaactggc    5460
gaactactta ctctagcttc ccggcaacaa ttaatagact ggatggaggc ggataaagtt    5520
```

-continued

```
gcaggaccac ttctgcgctc ggcccttccg gctggctggt ttattgctga taaatctgga      5580
gccggtgagc gtgggtctcg cggtatcatt gcagcactgg ggccagatgg taagccctcc      5640
cgtatcgtag ttatctacac gacggggagt caggcaacta tggatgaacg aaatagacag      5700
atcgctgaga taggtgcctc actgattaag cattggtaac tgtcagacca agtttactca      5760
tatatacttt agattgattt aaaacttcat ttttaattta aaaggatcta ggtgaagatc      5820 cttttttgata atctcatgac caaaatccct taacgtgagt tttcgttcca ctgagcgtca     5880
gaccccgtag aaaagatcaa aggatcttct tgagatcctt ttttttctgcg cgtaatctgc    5940 tgcttgcaaa caaaaaaacc accgctacca gcggtggttt gtttgccgga tcaagagcta      6000
ccaactcttt ttccgaaggt aactggcttc agcagagcgc agataccaaa tactgttctt      6060
ctagtgtagc cgtagttagg ccaccacttc aagaactctg tagcaccgcc tacatacctc      6120
gctctgctaa tcctgttacc agtggctgct gccagtggcg ataagtcgtg tcttaccggg      6180
ttggactcaa gacgatagtt accggataag gcgcagcggt cgggctgaac ggggggttcg      6240
tgcacacagc ccagcttgga gcgaacgacc tacaccgaac tgagatacct acagcgtgag      6300
ctatgagaaa gcgccacgct tcccgaaggg agaaaggcgg acaggtatcc ggtaagcggc      6360
agggtcggaa caggagagcg cacgagggag cttccagggg gaaacgcctg gtatctttat      6420
agtcctgtcg ggtttcgcca cctctgactt gagcgtcgat ttttgtgatg ctcgtcaggg      6480
gggcggagcc tatggaaaaa cgccagcaac gcggcctttt tacggttcct ggccttttgc      6540
tggccttttg ctcacatgtt ctttcctgcg ttatccctg attctgtgga taaccgtatt      6600
accgcctttg agtgagctga taccgctcgc cgcagccgaa cgaccgagcg cagcgagtca      6660
gtgagcgagg aagcggaaga gcgcccaata cgcaaaccgc ctctccccgc gcgttggccg      6720
attcattaat gcagctggca cgacaggttt cccgactgga aagcgggcag tgagcgcaac      6780
gcaattaatg tgagttagct cactcattag gcaccccagg ctttacactt tatgcttccg      6840
gctcgtatgt tgtgtggaat tgtgagcgga taacaatttc acacaggaaa cagctatgac      6900
catgattacg ccaagcgcgc aattaaccct cactaaaggg aacaaaagct ggagctgcaa      6960
gctt                                                                   6964
```

<210> SEQ ID NO 4
<211> LENGTH: 8634
<212> TYPE: DNA
<213> ORGANISM: Artificial
<220> FEATURE:
<223> OTHER INFORMATION: pLenti4/V5-DEST

<400> SEQUENCE: 4

```
aatgtagtct tatgcaatac tcttgtagtc ttgcaacatg gtaacgatga gttagcaaca       60
tgccttacaa ggagagaaaa agcaccgtgc atgccgattg gtggaagtaa ggtggtacga      120
tcgtgcctta ttaggaaggc aacagacggg tctgacatgg attggacgaa ccactgaatt      180
gccgcattgc agagatattg tatttaagtg cctagctcga tacataaacg ggtctctctg      240
gttagaccag atctgagcct gggagctctc tggctaacta gggaacccac tgcttaagcc      300
tcaataaagc ttgccttgag tgcttcaagt agtgtgtgcc cgtctgttgt gtgactctgg      360
taactagaga tccctcagac ccttttagtc agtgtggaaa atctctagca gtggcgcccg      420
aacagggact tgaaagcgaa agggaaacca ggagctctct cgacgcagga ctcggctt        480 gctgaagcgc gcacggcaag aggcgagggg cggcgactgg tgagtacgcc aaaaattttg      540
actagcggag gctagaagga gagagatggg tgcgagagcg tcagtattaa gcgggggaga      600
```

```
attagatcgc gatgggaaaa aattcggtta aggccagggg gaaagaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620 agttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgata   1800
agcttgggag ttccgcgtta cataacttac ggtaaatggc ccgcctggct gaccgcccaa   1860
cgacccccgc ccattgacgt caataatgac gtatgttccc atagtaacgc caatagggac   1920
tttccattga cgtcaatggg tggagtattt acggtaaact gcccacttgg cagtacatca   1980
agtgtatcat atgccaagta cgccccctat tgacgtcaat gacggtaaat ggcccgcctg   2040
gcattatgcc cagtacatga ccttatggga ctttcctact tggcagtaca tctacgtatt   2100
agtcatcgct attaccatgg tgatgcggtt ttggcagtac atcaatgggc gtggatagcg   2160
gtttgactca cggggatttc caagtctcca ccccattgac gtcaatggga gtttgttttg   2220
gcaccaaaat caacgggact ttccaaaatg tcgtaacaac tccgccccat tgacgcaaat   2280
gggcggtagg cgtgtacggt gggaggtcta tataagcaga gctcgtttag tgaaccgtca   2340
gatcgcctgg agacgccatc cacgctgttt tgacctccat agaagacacc gactctagag   2400
gatccactag tccagtgtgg tggaattctg cagatatcaa caagtttgta caaaaaagct   2460
gaacgagaaa cgtaaaatga tataaatatc aatatattaa attagatttt gcataaaaaa   2520
cagactacat aatactgtaa aacacaacat atccagtcac tatggcggcc gcattaggca   2580
ccccaggctt tacactttat gcttccggct cgtataatgt gtggattttg agttaggatc   2640
cggcgagatt tcaggagct aaggaagcta aaatggagaa aaaatcact ggatatacca   2700 ccgttgatat atcccaatgg catcgtaaag aacattttga ggcatttcag tcagttgctc   2760
aatgtaccta taaccagacc gttcagctgg atattacggc cttttaaag accgtaaaga   2820 aaaataagca caagtttat ccggccttta ttcacattct tgcccgcctg atgaatgctc   2880
atccggaatt ccgtatggca atgaaagacg gtgagctggt gatatgggat agtgttcacc   2940
cttgttacac cgttttccat gagcaaactg aaacgttttc atcgctctgg agtgaatacc   3000
```

```
acgacgattt ccggcagttt ctacacatat attcgcaaga tgtggcgtgt tacggtgaaa    3060
acctggccta tttccctaaa gggtttattg agaatatgtt tttcgtctca gccaatccct    3120
gggtgagttt caccagtttt gatttaaacg tggccaatat ggacaacttc ttcgcccccg    3180
ttttcaccat gggcaaatat tatacgcaag gcgacaaggt gctgatgccg ctggcgattc    3240
aggttcatca tgccgtctgt gatggcttcc atgtcggcag aatgcttaat gaattacaac    3300
agtactgcga tgagtggcag ggcggggcgt aaagatctgg atccggctta ctaaaagcca    3360
gataacagta tgcgtatttg cgcgctgatt tttgcggtat aagaatatat actgatatgt    3420
atacccgaag tatgtcaaaa agaggtgtgc tatgaagcag cgtattacag tgacagttga    3480
cagcgacagc tatcagttgc tcaaggcata tgatgtca atatctccgg tctggtaagc    3540
acaaccatgc agaatgaagc ccgtcgtctg cgtgccgaac gctggaaagc ggaaaatcag    3600
gaagggatgg ctgaggtcgc ccggtttatt gaaatgaacg gctcttttgc tgacgagaac    3660
agggactggt gaaatgcagt ttaaggttta cacctataaa agagagagcc gttatcgtct    3720
gtttgtggat gtacagagtg atattattga cacgcccggg cgacggatgg tgatccccct    3780
ggccagtgca cgtctgctgt cagataaagt ctcccgtgaa cttacccggt ggtgcatat    3840 cggggatgaa agctggcgca tgatgaccac cgatatggcc agtgtgccgg tctccgttat    3900
cggggaagaa gtggctgatc tcagccaccg cgaaaatgac atcaaaaacg ccattaacct    3960
gatgttctgg ggaatataaa tgtcaggctc cgttatacac agccagtctg caggtcgacc    4020
atagtgactg gatatgttgt gttttacagt attatgtagt ctgtttttta tgcaaaatct    4080
aatttaatat attgatattt atatcatttt acgtttctcg ttcagctttc ttgtacaaag    4140
tggttgatat ccagcacagt ggcggccgct cgagtctaga gggcccgcgg ttcgaaggta    4200
agcctatccc taaccctctc ctcggtctcg attctacgcg taccggttag taatgagttt    4260
ggaattaatt ctgtggaatg tgtgtcagtt agggtgtgga aagtccccag gctccccagg    4320
caggcagaag tatgcaaagc atgcatctca attagtcagc aaccaggtgt ggaaagtccc    4380
caggctcccc agcaggcaga agtatgcaaa gcatgcatct caattagtca gcaaccatag    4440
tcccgcccct aactccgccc atcccgcccc taactccgcc cagttccgcc cattctccgc    4500
cccatggctg actaattttt tttatttatg cagaggccga ggccgcctct gcctctgagc    4560
tattccagaa gtagtgagga ggcttttttg gaggcctagg cttttgcaaa aagctccccc    4620
tgttgacaat taatcatcgg catagtatat cggcatagta taatacgaca aggtgaggaa    4680
ctaaaccatg gccaagttga ccagtgccgt tccggtgctc accgcgcgcg acgtcgccgg    4740
agcggtcgag ttctggaccg accggctcgg gttctcccgg gacttcgtgg aggacgactt    4800
cgccggtgtg gtccgggacg acgtgaccct gttcatcagc gcggtccagg accaggtggt    4860 gccgacaac accctggcct gggtgtgggt gcgcggcctg gacgagctgt acgccgagtg    4920
gtcggaggtc gtgtccacga acttccggga cgcctccggg ccggccatga ccgagatcgg    4980
cgagcagccg tggggcggg agttcgccct gcgcgaccg gccggcaact gcgtgcactt    5040
cgtggccgag gagcaggact gacacgtgct acgagattta aatggtacct ttaagaccaa    5100
tgacttacaa ggcagctgta gatcttagcc acttttttaaa agaaaagggg ggactggaag    5160
ggctaattca ctcccaacga agacaagatc tgcttttttgc ttgtactggg tctctctggt    5220
tagaccagat ctgagcctgg gagctctctg gctaactagg gaacccactg cttaagcctc    5280
aataaagctt gccttgagtg cttcaagtag tgtgtgcccg tctgttgtgt gactctggta    5340
actagagatc cctcagaccc ttttagtcag tgtggaaaat ctctagcagt agtagttcat    5400
```

```
gtcatcttat tattcagtat ttataacttg caaagaaatg aatatcagag agtgagagga    5460
acttgtttat tgcagcttat aatggttaca aataaagcaa tagcatcaca aatttcacaa    5520
ataaagcatt ttttcactg cattctagtt gtggtttgtc caaactcatc aatgtatctt     5580
atcatgtctg gctctagcta tcccgcccct aactccgccc atcccgcccc taactccgcc    5640
cagttccgcc cattctccgc ccatggctg actaattttt tttatttatg cagaggccga     5700
ggccgcctcg gcctctgagc tattccagaa gtagtgagga ggcttttttg gaggcctagg    5760
gacgtaccca attcgcccta tagtgagtcg tattacgcgc gctcactggc cgtcgtttta    5820
caacgtcgtg actgggaaaa ccctggcgtt acccaactta atcgccttgc agcacatccc    5880
cctttcgcca gctggcgtaa tagcgaagag gcccgcaccg atcgcccttc ccaacagttg    5940
cgcagcctga atggcgaatg ggacgcgccc tgtagcggcg cattaagcgc ggcgggtgtg    6000
gtggttacgc gcagcgtgac cgctacactt gccagcgccc tagcgcccgc tcctttcgct    6060
ttcttccctt cctttctcgc cacgttcgcc ggctttcccc gtcaagctct aaatcggggg    6120
ctccctttag ggttccgatt tagtgcttta cggcacctcg accccaaaaa acttgattag    6180
ggtgatggtt cacgtagtgg gccatcgccc tgatagacgg ttttcgccc tttgacgttg     6240 gagtccacgt tctttaatag tggactcttg ttccaaactg gaacaacact caaccctatc    6300
tcggtctatt cttttgattt ataagggatt ttgccgattt cggcctattg gttaaaaaat    6360
gagctgattt aacaaaaatt taacgcgaat tttaacaaaa tattaacgct tacaatttag    6420
gtggcacttt tcggggaaat gtgcgcggaa cccctatttg tttattttc taaatacatt     6480 caaatatgta tccgctcatg agacaataac cctgataaat gcttcaataa tattgaaaaa    6540
ggaagagtat gagtattcaa catttccgtg tcgcccttat tccttttttt gcggcatttt    6600
gccttcctgt ttttgctcac ccagaaacgc tggtgaaagt aaaagatgct gaagatcagt    6660
tgggtgcacg agtgggttac atcgaactgg atctcaacag cggtaagatc cttgagagtt    6720
ttcgccccga agaacgtttt ccaatgatga gcacttttaa agttctgcta tgtggcgcgg    6780
tattatcccg tattgacgcc gggcaagagc aactcggtcg ccgcatacac tattctcaga    6840
atgacttggt tgagtactca ccagtcacag aaaagcatct tacggatggc atgacagtaa    6900
gagaattatg cagtgctgcc ataaccatga gtgataacac tgcggccaac ttacttctga    6960
caacgatcgg aggaccgaag gagctaaccg ctttttttgca caacatgggg gatcatgtaa    7020
ctcgccttga tcgttgggaa ccggagctga atgaagccat accaaacgac gagcgtgaca    7080
ccacgatgcc tgtagcaatg gcaacaacgt tgcgcaaact attaactggc gaactactta    7140
ctctagcttc ccggcaacaa ttaatagact ggatggaggc ggataaagtt gcaggaccac    7200
ttctgcgctc ggcccttccg gctggctggt ttattgctga taaatctgga gccggtgagc    7260
gtgggtctcg cggtatcatt gcagcactgg ggccagatgg taagccctcc cgtatcgtag    7320
ttatctacac gacggggagt caggcaacta tggatgaacg aaatagacag atcgctgaga    7380
taggtgcctc actgattaag cattggtaac tgtcagacca agtttactca tatatacttt    7440
agattgattt aaaacttcat ttttaattta aaaggatcta ggtgaagatc ctttttgata    7500
atctcatgac caaaatccct taacgtgagt tttcgttcca ctgagcgtca gaccccgtag    7560
aaaagatcaa aggatcttct tgagatcctt ttttctgcg cgtaatctgc tgcttgcaaa     7620
caaaaaaacc accgctacca gcggtggttt gtttgccgga tcaagagcta ccaactcttt    7680
ttccgaaggt aactggcttc agcagagcgc agataccaaa tactgttctt ctagtgtagc    7740
cgtagttagg ccaccacttc aagaactctg tagcaccgcc tacatacctc gctctgctaa    7800
```

| | |
|---|---|
| tcctgttacc agtggctgct gccagtggcg ataagtcgtg tcttaccggg ttggactcaa | 7860 |
| gacgatagtt accggataag gcgcagcggt cgggctgaac ggggggttcg tgcacacagc | 7920 |
| ccagcttgga gcgaacgacc tacaccgaac tgagatacct acagcgtgag ctatgagaaa | 7980 |
| gcgccacgct tcccgaaggg agaaaggcgg acaggtatcc ggtaagcggc agggtcggaa | 8040 |
| caggagagcg cacgagggag cttccagggg gaaacgcctg gtatctttat agtcctgtcg | 8100 |
| ggtttcgcca cctctgactt gagcgtcgat ttttgtgatg ctcgtcaggg gggcggagcc | 8160 |
| tatggaaaaa cgccagcaac gcggcctttt tacggttcct ggccttttgc tggccttttg | 8220 |
| ctcacatgtt ctttcctgcg ttatcccctg attctgtgga taaccgtatt accgcctttg | 8280 |
| agtgagctga taccgctcgc cgcagccgaa cgaccgagcg cagcgagtca gtgagcgagg | 8340 |
| aagcggaaga gcgcccaata cgcaaaccgc ctctccccgc gcgttggccg attcattaat | 8400 |
| gcagctggca cgacaggttt cccgactgga aagcgggcag tgagcgcaac gcaattaatg | 8460 |
| tgagttagct cactcattag gcaccccagg ctttacactt tatgcttccg gctcgtatgt | 8520 |
| tgtgtggaat tgtgagcgga taacaatttc acacaggaaa cagctatgac catgattacg | 8580 |
| ccaagcgcgc aattaaccct cactaaaggg aacaaaagct ggagctgcaa gctt | 8634 |

<210> SEQ ID NO 5
<211> LENGTH: 9320
<212> TYPE: DNA
<213> ORGANISM: Artificial
<220> FEATURE:
<223> OTHER INFORMATION: pLenti6/UBC/V5-DEST

<400> SEQUENCE: 5

| | |
|---|---|
| aatgtagtct tatgcaatac tcttgtagtc ttgcaacatg gtaacgatga gttagcaaca | 60 |
| tgccttacaa ggagagaaaa agcaccgtgc atgccgattg gtggaagtaa ggtggtacga | 120 |
| tcgtgcctta ttaggaaggc aacagacggg tctgacatgg attggacgaa ccactgaatt | 180 |
| gccgcattgc agagatattg tatttaagtg cctagctcga tacataaacg ggtctctctg | 240 |
| gttagaccag atctgagcct gggagctctc tggctaacta gggaacccac tgcttaagcc | 300 |
| tcaataaagc ttgccttgag tgcttcaagt agtgtgtgcc cgtctgttgt gtgactctgg | 360 |
| taactagaga tccctcagac ccttttagtc agtgtggaaa atctctagca gtggcgcccg | 420 |
| aacagggact tgaaagcgaa agggaaacca gaggagctct ctcgacgcag gactcggctt | 480 |
| gctgaagcgc gcacggcaag aggcgagggg cggcgactgg tgagtacgcc aaaaattttg | 540 |
| actagcggag gctagaagga gagagatggg tgcgagagcg tcagtattaa gcggggggaga | 600 |
| attagatcgc gatgggaaaa aattcggtta aggccagggg gaagaaaaaa atataaatta | 660 |
| aaacatatag tatgggcaag cagggagcta gaacgattcg cagttaatcc tggcctgtta | 720 |
| gaaacatcag aaggctgtag acaaatactg ggacagctac aaccatccct tcagacagga | 780 |
| tcagaagaac ttagatcatt atataataca gtagcaaccc tctattgtgt gcatcaaagg | 840 |
| atagagataa aagacaccaa ggaagcttta gacaagatag aggaagagca aaacaaaagt | 900 |
| aagaccaccg cacagcaagc ggccgctgat cttcagacct ggaggaggag atatgaggga | 960 |
| caattggaga agtgaattat ataaatataa agtagtaaaa attgaaccat taggagtagc | 1020 |
| acccaccaag gcaaagagaa gagtggtgca gagagaaaaa agagcagtgg aataggagc | 1080 |
| tttgttcctt gggttcttgg gagcagcagg aagcactatg gcgcagcgt caatgacgct | 1140 |
| gacggtacag gccagacaat tattgtctgg tatagtgcag cagcagaaca atttgctgag | 1200 |
| ggctattgag gcgcaacagc atctgttgca actcacagtc tggggcatca agcagctcca | 1260 |

```
ggcaagaatc ctggctgtgg aaagatacct aaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620 agttttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcggat    1800
ctggcctccg cgccgggttt tggcgcctcc cgcgggcgcc cccctcctca cggcgagcgc    1860
tgccacgtca gacgaagggc gcaggagcgt cctgatcctt ccgcccggac gctcaggaca    1920
gcggcccgct gctcataaga ctcggcctta gaacccagt atcagcagaa ggacatttta    1980
ggacgggact tgggtgactc tagggcactg gttttctttc cagagagcgg aacaggcgag    2040
gaaaagtagt cccttctcgg cgattctgcg gagggatctc cgtggggcgg tgaacgccga    2100
tgattatata aggacgcgcc gggtgtggca cagctagttc cgtcgcagcc gggatttggg    2160
tcgcggttct tgtttgtgga tcgctgtgat cgtcacttgg tgagtagcgg gctgctgggc    2220
tggccggggc tttcgtggcc gccgggccgc tcggtgggac ggaagcgtgt ggagagaccg    2280
ccaagggctg tagtctgggt ccgcgagcaa ggttgccctg aactgggggt tgggggagc    2340 gcagcaaaat ggcggctgtt cccgagtctt gaatggaaga cgcttgtgag gcgggctgtg    2400
aggtcgttga acaaggtgg ggggcatggt gggcggcaag aacccaaggt cttgaggcct    2460
tcgctaatgc gggaaagctc ttattcgggt gagatgggct ggggcaccat ctggggaccc    2520
tgacgtgaag tttgtcactg actgagaac tcggtttgtc gtctgttgcg ggggcggcag    2580
ttatgcggtg ccgttgggca gtgcacccgt acctttggga gcgcgcgccc tcgtcgtgtc    2640
gtgacgtcac ccgttctgtt ggcttataat gcagggtggg gccacctgcc ggtaggtgtg    2700
cggtaggctt ttctccgtcg caggacgcag ggttcgggcc tagggtaggc tctcctgaat    2760
cgacaggcgc cggacctctg gtgaggggag ggataagtga ggcgtcagtt tctttggtcg    2820
gttttatgta cctatcttct taagtagctg aagctccggt tttgaactat gcgctcgggg    2880
ttggcgagtg tgttttgtga agttttttag gcacccttttg aaatgtaatc atttgggtca    2940
atatgtaatt ttcagtgtta gactagtaaa ttgtccgcta aattctggcc gttttttggct    3000 tttttgttag acgaagcttg gtaccgagct cggatccact agtccagtgt ggtggaattc    3060
tgcagatatc aacaagtttg tacaaaaaag ctgaacgaga aacgtaaaat gatataaata    3120
tcaatatatt aaattagatt ttgcataaaa aacagactac ataatactgt aaaacacaac    3180
atatccagtc actatggcgg ccgcattagg cacccccaggc tttacacttt atgcttccgg    3240
ctcgtataat gtgtggattt tgagttagga tccggcgaga ttttcaggag ctaaggaagc    3300
taaaatggag aaaaaaatca ctggatatac caccgttgat atatcccaat ggcatcgtaa    3360
agaacatttt gaggcatttc agtcagttgc tcaatgtacc tataaccaga ccgttcagct    3420
ggatattacg gcctttttaa agaccgtaaa gaaaataag cacaagtttt atccggcctt    3480
tattcacatt cttgcccgcc tgatgaatgc tcatccggaa ttccgtatgg caatgaaaga    3540
cggtgagctg gtgatatggg atagtgttca cccttgttac accgttttcc atgagcaaac    3600
tgaaacgttt tcatcgctct ggagtgaata ccacgacgat ttccggcagt ttctacacat    3660
```

```
atattcgcaa gatgtggcgt gttacggtga aaacctggcc tatttccctaa aagggtttat    3720
tgagaatatg ttttcgtct cagccaatcc ctgggtgagt ttcaccagtt ttgatttaaa     3780
cgtggccaat atggacaact tcttcgcccc cgttttcacc atgggcaaat attatacgca     3840
aggcgacaag gtgctgatgc cgctggcgat tcaggttcat catgccgtct gtgatggctt    3900
ccatgtcggc agaatgctta atgaattaca acagtactgc gatgagtggc agggcggggc    3960
gtaaagatct ggatccggct tactaaaagc cagataacag tatgcgtatt tgcgcgctga    4020
ttttttgcggt ataagaatat atactgatat gtatacccga agtatgtcaa aaagaggtgt   4080
gctatgaagc agcgtattac agtgacagtt gacagcgaca gctatcagtt gctcaaggca    4140
tatatgatgt caatatctcc ggtctggtaa gcacaaccat gcagaatgaa gcccgtcgtc    4200
tgcgtgccga acgctggaaa gcggaaaatc aggaagggat ggctgaggtc gcccggttta    4260
ttgaaatgaa cggctctttt gctgacgaga acagggactg gtgaaatgca gtttaaggtt    4320
tacacctata aagagagag ccgttatcgt ctgtttgtgg atgtacagag tgatattatt     4380
gacacgcccg ggcgacggat ggtgatcccc ctggccagtg cacgtctgct gtcagataaa    4440
gtctcccgtg aactttaccc ggtggtgcat atcggggatg aaagctggcg catgatgacc    4500
accgatatgg ccagtgtgcc ggtctccgtt atcggggaag aagtggctga tctcagccac    4560
cgcgaaaatg acatcaaaaa cgccattaac ctgatgttct ggggaatata atgtcaggc    4620
tccgttatac acagccagtc tgcaggtcga ccatagtgac tggatatgtt gtgttttaca    4680
gtattatgta gtctgttttt tatgcaaaat ctaatttaat atattgatat ttatatcatt    4740
ttacgtttct cgttcagctt tcttgtacaa agtggttgat atccagcaca gtggcggccg    4800
ctcgagtcta gagggcccgc ggttcgaagg taagcctatc cctaaccctc tcctcggtct    4860
cgattctacg cgtaccggtt agtaatgagt ttggaattaa ttctgtggaa tgtgtgtcag    4920
ttagggtgtg aaagtccccc aggctcccca ggcaggcaga agtatgcaaa gcatgcatct    4980
caattagtca gcaaccaggt gtggaaagtc cccaggctcc ccagcaggca gaagtatgca    5040
aagcatgcat ctcaattagt cagcaaccat agtcccgccc ctaactccgc ccatcccgcc    5100
cctaactccg cccagttccg cccattctcc gccccatggc tgactaattt ttttatta     5160
tgcagaggcc gaggccgcct ctgcctctga gctattccag aagtagtgag gaggcttttt    5220
tggaggccta ggcttttgca aaaagctccc gggagcttgt atatccattt tcggatctga    5280
tcagcacgtg ttgacaatta atcatcggca tagtatatcg gcatagtata atacgacaag    5340
gtgaggaact aaaccatggc caagcctttg tctcaagaag aatccaccct cattgaaaga    5400
gcaacggcta caatcaacag catccccatc tctgaagact acagcgtcgc cagcgcagct    5460
ctctctagcg acggccgcat cttcactggt gtcaatgtat atcattttac tgggggacct    5520
tgtgcagaac tcgtggtgct gggcactgct gctgctgcgg cagctggcaa cctgacttgt    5580
atcgtcgcga tcggaaatga gaacaggggc atcttgagcc cctgcggacg gtgccgacag    5640
gtgcttctcg atctgcatcc tgggatcaaa gccatagtga aggacagtga tggacagccg    5700
acggcagttg ggattcgtga attgctgccc tctggttatg tgtgggaggg ctaagcacaa    5760
ttcgagctcg gtacctttaa gaccaatgac ttacaaggca gctgtagatc ttagccactt    5820
tttaaaagaa aagggggggac tggaagggct aattcactcc caacgaagac aagatctgct    5880
ttttgcttgt actgggtctc tctggttaga ccagatctga gcctgggagc tctctggcta    5940
actagggaac ccactgctta agcctcaata aagcttgcct tgagtgcttc aagtagtgtg    6000
tgcccgtctg ttgtgtgact ctggtaacta gagatccctc agacccttt agtcagtgtg    6060
```

```
gaaaatctct agcagtagta gttcatgtca tcttattatt cagtatttat aacttgcaaa    6120
gaaatgaata tcagagagtg agaggaactt gtttattgca gcttataatg gttacaaata    6180
aagcaatagc atcacaaatt tcacaaataa agcattttt tcactgcatt ctagttgtgg     6240
tttgtccaaa ctcatcaatg tatcttatca tgtctggctc tagctatccc gcccctaact    6300
ccgcccatcc cgcccctaac tccgcccagt tccgcccatt ctcgccccca tggctgacta    6360 attttttta tttatgcaga ggccgaggcc gcctcggcct ctgagctatt ccagaagtag     6420
tgaggaggct ttttggagg cctagggacg tacccaattc gccctatagt gagtcgtatt     6480
acgcgcgctc actggccgtc gttttacaac gtcgtgactg ggaaaaccct ggcgttaccc    6540
aacttaatcg ccttgcagca catccccctt tcgccagctg gcgtaatagc gaagaggccc    6600
gcaccgatcg cccttcccaa cagttgcgca gcctgaatgg cgaatgggac gcgccctgta    6660
gcggcgcatt aagcgcggcg ggtgtggtgg ttacgcgcag cgtgaccgct acacttgcca    6720
gcgccctagc gcccgctcct ttcgctttct tcccttcctt tctcgccacg ttcgccggct    6780
ttccccgtca gctctaaat cggggctcc ctttagggtt ccgatttagt gctttacggc       6840
acctcgaccc caaaaaactt gattagggtg atggttcacg tagtgggcca tcgccctgat    6900
agacggtttt tcgccctttg acgttggagt ccacgttctt taatagtgga ctcttgttcc    6960
aaactggaac aacactcaac cctatctcgg tctattcttt tgatttataa gggattttgc    7020
cgatttcggc ctattggtta aaaaatgagc tgatttaaca aaaatttaac gcgaatttta    7080
acaaaatatt aacgcttaca atttaggtgg cacttttcgg ggaaatgtgc gcggaacccc    7140
tatttgttta ttttctaaa tacattcaaa tatgtatccg ctcatgagac aataaccctg       7200
ataaatgctt caataatatt gaaaaggaa gagtatgagt attcaacatt tccgtgtcgc     7260
ccttattccc ttttttgcgg cattttgcct tcctgttttt gctcacccag aaacgctggt    7320
gaaagtaaaa gatgctgaag atcagttggg tgcacgagtg ggttacatcg aactggatct    7380
caacagcggt aagatccttg agagttttcg ccccgaagaa cgttttccaa tgatgagcac    7440
ttttaaagtt ctgctatgtg gcgcggtatt atcccgtatt gacgccgggc aagagcaact    7500
cggtcgccgc atacactatt ctcagaatga cttggttgag tactcaccag tcacagaaaa    7560
gcatcttacg gatggcatga cagtaagaga attatgcagt gctgccataa ccatgagtga    7620
taacactgcg gccaacttac ttctgacaac gatcggagga ccgaaggagc taaccgcttt    7680
tttgcacaac atgggggatc atgtaactcg ccttgatcgt tgggaaccgg agctgaatga    7740
agccatacca aacgacgagc gtgacaccac gatgcctgta gcaatggcaa caacgttgcg    7800
caaactatta actggcgaac tacttactct agcttcccgg caacaattaa tagactggat    7860
ggaggcggat aaagttgcag gaccacttct gcgctcggcc cttccggctg ctggttat      7920 tgctgataaa tctggagccg gtgagcgtgg gtctcgcggt atcattgcag cactggggcc    7980
agatggtaag ccctcccgta tcgtagttat ctacacgacg gggagtcagg caactatgga    8040
tgaacgaaat agacagatcg ctgagatagg tgcctcactg attaagcatt ggtaactgtc    8100
agaccaagtt tactcatata tactttagat tgatttaaaa cttcattttt aatttaaaag    8160
gatctaggtg aagatccttt ttgataatct catgaccaaa atcccttaac gtgagttttc    8220
gttccactga gcgtcagacc ccgtagaaaa gatcaaagga tcttcttgag atccttttt      8280 tctgcgcgta atctgctgct tgcaaacaaa aaaccaccg ctaccagcgg tggtttgttt     8340
gccggatcaa gagctaccaa ctctttttcc gaaggtaact ggcttcagca gagcgcagat    8400
accaaatact gttcttctag tgtagccgta gttaggccac cacttcaaga actctgtagc    8460
```

| | |
|---|---|
| accgcctaca tacctcgctc tgctaatcct gttaccagtg gctgctgcca gtggcgataa | 8520 |
| gtcgtgtctt accgggttgg actcaagacg atagttaccg gataaggcgc agcggtcggg | 8580 |
| ctgaacgggg ggttcgtgca cacagcccag cttggagcga acgacctaca ccgaactgag | 8640 |
| atacctacag cgtgagctat gagaaagcgc cacgcttccc gaagggagaa aggcggacag | 8700 |
| gtatccggta agcggcaggg tcggaacagg agagcgcacg agggagcttc caggggggaaa | 8760 |
| cgcctggtat ctttatagtc ctgtcgggtt tcgccacctc tgacttgagc gtcgattttt | 8820 |
| gtgatgctcg tcaggggggc ggagcctatg gaaaaacgcc agcaacgcgg ccttttacg | 8880 |
| gttcctggcc ttttgctggc cttttgctca catgttcttt cctgcgttat cccctgattc | 8940 |
| tgtggataac cgtattaccg cctttgagtg agctgatacc gctcgccgca gccgaacgac | 9000 |
| cgagcgcagc gagtcagtga gcgaggaagc ggaagagcgc ccaatacgca aaccgcctct | 9060 |
| ccccgcgcgt tggccgattc attaatgcag ctggcacgac aggtttcccg actggaaagc | 9120 |
| gggcagtgag cgcaacgcaa ttaatgtgag ttagctcact cattaggcac cccaggcttt | 9180 |
| acactttatg cttccggctc gtatgttgtg tggaattgtg agcggataac aatttcacac | 9240 |
| aggaaacagc tatgaccatg attacgccaa gcgcgcaatt aaccctcact aaagggaaca | 9300 |
| aaagctggag ctgcaagctt | 9320 |

<210> SEQ ID NO 6
<211> LENGTH: 8889
<212> TYPE: DNA
<213> ORGANISM: Artificial
<220> FEATURE:
<223> OTHER INFORMATION: pLP1

<400> SEQUENCE: 6

| | |
|---|---|
| ttggcccatt gcatacgttg tatccatatc ataatatgta catttatatt ggctcatgtc | 60 |
| caacattacc gccatgttga cattgattat tgactagtta ttaatagtaa tcaattacgg | 120 |
| ggtcattagt tcatagccca tatatggagt tccgcgttac ataacttacg gtaaatggcc | 180 |
| cgcctggctg accgcccaac gacccccgcc cattgacgtc aataatgacg tatgttccca | 240 |
| tagtaacgcc aatagggact ttccattgac gtcaatgggt ggagtattta cggtaaactg | 300 |
| cccacttggc agtacatcaa gtgtatcata tgccaagtac gccccctatt gacgtcaatg | 360 |
| acggtaaatg gcccgcctgg cattatgccc agtacatgac cttatgggac tttcctactt | 420 |
| ggcagtacat ctacgtatta gtcatcgcta ttaccatggt gatgcggttt tggcagtaca | 480 |
| tcaatgggcg tggatagcgg tttgactcac ggggatttcc aagtctccac cccattgacg | 540 |
| tcaatgggag tttgttttgg caccaaaatc aacgggactt tccaaaatgt cgtaacaact | 600 |
| ccgccccatt gacgcaaatg ggcggtaggc gtgtacggtg ggaggtctat ataagcagag | 660 |
| ctcgtttagt gaaccgtcag atcgcctgga gacgccatcc acgctgtttt gacctccata | 720 |
| gaagacaccg ggaccgatcc agcctcccct cgaagcttac atgtggtacc gagctcggat | 780 |
| cctgagaact tcagggtgag tctatgggac ccttgatgtt ttctttcccc ttcttttcta | 840 |
| tggttaagtt catgtcatag aaggggggaga agtaacaggg tacacatatt gaccaaatca | 900 |
| gggtaatttt gcatttgtaa ttttaaaaaa tgctttcttc ttttaatata cttttttgtt | 960 |
| tatcttattt ctaatacttt ccctaatctc tttctttcag gcaataatg atacaatgta | 1020 |
| tcatgcctct ttgcaccatt ctaaagaata acagtgataa tttctgggtt aaggcaatag | 1080 |
| caatatttct gcatataaat atttctgcat ataaattgta actgatgtaa gaggtttcat | 1140 |
| attgctaata gcagctacaa tccagctacc attctgcttt tattttatgg ttgggataag | 1200 |

```
gctggattat tctgagtcca agctaggccc ttttgctaat catgttcata cctcttatct    1260
tcctcccaca gctcctgggc aacgtgctgg tctgtgtgct ggcccatcac tttggcaaag    1320
cacgtgagat ctgaattcga gatctgccgc cgccatgggt gcgagagcgt cagtattaag    1380
cgggggagaa ttagatcgat gggaaaaaat tcggttaagg ccaggggaa agaaaaaata    1440 taaattaaaa catatagtat gggcaagcag ggagctagaa cgattcgcag ttaatcctgg    1500
cctgttagaa acatcagaag gctgtagaca aatactggga cagctacaac catcccttca    1560
gacaggatca gaagaactta gatcattata aatacagta gcaaccctct attgtgtgca    1620
tcaaaggata gagataaaag acaccaagga agctttagac aagatagagg aagagcaaaa    1680
caaaagtaag aaaaaagcac agcaagcagc agctgacaca ggacacagca atcaggtcag    1740
ccaaaattac cctatagtgc agaacatcca ggggcaaatg gtacatcagg ccatatcacc    1800
tagaacttta aatgcatggg taaaagtagt agaagagaag gctttcagcc cagaagtgat    1860
acccatgttt tcagcattat cagaaggagc cacccccaca gatttaaaca ccatgctaaa    1920
cacagtgggg ggacatcaag cagccatgca aatgttaaaa gagaccatca atgaggaagc    1980
tgcagaatgg gatagagtgc atccagtgca tgcagggcct attgcaccag gccagatgag    2040
agaaccaagg ggaagtgaca tagcaggaac tactagtacc cttcaggaac aaataggatg    2100
gatgacacat aatccaccta tcccagtagg agaaatctat aaaagatgga taatcctggg    2160
attaaataaa atagtaagaa tgtatagccc taccagcatt ctggacataa gacaaggacc    2220
aaaggaaccc tttagagact atgtagaccg attctataaa actctaagag ccgagcaagc    2280
ttcacaagag gtaaaaaatt ggatgacaga aaccttgttg gtccaaaatg cgaacccaga    2340
ttgtaagact atttttaaaag cattgggacc aggagcgaca ctagaagaaa tgatgacagc    2400
atgtcaggga gtgggggac ccggccataa agcaagagtt ttggctgaag caatgagcca    2460
agtaacaaat ccagctacca taatgataca gaaaggcaat tttaggaacc aaagaaagac    2520
tgttaagtgt ttcaattgtg gcaaagaagg gcacatagcc aaaaattgca gggcccctag    2580
gaaaaagggc tgttggaaat gtggaaagga aggacaccaa atgaaagatt gtactgagag    2640
acaggctaat ttttaggga agatctggcc ttcccacaag ggaaggccag ggaatttct    2700 tcagagcaga ccagagccaa cagccccacc agaagagagc ttcaggtttg gggaagagac    2760
aacaactccc tctcagaagc aggagccgat agacaaggaa ctgtatcctt tagcttccct    2820
cagatcactc tttggcagcg acccctcgtc acaataaaga tagggggca attaaaggaa    2880 gctctattag atacaggagc agatgataca gtattagaag aaatgaattt gccaggaaga    2940
tggaaaccaa aaatgatagg gggaattgga ggttttatca aagtaagaca gtatgatcag    3000
atactcatag aaatctgcgg acataaagct ataggtacag tattagtagg acctacacct    3060
gtcaacataa ttggaagaaa tctgttgact cagattggct gcacttttaaa ttttcccatt    3120 agtcctattg agactgtacc agtaaaatta aagccaggaa tggatggccc aaaagttaaa    3180
caatggccat tgacagaaga aaaaataaaa gcattagtag aaatttgtac agaaatggaa    3240
aaggaaggaa aaatttcaaa aattgggcct gaaaatccat acaatactcc agtatttgcc    3300
ataagaaaaa aagacagtac taatggaga aaattagtag atttcagaga acttaataag    3360
agaactcaag atttctggga agttcaatta ggaataccac atcctgcagg gttaaaacag    3420
aaaaaatcag taacagtact ggatgtgggc gatgcatatt tttcagttcc cttagataaa    3480
gacttcagga agtatactgc atttaccata cctagtataa acaatgagac accagggatt    3540
agatatcagt acaatgtgct tccacaggga tggaaaggat caccagcaat attccagtgt    3600
```

| | |
|---|---|
| agcatgacaa aaatcttaga gcctttaga aaacaaaatc cagacatagt catctatcaa | 3660 |
| tacatggatg atttgtatgt aggatctgac ttagaaatag ggcagcatag aacaaaaata | 3720 |
| gaggaactga gacaacatct gttgaggtgg ggatttacca caccagacaa aaaacatcag | 3780 |
| aaagaacctc cattcctttg gatgggttat gaactccatc ctgataaatg gacagtacag | 3840 |
| cctatagtgc tgccagaaaa ggacagctgg actgtcaatg acatacagaa attagtggga | 3900 |
| aaattgaatt gggcaagtca gatttatgca gggattaaag taaggcaatt atgtaaactt | 3960 |
| cttaggggaa ccaaagcact aacagaagta gtaccactaa cagaagaagc agagctagaa | 4020 |
| ctggcagaaa acagggagat tctaaaagaa ccggtacatg gagtgtatta tgacccatca | 4080 |
| aaagacttaa tagcagaaat acagaagcag gggcaaggcc aatggacata tcaaatttat | 4140 |
| caagagccat ttaaaaatct gaaaacagga aagtatgcaa gaatgaaggg tgcccacact | 4200 |
| aatgatgtga aacaattaac agaggcagta caaaaaatag ccacagaaag catagtaata | 4260 |
| tggggaaaga ctcctaaatt taaattaccc atacaaaagg aaacatggga agcatggtgg | 4320 |
| acagagtatt ggcaagccac ctggattcct gagtgggagt ttgtcaatac ccctccctta | 4380 |
| gtgaagttat ggtaccagtt agagaaagaa cccataatag gagcagaaac tttctatgta | 4440 |
| gatggggcag ccaatagggga aactaaatta ggaaaagcag gatatgtaac tgacagagga | 4500 |
| agacaaaaag ttgtcccect aacggacaca acaaatcaga agactgagtt acaagcaatt | 4560 |
| catctagctt tgcaggattc gggattagaa gtaaacatag tgacagactc acaatatgca | 4620 |
| ttgggaatca ttcaagcaca accagataag agtgaatcag agttagtcag tcaaataata | 4680 |
| gagcagttaa taaaaaagga aaaagtctac ctggcatggg taccagcaca caaaggaatt | 4740 |
| ggaggaaatg aacaagtaga taattggtc agtgctggaa tcaggaaagt actattttta | 4800 |
| gatggaatag ataaggccca agaagaacat gagaaatatc acagtaattg gagagcaatg | 4860 |
| gctagtgatt ttaacctacc acctgtagta gcaaaagaaa tagtagccag ctgtgataaa | 4920 |
| tgtcagctaa aggggaagc catgcatgga caagtagact gtagcccagg aatatggcag | 4980 |
| ctagattgta cacatttaga aggaaaagtt atcttggtag cagttcatgt agccagtgga | 5040 |
| tatatagaag cagaagtaat tccagcagag acagggcaag aaacagcata cttcctctta | 5100 |
| aaattagcag gaagatggcc agtaaaaaca gtacatacag acaatggcag caatttcacc | 5160 |
| agtactacag ttaaggccgc ctgttggtgg gcggggatca agcaggaatt tggcattccc | 5220 |
| tacaatcccc aaagtcaagg agtaatagaa tctatgaata agaattaaa gaaaattata | 5280 |
| ggacaggtaa gagatcaggc tgaacatctt aagacagcag tacaaatggc agtattcatc | 5340 |
| cacaatttta aaagaaaagg ggggattggg gggtacagtg caggggaaag aatagtagac | 5400 |
| ataatagcaa cagacataca aactaaagaa ttacaaaaac aaattacaaa aattcaaaat | 5460 |
| tttcgggttt attacaggga cagcagagat ccagtttgga aaggaccagc aaagctcctc | 5520 |
| tggaaaggtg aagggggcagt agtaatacaa gataatagtg acataaaagt agtgccaaga | 5580 |
| agaaaagcaa agatcatcag ggattatgga aaacagatgg caggtgatga ttgtgtggca | 5640 |
| agtagacagg atgaggatta acacatggaa ttccggagcg gccgcaggag ctttgttcct | 5700 |
| tgggttcttg ggagcagcag gaagcactat gggcgcagcg tcaatgacgc tgacggtaca | 5760 |
| ggccagacaa ttattgtctg gtatagtgca gcagcagaac aatttgctga gggctattga | 5820 |
| ggcgcaacag catctgttgc aactcacagt ctggggcatc aagcagctcc aggcaagaat | 5880 |
| cctggctgtg gaaagatacc taaaggatca acagctcctg gggatttggg gttgctctgg | 5940 |
| aaaactcatt tgcaccactg ctgtgccttg gaatgctagt tggagtaata atctctggaa | 6000 |

```
acagatttgg aatcacacga cctggatgga gtgggacaga gaaattaaca attacacaag   6060
cttccgcgga attcacccca ccagtgcagg ctgcctatca gaaagtggtg gctggtgtgg   6120
ctaatgccct ggcccacaag tatcactaag ctcgctttct tgctgtccaa tttctattaa   6180
aggttccttt gttccctaag tccaactact aaactggggg atattatgaa gggccttgag   6240
catctggatt ctgcctaata aaaacatttt attttcattg caatgatgta tttaaattat   6300
ttctgaatat tttactaaaa agggaatgtg ggaggtcagt gcatttaaaa cataaagaaa   6360
tgaagagcta gttcaaacct tgggaaaata cactatatct taaactccat gaaagaaggt   6420
gaggctgcaa acagctaatg cacattggca acagccctg atgcctatgc cttattcatc    6480
cctcagaaaa ggattcaagt agaggcttga tttggaggtt aaagttttgc tatgctgtat   6540
tttacattac ttattgtttt agctgtcctc atgaatgtct tttcactacc catttgctta   6600
tcctgcatct ctcagccttg actccactca gttctcttgc ttagagatac cacctttccc   6660
ctgaagtgtt ccttccatgt tttacggcga gatggtttct cctcgcctgg ccactcagcc   6720
ttagttgtct ctgttgtctt atagaggtct acttgaagaa ggaaaaacag ggggcatggt   6780
ttgactgtcc tgtgagccct tcttccctgc ctcccccact cacagtgacc cggaatccct   6840
cgacatggca gtctagcact agtgcggccg cagatctgct tcctcgctca ctgactcgct   6900
gcgctcggtc gttcggctgc ggcgagcggt atcagctcac tcaaaggcgg taatacggtt   6960
atccacagaa tcaggggata acgcaggaaa gaacatgtga gcaaaaggcc agcaaaaggc   7020
caggaaccgt aaaaaggccg cgttgctggc gtttttccat aggctccgcc ccctgacga    7080 gcatcacaaa aatcgacgct caagtcagag gtggcgaaac ccgacaggac tataaagata   7140
ccaggcgttt cccctggaa gctccctcgt gcgctctcct gttccgaccc tgccgcttac     7200
cggatacctg tccgccttc tcccttcggg aagcgtggcg ctttctcata gctcacgctg     7260
taggtatctc agttcggtgt aggtcgttcg ctccaagctg ggctgtgtgc acgaaccccc   7320
cgttcagccc gaccgctgcg ccttatccgg taactatcgt cttgagtcca acccggtaag   7380
acacgactta tcgccactgg cagcagccac tggtaacagg attagcagag cgaggtatgt   7440
aggcggtgct acagagttct tgaagtggtg gcctaactac ggctacacta agaacagt     7500 atttggtatc tgcgctctgc tgaagccagt taccttcgga aaaagagttg gtagctcttg   7560
atccggcaaa caaaccaccg ctggtagcgg tggttttttt gtttgcaagc agcagattac   7620
gcgcagaaaa aaaggatctc aagaagatcc tttgatcttt tctacggggt ctgacgctca   7680
gtggaacgaa aactcacgtt aagggatttt ggtcatgaga ttatcaaaaa ggatcttcac   7740
ctagatcctt ttaaattaaa aatgaagttt taaatcaatc taaagtatat atgagtaaac   7800
ttggtctgac agttaccaat gcttaatcag tgaggcacct atctcagcga tctgtctatt   7860
tcgttcatcc atagttgcct gactccccgt cgtgtagata actacgatac gggagggctt   7920
accatctggc cccagtgctg caatgatacc gcgagaccca cgctcaccgg ctccagattt   7980
atcagcaata aaccagccag ccggaagggc cgagcgcaga agtggtcctg caactttatc   8040
cgcctccatc cagtctatta attgttgccg ggaagctaga gtaagtagtt cgccagttaa   8100 tagtttcgc aacgttgttg ccattgctac aggcatcgtg gtgtcacgct cgtcgtttgg    8160
tatggcttca ttcagctccg gttcccaacg atcaaggcga gttacatgat cccccatgtt   8220
gtgcaaaaaa gcggttagct ccttcggtcc tccgatcgtt gtcagaagta agttggccgc   8280
agtgttatca ctcatggtta tggcagcact gcataattct cttactgtca tgccatccgt   8340
aagatgcttt tctgtgactg gtgagtactc aaccaagtca ttctgagaat agtgtatgcg   8400
```

```
gcgaccgagt tgctcttgcc cggcgtcaat acgggataat accgcgccac atagcagaac    8460
tttaaaagtg ctcatcattg gaaaacgttc ttcggggcga aaactctcaa ggatcttacc    8520
gctgttgaga tccagttcga tgtaacccac tcgtgcaccc aactgatctt cagcatcttt    8580
tactttcacc agcgtttctg ggtgagcaaa aacaggaagg caaaatgccg caaaaaggg     8640 aataagggcg acacggaaat gttgaatact catactcttc cttttcaat  attattgaag    8700 catttatcag ggttattgtc tcatgagcgg atacatattt gaatgtattt agaaaaataa    8760
acaaataggg gttccgcgca catttccccg aaaagtgcca cctgacggga tccctgagg     8820 gggcccccat gggctagagg atccggcctc ggcctctgca taaataaaaa aaattagtca    8880
gccatgagc                                                             8889
```

<210> SEQ ID NO 7
<211> LENGTH: 4180
<212> TYPE: DNA
<213> ORGANISM: Artificial
<220> FEATURE:
<223> OTHER INFORMATION: pLP2

<400> SEQUENCE: 7

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
ccgcattgca gagatattgt atttaagtgc ctagctcgat acaataaacg ccatttgacc     240
attcaccaca ttggtgtgca cctccaagct cgagctcgtt tagtgaaccg tcagatcgcc     300
tggagacgcc atccacgctg ttttgacctc catagaagac accgggaccg atccagcctc     360
ccctcgaagc tagtcgatta ggcatctcct atggcaggaa gaagcggaga cagcgacgaa     420
gacctcctca aggcagtcag actcatcaag tttctctatc aaagcaaccc acctcccaat     480
cccgagggga cccgacaggc ccgaaggaat agaagaagaa ggtggagaga gagacagaga     540
cagatccatt cgattagtga acggatcctt agcacttatc tgggacgatc tgcggagcct     600
gtgcctcttc agctaccacc gcttgagaga cttactcttg attgtaacga ggattgtgga     660
acttctggga cgcaggggt  gggaagccct caaatattgg tggaatctcc tacaatattg     720
gagtcaggag ctaagaaata gtgctgttag cttgctcaat gccacagcta tagcagtagc     780
tgaggggaca gatagggtta tagaagtagt acaagaagct tggcactggc cgtcgtttta     840
caacgtcgtg atctgagcct gggagatctc tggctaacta gggaacccac tgcttaagcc     900
tcaataaagc ttgccttgag tgcttcaagt agtgtgtgcc cgtctgttgt gtgactctgg     960
taactagaga tcaggaaaac cctggcgtta cccaacttaa tcgccttgca gcacatcccc    1020
ctttcgccag ctggcgtaat agcgaagagg cccgcaccga tcgcccttcc caacagttgc    1080
gcagcctgaa tggcgaatgg cgcctgatgc ggtattttct ccttacgcat ctgtgcggta    1140
tttcacaccg catacgtcaa agcaaccata gtacgcgccc tgtagcggcg cattaagcgc    1200
ggcgggtgtg gtggttacgc gcagcgtgac cgctacactt gccagcgccc tagcgcccgc    1260
tcctttcgct ttcttccctt cctttctcgc cacgttcgcc ggctttcccc gtcaagctct    1320
aaatcggggg ctccctttag ggttccgatt tagtgcttta cggcacctcg accccaaaaa    1380 acttgattt  ggtgatggtt cacgtagtgg gccatcgccc tgatagacgg ttttcgccc     1440 tttgacgttg gagtccacgt tctttaatag tggactcttg ttccaaactg gaacaacact    1500
caaccctatc tcgggctatt cttttgattt ataagggatt ttgccgattt cggcctattg    1560
```

```
gttaaaaaat gagctgattt aacaaaaatt taacgcgaat tttaacaaaa tattaacgtt   1620
tacaatttta tggtgcactc tcagtacaat ctgctctgat gccgcatagt taagccagcc   1680
ccgacacccg ccaacacccg ctgacgcgcc ctgacgggct tgtctgctcc cggcatccgc   1740
ttacagacaa gctgtgaccg tctccgggag ctgcatgtgt cagaggtttt caccgtcatc   1800
accgaaacgc gcgagacgaa agggcctcgt gatacgccta ttttttatagg ttaatgtcat   1860 gataataatg gtttcttaga cgtcaggtgg cacttttcgg ggaaatgtgc gcggaacccc   1920
tatttgttta ttttctaaa tacattcaaa tatgtatccg ctcatgagac aataaccctg   1980
ataaatgctt caataatatt gaaaaaggaa gagtatgagt attcaacatt tccgtgtcgc   2040
ccttattccc ttttttgcgg cattttgcct tcctgttttt gctcacccag aaacgctggt   2100
gaaagtaaaa gatgctgaag atcagttggg tgcacgagtg gttacatcg aactggatct   2160 caacagcggt aagatccttg agagttttcg ccccgaagaa cgttttccaa tgatgagcac   2220
ttttaaagtt ctgctatgtg gcgcggtatt atcccgtatt gacgccgggc aagagcaact   2280
cggtcgccgc atacactatt ctcagaatga cttggttgag tactcaccag tcacagaaaa   2340
gcatcttacg gatggcatga cagtaagaga attatgcagt gctgccataa ccatgagtga   2400
taacactgcg gccaacttac ttctgacaac gatcggagga ccgaaggagc taaccgcttt   2460
tttgcacaac atgggggatc atgtaactcg ccttgatcgt tgggaaccgg agctgaatga   2520
agccatacca aacgacgagc gtgacaccac gatgcctgta gcaatggcaa caacgttgcg   2580
caaactatta actggcgaac tacttactct agcttcccgg caacaattaa tagactggat   2640
ggaggcggat aaagttgcag gaccacttct gcgctcggcc cttccggctg gctggtttat   2700
tgctgataaa tctggagccg gtgagcgtgg gtctcgcggt atcattgcag cactggggcc   2760
agatggtaag ccctcccgta tcgtagttat ctacacgacg gggagtcagg caactatgga   2820
tgaacgaaat agacagatcg ctgagatagg tgcctcactg attaagcatt ggtaactgtc   2880
agaccaagtt tactcatata ctttagat tgatttaaaa cttcattttt aatttaaaag   2940
gatctaggtg aagatccttt ttgataatct catgaccaaa atcccttaac gtgagttttc   3000
gttccactga gcgtcagacc ccgtagaaaa gatcaaagga tcttcttgag atcctttttt   3060
tctgcgcgta atctgctgct tgcaaacaaa aaaaccaccg ctaccagcgg tggtttgttt   3120
gccggatcaa gagctaccaa ctctttttcc gaaggtaact ggcttcagca gagcgcagat   3180
accaaatact gttcttctag tgtagccgta gttaggccac cacttcaaga actctgtagc   3240
accgcctaca tacctcgctc tgctaatcct gttaccagtg gctgctgcca gtggcgataa   3300
gtcgtgtctt accgggttgg actcaagacg atagttaccg gataaggcgc agcggtcggg   3360
ctgaacgggg ggttcgtgca cacagcccag cttggagcga acgacctaca ccgaactgag   3420
atacctacag cgtgagctat gagaaagcgc cacgcttccc gaaggagaa aggcggacag   3480 gtatccggta agcggcaggg tcggaacagg agagcgcacg agggagcttc caggggggaaa   3540 cgcctggtat ctttatagtc ctgtcgggtt tcgccacctc tgacttgagc gtcgattttt   3600
gtgatgctcg tcaggggggc ggagcctatg gaaaaacgcc agcaacgcgg cctttttacg   3660
gttcctggcc ttttgctggc cttttgctca catgttcttt cctgcgttat cccctgattc   3720
tgtggataac cgtattaccg cctttgagtg agctgatacc gctcgccgca gccgaacgac   3780
cgagcgcagc gagtcagtga gcgaggaagc ggaagagcgc ccaatacgca aaccgcctct   3840
ccccgcgcgt tggccgattc attaatgcag ctggcacgac aggtttcccg actggaaagc   3900
gggcagtgag cgcaacgcaa ttaatgtgag ttagctcact cattaggcac cccaggcttt   3960
```

```
acactttatg cttccggctc gtatgttgtg tggaattgtg agcggataac aatttcacac    4020
aggaaacagc tatgacatga ttacgaattc gatgtacggg ccagatatac gcgtatctga    4080
ggggactagg gtgtgtttag gcgaaaagcg gggcttcggt tgtacgcggt taggagtccc    4140
ctcaggatat agtagtttcg cttttgcata gggaggggga                          4180

<210> SEQ ID NO 8
<211> LENGTH: 5821
<212> TYPE: DNA
<213> ORGANISM: Artificial
<220> FEATURE:
<223> OTHER INFORMATION: pLP/VSVG

<400> SEQUENCE: 8
ttggcccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gacccccgcc cattgacgtc aataatgacg tatgttccca     240
tagtaacgcc aatagggact ttccattgac gtcaatgggt ggagtattta cggtaaactg     300
cccacttggc agtacatcaa gtgtatcata tgccaagtac gccccctatt gacgtcaatg     360
acggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540
tcaatgggag tttgttttgg caccaaaatc aacgggactt tccaaaatgt cgtaacaact     600
ccgccccatt gacgcaaatg ggcggtaggc gtgtacggtg ggaggtctat ataagcagag     660
ctcgtttagt gaaccgtcag atcgcctgga gacgccatcc acgctgtttt gacctccata     720
gaagacaccg ggaccgatcc agcctcccct cgaagcttac atgtggtacc gagctcggat     780
cctgagaact tcagggtgag tctatgggac ccttgatgtt ttctttcccc ttcttttcta     840
tggttaagtt catgtcatag aaggggagaa gtaacaggg tacacatatt gaccaaatca     900
gggtaatttt gcatttgtaa ttttaaaaaa tgctttcttc ttttaatata cttttttgtt     960
tatcttattt ctaatacttt ccctaatctc tttctttcag gcaataatg atacaatgta    1020 tcatgcctct ttgcaccatt ctaaagaata acagtgataa tttctgggtt aaggcaatag    1080
caatatttct gcatataaat atttctgcat ataaattgta actgatgtaa gaggtttcat    1140
attgctaata gcagctacaa tccagctacc attctgcttt tattttatgg ttgggataag    1200
gctggattat tctgagtcca agctaggccc ttttgctaat catgttcata cctcttatct    1260
tcctcccaca gctcctgggc aacgtgctgg tctgtgtgct ggcccatcac tttggcaaag    1320
cacgtgagat ctgaattctg acactatgaa gtgccttttg tacttagcct ttttattcat    1380 tgggtgaat tgcaagttca ccatagtttt tccacacaac caaaaggaa actggaaaaa      1440 tgttccttct aattaccatt attgcccgtc aagctcagat ttaaattggc ataatgactt    1500
aataggcaca gccttacaag tcaaaatgcc caagagtcac aaggctattc aagcagacgg    1560
ttggatgtgt catgcttcca aatgggtcac tacttgtgat ttccgctggt atggaccgaa    1620
gtatataaca cattccatcc gatccttcac tccatctgta gaacaatgca ggaaagcat     1680 tgaacaaacg aaacaaggaa cttggctgaa tccaggcttc cctcctcaaa gttgtggata    1740
tgcaactgtg acggatgccg aagcagtgat tgtccaggtg actcctcacc atgtgctggt    1800
tgatgaatac acaggagaat gggttgattc acagttcatc aacggaaaat gcagcaatta    1860
```

| | |
|---|---|
| catatgcccc actgtccata actctacaac ctggcattct gactataagg tcaaagggct | 1920 |
| atgtgattct aacctcattt ccatggacat caccttcttc tcagaggacg gagagctatc | 1980 |
| atccctggga aggagggca cagggttcag aagtaactac tttgcttatg aaactggagg | 2040 |
| caaggcctgc aaaatgcaat actgcaagca ttggggagtc agactcccat caggtgtctg | 2100 |
| gttcgagatg gctgataagg atctctttgc tgcagccaga ttccctgaat gcccagaagg | 2160 |
| gtcaagtatc tctgctccat ctcagacctc agtggatgta agtctaattc aggacgttga | 2220 |
| gaggatcttg gattattccc tctgccaaga aacctggagc aaaatcagag cgggtcttcc | 2280 |
| aatctctcca gtggatctca gctatcttgc tcctaaaaac ccaggaaccg tcctgctttt | 2340 |
| caccataatc aatggtaccc taaaatactt tgagaccaga tacatcagag tcgatattgc | 2400 |
| tgctccaatc ctctcaagaa tggtcggaat gatcagtgga actaccacag aaagggaact | 2460 |
| gtgggatgac tgggcaccat atgaagacgt ggaaattgga cccaatggag ttctgaggac | 2520 |
| cagttcagga tataagtttc ctttatacat gattggacat ggtatgttgg actccgatct | 2580 |
| tcatcttagc tcaaaggctc aggtgttcga acatcctcac attcaagacg ctgcttcgca | 2640 |
| acttcctgat gatgagagtt tattttttgg tgatactggg ctatccaaaa atccaatcga | 2700 |
| gcttgtagaa ggttggttca gtagttggaa aagctctatt gcctcttttt tctttatcat | 2760 |
| agggttaatc attggactat tcttggttct ccgagttggt atccatcttt gcattaaatt | 2820 |
| aaagcacacc aagaaaagac agatttatac agacatagag atgaaccgac ttggaaagta | 2880 |
| actcaaatcc tgcacaacag attcttcatg tttggaccaa atcaacttgt gataccatgc | 2940 |
| tcaaagaggc ctcaattata tttgagtttt taatttttat gaaaaaaaaa aaaaaaaacg | 3000 |
| gaattcaccc caccagtgca ggctgcctat cagaaagtgg tggctggtgt ggctaatgcc | 3060 |
| ctggcccaca agtatcacta agctcgcttt cttgctgtcc aatttctatt aaaggttcct | 3120 |
| ttgttcccta agtccaacta ctaaactggg ggatatatg aagggccttg agcatctgga | 3180 |
| ttctgcctaa taaaaaacat ttattttcat tgcaatgatg tatttaaatt atttctgaat | 3240 |
| attttactaa aaagggaatg tgggaggtca gtgcatttaa aacataaaga aatgaagagc | 3300 |
| tagttcaaac cttgggaaaa tacactatat cttaaactcc atgaaagaag gtgaggctgc | 3360 |
| aaacagctaa tgcacattgg caacagcccc tgatgcctat gccttattca tccctcagaa | 3420 |
| aaggattcaa gtagaggctt gatttggagg ttaaagtttt gctatgctgt attttacatt | 3480 |
| acttattgtt ttagctgtcc tcatgaatgt cttttcacta cccatttgct tatcctgcat | 3540 |
| ctctcagcct tgactccact cagttctctt gcttagagat accacctttc ccctgaagtg | 3600 |
| ttccttccat gttttacggc gagatggttt ctcctcgcct ggccactcag ccttagttgt | 3660 |
| ctctgttgtc ttatagaggt ctacttgaag aaggaaaaac aggggcatg gtttgactgt | 3720 |
| cctgtgagcc cttcttccct gcctccccca ctcacagtga cccggaatcc ctcgacatgg | 3780 |
| cagtctagca ctagtgcggc cgcagatctg cttcctcgct cactgactcg ctgcgctcgg | 3840 |
| tcgttcggct gcggcgagcg gtatcagctc actcaaaggc ggtaatacgg ttatccacag | 3900 |
| aatcagggga taacgcagga agaacatgt gagcaaaagg ccagcaaaag ccaggaacc | 3960 |
| gtaaaaaggc cgcgttgctg gcgttttttcc ataggctccg ccccctgac gagcatcaca | 4020 |
| aaaatcgacg ctcaagtcag aggtggcgaa acccgacagg actataaaga taccaggcgt | 4080 |
| ttccccctgg aagctccctc gtgcgctctc ctgttccgac cctgccgctt accggatacc | 4140 |
| tgtccgcctt tctcccttcg ggaagcgtgg cgctttctca tagctcacgc tgtaggtatc | 4200 |
| tcagttcggt gtaggtcgtt cgctccaagc tgggctgtgt gcacgaaccc cccgttcagc | 4260 |

```
ccgaccgctg cgccttatcc ggtaactatc gtcttgagtc caacccggta agacacgact    4320
tatcgccact ggcagcagcc actggtaaca ggattagcag agcgaggtat gtaggcggtg    4380
ctacagagtt cttgaagtgg tggcctaact acgctacac tagaagaaca gtatttggta     4440
tctgcgctct gctgaagcca gttaccttcg aaaaagagt tggtagctct tgatccggca     4500
aacaaaccac cgctggtagc ggtggttttt ttgtttgcaa gcagcagatt acgcgcagaa    4560 aaaaggatc tcaagaagat cctttgatct tttctacggg gtctgacgct cagtggaacg     4620
aaaactcacg ttaagggatt ttggtcatga gattatcaaa aaggatcttc acctagatcc    4680
ttttaaatta aaaatgaagt tttaaatcaa tctaaagtat atatgagtaa acttggtctg    4740
acagttacca atgcttaatc agtgaggcac ctatctcagc gatctgtcta tttcgttcat    4800
ccatagttgc ctgactcccc gtcgtgtaga taactacgat acgggagggc ttaccatctg    4860
gccccagtgc tgcaatgata ccgcgagacc cacgctcacc ggctccagat ttatcagcaa    4920
taaaccagcc agccggaagg gccgagcgca gaagtggtcc tgcaacttta tccgcctcca    4980
tccagtctat taattgttgc cgggaagcta gagtaagtag ttcgccagtt aatagtttgc    5040
gcaacgttgt tgccattgct acaggcatcg tggtgtcacg ctcgtcgttt ggtatggctt    5100
cattcagctc cggttcccaa cgatcaaggc gagttacatg atcccccatg ttgtgcaaaa    5160
aagcggttag ctccttcggt cctccgatcg ttgtcagaag taagttggcc gcagtgttat    5220
cactcatggt tatggcagca ctgcataatt ctcttactgt catgccatcc gtaagatgct    5280
tttctgtgac tggtgagtac tcaaccaagt cattctgaga atagtgtatg cggcgaccga    5340
gttgctcttg cccggcgtca atacgggata ataccgcgcc acatagcaga actttaaaag    5400
tgctcatcat tggaaaacgt tcttcggggc gaaaactctc aaggatctta ccgctgttga    5460
gatccagttc gatgtaaccc actcgtgcac ccaactgatc ttcagcatct tttactttca    5520
ccagcgtttc tgggtgagca aaaacaggaa ggcaaaatgc cgcaaaaaag gaataagggc    5580 gacacggaa atgttgaata ctcatactct tccttttca atattattga agcatttatc      5640
agggttattg tctcatgagc ggatacatat ttgaatgtat ttagaaaaat aaacaaatag    5700
gggttccgcg cacatttccc cgaaaagtgc cacctgacgg gatccctga ggggccccc      5760 atgggctaga ggatccggcc tcggcctctg cataaataaa aaaaattagt cagccatgag    5820
c                                                                    5821

<210> SEQ ID NO 9
<211> LENGTH: 47
<212> TYPE: DNA
<213> ORGANISM: Artificial
<220> FEATURE:
<223> OTHER INFORMATION: lamin A/C control oligo

<400> SEQUENCE: 9
caccgtgttc ttctggaagt ccagcgaact ggacttccag aagaaca                  47

<210> SEQ ID NO 10
<211> LENGTH: 47
<212> TYPE: DNA
<213> ORGANISM: Artificial
<220> FEATURE:
<223> OTHER INFORMATION: lamin A/C control oligo

<400> SEQUENCE: 10
aaaatgttct tctggaagtc cagttcgctg gacttccaga agaacac                  47
```

```
<210> SEQ ID NO 11
<211> LENGTH: 20
<212> TYPE: DNA
<213> ORGANISM: Artificial
<220> FEATURE:
<223> OTHER INFORMATION: Sequencing primer

<400> SEQUENCE: 11
ggactatcat atgcttaccg                                              20

<210> SEQ ID NO 12
<211> LENGTH: 17
<212> TYPE: DNA
<213> ORGANISM: Artificial
<220> FEATURE:
<223> OTHER INFORMATION: Sequencing primer

<400> SEQUENCE: 12
caggaaacag ctatgac                                                 17

<210> SEQ ID NO 13
<211> LENGTH: 20
<212> TYPE: DNA
<213> ORGANISM: Artificial
<220> FEATURE:
<223> OTHER INFORMATION: U6 promoter sequence

<400> SEQUENCE: 13
aaggtcgggc aggaagaggg                                              20

<210> SEQ ID NO 14
<211> LENGTH: 20
<212> TYPE: DNA
<213> ORGANISM: Artificial
<220> FEATURE:
<223> OTHER INFORMATION: U6 promoter sequence

<400> SEQUENCE: 14
agcgagcacg gtgtttcgtc                                              20

<210> SEQ ID NO 15
<211> LENGTH: 29
<212> TYPE: DNA
<213> ORGANISM: Artificial
<220> FEATURE:
<223> OTHER INFORMATION: U6 promoter sequence with Asp718 and Not I at
      5' end

<400> SEQUENCE: 15
gtgggtacca aggtcgggca ggaagaggg                                    29

<210> SEQ ID NO 16
<211> LENGTH: 33
<212> TYPE: DNA
<213> ORGANISM: Artificial
<220> FEATURE:
<223> OTHER INFORMATION: U6 promoter with Asp718 and Not I at 5' end

<400> SEQUENCE: 16
gtggcggccg cggtgtttcg tcctttccac aag                               33

<210> SEQ ID NO 17
<211> LENGTH: 44
<212> TYPE: DNA
<213> ORGANISM: Artificial
<220> FEATURE:
<223> OTHER INFORMATION: primer for ccdB gene
```

```
<400> SEQUENCE: 17
gtggcggccg caaagatcct ccagtggatc cggcttacta aaag            44

<210> SEQ ID NO 18
<211> LENGTH: 57
<212> TYPE: DNA
<213> ORGANISM: Artificial
<220> FEATURE:
<223> OTHER INFORMATION: primer for ccdB gene

<400> SEQUENCE: 18
gtgctcgaga aaaagtcga cacggagccc tccagttata ttccccagaa catcagg    57

<210> SEQ ID NO 19
<211> LENGTH: 30
<212> TYPE: DNA
<213> ORGANISM: Artificial
<220> FEATURE:
<223> OTHER INFORMATION: part of double stranded oligo containing BsaI
      and NotI site to engineer BsaI vector

<400> SEQUENCE: 19
gagaccgcgg ccgcttctcg aggtctcatt                            30

<210> SEQ ID NO 20
<211> LENGTH: 30
<212> TYPE: DNA
<213> ORGANISM: Artificial
<220> FEATURE:
<223> OTHER INFORMATION: part of double stranded oligo containing BsaI
      and NotI site for engineering BsaI vector

<400> SEQUENCE: 20
tgagacctcg agaagcggcc gcggtctccg                            30

<210> SEQ ID NO 21
<211> LENGTH: 31
<212> TYPE: DNA
<213> ORGANISM: Artificial
<220> FEATURE:
<223> OTHER INFORMATION: Primer for new ccdB region with NotI site, BsaI
      site, XbaI site

<400> SEQUENCE: 21
cacgcggccg ctggatccgg cttactaaaa g                          31

<210> SEQ ID NO 22
<211> LENGTH: 43
<212> TYPE: DNA
<213> ORGANISM: Artificial
<220> FEATURE:
<223> OTHER INFORMATION: Primer for new ccdB region

<400> SEQUENCE: 22
cactctagaa aaatgagac cttatattcc ccagaacatc agg              43

<210> SEQ ID NO 23
<211> LENGTH: 7
<212> TYPE: PRT
<213> ORGANISM: Artificial
<220> FEATURE:
<223> OTHER INFORMATION: Consensus cleavage site
<220> FEATURE:
<221> NAME/KEY: wildcard
<222> LOCATION: (2)..(3)
<223> OTHER INFORMATION: x can be any amino acid
<220> FEATURE:
<221> NAME/KEY: wildcard
```

```
<222> LOCATION: (5)..(5)
<223> OTHER INFORMATION: x can be any amino acid
<220> FEATURE:
<221> NAME/KEY: wildcard
<222> LOCATION: (7)..(7)
<223> OTHER INFORMATION: x can be any amino acid except proline

<400> SEQUENCE: 23

Glu Xaa Xaa Tyr Xaa Gln Xaa
1               5

<210> SEQ ID NO 24
<211> LENGTH: 7
<212> TYPE: PRT
<213> ORGANISM: Artificial
<220> FEATURE:
<223> OTHER INFORMATION: TEV1 cleavage site
<220> FEATURE:
<221> NAME/KEY: wildcard
<222> LOCATION: (7)..(7)
<223> OTHER INFORMATION: x can be any amino acid except proline

<400> SEQUENCE: 24

Glu Asn Leu Tyr Phe Gln Xaa
1               5

<210> SEQ ID NO 25
<211> LENGTH: 7
<212> TYPE: PRT
<213> ORGANISM: Artificial
<220> FEATURE:
<223> OTHER INFORMATION: Tev 2 cleavage site
<220> FEATURE:
<221> NAME/KEY: wildcard
<222> LOCATION: (7)..(7)
<223> OTHER INFORMATION: x can be any amino acid except proline

<400> SEQUENCE: 25

Glu Thr Leu Tyr Ile Gln Xaa
1               5

<210> SEQ ID NO 26
<211> LENGTH: 5
<212> TYPE: PRT
<213> ORGANISM: Artificial
<220> FEATURE:
<223> OTHER INFORMATION: EK Cleavage site

<400> SEQUENCE: 26

Asp Asp Asp Asp Lys
1               5

<210> SEQ ID NO 27
<211> LENGTH: 7
<212> TYPE: PRT
<213> ORGANISM: Artificial
<220> FEATURE:
<223> OTHER INFORMATION: TEV1 cleavage site (cleaves between Gln and
      Gly)

<400> SEQUENCE: 27

Glu Asn Leu Tyr Phe Gln Gly
1               5

<210> SEQ ID NO 28
<211> LENGTH: 3
<212> TYPE: PRT
<213> ORGANISM: Artificial
<220> FEATURE:
<223> OTHER INFORMATION: ulp1 protease recognition site
```

```
<400> SEQUENCE: 28

Gly Gly Ser
1

<210> SEQ ID NO 29
<211> LENGTH: 5
<212> TYPE: PRT
<213> ORGANISM: Artificial
<220> FEATURE:
<223> OTHER INFORMATION: Peptide tag

<400> SEQUENCE: 29

Phe His His Thr Thr
1               5

<210> SEQ ID NO 30
<211> LENGTH: 6
<212> TYPE: PRT
<213> ORGANISM: Artificial
<220> FEATURE:
<223> OTHER INFORMATION: Flash tags
<220> FEATURE:
<221> NAME/KEY: wildcard
<222> LOCATION: (3)..(4)
<223> OTHER INFORMATION: x can be any amino acid. In many instances, x
      is an amino acid with high helical propensity

<400> SEQUENCE: 30

Cys Cys Xaa Xaa Cys Cys
1               5

<210> SEQ ID NO 31
<211> LENGTH: 32
<212> TYPE: DNA
<213> ORGANISM: Artificial
<220> FEATURE:
<223> OTHER INFORMATION: BsaI digestion site

<400> SEQUENCE: 31
acaccggaga ccggtctcat tttttttcta ga                                     32

<210> SEQ ID NO 32
<211> LENGTH: 32
<212> TYPE: DNA
<213> ORGANISM: Artificial
<220> FEATURE:
<223> OTHER INFORMATION: BsaI digestion site complementary sequence

<400> SEQUENCE: 32
gctagaaaaa aaatgagacc ggtctccggt gt                                     32

<210> SEQ ID NO 33
<211> LENGTH: 13
<212> TYPE: DNA
<213> ORGANISM: Artificial
<220> FEATURE:
<223> OTHER INFORMATION: BsaI digestion fragment

<400> SEQUENCE: 33 tttttttct aga                                                           13

<210> SEQ ID NO 34
<211> LENGTH: 24
<212> TYPE: DNA
<213> ORGANISM: Artificial
<220> FEATURE:
<223> OTHER INFORMATION: possible insert with overhang into pENTR/U6-
```

```
                         BsaI-ccdB
<220> FEATURE:
<221> NAME/KEY: wildcard
<222> LOCATION: (6)..(24)
<223> OTHER INFORMATION: n can be any nucleotide
<220> FEATURE:
<221> NAME/KEY: misc_feature
<222> LOCATION: (6)..(24)
<223> OTHER INFORMATION: n is a, c, g, or t

<400> SEQUENCE: 34
caccgnnnnn nnnnnnnnnn nnnn                                              24

<210> SEQ ID NO 35
<211> LENGTH: 24
<212> TYPE: DNA
<213> ORGANISM: Artificial
<220> FEATURE:
<223> OTHER INFORMATION: Possible insert (complementary seq. with
      overhang) into p-ENTR/U6-BsaI-ccd
<220> FEATURE:
<221> NAME/KEY: wildcard
<222> LOCATION: (5)..(23)
<223> OTHER INFORMATION: n can be any nucleotide
<220> FEATURE:
<221> NAME/KEY: misc_feature
<222> LOCATION: (5)..(23)
<223> OTHER INFORMATION: n is a, c, g, or t

<400> SEQUENCE: 35 aaaannnnn nnnnnnnnnn nnnc                                               24

<210> SEQ ID NO 36
<211> LENGTH: 21
<212> TYPE: DNA
<213> ORGANISM: Artificial
<220> FEATURE:
<223> OTHER INFORMATION: siRNA core molecule with overhang

<400> SEQUENCE: 36
uucagugagu agagucauau t                                                 21

<210> SEQ ID NO 37
<211> LENGTH: 21
<212> TYPE: DNA
<213> ORGANISM: Artificial
<220> FEATURE:
<223> OTHER INFORMATION: siRNA core molecule complementary seq. with
      overhang

<400> SEQUENCE: 37
uaugactcta ctcacugaau t                                                 21

<210> SEQ ID NO 38
<211> LENGTH: 34
<212> TYPE: DNA
<213> ORGANISM: Artificial
<220> FEATURE:
<223> OTHER INFORMATION: miRNA with sequence mismatches

<400> SEQUENCE: 38
gcgacuguaa acauccucga cuggaagcug ugaa                                   34

<210> SEQ ID NO 39
<211> LENGTH: 37
<212> TYPE: RNA
<213> ORGANISM: Artificial
<220> FEATURE:
<223> OTHER INFORMATION: miRNA complementary sequence with mismatches
```

```
<400> SEQUENCE: 39
gccacagaug ggcuuucagu cgguaguuug cagcugc                        37

<210> SEQ ID NO 40
<211> LENGTH: 24
<212> TYPE: RNA
<213> ORGANISM: Artificial
<220> FEATURE:
<223> OTHER INFORMATION: diced miRNA with mismatches

<400> SEQUENCE: 40
uguaaacauc cucgacugga agcu                                     24

<210> SEQ ID NO 41
<211> LENGTH: 22
<212> TYPE: RNA
<213> ORGANISM: Artificial
<220> FEATURE:
<223> OTHER INFORMATION: diced miRNA complementary sequence with
      mismatches

<400> SEQUENCE: 41
cuuucagucg gauguuugca gc                                       22

<210> SEQ ID NO 42
<211> LENGTH: 23
<212> TYPE: RNA
<213> ORGANISM: Artificial
<220> FEATURE:
<223> OTHER INFORMATION: siRNA

<400> SEQUENCE: 42
auuucgaagu auccgcgua cgu                                       23

<210> SEQ ID NO 43
<211> LENGTH: 23
<212> TYPE: RNA
<213> ORGANISM: Artificial
<220> FEATURE:
<223> OTHER INFORMATION: siRNA complentary sequence

<400> SEQUENCE: 43
acguacgcgg aauacuucga aau                                      23

<210> SEQ ID NO 44
<211> LENGTH: 25
<212> TYPE: RNA
<213> ORGANISM: Artificial
<220> FEATURE:
<223> OTHER INFORMATION: shRNA

<400> SEQUENCE: 44
auuucgaagu auccgcgua cguuu                                     25

<210> SEQ ID NO 45
<211> LENGTH: 28
<212> TYPE: RNA
<213> ORGANISM: Artificial
<220> FEATURE:
<223> OTHER INFORMATION: shRNA complementary sequence

<400> SEQUENCE: 45
cgacguacgc ggaauacuuc gaaauuuu                                 28

<210> SEQ ID NO 46
<211> LENGTH: 41
```

```
<212> TYPE: RNA
<213> ORGANISM: Artificial
<220> FEATURE:
<223> OTHER INFORMATION: miRNA with mismatches

<400> SEQUENCE: 46
cucgagaucu gcgccguacg cggaauacuu cgaaauguga a                41

<210> SEQ ID NO 47
<211> LENGTH: 47
<212> TYPE: RNA
<213> ORGANISM: Artificial
<220> FEATURE:
<223> OTHER INFORMATION: miRNA complementary sequence with mismatches

<400> SEQUENCE: 47
gccacagaug auuucgaagu auuccgcgua cguugcggau ccucgag          47

<210> SEQ ID NO 48
<211> LENGTH: 23
<212> TYPE: DNA
<213> ORGANISM: Artificial
<220> FEATURE:
<223> OTHER INFORMATION: Directional TOPO cloning site with gene of
      interest
<220> FEATURE:
<221> NAME/KEY: wildcard
<222> LOCATION: (13)..(18)
<223> OTHER INFORMATION: n can be any nucleotide
<220> FEATURE:
<221> NAME/KEY: misc_feature
<222> LOCATION: (13)..(18)
<223> OTHER INFORMATION: n is a, c, g, or t

<400> SEQUENCE: 48
cccttcacca tgnnnnnnaa ggg                                    23

<210> SEQ ID NO 49
<211> LENGTH: 27
<212> TYPE: DNA
<213> ORGANISM: Artificial
<220> FEATURE:
<223> OTHER INFORMATION: Complementary sequence of directional TOPO
      cloning site with gene
<220> FEATURE:
<221> NAME/KEY: wildcard
<222> LOCATION: (6)..(11)
<223> OTHER INFORMATION: n can be any nucleotide
<220> FEATURE:
<221> NAME/KEY: misc_feature
<222> LOCATION: (6)..(11)
<223> OTHER INFORMATION: n is a, c, g, or t

<400> SEQUENCE: 49
cccttnnnnn ncatggtggg tgaaggg                                27

<210> SEQ ID NO 50
<211> LENGTH: 11
<212> TYPE: DNA
<213> ORGANISM: Artificial
<220> FEATURE:
<223> OTHER INFORMATION: TOPO cloning site

<400> SEQUENCE: 50
cccttaaggg c                                                 11

<210> SEQ ID NO 51
<211> LENGTH: 15
<212> TYPE: DNA
<213> ORGANISM: Artificial
```

-continued

```
<220> FEATURE:
<223> OTHER INFORMATION: TOPO cloning site complementary sequence with
      overhang

<400> SEQUENCE: 51
gcccttggtg aaggg                                                    15
```